(12) United States Patent
Gray et al.

(10) Patent No.: US 9,758,522 B2
(45) Date of Patent: Sep. 12, 2017

(54) HYDROPHOBICALLY TAGGED SMALL MOLECULES AS INDUCERS OF PROTEIN DEGRADATION

(71) Applicants: Dana-Farber Cancer Institute, Inc., Boston, MA (US); Yale University, New Haven, CT (US)

(72) Inventors: Nathanael Gray, Boston, MA (US); Ting Xie, Boston, MA (US); Sang Min Lim, San Diego, CA (US); Pasi A. Janne, Needham, MA (US); Craig M. Crews, New Haven, CT (US)

(73) Assignees: Dana-Farber Cancer Institute, Inc., Boston, MA (US); Yale University, New Haven, CT (US)

( * ) Notice: Subject to any disclaimer, the term of this patent is extended or adjusted under 35 U.S.C. 154(b) by 0 days.

(21) Appl. No.: 14/436,657

(22) PCT Filed: Oct. 18, 2013

(86) PCT No.: PCT/US2013/065698
§ 371 (c)(1),
(2) Date: Apr. 17, 2015

(87) PCT Pub. No.: WO2014/063061
PCT Pub. Date: Apr. 24, 2014

(65) Prior Publication Data
US 2015/0274738 A1    Oct. 1, 2015

Related U.S. Application Data

(60) Provisional application No. 61/716,305, filed on Oct. 19, 2012.

(51) Int. Cl.
*A61K 31/519* (2006.01)
*C07D 487/04* (2006.01)

(52) U.S. Cl.
CPC .......... *C07D 487/04* (2013.01); *A61K 31/519* (2013.01)

(58) Field of Classification Search
CPC .................................................. C07D 487/04
See application file for complete search history.

(56) References Cited

U.S. PATENT DOCUMENTS

| | | | |
|---|---|---|---|
| 4,231,938 A | 11/1980 | Monaghan et al. | |
| 4,270,537 A | 6/1981 | Romaine et al. | |
| 4,596,556 A | 6/1986 | Morrow et al. | |
| 4,782,084 A | 11/1988 | Vyas et al. | |
| 4,790,824 A | 12/1988 | Morrow et al. | |
| 4,885,314 A | 12/1989 | Vyas et al. | |
| 4,886,499 A | 12/1989 | Cirelli et al. | |
| 4,940,460 A | 7/1990 | Casey et al. | |
| 4,941,880 A | 7/1990 | Burns et al. | |
| 5,015,235 A | 5/1991 | Crossman et al. | |
| 5,064,413 A | 11/1991 | McKinnon et al. | |
| 5,141,496 A | 8/1992 | Dalto et al. | |
| 5,190,521 A | 3/1993 | Hubbard et al. | |
| 5,312,335 A | 5/1994 | McKinnon et al. | |
| 5,328,483 A | 7/1994 | Jacoby et al. | |

(Continued)

FOREIGN PATENT DOCUMENTS

| CA | 2486101 A1 | 11/2003 |
|---|---|---|
| CA | 2503646 A1 | 5/2004 |

(Continued)

OTHER PUBLICATIONS

Extended European Search Report for EP 15160591.2, mailed Nov. 2, 2015.
International Search Report and Written Opinion for PCT/US2015/41360, mailed Dec. 15, 2015.
International Search Report and Written Opinion for PCT/US2015/41348, mailed Oct. 28, 2015.
Hart et al., SB 1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
Mallison et al., Macrocycles in new drug discovery. Future Med Chem. Jul. 2012;4(11):1409-38. doi: 10.4155/fmc.12.93.
U.S. Appl. No. 14/552,229, filed Nov. 24, 2014, Gray et al.
U.S. Appl. No. 14/921,894, filed Oct. 23, 2015, Gray et al.

(Continued)

*Primary Examiner* — Brian McDowell
(74) *Attorney, Agent, or Firm* — Wolf, Greenfield & Sacks, P.C.

(57) ABSTRACT

Provided are bifunctional small molecules of Formula (I): or pharmaceutically acceptable salts thereof, wherein M represents a small organic molecule which binds, covalently or non-covalently, a kinase, such as Her3 protein kinase; $L^1$ represents a linker; and $R^H$ represents a hydrophobic group. An example of a compound of Formula (I) is a compound of Formula (II): Also provided are pharmaceutical compositions comprising a compound of Formula (I) or (II) and methods of using such compounds for treating proliferative diseases.

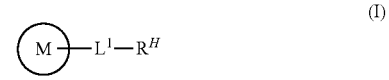

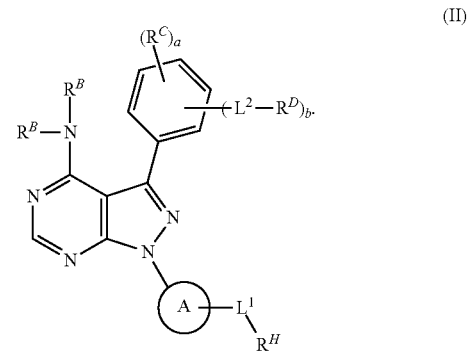

22 Claims, 5 Drawing Sheets

(56) References Cited

U.S. PATENT DOCUMENTS

| | | |
|---|---|---|
| 5,334,144 A | 8/1994 | Alchas et al. |
| 5,339,163 A | 8/1994 | Homma et al. |
| 5,383,851 A | 1/1995 | McKinnon et al. |
| 5,417,662 A | 5/1995 | Hjertman et al. |
| 5,420,245 A | 5/1995 | Brown et al. |
| 5,466,220 A | 11/1995 | Brenneman et al. |
| 5,480,381 A | 1/1996 | Weston et al. |
| 5,484,596 A | 1/1996 | Hanna et al. |
| 5,503,627 A | 4/1996 | McKinnon et al. |
| 5,510,510 A | 4/1996 | Patel et al. |
| 5,520,639 A | 5/1996 | Peterson et al. |
| 5,523,430 A | 6/1996 | Patel et al. |
| 5,527,288 A | 6/1996 | Gross et al. |
| 5,532,359 A | 7/1996 | Marsters et al. |
| 5,569,189 A | 10/1996 | Parsons et al. |
| 5,571,792 A | 11/1996 | Bolton et al. |
| 5,589,485 A | 12/1996 | Hochlowski et al. |
| 5,599,302 A | 2/1997 | Lilley et al. |
| 5,602,098 A | 2/1997 | Sebti et al. |
| 5,643,958 A | 7/1997 | Iwasawa et al. |
| 5,649,912 A | 7/1997 | Peterson et al. |
| 5,661,152 A | 8/1997 | Bishop et al. |
| 5,704,911 A | 1/1998 | Parsons et al. |
| 5,750,567 A | 5/1998 | Baudoin et al. |
| 5,756,466 A | 5/1998 | Bemis et al. |
| 5,856,439 A | 1/1999 | Clerc et al. |
| 5,889,053 A | 3/1999 | Baudoin et al. |
| 5,893,397 A | 4/1999 | Peterson et al. |
| 5,925,641 A | 7/1999 | Kanda et al. |
| 5,936,097 A | 8/1999 | Commercon et al. |
| 5,993,412 A | 11/1999 | Deily et al. |
| 6,069,134 A | 5/2000 | Roth et al. |
| 6,921,763 B2 * | 7/2005 | Hirst .................. C07F 9/6561 514/262.1 |
| 6,939,874 B2 | 9/2005 | Harmange et al. |
| 7,115,617 B2 | 10/2006 | Buchanan et al. |
| 7,312,225 B2 | 12/2007 | Luecking et al. |
| 7,884,117 B2 | 2/2011 | Zhang et al. |
| 7,928,140 B2 | 4/2011 | Booker et al. |
| 8,088,781 B2 | 1/2012 | Honigberg et al. |
| 8,394,818 B2 | 3/2013 | Gray et al. |
| 8,765,747 B2 | 7/2014 | Choi et al. |
| 8,889,706 B2 | 11/2014 | Gray et al. |
| 8,987,275 B2 | 3/2015 | Gray et al. |
| 9,180,127 B2 | 11/2015 | Gray et al. |
| 9,358,231 B2 | 6/2016 | Gray et al. |
| 9,382,239 B2 | 7/2016 | Gray et al. |
| 9,505,784 B2 | 11/2016 | Choi et al. |
| 2003/0139416 A1 | 7/2003 | Buchanan et al. |
| 2004/0106634 A1 | 6/2004 | Satoh et al. |
| 2004/0235892 A1 | 11/2004 | Dai et al. |
| 2005/0250837 A1 | 11/2005 | D'Mello et al. |
| 2006/0106083 A1 | 5/2006 | Martina et al. |
| 2006/0189627 A1 | 8/2006 | Laird et al. |
| 2007/0093537 A1 | 4/2007 | Hynes et al. |
| 2007/0185171 A1 | 8/2007 | Germain et al. |
| 2007/0225286 A1 | 9/2007 | Ren et al. |
| 2007/0281907 A1 | 12/2007 | Watkins |
| 2008/0039629 A1 | 2/2008 | Ramesh et al. |
| 2008/0090849 A1 | 4/2008 | Bordon-Pallier et al. |
| 2008/0103167 A1 | 5/2008 | Bebernitz et al. |
| 2008/0214501 A1 | 9/2008 | Pan et al. |
| 2008/0300267 A1 | 12/2008 | Okram et al. |
| 2009/0054392 A1 | 2/2009 | Pelletier et al. |
| 2009/0082346 A1 | 3/2009 | Brasca et al. |
| 2009/0105250 A1 | 4/2009 | Sim et al. |
| 2010/0197688 A1 | 8/2010 | Nantermet et al. |
| 2011/0086858 A1 | 4/2011 | Wang et al. |
| 2011/0098280 A1 | 4/2011 | Garcia-Echeverria et al. |
| 2011/0178070 A1 | 7/2011 | Gong et al. |
| 2011/0212053 A1 | 9/2011 | Qian et al. |
| 2012/0088766 A1 | 4/2012 | Choi et al. |
| 2012/0094999 A1 | 4/2012 | Gray et al. |
| 2012/0165309 A1 | 6/2012 | Takahashi et al. |
| 2012/0202809 A1 | 8/2012 | Li et al. |
| 2012/0277248 A1 | 11/2012 | Caruso et al. |
| 2012/0329771 A1 | 12/2012 | Treu et al. |
| 2013/0040949 A1 | 2/2013 | Gray et al. |
| 2013/0184264 A1 | 7/2013 | Bradner et al. |
| 2014/0303112 A1 | 10/2014 | Chen et al. |
| 2014/0309249 A1 | 10/2014 | Gray et al. |
| 2015/0094315 A1 | 4/2015 | Choi et al. |
| 2015/0157629 A1 | 6/2015 | Gray et al. |
| 2015/0166532 A1 | 6/2015 | Gray et al. |
| 2015/0246913 A1 | 9/2015 | Gray et al. |
| 2016/0046636 A1 | 2/2016 | Gray et al. |
| 2016/0122323 A1 | 5/2016 | Gray et al. |
| 2016/0368910 A1 | 12/2016 | Gray et al. |
| 2017/0044111 A1 | 2/2017 | Gray et al. |
| 2017/0044112 A1 | 2/2017 | Gray et al. |

FOREIGN PATENT DOCUMENTS

| | | |
|---|---|---|
| CA | 2526430 A1 | 12/2004 |
| CA | 2550128 A1 | 6/2005 |
| CA | 2563212 A1 | 10/2005 |
| EP | 0604181 A1 | 12/1993 |
| EP | 0618221 A2 | 3/1994 |
| EP | 0675112 A1 | 3/1995 |
| EP | 0696593 A2 | 8/1995 |
| EP | 1 935 890 A1 | 6/2008 |
| EP | 2 311 842 A2 | 4/2011 |
| JP | 2003-503481 A | 1/2003 |
| JP | 2004-529140 A | 9/2004 |
| JP | 2005-501860 A | 1/2005 |
| JP | 2005-505535 A | 2/2005 |
| JP | 2005-530711 A | 10/2005 |
| JP | 2005-534635 A | 11/2005 |
| JP | 2005-538100 A | 12/2005 |
| JP | 2006-521394 A | 9/2006 |
| JP | 2007-500226 A | 1/2007 |
| JP | 2007-500725 A | 1/2007 |
| JP | 2008-500320 A | 1/2008 |
| JP | 2008-501669 A | 1/2008 |
| JP | 2008-502610 A | 1/2008 |
| JP | 2009-510110 A | 3/2009 |
| JP | 2010-511655 A | 4/2010 |
| JP | 2010-521487 A | 6/2010 |
| JP | 2011-516533 A | 5/2011 |
| JP | 2012-530071 A | 11/2012 |
| JP | 2016-533379 | 10/2016 |
| JP | 2017-504651 | 2/2017 |
| MX | 2016-009974 | 10/2016 |
| MX | 2016-009975 | 10/2016 |
| MX | 2016-009976 | 11/2016 |
| WO | WO 84/02131 A1 | 6/1984 |
| WO | WO 94/19357 A | 9/1994 |
| WO | WO 95/08542 A1 | 3/1995 |
| WO | WO 95/10514 A1 | 4/1995 |
| WO | WO 95/10515 A1 | 4/1995 |
| WO | WO 95/10516 A1 | 4/1995 |
| WO | WO 95/11917 A1 | 5/1995 |
| WO | WO 95/12572 A1 | 5/1995 |
| WO | WO 95/12612 A1 | 5/1995 |
| WO | WO 95/24612 A1 | 9/1995 |
| WO | WO 95/25086 A1 | 9/1995 |
| WO | WO 95/26412 A1 | 10/1995 |
| WO | WO 95/32987 A1 | 12/1995 |
| WO | WO 95/34535 A1 | 12/1995 |
| WO | WO 96/00736 A1 | 1/1996 |
| WO | WO 96/05168 A1 | 2/1996 |
| WO | WO 96/05169 A1 | 2/1996 |
| WO | WO 96/05529 A1 | 2/1996 |
| WO | WO 96/06138 A1 | 2/1996 |
| WO | WO 96/06193 A1 | 2/1996 |
| WO | WO 96/16443 A1 | 5/1996 |
| WO | WO 96/17861 A1 | 6/1996 |
| WO | WO 96/21456 A1 | 7/1996 |
| WO | WO 96/21701 A2 | 7/1996 |
| WO | WO 96/22278 A1 | 7/1996 |
| WO | WO 96/24611 A1 | 8/1996 |
| WO | WO 96/24612 A1 | 8/1996 |
| WO | WO 96/30017 A1 | 10/1996 |
| WO | WO 96/30018 A1 | 10/1996 |

(56) References Cited

FOREIGN PATENT DOCUMENTS

| | | |
|---|---|---|
| WO | WO 96/30343 A1 | 10/1996 |
| WO | WO 96/30362 A1 | 10/1996 |
| WO | WO 96/30363 A1 | 10/1996 |
| WO | WO 96/31111 A1 | 10/1996 |
| WO | WO 96/31477 A1 | 10/1996 |
| WO | WO 96/31478 A1 | 10/1996 |
| WO | WO 96/31501 A1 | 10/1996 |
| WO | WO 96/33159 A1 | 10/1996 |
| WO | WO 96/34850 A1 | 11/1996 |
| WO | WO 96/34851 A1 | 11/1996 |
| WO | WO 97/00252 A1 | 1/1997 |
| WO | WO 97/02920 A1 | 1/1997 |
| WO | WO 97/03047 A1 | 1/1997 |
| WO | WO 97/03050 A1 | 1/1997 |
| WO | WO 97/04785 A1 | 2/1997 |
| WO | WO 97/13537 A1 | 4/1997 |
| WO | WO 97/17070 A1 | 5/1997 |
| WO | WO 97/18813 A1 | 5/1997 |
| WO | WO 97/21701 A1 | 6/1997 |
| WO | WO 97/23478 A1 | 7/1997 |
| WO | WO 97/26246 A1 | 7/1997 |
| WO | WO 97/30053 A1 | 8/1997 |
| WO | WO 97/37705 A1 | 10/1997 |
| WO | WO 97/38665 A1 | 10/1997 |
| WO | WO 97/44350 A1 | 11/1997 |
| WO | WO 98/02436 A2 | 1/1998 |
| WO | WO 98/28980 A1 | 7/1998 |
| WO | WO 98/29119 A1 | 7/1998 |
| WO | WO 99/34850 A1 | 7/1999 |
| WO | WO 00/44777 A1 | 8/2000 |
| WO | WO 00/50032 A1 | 8/2000 |
| WO | WO 00/61186 A1 | 10/2000 |
| WO | WO 01/02369 A2 | 1/2001 |
| WO | WO 0119829 * | 3/2001 |
| WO | WO 02/076986 A1 | 10/2002 |
| WO | WO 02/079197 A1 | 10/2002 |
| WO | WO 02/080926 A1 | 10/2002 |
| WO | WO 02/096905 A1 | 12/2002 |
| WO | WO 02/102800 A1 | 12/2002 |
| WO | WO 03/018021 A1 | 3/2003 |
| WO | WO 03/018022 A1 | 3/2003 |
| WO | WO 03/026664 A1 | 4/2003 |
| WO | WO 03/051847 A1 | 6/2003 |
| WO | WO 03/078403 A2 | 9/2003 |
| WO | WO 03/097610 A1 | 11/2003 |
| WO | WO 2004/005283 A1 | 1/2004 |
| WO | WO 2004/009601 A1 | 1/2004 |
| WO | WO 2004/010995 A1 | 2/2004 |
| WO | WO 2004/039796 A1 | 5/2004 |
| WO | WO 2004/078757 A2 | 9/2004 |
| WO | WO 2004/087699 A2 | 10/2004 |
| WO | WO 2004/100868 A2 | 11/2004 |
| WO | WO 2004/113303 A1 | 12/2004 |
| WO | WO 2004/113304 A1 | 12/2004 |
| WO | WO 2005/011597 A2 | 2/2005 |
| WO | WO 2005/058891 A1 | 6/2005 |
| WO | WO 2005/097790 A1 | 10/2005 |
| WO | WO 2005/108397 A1 | 11/2005 |
| WO | WO 2005/116025 A2 | 12/2005 |
| WO | WO 2006/003276 A1 | 1/2006 |
| WO | WO 2006/024834 A1 | 3/2006 |
| WO | WO 2006/031806 A2 | 3/2006 |
| WO | WO 2006/034341 A2 | 3/2006 |
| WO | WO 2006/040568 A1 | 4/2006 |
| WO | WO 2007/002325 A1 | 1/2007 |
| WO | WO 2007/002433 A1 | 1/2007 |
| WO | WO 2007/024680 A1 | 3/2007 |
| WO | WO 2007/035428 A1 | 3/2007 |
| WO | WO 2007/042786 A2 | 4/2007 |
| WO | WO 2007/048070 A2 | 4/2007 |
| WO | WO 2007/075869 A2 | 7/2007 |
| WO | WO 2007/129195 A2 | 11/2007 |
| WO | WO 2007/138277 A1 | 12/2007 |
| WO | WO 2008/063888 A2 | 5/2008 |
| WO | WO 2008/068171 A1 | 6/2008 |
| WO | WO 2008/074749 A1 | 6/2008 |
| WO | WO 2008/080015 A2 | 7/2008 |
| WO | WO 2008/112913 A1 | 9/2008 |
| WO | WO 2008/124393 A1 | 10/2008 |
| WO | WO 2008/144253 A1 | 11/2008 |
| WO | WO 2008/151183 A1 | 12/2008 |
| WO | WO 2009/017822 A2 | 2/2009 |
| WO | WO 2009/028655 A1 | 3/2009 |
| WO | WO 2009/032694 A1 | 3/2009 |
| WO | WO 2009/145360 A1 | 12/2009 |
| WO | WO 2009/155017 A2 | 12/2009 |
| WO | WO 2010/008847 A2 | 1/2010 |
| WO | WO 2010/051781 A1 | 5/2010 |
| WO | WO 2010/125799 A1 | 11/2010 |
| WO | WO 2010/144909 A1 | 12/2010 |
| WO | WO 2011/115725 A2 | 9/2011 |
| WO | WO 2013/014162 A1 | 1/2013 |
| WO | WO 2013/040436 A2 | 3/2013 |
| WO | WO 2013/074986 A1 | 5/2013 |
| WO | WO 2013/136070 A1 | 9/2013 |
| WO | WO 2013/154778 A1 | 10/2013 |
| WO | WO 2014/063054 A1 | 4/2014 |
| WO | WO 2014/063054 A8 | 4/2014 |
| WO | WO 2014/063061 A1 | 4/2014 |
| WO | WO 2014/063068 A1 | 4/2014 |
| WO | WO 2015/013635 | 1/2015 |
| WO | WO 2015/058126 A1 | 4/2015 |
| WO | WO 2015/058140 A1 | 4/2015 |
| WO | WO 2015/117087 A1 | 8/2015 |
| WO | WO 2015/154022 A1 | 10/2015 |
| WO | WO 2015/164604 A1 | 10/2015 |
| WO | WO 2015/164614 A1 | 10/2015 |
| WO | WO 2016/014542 A1 | 1/2016 |
| WO | WO 2016/014551 A1 | 1/2016 |
| WO | WO 2016/023014 A2 | 2/2016 |
| WO | WO 2016/105528 A2 | 6/2016 |

OTHER PUBLICATIONS

International Search Report and Written Opinion for PCT/US2012/065618, mailed Mar. 19, 2013.
International Preliminary Report on Patentability for PCT/US2012/065618, mailed May 30, 2014.
International Search Report and Written Opinion for PCT/US2013/065708, mailed Feb. 4, 2014.
International Preliminary Report on Patentability for PCT/US2013/065708, mailed Apr. 30, 2015.
International Search Report and Written Opinion for PCT/US2013/065689, mailed Mar. 4, 2014.
International Preliminary Report on Patentability for PCT/US2013/065689, mailed Apr. 30, 2015.
International Search Report and Written Opinion for PCT/US2013/065698, mailed Feb. 20, 2014.
International Preliminary Report on Patentability for PCT/US2013/065698, mailed Apr. 30, 2015.
International Search Report and Written Opinion for PCT/US2014/061232, mailed Dec. 23, 2014.
International Search Report and Written Opinion for PCT/US2015/027312, mailed Jul. 10, 2015.
International Search Report and Written Opinion for PCT/US2015/027294, mailed Jul. 10, 2015.
Invitation to Pay Additional Fees for PCT/US2015/041360, mailed Sep. 24, 2015.
Extended European Search Report for EP 10786967.9, mailed Oct. 23, 2012.
International Search Report and Written Opinion for PCT/US2010/038518, mailed Aug. 6, 2010.
International Preliminary Report on Patentability for PCT/US2010/038518, mailed Dec. 22, 2011.
Extended European Search Report for EP 10844280.7, mailed Apr. 17, 2013.
Partial European Search Report for EP 15160591.2, dated Jul. 1, 2015.
International Search Report and Written Opinion for PCT/US2010/062310, mailed Oct. 4, 2011.

(56) References Cited

OTHER PUBLICATIONS

International Preliminary Report on Patentability for PCT/US2010/062310, mailed Jul. 12, 2012.
Berge et al., Pharmaceutical salts. J Pharm Sci. Jan. 1977;66(1):1-19.
Cai et al., Discovery of orally active pyrrolopyridine- and aminopyridine-based Met kinase inhibitors. Bioorg Med Chem Lett. Jun. 1, 2008;18(11):3224-9. doi: 10.1016/j.bmcl.2008.04.047. Epub Apr. 25, 2008.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009.
Choi et al., Discovery and structural analysis of Eph receptor tyrosine kinase inhibitors. Bioorg Med Chem Lett. Aug. 1, 2009;19(15):4467-70. doi: 10.1016/j.bmcl.2009.05.029. Epub May 13, 2009. Supplementary Materials. 16 pages.
Hur et al., Clinical stage EGFR inhibitors irreversibly alkylate Bmx kinase. Bioorg Med Chem Lett. Nov. 15, 2008;18(22):5916-9. doi: 10.1016/j.bmcl.2008.07.062. Epub Jul. 18, 2008.
Jouve et al., Oxidative cyclization of n-methyl- and n-benzoylpyridylthioureas. Preparation of new thiazolo[4,5-b] and [5,4-b] pyridine derivatives. J Heterocyclic Chemistry. 2003;40(2):261-68.
Kim et al., Discovery of pyrrolopyridine-pyridone based inhibitors of Met kinase: synthesis, X-ray crystallographic analysis, and biological activities. J Med Chem. Sep. 11, 2008;51(17):5330-41. doi: 10.1021/jm800476q. Epub Aug. 9, 2008.
Liu et al., Discovery and optimization of potent and selective benzonaphthyridinone analogs as small molecule mTOR inhibitors with improved mouse microsome stability. Bioorg Med Chem Lett. Jul. 1, 2011;21(13):4036-40. doi: 10.1016/j.bmcl.2011.04.129. Epub May 7, 2011.
Liu et al., Discovery of 1-(4-(4-propionylpiperazin-1-yl)-3-(trifluoromethyl)phenyl)-9-(quinolin-3-yl)benzo[h][1,6]naphthyridin-2(1H)-one as a highly potent, selective mammalian target of rapamycin (mTOR) inhibitor for the treatment of cancer. J Med Chem. Oct. 14, 2010;53(19):7146-55. doi: 10.1021/jm101144f.
Schroeder et al., Discovery of N-(4-(2-amino-3-chloropyridin-4-yloxy)-3-fluorophenyl)-4-ethoxy-1-(4-fluorophenyl)-2-oxo-1,2-dihydropyridine-3-carboxamide (BMS-777607), a selective and orally efficacious inhibitor of the Met kinase superfamily. J Med Chem. Mar. 12, 2009;52(5):1251-4. doi: 10.1021/jm801586s.
Smith et al., The effect of the nature of the amine leaving group on the nature of the E2 transition state for the reaction of 1-phenylethylammonium ions sodium ethoxide in ethanol. Mar. 28, 1989;67:1457-67.
Stachlewitz et al., A-770041, a novel and selective small-molecule inhibitor of Lck, prevents heart allograft rejection. J Pharmacol Exp Ther. Oct. 2005;315(1):36-41. Epub Jul. 12, 2005.
Stanovnik et al., The Tautomerism of Heterocycles: Substituent Tautomerism of Six-Membered Ring Heterocycles. Advances in Heterocyclic Chemistry. 2006;91:1-134.
Wang et al., Pharmacophore and structure-activity relationships of integrase inhibition within a dual inhibitor scaffold of HIV reverse transcriptase and integrase. Bioorg Med Chem. Jun. 15, 2010;18(12):4202-11. doi: 10.1016/j.bmc.2010.05.004. Epub May 7, 2010.
Zhang et al., Discovery of potent and selective covalent inhibitors of JNK. Chem Biol. Jan. 27, 2012;19(1):140-54. doi: 10.1016/j.chembiol.2011.11.010.
International Search Report and Written Opinion for PCT/US2015/000297, mailed Mar. 4, 2016.
Invitation to Pay Additional Fees for PCT/US2015/044387, mailed Jan. 28, 2016.
International Search Report and Written Opinion for PCT/US2015/044387, mailed Mar. 25, 2016.
CAS Registry No. 916173-61-0, STN Entry Date Dec. 21, 2006.
CAS Registry No. 769961-42-4, STN Entry Date Oct. 27, 2004.
CAS Registry No. 769961-59-3, STN Entry Date Oct. 27, 2004.
Chong et al., Positive and negative regulation of Raf kinase activity and function by phosphorylation EMBO J. Jul. 16, 2001;20(14):3716-27.
Davies et al., Mutations of the BRAF gene in human cancer Nature. Jun. 27, 2002;417(6892):949-54. Epub Jun. 9, 2002.
Downward, Targeting RAS signalling pathways in cancer therapy Nat Rev Cancer. Jan. 2003;3(1):11-22.
Garnett et al., Guilty as charged: B-RAF is a human oncogene Cancer Cell. Oct. 2004;6(4):313-9.
Hart et al., SB1518, a novel macrocyclic pyrimidine-based JAK2 inhibitor for the treatment of myeloid and lymphoid malignancies. Leukemia. Nov. 2011;25(11):1751-9. doi: 10.1038/leu.2011.148. Epub Jun. 21, 2011.
King et al., Demonstration of a genetic therapeutic index for tumors expressing oncogenic BRAF by the kinase inhibitor SB-590885. Cancer Res. Dec. 1, 2006;66(23):11100-5.
Mallinson et al., Macrocycles in new drug discovery. Future Med Chem. Jul. 2012;4(11):1409-38. doi: 10.4155/fmc.12.93.
Smith et al., Recent advances in the research and development of RAF kinase inhibitors. Curr. Top Med. Chem. 2006; 6(11):1071-89.
Wellbrock et al., The RAF proteins take centre stage Nat Rev Mol Cell Biol. Nov. 2004;5(11):875-85.
Zebisch et al., Back to the roots: the remarkable RAF oncogene story Cell Mol Life Sci. Jun. 2006;63(11):1314-30.
U.S. Appl. No. 15/188,545, filed Jun. 21, 2016, Gray et al.
U.S. Appl. No. 15/305,801, filed Oct. 21, 2016, Gray et al.
U.S. Appl. No. 15/305,845, filed Oct. 21, 2016, Gray et al.
International Preliminary Report on Patentability for PCT/US2015/027312, mailed Nov. 3, 2016.
International Preliminary Report on Patentability for PCT/US2015/027294, mailed Nov. 3, 2016.
Invitation to Pay Additional Fees for PCT/US2015/041360 mailed Sep. 24, 2015.
International Search Report and Written Opinion for PCT/US2015/041360 mailed Dec. 15, 2015.
International Search Report and Written Opinion for PCT/US2016/037086, mailed Sep. 2, 2016.
Invitation to Pay Additional Fees for PCT/US2016/024345, mailed Aug. 9, 2016.
International Search Report and Written Opinion for PCT/US2016/024345, mailed Oct. 6, 2016.
PubChem-CID-68365059. Available at https://pubchem.ncbi.nlm.nih.gov/compound/68365059. Accessed Jun. 17, 2016.
Christensen et al., Targeting transcriptional addictions in small cell lung cancer with a covalent CDK7 inhibitor. Cancer Cell. Dec. 8, 2014;26(6):909-22.
Davis et al., Comprehensive analysis of kinase inhibitor selectivity. Nat Biotechnol. Oct. 30, 2011;29(11):1046-51. doi: 10.1038/nbt.1990.
Ercan et al., Reactivation of ERK signaling causes resistance to EGFR kinase inhibitors. Cancer Discov. Oct. 2012;2(10):934-47.
Filippakopoulos et al., Selective inhibition of BET bromodomains. Nature. Dec. 23, 2010;468(7327):1067-73.
Fraser et al., Dasatinib inhibits the secretion of TNF-alpha following TLR stimulation in vitro and in vivo. Exp Hematol. Dec. 2009;37(12):1435-44. doi: 10.1016/j.exphem.2009.09.007. Epub Sep. 26, 2009.
Fry et al., Specific inhibition of cyclin-dependent kinase 4/6 by PD 0332991 and associated antitumor activity in human tumor xenografts. Mol Cancer Ther. Nov. 2004;3(11):1427-37.
Gojo et al., The cyclin-dependent kinase inhibitor flavopiridol induces apoptosis in multiple myeloma cells through transcriptional repression and down-regulation of Mcl-1. Clin Cancer Res. Nov. 2002;8(11):3527-38.
Kantarjian et al., Dasatinib versus imatinib in newly diagnosed chronic-phase chronic myeloid leukemia. N Engl J Med. Jun. 17, 2010;362(24):2260-70.
Konig et al., The novel cyclin-dependent kinase inhibitor flavopiridol downregulates Bcl-2 and induces growth arrest and apoptosis in chronic B-cell leukemia lines. Blood. Dec. 1, 1997;90(11):4307-12.

(56) References Cited

OTHER PUBLICATIONS

Kwiatkowski et al., Targeting transcription regulation in cancer with a covalent CDK7 inhibitor. Nature. Jul. 31, 2014;511(7511):616-20.
Kwong et al., Targeted therapy for melanoma: rational combinatorial approaches. Oncogene. Jan. 2, 2014;33(1):1-9. doi: 10.1038/onc.2013.34. Epub Feb. 18, 2013.
Lin et al., Phase II study of flavopiridol in relapsed chronic lymphocytic leukemia demonstrating high response rates in genetically high-risk disease. J Clin Oncol. Dec. 10, 2009;27(35):6012-8.
Odingo et al., Synthesis and evaluation of the 2,4-diaminoquinazoline series as anti-tubercular agents. Bioorg Med Chem. Dec. 15, 2014;22(24):6965-79. doi: 10.1016/j.bmc.2014.10.007. Epub Oct. 22, 2014.
Sharma et al., A chromatin-mediated reversible drug-tolerant state in cancer cell subpopulations. Cell. Apr. 2, 2010;141(1):69-80.
Stuhlmiller et al., Inhibition of Lapatinib-Induced Kinome Reprogramming in ERBB2-Positive Breast Cancer by Targeting BET Family Bromodomains. Cell Rep. Apr. 21, 2015;11(3):390-404.
Terai et al., Activation of the FGF2-FGFR1 autocrine pathway: a novel mechanism of acquired resistance to gefitinib in NSCLC. Mol Cancer Res. Jul. 2013;11(7):759-67.
Zhou et al., Novel mutant-selective EGFR kinase inhibitors against EGFR T790M. Nature. Dec. 24, 2009;462(7276):1070-4.
Invitation to Pay Additional Fees for PCT/US2016/051118, mailed Dec. 1, 2016.
International Search Report and Written Opinion for PCT/US2016/051118, mailed Mar. 13, 2017.
Invitation to Pay Additional Fees for PCT/US2011/025423, mailed May 31, 2011.
International Preliminary Report on Patentability PCT/US2011/025423, mailed Nov. 20, 2012.
International Search Report and Written Opinion from PCT/US2011/025423, dated Nov. 5, 2012.
CAS Registry No. 1334419-59-8, STN Entry Date Dec. 30, 2013.
GenBank Accession No. M80629. Lapidot-Lifson et al., Dec. 31, 1994. 2 pages.
GenBank Accession No. NP_001790. Yang et al., Oct. 6, 2016. 4 pages.
Uniprot No. Q9NYV4. Last modified Mar. 15, 2017. 14 pages.
Akhtar et al., TFIIH kinase places bivalent marks on the carboxy-terminal domain of RNA polymerase II. Mol Cell. May 15, 2009;34(3):387-93. doi: 10.1016/j.molcel.2009.04.016.
Bajrami et al., Genome-wide profiling of genetic synthetic lethality identifies CDK12 as a novel determinant of PARP1/2 inhibitor sensitivity. Cancer Res. Jan. 1, 2014;74(1):287-97. doi: 10.1158/0008-5472.CAN-13-2541. Epub Nov. 15, 2013.
Bartkowiak et al., CDK12 is a transcription elongation-associated CTD kinase, the metazoan ortholog of yeast Ctk1. Genes Dev. Oct. 15, 2010;24(20):2303-16. doi: 10.1101/gad.1968210.
Bell et al., Integrated genomic analyses of ovarian carcinoma. Nature. Jun. 29, 2011;474(7353):609-15. doi: 10.1038/nature10166.
Ben-Av et al., Induction of vascular endothelial growth factor expression in synovial fibroblasts by prostaglandin E and interleukin-1: a potential mechanism for inflammatory angiogenesis. FEBS Letters 1995;372:83-7.
Benezra et al., In vivo angiogenic activity of interleukins. Archives of Opthamology 1990;108:573.
Blazek et al., The Cyclin K/Cdk12 complex maintains genomic stability via regulation of expression of DNA damage response genes. Genes Dev. Oct. 15, 2011;25(20):2158-72. doi: 10.1101/gad.16962311.
Blazek et al., The cyclin K/Cdk12 complex: an emerging new player in the maintenance of genome stability. Cell Cycle. Mar. 15, 2012;11(6):1049-50. doi: 10.4161/cc.11.6.19678. Epub Mar. 15, 2012.
Bosken et al., The structure and substrate specificity of human Cdk12/Cyclin K. Nat Commun. Mar. 24, 2014;5:3505. doi: 10.1038/ncomms4505.
Brower et al., Tumor Angiogenesis: New drugs on the block. Nature Biotechnology 1999;17:963-8.

Brunton et al., eds., Chemotherapy of Neoplastic Diseases. In Goodman & Gilman's the Pharmacological Basis of Therapeutics. 2008; 11th edition:853-908.
Cappuzzo et al., Increased MET gene copy number negatively affects survival of surgically resected non-small-cell lung cancer patients. J Clin Oncol. Apr. 1, 2009;27(10):1667-74. doi: 10.1200/JCO.2008.19.1635. Epub Mar. 2, 2009.
Chakraborty et al., Developmental expression of the cyclooxygenase-1 and cyclooxygenase-2 genes in the peri-implantation mouse uterus and their differential regulation by the blastocyst and ovarian steroids. Journal of Molecular Endocrinology 1996;16:107-122.
Chen et al., Cdk12 and Cdk13 regulate axonal elongation through a common signaling pathway that modulates Cdk5 expression. Exp Neurol. Nov. 2014;261:10-21. doi: 10.1016/j.expneurol.2014.06.024. Epub Jul. 3, 2014.
Chiarugi et al., Cox-2, iNOS and p53 as play-makers of tumor angiogenesis. International Journal of Molecular Medicine 1998;2:715-9.
Christensen et al., Cytoreductive antitumor activity of PF-2341066, a novel inhibitor of anaplastic lymphoma kinase and c-Met, in experimental models of anaplastic large-cell lymphoma. Mol Cancer Ther. Dec. 2007;6(12 Pt 1):3314-22.
Christian et al., Flavopiridol in chronic lymphocytic leukemia: a concise review. Clin Lymphoma Myeloma. 2009;9 Suppl 3:S179-85. doi: 10.3816/CLM.2009.s.009.
Desai et al., Effects of phosphorylation by CAK on cyclin binding by CDC2 and CDK2. Mol Cell Biol. Jan. 1995;15(1):345-50.
Diaz-Flores et al., Intense vascular sprouting from rat femoral vein induced by prostaglandins E1 and E2. Anatomical Record 1994;238:68-76.
Drapkin et al., Human cyclin-dependent kinase-activating kinase exists in three distinct complexes. Proc Natl Acad Sci U S A. Jun. 25, 1996;93(13):6488-93.
Even et al., CDC2L5, a Cdk-like kinase with RS domain, interacts with the ASF/SF2-associated protein p32 and affects splicing in vivo. J Cell Biochem. Oct. 15, 2006;99(3):890-904.
Fernandez et al., Neovascularization produced by angiotensin I.Journal of Laboratory and Clinical Medicine 1985;105(2):141-5.
Finn et al., Dasatinib, an orally active small molecule inhibitor of both the src and abl kinases, selectively inhibits growth of basal-type/"triple-negative" breast cancer cell lines growing in vitro. Breast Cancer Res Treat. Nov. 2007;105(3):319-26. Epub Feb. 1, 2007.
Fizazi, The role of Src in prostate cancer. Ann Oncol. Nov. 2007;18(11):1765-73. Epub Apr. 10, 2007.
Fleisher et al., Improved oral drug delivery: solubility limitations overcome by the use of prodrugs. Advanced Drug Delivery Reviews 1996;19:115-30.
Glover-Cutter et al., TFIIH-associated Cdk7 kinase functions in phosphorylation of C-terminal domain Ser7 residues, promoter-proximal pausing, and termination by RNA polymerase II. Mol Cell Biol. Oct. 2009;29(20):5455-64. doi: 10.1128/MCB.00637-09. Epub Aug. 10, 2009.
Gu et al., Effect of novel CAAX peptidomimetic farnesyltransferase inhibitor on angiogenesis in vitro and in vivo. European Journal of Cancer 1999;35(9):1394-1401.
Harada et al., Expression and regulation of vascular endothelial growth factor in osteoblasts. Clinical Orthopedics 1995;313:76-80.
Hla et al., Human cyclooxygenase-2 cDNA. Proceedings of the National Academy of Sciences 1992;89(16):7384-8.
Iorns et al., CRK7 modifies the MAPK pathway and influences the response to endocrine therapy. Carcinogenesis. Oct. 2009;30(10):1696-701. doi: 10.1093/carcin/bgp187. Epub Aug. 3, 2009.
Janne et al., Factors underlying sensitivity of cancers to small-molecule kinase inhibitors. Nat Rev Drug Discov. Sep. 2009;8(9):709-23. doi: 10.1038/nrd2871. Epub Jul. 24, 2009.
Joshi et al., Ovarian cancer-associated mutations disable catalytic activity of CDK12, a kinase that promotes homologous recombination repair and resistance to cisplatin and poly(ADP-ribose) polymerase inhibitors. J Biol Chem. Mar. 28, 2014;289(13):9247-53. doi: 10.1074/jbc.M114.551143. Epub Feb. 19, 2014.

(56) References Cited

OTHER PUBLICATIONS

Kaldis et al., Analysis of CAK activities from human cells. Eur J Biochem. Jul. 2000;267(13):4213-21.
Kauraniemi et al., New amplified and highly expressed genes discovered in the ERBB2 amplicon in breast cancer by cDNA microarrays. Cancer Res. Nov. 15, 2001;61(22):8235-40.
Kim et al., Inhibition of vascular endothelial growth factor-induced angiogenesis suppresses tumour growth in vivo. Nature 1993;362:841.
Ko et al., CrkRS: a novel conserved Cdc2-related protein kinase that colocalises with SC35 speckles. J Cell Sci. Jul. 2001;114(Pt 14):2591-603.
Koivunen et al., EML4-ALK fusion gene and efficacy of an ALK kinase inhibitor in lung cancer. Clin Cancer Res. Jul. 1, 2008;14(13):4275-83. doi: 10.1158/1078-0432.CCR-08-0168.
Larochelle et al., Requirements for Cdk7 in the assembly of Cdk1/cyclin B and activation of Cdk2 revealed by chemical genetics in human cells. Mol Cell. Mar. 23, 2007;25(6):839-50.
Lavis et al., Bright ideas for chemical biology. ACS Chem Biol. Mar. 20, 2008;3(3):142-55. doi: 10.1021/cb700248m.
Liu et al., Two cyclin-dependent kinases promote RNA polymerase II transcription and formation of the scaffold complex. Mol Cell Biol. Feb. 2004;24(4):1721-35.
Llambi et al., Apoptosis and oncogenesis: give and take in the BCL-2 family. Curr Opin Genet Dev. Feb. 2011;21(1):12-20. doi: 10.1016/j.gde.2010.12.001. Epub Jan. 13, 2011.
Majima et al., Significant Roles of Inducible Cyclooxygenase (COX)-2 in Angiogenesis in Rat Sponge Implants. Japanese Journal of Pharmacology 1997;75;105-14.
Marques et al., A new subfamily of high molecular mass CDC2-related kinases with PITAI/VRE motifs. Biochem Biophys Res Commun. Dec. 29, 2000;279(3):832-7.
Mukaiyama et al., The unexpected and the unpredictable in organic synthesis. Tetrahedron Jul. 1999;55(29):8609-70.
Neklesa et al., Small-molecule hydrophobic tagging-induced degradation of HaloTag fusion proteins. Nat Chem Biol. Jul. 3, 2011;7(8):538-43. doi: 10.1038/nchembio.597.
Obenauf et al., Therapy-induced tumour secretomes promote resistance and tumour progression. Nature. Apr. 16, 2015;520(7547):368-72. doi: 10.1038/nature14336. Epub Mar. 25, 2015.
Ou et al., Activity of crizotinib (PF02341066), a dual mesenchymal-epithelial transition (MET) and anaplastic lymphoma kinase (ALK) inhibitor, in a non-small cell lung cancer patient with de novo MET amplification. J Thorac Oncol. May 2011;6(5):942-6. doi: 10.1097/JTO.0b013e31821528d3.
Robinson et al., Discovery of the hemifumarate and (alpha-L-alanyloxy)methyl ether as prod rugs of an anti rheumatic oxindole: prod rugs for the enolic OH group. J. Med. Chem. 1996;39:10-8.
Seed et al., The Inhibition of colon-26 Adenocarcinoma Development and Angiogenesis by Topical Diclofenac in 2.5% Hyaluronan. Cancer Research 1997;57:1625-9.
Serizawa et al., Association of Cdk-activating kinase subunits with transcription factor TFIIH. Nature. Mar. 16, 1995;374(6519):280-2.
Shiekhattar et al., Cdk-activating kinase complex is a component of human transcription factor TFIIH. Nature. Mar. 16, 1995;374(6519):283-7.
Tsai et al., Discovery of a selective inhibitor of oncogenic B-Raf kinase with potent antimelanoma activity. Proc Natl Acad Sci U S A. Feb. 26, 2008;105(8):3041-6. doi: 10.1073/pnas.0711741105. Epub Feb. 19, 2008.
Tsujii et al., Cyclooxygenase regulates angiogenesis induced by colon cancer cells. Cell. May 29, 1998;93(5):705-16.
Wang et al., Ligand-associated ERBB2/3 activation confers acquired resistance to FGFR inhibition in FGFR3-dependent cancer cells. Oncogene. Apr. 23, 2015;34(17):2167-77. doi: 10.1038/onc.2014.161. Epub Jun. 9, 2014.
Xin et al., Peroxisome proliferator-activated receptor gamma ligands are potent inhibitors of angiogenesis in vitro and in vivo. Journal of Biological Chemistry 1996;274(13):9116-21.
Yalpani, Cholesterol Lowering Drugs. Chemistry and Industry Feb. 1996;3:85-89.
Zang et al., Genetic and structural variation in the gastric cancer kinome revealed through targeted deep sequencing. Cancer Res. Jan. 1, 2011;71(1):29-39. doi: 10.1158/0008-5472.CAN-10-1749. Epub Nov. 19, 2010.
Ziche et al., Role of prostaglandin E1 and copper in angiogenesis. Journal of the National Cancer Institute 1982;69(2):475.
Zambon et al., Small molecule inhibitors of BRAF in clinical trials. Bioorg Med Chem Lett. Jan. 15, 2012;22(2):789-92. doi: 10.1016/j.bmcl.2011.11.060. Epub Dec. 3, 2011.

\* cited by examiner

HYDROPHOBICALLY TAGGED SMALL MOLECULES AS INDUCERS OF PROTEIN DEGRADATION

RELATED APPLICATIONS

The present application is a national stage filing under 35 U.S.C. §371 of international PCT application, PCT/US2013/065698, filed Oct. 18, 2013, which claims priority under 35 U.S.C. §119(e) to U.S. provisional patent application, U.S. Ser. No. 61/716,305, filed Oct. 19, 2012, the entirety of each of which is incorporated herein by reference.

GOVERNMENT SUPPORT

This invention was made with government support under grant number R01AI084140 awarded by The National Institutes of Health. The government has certain rights in the invention.

BACKGROUND OF THE INVENTION

Inducing protein degradation using hydrophobic tags is a strategy that has recently received active attention from the scientific community. For example, Crews and coworkers discovered that covalent attachment of a hydrophobic tag to a dehalogenase fusion protein is effective in modulating the level of the transgenic fusion protein. See, e.g., Neklesa et al., Nature Chemical Biology (2011) 7:538-543. Hydrophobic tags used to induce protein degradation may eventually be found useful in a variety of applications, such as, for example, tagged therapeutic agents and tagged research tools for inducing protein degradatation in vivo and in vitro. However, the development of such hydrophobically tagged agents and tools is underrealized and continues to remain of great interest.

SUMMARY OF THE INVENTION

The present invention is based on the development of bifunctional compounds (i.e., a kinase binding small molecule tagged with a hydrophobic moiety) that can induce the degradation of a kinase of interest. These bifunctional compounds possess a kinase recognition element that can bind either covalently or noncovalently and a 'hydrophobic' tag element that signals to the intracellular protein homeostasis machinery to induce degradation of the targeted kinase. In contrast to all currently reported small molecule approaches to modulating kinase activity which typically involve inhibition of enzymatic activity, these bifunctional compounds are designed to induce the physical elimination of the protein from the cell. Without wishing to be bound by any particular theory, the protein degradation induced by the bifunctional compounds studied appears to be dependent upon the molecular chaperone protein Hsp90 and/or on the proteasome, the central proteolytic enzyme in the cell.

Bifunctional compounds contemplated herein are generally represented by Formula (I):

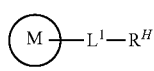
(I)

or a pharmaceutically acceptable salt thereof;
wherein:
M represents a small organic molecule which binds to a kinase;

$L^1$ represents a linker selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene; substituted and unsubstituted heteroarylene, and combinations thereof; and $R^H$ represents a hydrophobic group selected from the group consisting of substituted and unsubstituted aryl, substituted and unsubstituted heteroaryl, substituted and unsubstituted carbocyclyl, substituted and unsubstituted heterocyclyl, substituted and unsubstituted aralkyl, substituted and unsubstituted heteroarylalkyl, substituted and unsubstituted carbocyclylalkyl, and substituted and unsubstituted heterocyclylalkyl.

Binding of a small molecule M refers to covalent or noncovalent binding to a kinase, e.g., a protein kinase. In certain embodiments, M covalently binds a protein kinase. In other embodiments, M noncovalently binds a protein kinase. Exemplary kinases are listed herein. In certain embodiments, M represents a small organic molecule which covalently or noncovalently binds to Her3 kinase.

The small organic molecule M is substituted with a group -$L^2$-$R^D$, wherein:

$L^2$ represents a bond or a linker selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof; and $R^D$ is of the formula:

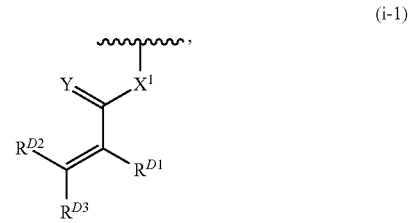
(i-1)

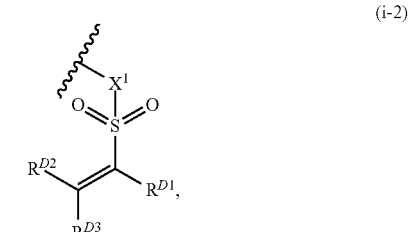
(i-2)

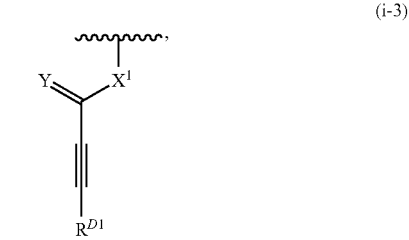
(i-3)

-continued
(i-4)
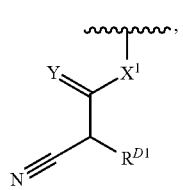
(i-5)
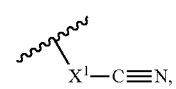
(i-6)
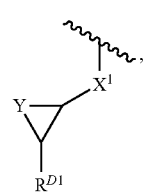
(i-7)
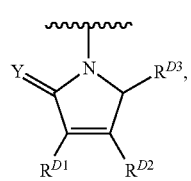
(i-8)
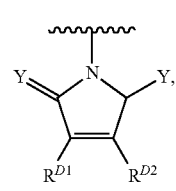
(i-9)
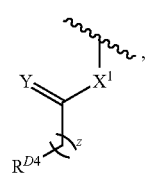
(i-10)
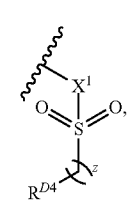
(i-11)
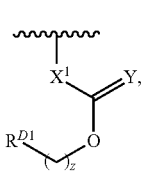
(i-12)
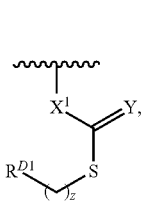
-continued
(i-13)
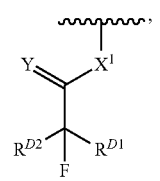
(i-14)
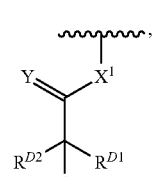
(i-15)
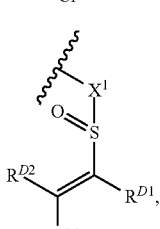
(i-16)
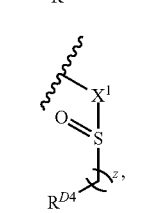
(i-17)
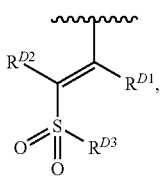
(i-18)
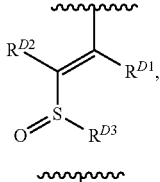
(i-19)
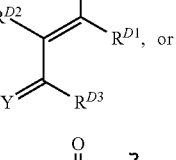
(i-20)
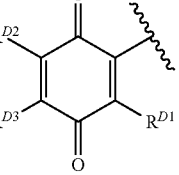
wherein Y, $X^1$, $R^{D1}$, $R^{D2}$, $R^{D3}$, $R^{D4}$, and z are as define herein.
In certain embodiments, the compound of Formula (I) is a compound of Formula (II):

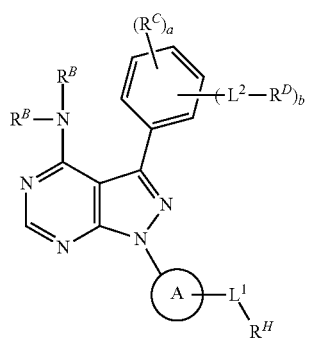

(II)

or a pharmaceutically acceptable salt thereof; wherein Ring A, $R^B$, $R^C$, $R^D$, $R^H$, $L^1$, $L^2$, a, and b are as defined herein.

In certain embodiments, Ring A is substituted or unsubstituted phenyl. In certain embodiments, Ring A is a substituted or unsubstituted 5 to 6-membered heteroaryl ring. In certain embodiments, Ring A is a substituted or unsubstituted $C_{3-8}$ carbocyclyl ring. In certain embodiments, Ring A is a substituted or unsubstituted 3 to 8-membered heterocyclyl ring.

In certain embodiments, $R^H$ is a substituted or unsubstituted hydrophobic group of formula:

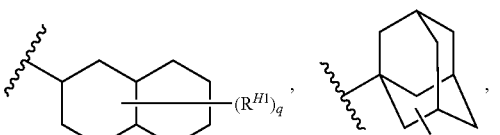

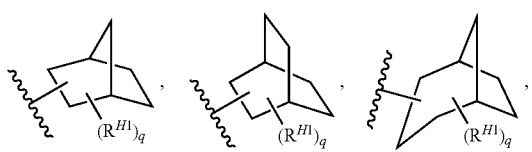

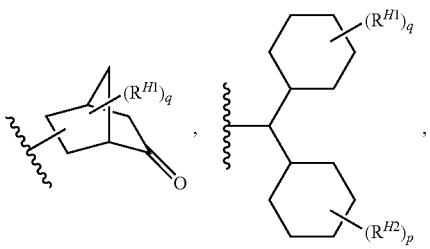

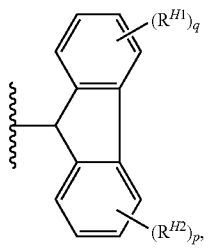

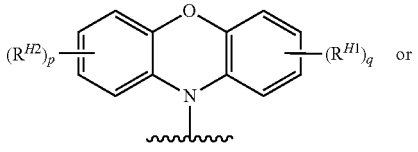

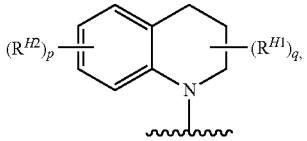

wherein $R^{H1}$, $R^{H2}$, $R^{H3}$, q, and p are as defined herein.

In certain embodiments, $L^1$ represents a linker 4 to 20 consecutive covalently bonded atoms in length, inclusive. In certain embodiments, $L^1$ represents a linker 5, 6, 7, 8, 9, 10, 11, 12, 13, 14, or 15 consecutive covalently bonded atoms in length.

In certain embodiments, $L^1$ represents a linker consisting of a combination of one or more groups of the formulae:

—$NR^{W1}$—; —$NR^{W1}$—$NR^{W1}$—; —O—$NR^{W1}$—;

—$NR^{W1}$—O—; —S—; —O—;

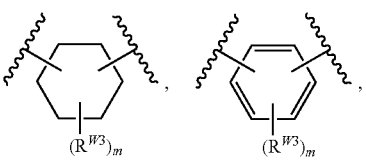

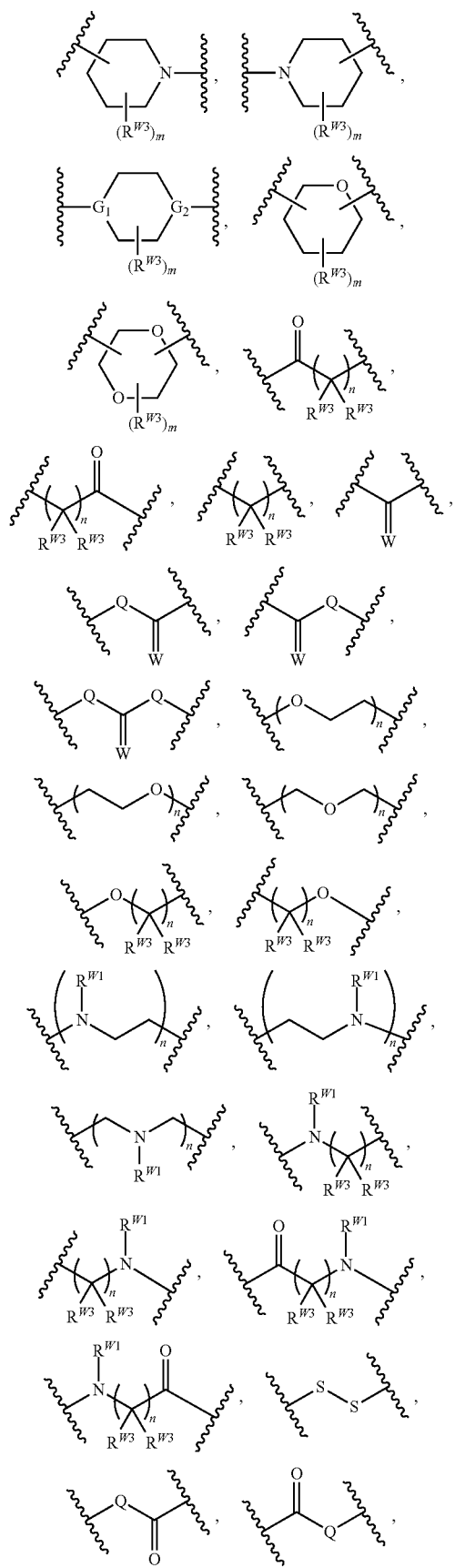
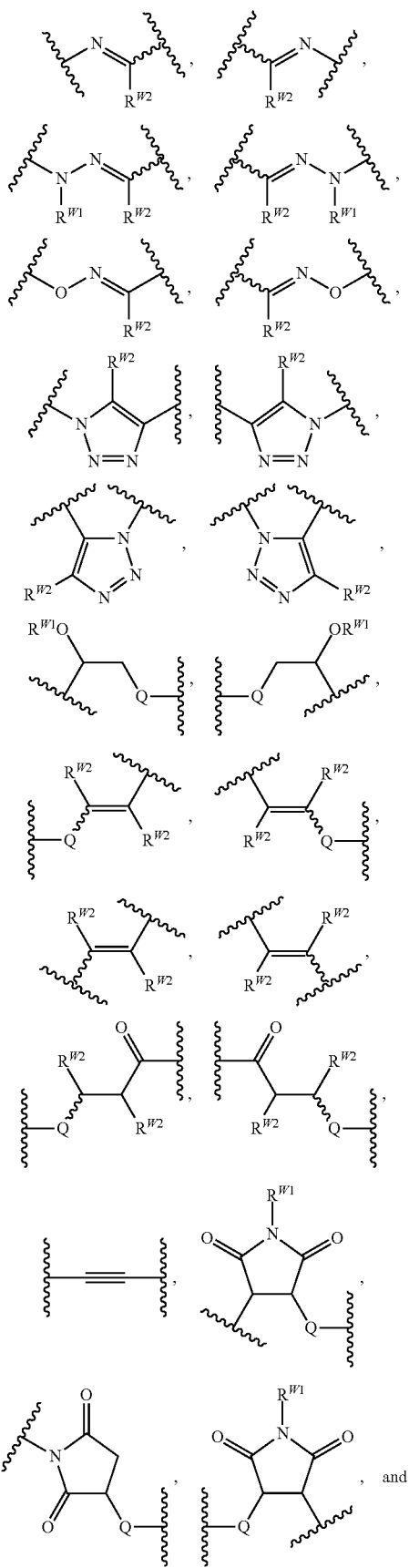

-continued

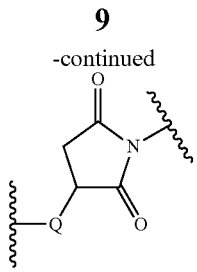

wherein n, m, Q, W, G$_1$, G$_2$, R$^{W1}$, R$^{W2}$, and R$^{W3}$ are as defined herein.

In certain embodiments, the compound of Formula (I) has a molecular weight of between about 200 to about 800 g/mol, inclusive. In certain embodiments, the compound has a c Log P less than 5, e.g., between about 8 to about 4.9 c Log P, inclusive. In certain embodiments, the compound has 0, 1, 2, 3, 4, or 5 hydrogen bond donors. In certain embodiments, the compound has 0, 1, 2, 3, 4, 5, 6, 7, 8, 9, or 10 hydrogen bond acceptors.

In another aspect, provided are pharmaceutical compositions comprising a compound of Formula (I), or a pharmaceutically acceptable salt thereof, and optionally a pharmaceutically acceptable excipient. The pharmaceutical composition may be useful in treating proliferative diseases, such as cancer.

In yet another aspect, provided are methods of treating a condition associated with aberrant activity of a kinase, e.g., a protein kinase, the method comprising administering a compound of Formula (I), or a pharmaceutical composition thereof, to a subject in need thereof in an amount sufficient to reduce kinase activity. In certain embodiments, the compound reduces kinase activity by targeted degradation of the protein kinase. In certain embodiments, the compound reduces kinase activity by inducing unfolding of the protein kinase. In certain embodiments, the compound reduces kinase activity by covalently binding to the protein kinase. In certain embodiments, the compound reduces kinase activity by non covalently binding to the protein kinase. In certain embodiments, the condition being treated is a proliferative disorder. In certain embodiments, the proliferative disorder is cancer.

The details of one or more embodiments of the invention are set forth in the accompanying Figures, the Detailed Description, and the Examples. Other features, objects, and advantages of the invention will be apparent from the description and from the claims.

DEFINITIONS

Chemical Definitions

Figure 1:
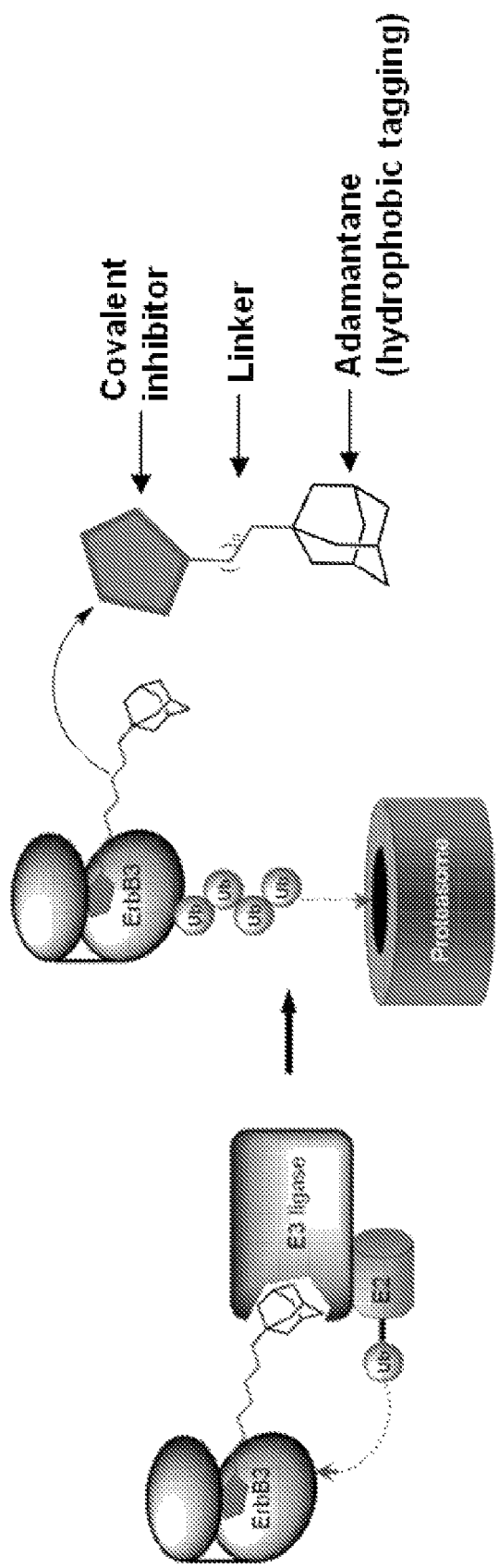
FIG. 1 depicts the general hydrophobic tagging induced degradation strategy.

Definitions of specific functional groups and chemical terms are described in more detail below. The chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in *Organic Chemistry*, Thomas Sorrell, University Science Books, Sausalito, 1999; Smith and March *March's Advanced Organic Chemistry*, 5$^{th}$ Edition, John Wiley & Sons, Inc., New York, 2001; Larock, *Comprehensive Organic Transformations*, VCH Publishers, Inc., New York, 1989; and Carruthers, *Some Modern Methods of Organic Synthesis*, 3$^{rd}$ Edition, Cambridge University Press, Cambridge, 1987.

Compounds described herein can comprise one or more asymmetric centers, and thus can exist in various stereoisomeric forms, e.g., enantiomers and/or diastereomers. For example, the compounds described herein can be in the form of an individual enantiomer, diastereomer or geometric isomer, or can be in the form of a mixture of stereoisomers, including racemic mixtures and mixtures enriched in one or more stereoisomer. "Racemic" refers to a compound in which the percent by weight of one enantiomer is equal to the percent by weight of the other enantiomer.

The terms "enantiomerically enriched," "enantiomerically pure" and "non racemic," as used interchangeably herein, refer to a compound in which the percent by weight of one enantiomer is greater than the amount of that one enantiomer compared to a control mixture of the racemic composition (e.g., greater than 1:1 by weight). For example, an enantiomerically enriched enantiomer, means a compound having greater than 50% by weight of one enantiomer relative to the other enantiomer, e.g., at least 75% by weight, or at least 80% by weight. In some embodiments, the enrichment can be much greater than 80% by weight, providing a "substantially enantiomerically enriched," "substantially enantiomerically pure" or a "substantially nonracemic" compound, which refers to a compound with at least 85% by weight of one enantiomer relative to other enantiomer, e.g., at least 90% by weight, or at least 95% by weight.

Enantiomers can be isolated from mixtures by methods known to those skilled in the art, including chiral high pressure liquid chromatography (HPLC) and the formation and crystallization of chiral salts; or preferred enantiomers can be prepared by asymmetric syntheses. See, for example, Jacques, et al., *Enantiomers, Racemates and Resolutions* (Wiley Interscience, New York, 1981); Wilen, S. H., et al., *Tetrahedron* 33:2725 (1977); Eliel, E. L. *Stereochemistry of Carbon Compounds* (McGraw-Hill, NY, 1962); and Wilen, S. H. *Tables of Resolving Agents and Optical Resolutions* p. 268 (E. L. Eliel, Ed., Univ. of Notre Dame Press, Notre Dame, Ind. 1972).

When a range of values is listed, it is intended to encompass each value and sub-range within the range. For example "C$_{1-6}$ alkyl" is intended to encompass, C$_1$, C$_2$, C$_3$, C$_4$, C$_5$, $C_6$, $C_{1-6}$, $C_{1-5}$, $C_{1-4}$, $C_{1-3}$, $C_{1-2}$, $C_{2-6}$, $C_{2-5}$, $C_{2-4}$, $C_{2-3}$, $C_{3-6}$, $C_{3-5}$, $C_{3-4}$, $C_{4-6}$, $C_{4-5}$, and $C_{5-6}$ alkyl.

As used herein, "alkyl" refers to a radical of a straight-chain or branched saturated hydrocarbon group having from 1 to 10 carbon atoms ("$C_{1-10}$ alkyl"). In some embodiments, an alkyl group has 1 to 9 carbon atoms ("$C_{1-9}$ alkyl"). In some embodiments, an alkyl group has 1 to 8 carbon atoms ("$C_{1-8}$ alkyl"). In some embodiments, an alkyl group has 1 to 7 carbon atoms ("$C_{1-7}$ alkyl"). In some embodiments, an alkyl group has 1 to 6 carbon atoms ("$C_{1-6}$ alkyl"). In some embodiments, an alkyl group has 1 to 5 carbon atoms ("$C_{1-5}$ alkyl"). In some embodiments, an alkyl group has 1 to 4 carbon atoms ("$C_{1-4}$ alkyl"). In some embodiments, an alkyl group has 1 to 3 carbon atoms ("$C_{1-3}$ alkyl"). In some embodiments, an alkyl group has 1 to 2 carbon atoms ("$C_{1-2}$ alkyl"). In some embodiments, an alkyl group has 1 carbon atom ("$C_1$ alkyl"). In some embodiments, an alkyl group has 2 to 6 carbon atoms ("$C_{2-6}$ alkyl"). Examples of $C_{1-6}$ alkyl groups include methyl ($C_1$), ethyl ($C_2$), n-propyl ($C_3$), iso-propyl ($C_3$), n-butyl ($C_4$), tert-butyl ($C_4$), sec-butyl ($C_4$), iso-butyl ($C_4$), n-pentyl ($C_5$), 3-pentanyl ($C_5$), amyl ($C_5$), neopentyl ($C_5$), 3-methyl-2-butanyl ($C_5$), tertiary amyl ($C_5$), and n-hexyl ($C_6$). Additional examples of alkyl groups include n-heptyl ($C_7$), n-octyl ($C_8$) and the like. Unless otherwise specified, each instance of an alkyl group is independently unsubstituted (an "unsubstituted alkyl") or substituted (a "substituted alkyl") with one or more substituents. In certain embodiments, the alkyl group is an unsubstituted $C_{1-10}$ alkyl (e.g., $-CH_3$). In certain embodiments, the alkyl group is a substituted $C_{1-10}$ alkyl.

As used herein, "haloalkyl" is a substituted alkyl group as defined herein wherein one or more of the hydrogen atoms are independently replaced by a halogen, e.g., fluoro, bromo, chloro, or iodo. "Perhaloalkyl" is a subset of haloalkyl, and refers to an alkyl group wherein all of the hydrogen atoms are independently replaced by a halogen, e.g., fluoro, bromo, chloro, or iodo. In some embodiments, the haloalkyl moiety has 1 to 8 carbon atoms ("$C_{1-8}$ haloalkyl"). In some embodiments, the haloalkyl moiety has 1 to 6 carbon atoms ("$C_{1-6}$ haloalkyl"). In some embodiments, the haloalkyl moiety has 1 to 4 carbon atoms ("$C_{1-4}$ haloalkyl"). In some embodiments, the haloalkyl moiety has 1 to 3 carbon atoms ("$C_{1-3}$ haloalkyl"). In some embodiments, the haloalkyl moiety has 1 to 2 carbon atoms ("$C_{1-2}$ haloalkyl"). In some embodiments, all of the haloalkyl hydrogen atoms are replaced with fluoro to provide a perfluoroalkyl group. In some embodiments, all of the haloalkyl hydrogen atoms are replaced with chloro to provide a "perchloroalkyl" group. Examples of haloalkyl groups include $CF_3$, $CF_2CF_3$, $CF_2CF_2CF_3$, $CCl_3$, $CFCl_2$, $CF_2Cl$, and the like.

As used herein, "heteroalkyl" refers to an alkyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkyl group refers to a saturated group having from 1 to 10 carbon atoms and 1, 2, 3, or 4 heteroatoms within the parent chain ("hetero$C_{1-10}$ alkyl"). In some embodiments, a heteroalkyl group is a saturated group having 1 to 9 carbon atoms and 1, 2, 3, or 4 heteroatoms within the parent chain ("hetero$C_{1-9}$ alkyl"). In some embodiments, a heteroalkyl group is a saturated group having 1 to 8 carbon atoms and 1, 2, 3, or 4 heteroatoms within the parent chain ("hetero$C_{1-8}$ alkyl"). In some embodiments, a heteroalkyl group is a saturated group having 1 to 7 carbon atoms and 1, 2, 3, or 4 heteroatoms within the parent chain ("hetero$C_{1-7}$ alkyl"). In some embodiments, a heteroalkyl group is a saturated group having 1 to 6 carbon atoms and 1, 2, or 3 heteroatoms within the parent chain ("hetero$C_{1-6}$ alkyl"). In some embodiments, a heteroalkyl group is a saturated group having 1 to 5 carbon atoms and 1 or 2 heteroatoms within the parent chain ("hetero$C_{1-5}$ alkyl"). In some embodiments, a heteroalkyl group is a saturated group having 1 to 4 carbon atoms and for 2 heteroatoms within the parent chain ("hetero$C_{1-4}$ alkyl"). In some embodiments, a heteroalkyl group is a saturated group having 1 to 3 carbon atoms and 1 heteroatom within the parent chain ("hetero$C_{1-3}$ alkyl"). In some embodiments, a heteroalkyl group is a saturated group having 1 to 2 carbon atoms and 1 heteroatom within the parent chain ("hetero$C_{1-2}$ alkyl"). In some embodiments, a heteroalkyl group is a saturated group having 1 carbon atom and 1 heteroatom ("hetero$C_1$ alkyl"). In some embodiments, a heteroalkyl group is a saturated group having 2 to 6 carbon atoms and 1 or 2 heteroatoms within the parent chain ("hetero$C_{2-6}$ alkyl"). Unless otherwise specified, each instance of a heteroalkyl group is independently unsubstituted (an "unsubstituted heteroalkyl") or substituted (a "substituted heteroalkyl") with one or more substituents. In certain embodiments, the heteroalkyl group is an unsubstituted hetero$C_{1-10}$ alkyl. In certain embodiments, the heteroalkyl group is a substituted hetero$C_{1-10}$ alkyl.

As used herein, "alkenyl" refers to a radical of a straight-chain or branched hydrocarbon group having from 2 to 10 carbon atoms and one or more double bonds (e.g., 1, 2, 3, or 4 double bonds) and no triple bonds. In some embodiments, an alkenyl group has 2 to 9 carbon atoms ("$C_{2-9}$ alkenyl"). In some embodiments, an alkenyl group has 2 to 8 carbon atoms ("$C_{2-8}$ alkenyl"). In some embodiments, an alkenyl group has 2 to 7 carbon atoms ("$C_{2-7}$ alkenyl"). In some embodiments, an alkenyl group has 2 to 6 carbon atoms ("$C_{2-6}$ alkenyl"). In some embodiments, an alkenyl group has 2 to 5 carbon atoms ("$C_{2-5}$ alkenyl"). In some embodiments, an alkenyl group has 2 to 4 carbon atoms ("$C_{2-4}$ alkenyl"). In some embodiments, an alkenyl group has 2 to 3 carbon atoms ("$C_{2-3}$ alkenyl"). In some embodiments, an alkenyl group has 2 carbon atoms ("$C_2$ alkenyl"). The one or more carbon-carbon double bonds can be internal (such as in 2-butenyl) or terminal (such as in 1-butenyl). Examples of $C_{2-4}$ alkenyl groups include ethenyl ($C_2$), 1-propenyl ($C_3$), 2-propenyl ($C_3$), 1-butenyl ($C_4$), 2-butenyl ($C_4$), butadienyl ($C_4$), and the like. Examples of $C_{2-6}$ alkenyl groups include the aforementioned $C_{2-4}$ alkenyl groups as well as pentenyl ($C_5$), pentadienyl ($C_5$), hexenyl ($C_6$), and the like. Additional examples of alkenyl include heptenyl ($C_7$), octenyl ($C_8$), octatrienyl ($C_8$), and the like. Unless otherwise specified, each instance of an alkenyl group is independently unsubstituted (an "unsubstituted alkenyl") or substituted (a "substituted alkenyl") with one or more substituents. In certain embodiments, the alkenyl group is an unsubstituted $C_{2-10}$ alkenyl. In certain embodiments, the alkenyl group is a substituted $C_{2-10}$ alkenyl.

As used herein, "heteroalkenyl" refers to an alkenyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkenyl group refers to a group having from 2 to 10 carbon atoms, at least one double bond, and 1, 2, 3, or 4 heteroatoms within the parent chain ("hetero$C_{2-10}$ alkenyl"). In some embodiments, a heteroalkenyl group has 2 to 9 carbon atoms at least one double bond, and 1, 2, 3, or 4 heteroatoms within the parent chain ("hetero$C_{2-9}$ alkenyl"). In some embodiments, a heteroalkenyl group has 2 to 8 carbon atoms, at least one double bond, and 1, 2, 3, or 4 heteroatoms within the parent chain ("heteroC$_{2-8}$ alkenyl"). In some embodiments, a heteroalkenyl group has 2 to 7 carbon atoms, at least one double bond, and 1, 2, 3, or 4 heteroatoms within the parent chain ("heteroC$_{2-7}$ alkenyl"). In some embodiments, a heteroalkenyl group has 2 to 6 carbon atoms, at least one double bond, and 1, 2, or 3 heteroatoms within the parent chain ("heteroC$_{2-6}$ alkenyl"). In some embodiments, a heteroalkenyl group has 2 to 5 carbon atoms, at least one double bond, and 1 or 2 heteroatoms within the parent chain ("heteroC$_{2-5}$ alkenyl"). In some embodiments, a heteroalkenyl group has 2 to 4 carbon atoms, at least one double bond, and for 2 heteroatoms within the parent chain ("heteroC$_{2-4}$ alkenyl"). In some embodiments, a heteroalkenyl group has 2 to 3 carbon atoms, at least one double bond, and 1 heteroatom within the parent chain ("heteroC$_{2-3}$ alkenyl"). In some embodiments, a heteroalkenyl group has 2 to 6 carbon atoms, at least one double bond, and 1 or 2 heteroatoms within the parent chain ("heteroC$_{2-6}$ alkenyl"). Unless otherwise specified, each instance of a heteroalkenyl group is independently unsubstituted (an "unsubstituted heteroalkenyl") or substituted (a "substituted heteroalkenyl") with one or more substituents. In certain embodiments, the heteroalkenyl group is an unsubstituted heteroC$_{2-10}$ alkenyl. In certain embodiments, the heteroalkenyl group is a substituted heteroC$_{2-10}$ alkenyl.

As used herein, "alkynyl" refers to a radical of a straight-chain or branched hydrocarbon group having from 2 to 10 carbon atoms and one or more triple bonds (e.g., 1, 2, 3, or 4 triple bonds) and optionally one or more double bonds (e.g., 1, 2, 3, or 4 double bonds) ("C$_{2-10}$ alkynyl"). An alkynyl group that has one or more triple bonds and one or more double bonds is also referred to as an "ene-yene" group. In some embodiments, an alkynyl group has 2 to 9 carbon atoms ("C$_{2-9}$ alkynyl"). In some embodiments, an alkynyl group has 2 to 8 carbon atoms ("C$_{2-8}$ alkynyl"). In some embodiments, an alkynyl group has 2 to 7 carbon atoms ("C$_{2-7}$ alkynyl"). In some embodiments, an alkynyl group has 2 to 6 carbon atoms ("C$_{2-6}$ alkynyl"). In some embodiments, an alkynyl group has 2 to 5 carbon atoms ("C$_{2-5}$ alkynyl"). In some embodiments, an alkynyl group has 2 to 4 carbon atoms ("C$_{2-4}$ alkynyl"). In some embodiments, an alkynyl group has 2 to 3 carbon atoms ("C$_{2-3}$ alkynyl"). In some embodiments, an alkynyl group has 2 carbon atoms ("C$_2$ alkynyl"). The one or more carbon-carbon triple bonds can be internal (such as in 2-butynyl) or terminal (such as in 1 Examples of C$_{2-4}$ alkynyl groups include, without limitation, ethynyl (C$_2$), 1 (C$_3$), 2-propynyl (C$_3$), 1-butynyl (C$_4$), 2-butynyl (C$_4$), and the like. Examples of C$_{2-6}$ alkenyl groups include the aforementioned C$_{2-4}$ alkynyl groups as well as pentynyl (C$_5$), hexynyl (C$_6$), and the like. Additional examples of alkynyl include heptynyl (C$_7$), octynyl (C$_8$), and the like. Unless otherwise specified, each instance of an alkynyl group is independently unsubstituted (an "unsubstituted alkynyl") or substituted (a "substituted alkynyl") with one or more substituents. In certain embodiments, the alkynyl group is an unsubstituted C$_{2-10}$ alkynyl. In certain embodiments, the alkynyl group is a substituted C$_{2-10}$ alkynyl.

As used herein, "heteroalkynyl" refers to an alkynyl group as defined herein which further includes at least one heteroatom (e.g., 1, 2, 3, or 4 heteroatoms) selected from oxygen, nitrogen, or sulfur within (i.e., inserted between adjacent carbon atoms of) and/or placed at one or more terminal position(s) of the parent chain. In certain embodiments, a heteroalkynyl group refers to a group having from 2 to 10 carbon atoms, at least one triple bond, and 1, 2, 3, or 4 heteroatoms within the parent chain ("heteroC$_{2-10}$ alkynyl"). In some embodiments, a heteroalkynyl group has 2 to 9 carbon atoms, at least one triple bond, and 1, 2, 3, or 4 heteroatoms within the parent chain ("heteroC$_{2-9}$ alkynyl"). In some embodiments, a heteroalkynyl group has 2 to 8 carbon atoms, at least one triple bond, and 1, 2, 3, or 4 heteroatoms within the parent chain ("heteroC$_{2-8}$ alkynyl"). In some embodiments, a heteroalkynyl group has 2 to 7 carbon atoms, at least one triple bond, and 1, 2, 3, or 4 heteroatoms within the parent chain ("heteroC$_{2-7}$ alkynyl"). In some embodiments, a heteroalkynyl group has 2 to 6 carbon atoms, at least one triple bond, and 1, 2, or 3 heteroatoms within the parent chain ("heteroC$_{2-6}$ alkynyl"). In some embodiments, a heteroalkynyl group has 2 to 5 carbon atoms, at least one triple bond, and 1 or 2 heteroatoms within the parent chain ("heteroC$_{2-5}$ alkynyl"). In some embodiments, a heteroalkynyl group has 2 to 4 carbon atoms, at least one triple bond, and for 2 heteroatoms within the parent chain ("heteroC$_{2-4}$ alkynyl"). In some embodiments, a heteroalkynyl group has 2 to 3 carbon atoms, at least one triple bond, and 1 heteroatom within the parent chain ("heteroC$_{2-3}$ alkynyl"). In some embodiments, a heteroalkynyl group has 2 to 6 carbon atoms, at least one triple bond, and 1 or 2 heteroatoms within the parent chain ("heteroC$_{2-6}$ alkynyl"). Unless otherwise specified, each instance of a heteroalkynyl group is independently unsubstituted (an "unsubstituted heteroalkynyl") or substituted (a "substituted heteroalkynyl") with one or more substituents. In certain embodiments, the heteroalkynyl group is an unsubstituted heteroC$_{2-10}$ alkynyl. In certain embodiments, the heteroalkynyl group is a substituted heteroC$_{2-10}$ alkynyl.

As used herein, "carbocyclyl" or "carbocyclic" refers to a radical of a non aromatic cyclic hydrocarbon group having from 3 to 14 ring carbon atoms ("C$_{3-14}$ carbocyclyl") and zero heteroatoms in the nonaromatic ring system. In some embodiments, a carbocyclyl group has 3 to 10 ring carbon atoms ("C$_{3-10}$ carbocyclyl"). In some embodiments, a carbocyclyl group has 3 to 9 ring carbon atoms ("C$_{3-9}$ carbocyclyl"). In some embodiments, a carbocyclyl group has 3 to 8 ring carbon atoms ("C$_{3-8}$ carbocyclyl"). In some embodiments, a carbocyclyl group has 3 to 7 ring carbon atoms ("C$_{3-7}$ carbocyclyl"). In some embodiments, a carbocyclyl group has 3 to 6 ring carbon atoms ("C$_{3-6}$ carbocyclyl"). In some embodiments, a carbocyclyl group has 5 to 10 ring carbon atoms ("C$_{5-10}$ carbocyclyl"). Exemplary C$_{3-6}$ carbocyclyl groups include, without limitation, cyclopropyl (C$_3$), cyclopropenyl (C$_3$), cyclobutyl (C$_4$), cyclobutenyl (C$_4$), cyclopentyl (C$_5$), cyclopentenyl (C$_5$), cyclohexyl (C$_6$), cyclohexenyl (C$_6$), cyclohexadienyl (C$_6$), and the like. Exemplary C$_{3-8}$ carbocyclyl groups include, without limitation, the aforementioned C$_{3-6}$ carbocyclyl groups as well as cycloheptyl (C$_7$), cycloheptenyl (C$_7$), cycloheptadienyl (C$_7$), cycloheptatrienyl (C$_7$), cyclooctyl (C$_8$), cyclooctenyl (C$_8$), bicyclo[2.2.1]heptanyl (C$_7$), bicyclo[2.2.2]octanyl (C$_8$), and the like. Exemplary C$_{3-10}$ carbocyclyl groups include, without limitation, the aforementioned C$_{3-8}$ carbocyclyl groups as well as cyclononyl (C$_9$), cyclononenyl (C$_9$), cyclodecyl (C$_{10}$), cyclodecenyl (C$_{10}$), octahydro-1H-indenyl (C$_9$), decahydronaphthalenyl (C$_{10}$), spiro[4.5]decanyl (C$_m$), and the like. In certain embodiments, the carbocyclyl group is either monocyclic ("monocyclic carbocyclyl") or polycyclic (e.g., containing a fused, bridged or spirofused ring system such as a bicyclic system ("bicyclic carbocyclyl") or tricyclic system ("tricyclic carbocyclyl")) and can be saturated or can contain one or more carbon carbon double or triple bonds. Exemplary fused bicyclic systems include, but are not limited to, decalin (cis or trans decalin). Exemplary fused tricyclic systems include, but are not limited to, fluorenyl. Exemplary spirofused bicyclic systems include, but are not limited to, spiropentane. Exemplary bridged bicyclic systems include, but are not limited to, norbornane, norbornene, bicyclo[2.2.2]octane, bicyclo[2.2.2]oct-2-ene, bicyclo[3.2.1]octane, and bicyclo[2.2.1]heptan-2-one. Exemplary bridged tricyclic systems include, but are not limited to adamantane. "Carbocyclyl" includes ring systems wherein the carbocyclyl ring, as defined above, is fused with one or more aryl or heteroaryl groups wherein the point of attachment is on the carbocyclyl ring, and in such instances, the number of carbons continue to designate the number of carbons in the carbocyclic ring system. Unless otherwise specified, each instance of a carbocyclyl group is independently unsubstituted (an "unsubstituted carbocyclyl") or substituted (a "substituted carbocyclyl") with one or more substituents. In certain embodiments, the carbocyclyl group is an unsubstituted $C_{3-14}$ carbocyclyl. In certain embodiments, the carbocyclyl group is a substituted $C_{3-14}$ carbocyclyl.

"Carbocyclylalkyl" is a subset of "alkyl" and refers to an alkyl group, as defined herein, substituted by an carbocyclyl group, as defined herein, wherein the point of attachment is on the alkyl moiety.

As used herein, "heterocyclyl" or "heterocyclic" refers to a radical of a 3 to 14 nonaromatic ring system having ring carbon atoms and 1 to 4 ring heteroatoms, wherein each heteroatom is independently selected from nitrogen, oxygen, and sulfur ("3-14 membered heterocyclyl"). In heterocyclyl groups that contain one or more nitrogen atoms, the point of attachment can be a carbon or nitrogen atom, as valency permits. A heterocyclyl group can either be monocyclic ("monocyclic heterocyclyl") or polycyclic (e.g., a fused, bridged or spiro ring system such as a bicyclic system ("bicyclic heterocyclyl") or tricyclic system ("tricyclic heterocyclyl")), and can be saturated or can contain one or more carbon carbon double or triple bonds. Heterocyclyl polycyclic ring systems can include one or more heteroatoms in one or both rings. In certain embodiments, the heterocyclyl group is either monocyclic ("monocyclic heterocyclyl") or polycyclic (e.g., containing a fused, bridged or spirofused ring system such as a bicyclic system ("bicyclic heterocyclyl") or tricyclic system ("tricyclic heterocyclyl")) and can be saturated or can contain one or more carbon carbon double or triple bonds. "Heterocyclyl" also includes ring systems wherein the heterocyclyl ring, as defined above, is fused with one or more carbocyclyl groups wherein the point of attachment is either on the carbocyclyl or heterocyclyl ring, or ring systems wherein the heterocyclyl ring, as defined above, is fused with one or more aryl or heteroaryl groups, wherein the point of attachment is on the heterocyclyl ring, and in such instances, the number of ring members continue to designate the number of ring members in the heterocyclyl ring system. Unless otherwise specified, each instance of heterocyclyl is independently unsubstituted (an "unsubstituted heterocyclyl") or substituted (a "substituted heterocyclyl") with one or more substituents. In certain embodiments, the heterocyclyl group is an unsubstituted 3-14 membered heterocyclyl. In certain embodiments, the heterocyclyl group is a substituted 3-14 membered heterocyclyl.

In some embodiments, a heterocyclyl group is a 5-10 membered nonaromatic ring system having ring carbon atoms and 1-4 ring heteroatoms, wherein each heteroatom is independently selected from nitrogen, oxygen, and sulfur ("5-10 membered heterocyclyl"). In some embodiments, a heterocyclyl group is a 5-8 membered nonaromatic ring system having ring carbon atoms and 1-4 ring heteroatoms, wherein each heteroatom is independently selected from nitrogen, oxygen, and sulfur ("5-8 membered heterocyclyl"). In some embodiments, a heterocyclyl group is a 5-6 membered nonaromatic ring system having ring carbon atoms and 1-4 ring heteroatoms, wherein each heteroatom is independently selected from nitrogen, oxygen, and sulfur ("5-6 membered heterocyclyl"). In some embodiments, the 5-6 membered heterocyclyl has 1-3 ring heteroatoms selected from nitrogen, oxygen, and sulfur. In some embodiments, the 5-6 membered heterocyclyl has 1-2 ring heteroatoms selected from nitrogen, oxygen, and sulfur. In some embodiments, the 5-6 membered heterocyclyl has 1 ring heteroatom selected from nitrogen, oxygen, and sulfur.

Exemplary 3-membered heterocyclyl groups containing 1 heteroatom include, without limitation, azirdinyl, oxiranyl, thiorenyl. Exemplary 4-membered heterocyclyl groups containing 1 heteroatom include, without limitation, azetidinyl, oxetanyl and thietanyl. Exemplary 5-membered heterocyclyl groups containing 1 heteroatom include, without limitation, tetrahydrofuranyl, dihydrofuranyl, tetrahydrothiophenyl, dihydrothiophenyl, pyrrolidinyl, dihydropyrrolyl and pyrrolyl-2,5-dione. Exemplary 5 heterocyclyl groups containing 2 heteroatoms include, without limitation, dioxolanyl, oxathiolanyl, and dithiolanyl. Exemplary 5-membered heterocyclyl groups containing 3 heteroatoms include, without limitation, triazolinyl, oxadiazolinyl, and thiadiazolinyl. Exemplary 6-membered heterocyclyl groups containing 1 heteroatom include, without limitation, piperidinyl, tetrahydropyranyl, dihydropyridinyl, and thianyl. Exemplary 6-membered heterocyclyl groups containing 2 heteroatoms include, without limitation, piperazinyl, morpholinyl, dithianyl, dioxanyl. Exemplary 6-membered heterocyclyl groups containing 2 heteroatoms include, without limitation, triazinanyl. Exemplary 7-membered heterocyclyl groups containing 1 heteroatom include, without limitation, azepanyl, oxepanyl and thiepanyl. Exemplary 8-membered heterocyclyl groups containing 1 heteroatom include, without limitation, azocanyl, oxecanyl and thiocanyl. Exemplary bicyclic heterocyclyl groups include, without limitation, indolinyl, isoindolinyl, dihydrobenzofuranyl, dihydrobenzothienyl, tetrahydrobenzothienyl, tetrahydrobenzofuranyl, tetrahydroindolyl, tetrahydroquinolinyl, tetrahydroisoquinolinyl, decahydroquinolinyl, decahydroisoquinolinyl, octahydrochromenyl, octahydroisochromenyl, decahydronaphthyridinyl, decahydro-1,8-naphthyridinyl, octahydropyrrolo[3,2-b]pyrrole, indolinyl, phthalimidyl, naphthalimidyl, chromanyl, chromenyl, 1H-benzo[e][1,4]diazepinyl, 1,4,5,7-tetrahydropyrano[3,4-b]pyrrolyl, 5,6-dihydro-4H-furo[3,2-b]pyrrolyl, 6,7-dihydro-5H-furo[3,2-b]pyranyl, 5,7-dihydro-4H-thieno[2,3-c]pyranyl, 2,3-dihydro-1H-pyrrolo[2,3-b]pyridinyl, 2,3-dihydrofuro[2,3-b]pyridinyl, 4,5,6,7-tetrahydro-1H-pyrrolo-[2,3-b]pyridinyl, 4,5,6,7-tetrahydrofuro[3,2-c]pyridinyl, 4,5,6,7-tetrahydrothieno[3,2-b]pyridinyl, 1,2,3,4-tetrahydro-1,6-naphthyridinyl, and the like.

"Heterocyclylalkyl" is a subset of "alkyl" and refers to an alkyl group, as defined herein, substituted by an heterocyclyl group, as defined herein, wherein the point of attachment is on the alkyl moiety.

As used herein, "aryl" refers to a radical of a monocyclic or polycyclic (e.g., bicyclic or tricyclic) 4n+2 aromatic ring system (e.g., having 6, 10, or 14 π electrons shared in a cyclic array) having 6-14 ring carbon atoms and zero heteroatoms provided in the aromatic ring system ("$C_{6-14}$ aryl"). In some embodiments, an aryl group has 6 ring carbon atoms ("C₆ aryl"; e.g., phenyl). In some embodiments, an aryl group has 10 ring carbon atoms ("C₁₀ aryl"; e.g., naphthyl such as 1-naphthyl and 2-naphthyl). In some embodiments, an aryl group has 14 ring carbon atoms ("C₁₄ aryl"; e.g., anthracenyl). "Aryl" also includes ring systems wherein the aryl ring, as defined above, is fused with one or more carbocyclyl or heterocyclyl groups wherein the radical or point of attachment is on the aryl ring, and in such instances, the number of carbon atoms continue to designate the number of carbon atoms in the aryl ring system. Unless otherwise specified, each instance of an aryl group is independently unsubstituted (an "unsubstituted aryl") or substituted (a "substituted aryl") with one or more substituents. In certain embodiments, the aryl group is an unsubstituted $C_{6-14}$ aryl. In certain embodiments, the aryl group is a substituted $C_{6-14}$ aryl.

"Aralkyl" is a subset of "alkyl" and refers to an alkyl group, as defined herein, substituted by an aryl group, as defined herein, wherein the point of attachment is on the alkyl moiety.

As used herein, "heteroaryl" refers to a radical of a 5-14 membered monocyclic or polycyclic (e.g., bicyclic, tricyclic) 4n+2 aromatic ring system (e.g., having 6, 10, or 14 π electrons shared in a cyclic array) having ring carbon atoms and 1-4 ring heteroatoms provided in the aromatic ring system, wherein each heteroatom is independently selected from nitrogen, oxygen and sulfur ("5-14 membered heteroaryl"). In heteroaryl groups that contain one or more nitrogen atoms, the point of attachment can be a carbon or nitrogen atom, as valency permits. Heteroaryl polycyclic ring systems can include one or more heteroatoms in one or both rings. "Heteroaryl" includes ring systems wherein the heteroaryl ring, as defined above, is fused with one or more carbocyclyl or heterocyclyl groups wherein the point of attachment is on the heteroaryl ring, and in such instances, the number of ring members continue to designate the number of ring members in the heteroaryl ring system. "Heteroaryl" also includes ring systems wherein the heteroaryl ring, as defined above, is fused with one or more aryl groups wherein the point of attachment is either on the aryl or heteroaryl ring, and in such instances, the number of ring members designates the number of ring members in the fused polycyclic (aryl/heteroaryl) ring system. Polycyclic heteroaryl groups wherein one ring does not contain a heteroatom (e.g., indolyl, quinolinyl, carbazolyl, and the like) the point of attachment can be on either ring, i.e., either the ring bearing a heteroatom (e.g., 2-indolyl) or the ring that does not contain a heteroatom (e.g., 5-indolyl).

In some embodiments, a heteroaryl group is a 5-10 membered aromatic ring system having ring carbon atoms and 1-4 ring heteroatoms provided in the aromatic ring system, wherein each heteroatom is independently selected from nitrogen, oxygen, and sulfur ("5-10 membered heteroaryl"). In some embodiments, a heteroaryl group is a 5-8 membered aromatic ring system having ring carbon atoms and 1-4 ring heteroatoms provided in the aromatic ring system, wherein each heteroatom is independently selected from nitrogen, oxygen, and sulfur ("5-8 membered heteroaryl"). In some embodiments, a heteroaryl group is a 5-6 membered aromatic ring system having ring carbon atoms and 1-4 ring heteroatoms provided in the aromatic ring system, wherein each heteroatom is independently selected from nitrogen, oxygen, and sulfur ("5-6 membered heteroaryl"). In some embodiments, the 5-6 membered heteroaryl has 1-3 ring heteroatoms selected from nitrogen, oxygen, and sulfur. In some embodiments, the 5-6 membered heteroaryl has 1-2 ring heteroatoms selected from nitrogen, oxygen, and sulfur. In some embodiments, the 5-6 membered heteroaryl has 1 ring heteroatom selected from nitrogen, oxygen, and sulfur. Unless otherwise specified, each instance of a heteroaryl group is independently unsubstituted (an "unsubstituted heteroaryl") or substituted (a "substituted heteroaryl") with one or more substituents. In certain embodiments, the heteroaryl group is an unsubstituted 5-14 membered heteroaryl. In certain embodiments, the heteroaryl group is a substituted 5-14 membered heteroaryl.

Exemplary 5-membered heteroaryl groups containing 1 heteroatom include, without limitation, pyrrolyl, furanyl, and thiophenyl. Exemplary 5-membered heteroaryl groups containing 2 heteroatoms include, without limitation, imidazolyl, pyrazolyl, oxazolyl, isoxazolyl, thiazolyl, and isothiazolyl. Exemplary 5-membered heteroaryl groups containing 3 heteroatoms include, without limitation, triazolyl, oxadiazolyl, and thiadiazolyl. Exemplary 5-membered heteroaryl groups containing 4 heteroatoms include, without limitation, tetrazolyl. Exemplary 6-membered heteroaryl groups containing 1 heteroatom include, without limitation, pyridinyl. Exemplary 6-membered heteroaryl groups containing 2 heteroatoms include, without limitation, pyridazinyl, pyrimidinyl, and pyrazinyl. Exemplary 6-membered heteroaryl groups containing 3 or 4 heteroatoms include, without limitation, triazinyl and tetrazinyl, respectively. Exemplary 7-membered heteroaryl groups containing 1 heteroatom include, without limitation, azepinyl, oxepinyl, and thiepinyl. Exemplary 5,6-heteroaryl groups include, without limitation, indolyl, isoindolyl, indazolyl, benzotriazolyl, benzothiophenyl, isobenzothiophenyl, benzofuranyl, benzoisofuranyl, benzimidazolyl, benzoxazolyl, benzisoxazolyl, benzoxadiazolyl, benzthiazolyl, benzisothiazolyl, benzthiadiazolyl, indolizinyl, and purinyl. Exemplary 6,6-bicyclic heteroaryl groups include, without limitation, naphthyridinyl, pteridinyl, quinolinyl, isoquinolinyl, cinnolinyl, quinoxalinyl, phthalazinyl, and quinazolinyl. Exemplary tricyclic heteroaryl groups include, without limitation, phenanthridinyl, dibenzofuranyl, carbazolyl, acridinyl, phenothiazinyl, phenoxazinyl and phenazinyl.

"Heteroaralkyl" is a subset of "alkyl" and refers to an alkyl group, as defined herein, substituted by a heteroaryl group, as defined herein, wherein the point of attachment is on the alkyl moiety.

As used herein, the term "partially unsaturated" refers to a ring moiety that includes at least one double or triple bond. The term "partially unsaturated" is intended to encompass rings having multiple sites of unsaturation, but is not intended to include aromatic groups (e.g., aryl or heteroaryl moieties) as herein defined.

As used herein, the term "saturated" refers to a ring moiety that does not contain a double or triple bond, i.e., the ring contains all single bonds.

Affixing the suffix "-ene" to a group indicates the group is a divalent moiety, e.g., alkylene is the divalent moiety of alkyl, alkenylene is the divalent moiety of alkenyl, alkynylene is the divalent moiety of alkynyl, heteroalkylene is the divalent moiety of heteroalkyl, heteroalkenylene is the divalent moiety of heteroalkenyl, heteroalkynylene is the divalent moiety of heteroalkynyl, carbocyclylene is the divalent moiety of carbocyclyl, heterocyclylene is the divalent moiety of heterocyclyl, arylene is the divalent moiety of aryl, and heteroarylene is the divalent moiety of heteroaryl.

As understood from the above, alkyl, alkenyl, alkynyl, heteroalkyl, heteroalkenyl, heteroalkynyl, carbocyclyl, heterocyclyl, aryl, and heteroaryl groups, as defined herein, are, in certain embodiments, optionally substituted. Optionally substituted refers to a group which may be substituted or unsubstituted (e.g., "substituted" or "unsubstituted" alkyl, "substituted" or "unsubstituted" alkenyl, "substituted" or "unsubstituted" alkynyl, "substituted" or "unsubstituted" heteroalkyl, "substituted" or "unsubstituted" heteroalkenyl, "substituted" or "unsubstituted" heteroalkynyl, "substituted" or "unsubstituted" carbocyclyl, "substituted" or "unsubstituted" heterocyclyl, "substituted" or "unsubstituted" aryl or "substituted" or "unsubstituted" heteroaryl group). In general, the term "substituted", whether preceded by the term "optionally" or not, means that at least one hydrogen present on a group (e.g., a carbon or nitrogen atom) is replaced with a permissible substituent, e.g., a substituent which upon substitution results in a stable compound, e.g., a compound which does not spontaneously undergo transformation such as by rearrangement, cyclization, elimination, or other reaction. Unless otherwise indicated, a "substituted" group has a substituent at one or more substitutable positions of the group, and when more than one position in any given structure is substituted, the substituent is either the same or different at each position. The term "substituted" is contemplated to include substitution with all permissible substituents of organic compounds, any of the substituents described herein that results in the formation of a stable compound. The present invention contemplates any and all such combinations in order to arrive at a stable compound. For purposes of this invention, heteroatoms such as nitrogen may have hydrogen substituents and/or any suitable substituent as described herein which satisfy the valencies of the heteroatoms and results in the formation of a stable moiety.

Exemplary carbon atom substituents include, but are not limited to, halogen, —CN, —NO$_2$, —N$_3$, —SO$_2$H, —SO$_3$H, —OH, —OR$^{aa}$, —ON(R$^{bb}$)$_2$, —N(R$^{bb}$)$_2$, —N(R$^{bb}$)$_3$$^+$X$^-$, —N(OR$^{cc}$)R$^{bb}$, —SH, —SR$^{aa}$, —SSR$^{cc}$, —C(=O)R$^{aa}$, —CO$_2$H, —CHO, —C(OR$^{cc}$)$_2$, —CO$_2$R$^{aa}$, —OC(=O)R$^{aa}$, —OCO$_2$R$^{aa}$, —C(=O)N(R$^{bb}$)$_2$, —OC(=O)N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —C(=NR$^{bb}$)R$^{aa}$, —C(=NR$^{bb}$)OR$^{aa}$, —OC(=NR$^{bb}$)R$^{aa}$, —OC(=NR$^{bb}$)OR$^{aa}$, —C(=NR$^{bb}$)N(R$^{bb}$)$_2$, —OC(=NR$^{bb}$)N(R$^{bb}$)$_2$, —NR$^{bb}$C(=NR$^{bb}$)N(R$^{bb}$)$_2$, —C(=O)NR$^{bb}$SO$_2$R$^{aa}$, —NR$^{bb}$SO$_2$R$^{aa}$, —SO$_2$N(R$^{bb}$)$_2$, —SO$_2$R$^{aa}$, —SO$_2$OR$^{aa}$, —OSO$_2$R$^{aa}$, —S(=O)R$^{aa}$, —OS(=O)R$^{aa}$, —Si(R$^{aa}$)$_3$, —OSi(R$^{aa}$)$_3$ —C(=S)N(R$^{bb}$)$_2$, —C(=O)SR$^{aa}$, —C(=S)SR$^{aa}$, —SC(=S)SR$^{aa}$, —SC(=O)SR$^{aa}$, —OC(=O)SR$^{aa}$, —SC(=O)OR$^{aa}$, —SC(=O)R$^{aa}$, —P(=O)$_2$R$^{aa}$, —OP(=O)$_2$R$^{aa}$, —P(=O)(R$^{aa}$)$_2$, —OP(=O)(R$^{aa}$)$_2$, —OP(=O)(OR$^{cc}$)$_2$, —P(=O)$_2$N(R$^{bb}$)$_2$, —OP(=O)$_2$N(R$^{bb}$)$_2$, —P(=O)(NR$^{bb}$)$_2$, —OP(=O)(NR$^{bb}$)$_2$, —NR$^{bb}$P(=O)(OR$^{cc}$)$_2$, —NR$^{bb}$P(=O)(NR$^{bb}$)$_2$, —P(R$^{cc}$)$_2$, —P(R$^{cc}$)$_3$, —OP(R$^{cc}$)$_2$, —OP(R$^{cc}$)$_3$, —B(R$^{aa}$)$_2$, —B(OR$^{cc}$)$_2$, —BR$^{aa}$(OR$^{cc}$), C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-14}$ carbocyclyl, 3-14 membered heterocyclyl, C$_{6-14}$ aryl, and 5-14 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

or two geminal hydrogens on a carbon atom are replaced with the group =O, =S, =NN(R$^{bb}$)$_2$, =NNR$^{bb}$C(=O)R$^{aa}$, =NNR$^{bb}$C(=O)OR$^{aa}$, =NNR$^{bb}$S(=O)$_2$R$^{aa}$, =NR$^{bb}$, or =NOR$^{cc}$;

each instance of R$^{aa}$ is, independently, selected from C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{aa}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{bb}$ is, independently, selected from hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_{3-10}$ carbocyclyl, 3-14 membered heterocyclyl, C$_{6-14}$ aryl, and 5-14 membered heteroaryl, or two R$^{bb}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{cc}$ is, independently, selected from hydrogen, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$heteroalkynyl, C$_3$-10 carbocyclyl, 3-14 membered heterocyclyl, C$_{6-14}$ aryl, and 5-14 membered heteroaryl, or two R$^{cc}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups;

each instance of R$^{dd}$ is, independently, selected from halogen, —CN, —NO$_2$, —N$_3$, —SO$_2$H, —SO$_3$H, —OH, —OR$^{ee}$, —ON(R$^{ff}$)$_2$, —N(R$^{ff}$)$_2$, —N(R$^{ff}$)$_3$$^+$X$^-$, —N(OR$^{ee}$)R$^{ff}$, —SH, —SR$^{ee}$, —SSR$^{ee}$, —C(=O)R$^{ee}$, —CO$_2$H, —CO$_2$R$^{ee}$, —OC(=O)R$^{ee}$, —OCO$_2$R$^{ee}$, —C(=O)N(R$^{ff}$)$_2$, —OC(=O)N(R$^{ff}$)$_2$, —NR$^{ff}$C(=O)R$^{ee}$, —NR$^{ff}$CO$_2$R$^{ee}$, —NR$^{ff}$C(=O)N(R$^{ff}$)$_2$, —C(=NR$^{ff}$)OR$^{ee}$, OC(=NR$^{ff}$)R$^{ee}$, —OC(=NR$^{ff}$)OR$^{ee}$, —C(=NR$^{ff}$)N(R$^{ff}$)$_2$, —OC(=NR$^{ff}$)N(R$^{ff}$)$_2$, —NR$^{ff}$C(=NR$^{ff}$)N(R$^{ff}$)$_2$, —NR$^{ff}$SO$_2$R$^{ee}$, —SO$_2$N(R$^{ff}$)$_2$, —SO$_2$R$^{ee}$, —SO$_2$OR$^{ee}$, —OSO$_2$R$^{ee}$, —S(=O)R$^{ee}$, —Si(R$^{ee}$)$_3$, —OSi(R$^{ee}$)$_3$, —C(=S)N(R$^{ff}$)$_2$, —C(=O)SR$^{ee}$, —C(=S)SR$^{ee}$, —SC(=S)SR$^{ee}$, —P(=O)$_2$R$^{ee}$, —P(=O)(R$^{ee}$)$_2$, —OP(=O)(R$^{ee}$)$_2$, —OP(=O)(OR$^{ee}$)$_2$, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl, 5-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups, or two geminal R$^{dd}$ substituents can be joined to form =O or =S;

each instance of R$^{ee}$ is, independently, selected from C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, and 3-10 membered heteroaryl, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{gg}$ groups;

each instance of R$^{ff}$ is, independently, selected from hydrogen, C$_{1-6}$ alkyl, C$_{1-6}$ perhaloalkyl, C$_{2-6}$ alkenyl, C$_{2-6}$ alkynyl, C$_{1-6}$ heteroalkyl, C$_{2-6}$ heteroalkenyl, C$_{2-6}$heteroalkynyl, C$_{3-10}$ carbocyclyl, 3-10 membered heterocyclyl, C$_{6-10}$ aryl and 5-10 membered heteroaryl, or two R$^{ff}$ groups are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 $R^{gg}$ groups; and each instance of $R^{gg}$ is, independently, halogen, —CN, —NO$_2$, —N$_3$, —SO$_2$H, —SO$_3$H, —OH, —OC$_{1-6}$ alkyl, —ON(C$_{1-6}$ alkyl)$_2$, —N(C$_{1-6}$ alkyl)$_2$, —N(C$_{1-6}$ alkyl)$_3$$^+$X$^-$, —NH(C$_{1-6}$ alkyl)$_2$$^+$X$^-$, —NH$_2$(C$_{1-6}$ alkyl)$^+$X$^-$, —NH$_3$$^+$X$^-$, —N(OC$_{1-6}$ alkyl)(C$_{1-6}$ alkyl), —N(OH)(C$_{1-6}$ alkyl), —NH(OH), —SH, —SC$_{1-6}$ alkyl, —SS(C$_{1-6}$ alkyl), —C(=O)(C$_{1-6}$ alkyl), —CO$_2$H, —CO$_2$(C$_{1-6}$ alkyl), —OC(=O)(C$_{1-6}$ alkyl), —OCO$_2$(C$_{1-6}$ alkyl), —C(=O)NH$_2$, —C(=O)N(C$_{1-6}$ alkyl)$_2$, —OC(=O)NH(C$_{1-6}$ alkyl), —NHC(=O)(C$_{1-6}$ alkyl), —N(C$_{1-6}$ alkyl)C(=O)(C$_{1-6}$ alkyl), —NHCO$_2$(C$_{1-6}$ alkyl), —NHC(=O)N(C$_{1-6}$ alkyl)$_2$, —NHC(=O)NH(C$_{1-6}$ alkyl), —NHC(=O)NH$_2$, —C(=NH)O(C$_{1-6}$ alkyl), —OC(=NH)(C$_{1-6}$ alkyl), —OC(=NH)OC$_{1-6}$ alkyl, —C(=NH)N(C$_{1-6}$ alkyl)$_2$, —C(=NH)NH(C$_{1-6}$ alkyl), —C(=NH)NH$_2$, —OC(=NH)N(C$_{1-6}$ alkyl)$_2$, —OC(NH)NH(C$_{1-6}$ alkyl), —OC(NH)NH$_2$, —NHC(NH)N(C$_{1-6}$ alkyl)$_2$, —NHC(=NH)NH$_2$, —NHSO$_2$(C$_{1-6}$ alkyl), —SO$_2$N(C$_{1-6}$ alkyl)$_2$, —SO$_2$NH(C$_{1-6}$ alkyl), —SO$_2$NH$_2$, —SO$_2$C$_{1-6}$ alkyl, —SO$_2$OC$_{1-6}$ alkyl, —OSO$_2$C$_{1-6}$ alkyl, —SOC$_{1-6}$ alkyl, —Si(C$_{1-6}$ alkyl)$_3$, —OSi(C$_{1-6}$ alkyl)$_3$-C(=S)N(C$_{1-6}$ alkyl)$_2$, —C(=S)NH(C$_{1-6}$ alkyl), —C(=S)NH$_2$, —C(=O)S(C$_{1-6}$ alkyl), —C(=S)SC$_{1-6}$ alkyl, —SC(=S)SC$_{1-6}$ alkyl, —P(=O)$_2$(C$_{1-6}$ alkyl), —P(=O)(C$_{1-6}$ alkyl)$_2$, —OP(=O)(C$_{1-6}$ alkyl)$_2$, —OP(=O)(OC$_{1-6}$ alkyl)$_2$, C$_{1-6}$ alkyl, C$_{1-6}$ perhaloalkyl, C$_{2-6}$ alkenyl, C$_{2-6}$ alkynyl, C$_{1-6}$heteroalkyl, C$_{2-6}$ heteroalkenyl, C$_{2-6}$heteroalkynyl, C$_{3-10}$ carbocyclyl, C$_{6-10}$ aryl, 3-10 membered heterocyclyl, 5-10 membered heteroaryl; or two geminal $R^{gg}$ substituents can be joined to form =O or =S; wherein X$^-$ is a counterion.

As used herein, the term "halo" or "halogen" refers to fluorine (fluoro, —F), chlorine (chloro, —Cl), bromine (bromo, —Br), or iodine (iodo, —I).

As used herein, a "counterion" is a negatively charged group associated with a positively charged quarternary amine in order to maintain electronic neutrality. Exemplary counterions include halide ions (e.g., F$^-$, Cl$^-$, Br$^-$, I$^-$), NO$_3$$^-$, ClO$_4$$^-$, OH$^-$, H$_2$PO$_4$$^-$, HSO$_4$$^-$, sulfonate ions (e.g., methansulfonate, trifluoromethanesulfonate, p-toluenesulfonate, benzenesulfonate, 10-camphor sulfonate, naphthalene-2-sulfonate, naphthalene-1-sulfonic acid-5-sulfonate, ethan-1-sulfonic acid-2-sulfonate, and the like), and carboxylate ions (e.g., acetate, ethanoate, propanoate, benzoate, glycerate, lactate, tartrate, glycolate, and the like).

As used herein, the term "hydroxyl" or "hydroxy" refers to the group —OH. The term "substituted hydroxyl" or "substituted hydroxyl," by extension, refers to a hydroxyl group wherein the oxygen atom directly attached to the parent molecule is substituted with a group other than hydrogen, and includes groups selected from —OR$^{aa}$, —ON(R$^{bb}$)$_2$, —OC(=O)SR$^{aa}$, —OC(=O)R$^{aa}$, —OCO$_2$R$^{aa}$, —OC(=O)N(R$^{bb}$)$_2$, —OC(=NR$^{bb}$)R$^{aa}$, —OC(=NR$^{bb}$)OR$^{aa}$, —OC(=NR$^{bb}$)N(R$^{bb}$)$_2$, —OS(=O)R$^{aa}$, —OSO$_2$R$^{aa}$, —OSi(R$^{aa}$)$_3$, —OP(R$^{cc}$)$_2$, —OP(R$^{cc}$)$_3$, —OP(=O)$_2$R$^{aa}$, —OP(=O)(R$^{aa}$)$_2$, —OP(=O)(OR$^{cc}$)$_2$, —OP(=O)$_2$N(R$^{bb}$)$_2$, and —OP(=O)(NR$^{bb}$)$_2$, wherein R$^{aa}$, R$^{bb}$, and R$^{cc}$ are as defined herein.

As used herein, the term "thiol" or "thio" refers to the group —SH. The term "substituted thiol" or "substituted thio," by extension, refers to a thiol group wherein the sulfur atom directly attached to the parent molecule is substituted with a group other than hydrogen, and includes groups selected from —SR$^{aa}$, —S=SR$^{cc}$, —SC(=S)SR$^{aa}$, —SC(=O)SR$^{aa}$, —SC(=O)OR$^{aa}$, and —SC(=O)R$^{aa}$, wherein R$^{aa}$ and R$^{cc}$ are as defined herein.

As used herein, the term, "amino" refers to the group —NH$_2$. The term "substituted amino," by extension, refers to a monosubstituted amino, a disubstituted amino, or a trisubstituted amino, as defined herein. In certain embodiments, the "substituted amino" is a monosubstituted amino or a disubstituted amino group.

As used herein, the term "monosubstituted amino" refers to an amino group wherein the nitrogen atom directly attached to the parent molecule is substituted with one hydrogen and one group other than hydrogen, and includes groups selected from —NH(R$^{bb}$), —NHC(=O)R$^{aa}$, —NHCO$_2$R$^{aa}$, —NHC(=O)N(R$^{bb}$)$_2$, —NHC(=NR$^{bb}$)N(R$^{bb}$)$_2$, —NHSO$_2$R$^{aa}$, —NHP(=O)(OR$^{cc}$)$_2$, and —NHP(=O)(NR$^{bb}$)$_2$, wherein R$^{aa}$, R$^{bb}$ and R$^{cc}$ are as defined herein, and wherein R$^{bb}$ of the group —NH(R$^{bb}$) is not hydrogen.

As used herein, the term "disubstituted amino" refers to an amino group wherein the nitrogen atom directly attached to the parent molecule is substituted with two groups other than hydrogen, and includes groups selected from —N(R$^{bb}$)$_2$, —NR$^{bb}$C(=O)R$^{aa}$, —NR$^{bb}$CO$_2$R$^{aa}$, —NR$^{bb}$C(=O)N(R$^{bb}$)$_2$, —NR$^{bb}$C(=NR$^{bb}$)N(R$^{bb}$)$_2$, —NR$^{bb}$SO$_2$R$^{aa}$, —NR$^{bb}$P(=O)(OR$^{cc}$)$_2$, and —NR$^{bb}$P(=O)(NR$^{bb}$)$_2$, wherein R$^{aa}$, R$^{bb}$, and R$^{cc}$ are as defined herein, with the proviso that the nitrogen atom directly attached to the parent molecule is not substituted with hydrogen.

As used herein, the term "trisubstituted amino" refers to an amino group wherein the nitrogen atom directly attached to the parent molecule is substituted with three groups, and includes groups selected from —N(R$^{bb}$)$_3$ and —N(R$^{bb}$)$_3$$^+$X$^-$, wherein R$^{bb}$ and X$^-$ are as defined herein.

As used herein, the term "oxo" refers to the group =O, and the term "thiooxo" refers to the group =S.

Nitrogen atoms can be substituted or unsubstituted as valency permits, and include primary, secondary, tertiary, and quarternary nitrogen atoms. Exemplary nitrogen atom substitutents include, but are not limited to, hydrogen, —OH, —OR$^{aa}$, —N(R$^{cc}$)$_2$, —CN, —C(=O)R$^{aa}$, —C(=O)N(R$^{cc}$)$_2$, —CO$_2$R$^{aa}$, —SO$_2$R$^{aa}$, —C(=NR$^{bb}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, —P(=O)$_2$R$^{aa}$, —P(=O)(R$^{aa}$)$_2$, —P(=O)$_2$N(R$^{cc}$)$_2$, —P(=O)(NR$^{cc}$)$_2$, C$_{1-10}$ alkyl, C$_{1-10}$ perhaloalkyl, C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl, or two R$^{cc}$ groups attached to an N atom are joined to form a 3-14 membered heterocyclyl or 5-14 membered heteroaryl ring, wherein each alkyl, alkenyl, alkynyl, heteroalkyl, heteroalkenyl, heteroalkynyl, carbocyclyl, heterocyclyl, aryl, and heteroaryl is independently substituted with 0, 1, 2, 3, 4, or 5 R$^{dd}$ groups, and wherein R$^{aa}$, R$^{bb}$, R$^{cc}$ and R$^{dd}$ are as defined above.

In certain embodiments, the substituent present on the nitrogen atom is an nitrogen protecting group (also referred to herein as an "amino protecting group"). Nitrogen protecting groups include, but are not limited to, —OH, —OR$^{aa}$, —N(R$^{cc}$)$_2$, —C(=O)R$^{aa}$, —C(=O)N(R$^{cc}$)$_2$, —CO$_2$R$^{aa}$, —SO$_2$R$^{aa}$, —C(=NR$^{cc}$)R$^{aa}$, —C(=NR$^{cc}$)OR$^{aa}$, —C(=NR$^{cc}$)N(R$^{cc}$)$_2$, —SO$_2$N(R$^{cc}$)$_2$, —SO$_2$R$^{cc}$, —SO$_2$OR$^{cc}$, —SOR$^{aa}$, —C(=S)N(R$^{cc}$)$_2$, —C(=O)SR$^{cc}$, —C(=S)SR$^{cc}$, C$_{1-10}$ alkyl (e.g., aralkyl, heteroaralkyl), C$_{2-10}$ alkenyl, C$_{2-10}$ alkynyl, C$_{1-10}$ heteroalkyl, C$_{2-10}$ heteroalkenyl, C$_{2-10}$ heteroalkynyl, C$_{3-10}$ carbocyclyl, 3-14 membered heterocyclyl, C$_{6-14}$ aryl, and 5-14 membered heteroaryl groups, wherein each alkyl, alkenyl, alkynyl, heteroalkyl, heteroalkenyl, heteroalkynyl, carbocyclyl, heterocyclyl, aralkyl, aryl, and heteroaryl is independently substituted with 0, 1, 2, 3, 4, or 5 $R^{dd}$ groups, and wherein $R^{aa}$, $R^{bb}$, $R^{cc}$ and $R^{dd}$ are as defined herein. Nitrogen protecting groups are well known in the art and include those described in detail in *Protecting Groups in Organic Synthesis*, T. W. Greene and P. G. M. Wuts, $3^{rd}$ edition, John Wiley & Sons, 1999, incorporated herein by reference.

For example, nitrogen protecting groups such as amide groups (e.g., —C(=O)$R^{aa}$) include, but are not limited to, formamide, acetamide, chloroacetamide, trichloroacetamide, trifluoroacetamide, phenylacetamide, 3-phenylpropanamide, picolinamide, 3-pyridylcarboxamide, N-benzoylphenylalanyl derivative, benzamide, p-phenylbenzamide, o-nitrophenylacetamide, o-nitrophenoxyacetamide, acetoacetamide, (N'-dithiobenzyloxyacylamino)acetamide, 3-(p-hydroxyphenyl)propanamide, 3-(o-nitrophenyl)propanamide, 2-methyl-2-(o-nitrophenoxy)propanamide, 2-methyl-2-(o-phenylazophenoxy)propanamide, 4-chlorobutanamide, 3-methyl-3-nitrobutanamide, o-nitrocinnamide, N-acetylmethionine derivative, o-nitrobenzamide and o-(benzoyloxymethyl)benzamide.

Nitrogen protecting groups such as carbamate groups (e.g., —C(=O)O$R^{aa}$) include, but are not limited to, methyl carbamate, ethyl carbamante, 9-fluorenylmethyl carbamate (Fmoc), 9-(2-sulfo)fluorenylmethyl carbamate, 9-(2,7-dibromo)fluoroenylmethyl carbamate, 2,7-di-t-butyl-[9-(10,10-dioxo-10,10,10,10-tetrahydrothioxanthyl)]methyl carbamate (DBD-Tmoc), 4-methoxyphenacyl carbamate (Phenoc), 2,2,2-trichloroethyl carbamate (Troc), 2-trimethylsilylethyl carbamate (Teoc), 2-phenylethyl carbamate (hZ), 1-(1-adamantyl)-1-methylethyl carbamate (Adpoc), 1,1-dimethyl-2-haloethyl carbamate, 1,1-dimethyl-2,2-dibromoethyl carbamate (DB-t-BOC), 1,1-dimethyl-2,2,2-trichloroethyl carbamate (TCBOC), 1-methyl-1-(4-biphenylyl)ethyl carbamate (Bpoc), 1-(3,5-di-t-butylphenyl)-1-methylethyl carbamate (t-Bumeoc), 2-(2'- and 4'-pyridyl) ethyl carbamate (Pyoc), 2-(N,N-dicyclohexylcarboxamido) ethyl carbamate, t-butyl carbamate (BOC), 1-adamantyl carbamate (Adoc), vinyl carbamate (Voc), allyl carbamate (Alloc), 1-isopropylallyl carbamate (Ipaoc), cinnamyl carbamate (Coc), 4-nitrocinnamyl carbamate (Noc), 8-quinolyl carbamate, N-hydroxypiperidinyl carbamate, alkyldithio carbamate, benzyl carbamate (Cbz), p-methoxybenzyl carbamate (Moz), p-nitobenzyl carbamate, p-bromobenzyl carbamate, p-chlorobenzyl carbamate, 2,4-dichlorobenzyl carbamate, 4-methylsulfinylbenzyl carbamate (Msz), 9-anthrylmethyl carbamate, diphenylmethyl carbamate, 2-methylthioethyl carbamate, 2-methylsulfonylethyl carbamate, 2-(p-toluenesulfonyl)ethyl carbamate, [2-(1,3-dithianyl)]methyl carbamate (Dmoc), 4-methylthiophenyl carbamate (Mtpc), 2,4-dimethylthiophenyl carbamate (Bmpc), 2-phosphonioethyl carbamate (Peoc), 2-triphenylphosphonioisopropyl carbamate (Ppoc), 1,1-dimethyl-2-cyanoethyl carbamate, m-chloro-p-acyloxybenzyl carbamate, p-(dihydroxyboryl)benzyl carbamate, 5-benzisoxazolylmethyl carbamate, 2-(trifluoromethyl)-6-chromonylmethyl carbamate (Tcroc), m-nitrophenyl carbamate, 3,5-dimethoxybenzyl carbamate, o-nitrobenzyl carbamate, 3,4-dimethoxy-6-nitrobenzyl carbamate, phenyl(o-nitrophenyl)methyl carbamate, t-amyl carbamate, S-benzyl thiocarbamate, p-cyanobenzyl carbamate, cyclobutyl carbamate, cyclohexyl carbamate, cyclopentyl carbamate, cyclopropylmethyl carbamate, p-decyloxybenzyl carbamate, 2,2-dimethoxyacylvinyl carbamate, o-(N,N-dimethylcarboxamido)benzyl carbamate, 1,1-dimethyl-3-(N,N-dimethylcarboxamido)propyl carbamate, 1,1-dimethylpropynyl carbamate, di(2-pyridyl)methyl carbamate, 2-furanylmethyl carbamate, 2-iodoethyl carbamate, isobornyl carbamate, isobutyl carbamate, isonicotinyl carbamate, p-(p'-methoxyphenylazo)benzyl carbamate, 1-methylcyclobutyl carbamate, 1-methylcyclohexyl carbamate, 1-methyl-1-cyclopropylmethyl carbamate, 1-methyl-1-(3,5-dimethoxyphenyl)ethyl carbamate, 1-methyl-1-(p-phenylazophenyl)ethyl carbamate, 1-methyl-1-phenylethyl carbamate, 1-methyl-1-(4-pyridyl)ethyl carbamate, phenyl carbamate, p-(phenylazo)benzyl carbamate, 2,4,6-tri-t-butylphenyl carbamate, 4-(trimethylammonium) benzyl carbamate, and 2,4,6-trimethylbenzyl carbamate.

Nitrogen protecting groups such as sulfonamide groups (e.g., —S(=O)$_2$$R^{aa}$) include, but are not limited to, p-toluenesulfonamide (Ts), benzenesulfonamide, 2,3,6,-trimethyl-4-methoxybenzenesulfonamide (Mtr), 2,4,6-trimethoxybenzenesulfonamide (Mtb), 2,6-dimethyl-4-methoxybenzenesulfonamide (Pme), 2,3,5,6-tetramethyl-4-methoxybenzenesulfonamide (Mte), 4-methoxybenzenesulfonamide (Mbs), 2,4,6-trimethylbenzenesulfonamide (Mts), 2,6-dimethoxy-4-methylbenzenesulfonamide (iMds), 2,2,5,7,8-pentamethylchroman-6-sulfonamide (Pmc), methanesulfonamide (Ms), β-trimethylsilylethanesulfonamide (SES), 9-anthracenesulfonamide, 4-(4',8'-dimethoxynaphthylmethyl)benzenesulfonamide (DNMBS), benzylsulfonamide, trifluoromethylsulfonamide, and phenacylsulfonamide.

Other nitrogen protecting groups include, but are not limited to, phenothiazinyl-(10)-acyl derivative, N'-p-toluenesulfonylaminoacyl derivative, N'-phenylaminothioacyl derivative, N-benzoylphenylalanyl derivative, N-acetylmethionine derivative, 4,5-diphenyl-3-oxazolin-2-one, N-phthalimide, N-dithiasuccinimide (Dts), N-2,3-diphenylmaleimide, N-2,5-dimethylpyrrole, N-1,1,4,4-tetramethyldisilylazacyclopentane adduct (STABASE), 5-substituted 1,3-dimethyl-1,3,5-triazacyclohexan-2-one, 5-substituted 1,3-dibenzyl-1,3,5-triazacyclohexan-2-one, 1-substituted 3,5-dinitro-4-pyridone, N-methylamine, N-allylamine, N-[2-(trimethylsilyl)ethoxy]methylamine (SEM), N-3-acetoxypropylamine, N-(1-isopropyl-4-nitro-2-oxo-3-pyroolin-3-yl)amine, quaternary ammonium salts, N-benzylamine, N-di(4-methoxyphenyl)methylamine, N-5-dibenzosuberylamine, N-triphenylmethylamine (Tr), N-[(4-methoxyphenyl)diphenylmethyl]amine (MMTr), N-9-phenylfluorenylamine (PhF), N-2,7-dichloro-9-fluorenylmethyleneamine, N-ferrocenylmethylamino (Fcm), N-2-picolylamino N'-oxide, N-1,1-dimethylthiomethyleneamine, N-benzylideneamine, N-p-methoxybenzylideneamine, N-diphenylmethyleneamine, N-[(2-pyridyl)mesityl]methyleneamine, N—(N',N'-dimethylaminomethylene)amine, N,N'-isopropylidenediamine, N-p-nitrobenzylideneamine, N-salicylideneamine, N-5-chlorosalicylideneamine, N-(5-chloro-2-hydroxyphenyl)phenylmethyleneamine, N-cyclohexylideneamine, N-(5,5-dimethyl-3-oxo-1-cyclohexenyl)amine, N-borane derivative, N-diphenylborinic acid derivative, N-[phenyl(pentaacylchromium- or tungsten)acyl]amine, N-copper chelate, N-zinc chelate, N-nitroamine, N-nitrosoamine, amine N-oxide, diphenylphosphinamide (Dpp), dimethylthiophosphinamide (Mpt), diphenylthiophosphinamide (Ppt), dialkyl phosphoramidates, dibenzyl phosphoramidate, diphenyl phosphoramidate, benzenesulfenamide, o-nitrobenzenesulfenamide (Nps), 2,4-dinitrobenzenesulfenamide, pentachlorobenzenesulfenamide, 2-nitro-4-methoxybenzenesulfenamide, triphenylmethylsulfenamide, and 3-nitropyridinesulfenamide (Npys).

In certain embodiments, the substituent present on an oxygen atom is an oxygen protecting group (also referred to herein as an "hydroxyl protecting group"). Oxygen protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Oxygen protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

Exemplary oxygen protecting groups include, but are not limited to, methyl, methoxylmethyl (MOM), methylthiomethyl (MTM), t-butylthiomethyl, (phenyldimethylsilyl)methoxymethyl (SMOM), benzyloxymethyl (BOM), p-methoxybenzyloxymethyl (PMBM), (4-methoxyphenoxy)methyl (p-AOM), guaiacolmethyl (GUM), t-butoxymethyl, 4-pentenyloxymethyl (POM), siloxymethyl, 2-methoxyethoxymethyl (MEM), 2,2,2-trichloroethoxymethyl, bis(2-chloroethoxy)methyl, 2-(trimethylsilyl)ethoxymethyl (SEMOR), tetrahydropyranyl (THP), 3-bromotetrahydropyranyl, tetrahydrothiopyranyl, 1-methoxycyclohexyl, 4-methoxytetrahydropyranyl (MTHP), 4-methoxytetrahydrothiopyranyl, 4-methoxytetrahydrothiopyranyl S,S-dioxide, 1-[(2-chloro-4-methyl)phenyl]-4-methoxypiperidin-4-yl (CTMP), 1,4-dioxan-2-yl, tetrahydrofuranyl, tetrahydrothiofuranyl, 2,3,3a,4,5,6,7,7a-octahydro-7,8,8-trimethyl-4,7-methanobenzofuran-2-yl, 1-ethoxyethyl, 1-(2-chloroethoxy)ethyl, 1-methyl-1-methoxyethyl, 1-methyl-1-benzyloxyethyl, 1-methyl-1-benzyloxy-2-fluoroethyl, 2,2,2-trichloroethyl, 2-trimethylsilylethyl, 2-(phenylselenyl)ethyl, t-butyl, allyl, p-chlorophenyl, p-methoxyphenyl, 2,4-dinitrophenyl, benzyl (Bn), p-methoxybenzyl, 3,4-dimethoxybenzyl, o-nitrobenzyl, p-nitrobenzyl, p-halobenzyl, 2,6-dichlorobenzyl, p-cyanobenzyl, p-phenylbenzyl, 2-picolyl, 4-picolyl, 3-methyl-2-picolyl N-oxido, diphenylmethyl, p,p'-dinitrobenzhydryl, 5-dibenzosuberyl, triphenylmethyl, α-naphthyldiphenylmethyl, p-methoxyphenyldiphenylmethyl, di(p-methoxyphenyl)phenylmethyl, tri(p-methoxyphenyl)methyl, 4-(4'-bromophenacyloxyphenyl)diphenylmethyl, 4,4',4"-tris(4,5-dichlorophthalimidophenyl)methyl, 4,4',4"-tris(levulinoyloxyphenyl)methyl, 4,4',4"-tris(benzoyloxyphenyl)methyl, 3-(imidazol-1-yl)bis(4',4"-dimethoxyphenyl)methyl, 1,1-bis(4-methoxyphenyl)-1'-pyrenylmethyl, 9-anthryl, 9-(9-phenyl)xanthenyl, 9-(9-phenyl-10-oxo)anthryl, 1,3-benzodithiolan-2-yl, benzisothiazolyl S,S-dioxido, trimethylsilyl (TMS), triethylsilyl (TES), triisopropylsilyl (TIPS), dimethylisopropylsilyl (IPDMS), diethylisopropylsilyl (DEIPS), dimethylthexylsilyl, t-butyldimethylsilyl (TBDMS), t-butyldiphenylsilyl (TBDPS), tribenzylsilyl, tri-p-xylylsilyl, triphenylsilyl, diphenylmethylsilyl (DPMS), t-butylmethoxyphenylsilyl (TBMPS), formate, benzoylformate, acetate, chloroacetate, dichloroacetate, trichloroacetate, trifluoroacetate, methoxyacetate, triphenylmethoxyacetate, phenoxyacetate, p-chlorophenoxyacetate, 3-phenylpropionate, 4-oxopentanoate (levulinate), 4,4-(ethylenedithio)pentanoate (levulinoyldithioacetal), pivaloate, adamantoate, crotonate, 4-methoxycrotonate, benzoate, p-phenylbenzoate, 2,4,6-trimethylbenzoate (mesitoate), alkyl methyl carbonate, 9-fluorenylmethyl carbonate (Fmoc), alkyl ethyl carbonate, alkyl 2,2,2-trichloroethyl carbonate (Troc), 2-(trimethylsilyl)ethyl carbonate (TMSEC), 2-(phenylsulfonyl) ethyl carbonate (Psec), 2-(triphenylphosphonio) ethyl carbonate (Peoc), alkyl isobutyl carbonate, alkyl vinyl carbonate alkyl allyl carbonate, alkyl p-nitrophenyl carbonate, alkyl benzyl carbonate, alkyl p-methoxybenzyl carbonate, alkyl 3,4-dimethoxybenzyl carbonate, alkyl o-nitrobenzyl carbonate, alkyl p-nitrobenzyl carbonate, alkyl S-benzyl thiocarbonate, 4-ethoxy-1-napthyl carbonate, methyl dithiocarbonate, 2-iodobenzoate, 4-azidobutyrate, 4-nitro-4-methylpentanoate, o-(dibromomethyl)benzoate, 2-formylbenzenesulfonate, 2-(methylthiomethoxy)ethyl, 4-(methylthiomethoxy)butyrate, 2-(methylthiomethoxymethyl)benzoate, 2,6-dichloro-4-methylphenoxyacetate, 2,6-dichloro-4-(1,1,3,3-tetramethylbutyl)phenoxyacetate, 2,4-bis(1,1-dimethylpropyl)phenoxyacetate, chlorodiphenylacetate, isobutyrate, monosuccinoate, (E)-2-methyl-2-butenoate, o-(methoxyacyl)benzoate, α-naphthoate, nitrate, alkyl N,N,N',N'-tetramethylphosphorodiamidate, alkyl N-phenylcarbamate, borate, dimethylphosphinothioyl, alkyl 2,4-dinitrophenylsulfenate, sulfate, methanesulfonate (mesylate, Ms), benzylsulfonate, benzenesulfonate (besylate, Bs), and toluenesulfonate (tosylate, Ts).

In certain embodiments, the substituent present on an sulfur atom is a sulfur protecting group (also referred to as a "thiol protecting group"). Sulfur protecting groups include, but are not limited to, —$R^{aa}$, —$N(R^{bb})_2$, —$C(=O)SR^{aa}$, —$C(=O)R^{aa}$, —$CO_2R^{aa}$, —$C(=O)N(R^{bb})_2$, —$C(=NR^{bb})R^{aa}$, —$C(=NR^{bb})OR^{aa}$, —$C(=NR^{bb})N(R^{bb})_2$, —$S(=O)R^{aa}$, —$SO_2R^{aa}$, —$Si(R^{aa})_3$, —$P(R^{cc})_2$, —$P(R^{cc})_3$, —$P(=O)_2R^{aa}$, —$P(=O)(R^{aa})_2$, —$P(=O)(OR^{cc})_2$, —$P(=O)_2N(R^{bb})_2$, and —$P(=O)(NR^{bb})_2$, wherein $R^{aa}$, $R^{bb}$, and $R^{cc}$ are as defined herein. Sulfur protecting groups are well known in the art and include those described in detail in *Protecting Groups in Organic Synthesis*, T. W. Greene and P. G. M. Wuts, 3$^{rd}$ edition, John Wiley & Sons, 1999, incorporated herein by reference.

These and other exemplary substituents are described in more detail in the Detailed Description, Examples, and claims. The invention is not intended to be limited in any manner by the above exemplary listing of substituents.

The term "pharmaceutically acceptable salt" refers to those salts which are, within the scope of sound medical judgment, suitable for use in contact with the tissues of humans and lower animals without undue toxicity, irritation, allergic response, and the like, and are commensurate with a reasonable benefit/risk ratio. Pharmaceutically acceptable salts are well known in the art. For example, Berge et al., describes pharmaceutically acceptable salts in detail in *J. Pharmaceutical Sciences* (1977) 66:1-19. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Pharmaceutically acceptable salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate, and aryl sulfonate.

As used herein, a "leaving group" is an art-understood term referring to a molecular fragment that departs with a pair of electrons in heterolytic bond cleavage, wherein the molecular fragment is an anion or neutral molecule. See, for example, Smith, March *Advanced Organic Chemistry* 6th ed. (501-502). Exemplary leaving groups include, but are not limited to, halo (e.g., chloro, bromo, iodo) and sulfonyl substituted hydroxyl groups (e.g., tosyl, mesyl, besyl).

Other Definitions

A "subject" to which administration is contemplated includes, but is not limited to, humans (i.e., a male or female of any age group, e.g., a pediatric subject (e.g, infant, child, adolescent) or adult subject (e.g., young adult, middle-aged adult or senior adult)) and/or other non-human animals, for example mammals (e.g., primates (e.g., cynomolgus monkeys, rhesus monkeys); commercially relevant mammals such as cattle, pigs, horses, sheep, goats, cats, and/or dogs), birds (e.g., commercially relevant birds such as chickens, ducks, geese, and/or turkeys), reptiles, amphibians, and fish. In certain embodiments, the non-human animal is a mammal. The non-human animal may be a male or female and at any stage of development. A non-human animal may be a transgenic animal.

A "condition," "disease," and "disorder" are used interchangeably herein.

As used herein, and unless otherwise specified, the terms "treat," "treating" and "treatment" contemplate an action that occurs while a subject is suffering from the specified disease, disorder or condition, which reduces the severity of the disease, disorder or condition, or retards or slows the progression of the disease, disorder or condition ("therapeutic treatment"), and also contemplates an action that occurs before a subject begins to suffer from the specified disease, disorder or condition ("prophylactic treatment").

In general, the "effective amount" of a compound refers to an amount sufficient to elicit the desired biological response. As will be appreciated by those of ordinary skill in this art, the effective amount of a compound of the invention may vary depending on such factors as the desired biological endpoint, the pharmacokinetics of the compound, the disease being treated, the mode of administration, and the age, health, and condition of the subject. An effective amount encompasses therapeutic and prophylactic treatment.

As used herein, and unless otherwise specified, a "therapeutically effective amount" of a compound is an amount sufficient to provide a therapeutic benefit in the treatment of a disease, disorder or condition, or to delay or minimize one or more symptoms associated with the disease, disorder or condition. A therapeutically effective amount of a compound means an amount of therapeutic agent, alone or in combination with other therapies, which provides a therapeutic benefit in the treatment of the disease, disorder or condition. The term "therapeutically effective amount" can encompass an amount that improves overall therapy, reduces or avoids symptoms or causes of disease or condition, or enhances the therapeutic efficacy of another therapeutic agent. In the context of treatment of conditions associated with aberrant Her3 activity, in certain embodiments, a therapeutically effective amount is an amount sufficient to reduce Her3 activity, reduce Her3 protein levels, and/or inhibit cell proliferation.

As used herein, and unless otherwise specified, a "prophylactically effective amount" of a compound is an amount sufficient to prevent a disease, disorder or condition, or one or more symptoms associated with the disease, disorder or condition, or prevent its recurrence. A prophylactically effective amount of a compound means an amount of a therapeutic agent, alone or in combination with other agents, which provides a prophylactic benefit in the prevention of the disease, disorder or condition. The term "prophylactically effective amount" can encompass an amount that improves overall prophylaxis or enhances the prophylactic efficacy of another prophylactic agent.

As used herein an "inhibitor" refers to the ability of a compound to reduce (e.g., slow, halt) or prevent activity of a particular biological process (kinase activity) in a cell relative to vehicle.

As used herein, use of the phrase "at least one instance" refers to 1, 2, 3, 4, or more instances, but also encompasses a range, e.g., for example, from 1 to 4, from 1 to 3, from 1 to 2, from 2 to 4, from 2 to 3, or from 3 to 4 instances, inclusive.

"Kinase." A kinase is a type of enzyme that transfers phosphate groups from high energy donor molecules, such as ATP, to specific substrates, referred to as phosphorylation. Kinases are part of the larger family of phosphotransferases. One of the largest groups of kinases are protein kinases, which act on and modify the activity of specific proteins. Kinases are used extensively to transmit signals and control complex processes in cells. Various other kinases act on small molecules such as lipids, carbohydrates, amino acids, and nucleotides, either for signaling or to prime them for metabolic pathways. Kinases are often named after their substrates. More than 500 different protein kinases have been identified in humans. These exemplary human protein kinases include, but are not limited to, AAK1, ABL, ACK, ACTR2, ACTR2B, AKT1, AKT2, AKT3, ALK, ALK1, ALK2, ALK4, ALK7, AMPKa1, AMPKa2, ANKRD3, ANPa, ANPb, ARAF, ARAFps, ARG, AurA, AurAps1, AurAps2, AurB, AurBps1, AurC, AXL, BARK1, BARK2, BIKE, BLK, BMPR1A, BMPR1Aps1, BMPR1Aps2, BMPR1B, BMPR2, BMX, BRAF, BRAFps, BRK, BRSK1, BRSK2, BTK, BUB1, BUBR1, CaMK1a, CaMK1b, CaMK1d, CaMK1g, CaMK2a, CaMK2b, CaMK2d, CaMK2g, CaMK4, CaMKK1, CaMKK2, caMLCK, CASK, CCK4, CCRK, CDC2, CDC7, CDK10, CDK11, CDK2, CDK3, CDK4, CDK4ps, CDK5, CDK5ps, CDK6, CDK7, CDK7ps, CDK8, CDK8ps, CDK9, CDKL1, CDKL2, CDKL3, CDKL4, CDKL5, CGDps, CHED, CHK1, CHK2, CHK2ps1, CHK2ps2, CK1a, CK1a2, CK1aps1, CK1aps2, CK1aps3, CK1d, CK1e, CK1g1, CK1g2, CK1g2ps, CK1g3, CK2a1, CK2a1-rs, CK2a2, CLIK1, CLIK1L, CLK1, CLK2, CLK2ps, CLK3, CLK3ps, CLK4, COT, CRIK, CRK7, CSK, CTK, CYGD, CYGF, DAPK1, DAPK2, DAPK3, DCAMKL1, DCAMKL2, DCAMKL3, DDR1, DDR2, DLK, DMPK1, DMPK2, DRAK1, DRAK2, DYRK1A, DYRK1B, DYRK2, DYRK3, DYRK4, EGFR, EphA1, EphA10, EphA2, EphA3, EphA4, EphA5, EphA6, EphA7, EphA8, EphB1, EphB2, EphB3, EphB4, EphB6, Erk1, Erk2, Erk3, Erk3ps1, Erk3ps2, Erk3ps3, Erk3ps4, Erk4, Erk5, Erk7, FAK, FER, FERps, FES, FGFR1, FGFR2, FGFR3, FGFR4, FGR, FLT1, FLT1ps, FLT3, FLT4, FMS, FRK, Fused, FYN, GAK, GCK, GCN2, GCN22, GPRK4, GPRK5, GPRK6, GPRK6ps, GPRK7, GSK3A, GSK3B, Haspin, HCK, HER2/ErbB2, HER3/ErbB3, HER4/ErbB4, HH498, HIPK1, HIPK2, HIPK3, HIPK4, HPK1, HRI, HRIps, HSER, HUNK, ICK, IGF1R, IKKa, IKKb, IKKe, ILK, INSR, IRAK1, IRAK2, IRAK3, IRAK4, IRE1, IRE2, IRR, ITK, JAK1, JAK12, JAK2, JAK22, JAK3, JAK32, JNK1, JNK2, JNK3, KDR, KHS1, KHS2, KIS, KIT, KSGCps, KSR1, KSR2, LATS1, LATS2, LCK, LIMK1, LIMK2, LIMK2ps, LKB1, LMR1, LMR2, LMR3, LOK, LRRK1, LRRK2, LTK, LYN, LZK, MAK, MAP2K1, MAP2K1ps, MAP2K2, MAP2K2ps, MAP2K3, MAP2K4, MAP2K5, MAP2K6, MAP2K7, MAP3K1, MAP3K2, MAP3K3, MAP3K4, MAP3K5, MAP3K6, MAP3K7, MAP3K8, MAPKAPK2, MAPKAPK3, MAPKAPK5, MAPKAPKps1, MARK1, MARK2, MARK3, MARK4, MARKps01, MARKps02, MARKps03, MARKps04, MARKps05, MARKps07, MARKps08, MARKps09, MARKps10, MARKps11, MARKps12, MARKps13, MARKps15, MARKps16, MARKps17, MARKps18, MARKps19, MARKps20, MARKps21, MARKps22, MARKps23, MARKps24, MARKps25, MARKps26, MARKps27, MARKps28, MARKps29, MARKps30, MAST1, MAST2, MAST3, MAST4, MASTL, MELK, MER, MET, MISR2, MLK1, MLK2, MLK3, MLK4, MLKL, MNK1, MNK1ps, MNK2, MOK, MOS, MPSK1, MPSK1ps, MRCKa, MRCKb, MRCKps, MSK1, MSK12, MSK2, MSK22, MSSK1, MST1, MST2, MST3, MST3ps, MST4, MUSK, MYO3A, MYO3B, MYT1, NDR1, NDR2, NEK1, NEK10, NEK11, NEK2, NEK2ps1, NEK2ps2, NEK2ps3, NEK3, NEK4, NEK4ps, NEK5, NEK6, NEK7, NEK8, NEK9, NIK, NIM1, NLK, NRBP1, NRBP2, NuaK1, NuaK2, Obscn, Obscn2, OSR1, p38a, p38b, p38d, p38g, p70S6K, p70S6Kb, p70S6Kps1, p70S6Kps2, PAK1, PAK2, PAK2ps, PAK3, PAK4, PAK5, PAK6, PASK, PBK, PCTAIRE1, PCTAIRE2, PCTAIRE3, PDGFRa, PDGFRb, PDK1, PEK, PFTAIRE1, PFTAIRE2, PHKg1, PHKg1ps1, PHKg1ps2, PHKg1ps3, PHKg2, PIK3R4, PIM1, PIM2, PIM3, PINK1, PITSLRE, PKACa, PKACb, PKACg, PKCa, PKCb, PKCd, PKCe, PKCg, PKCh, PKCi, PKCips, PKCt, PKCz, PKD1, PKD2, PKD3, PKG1, PKG2, PKN1, PKN2, PKN3, PKR, PLK1, PLK1ps1, PLK1ps2, PLK2, PLK3, PLK4, PRKX, PRKXps, PRKY, PRP4, PRP4ps, PRPK, PSKH1, PSKH1ps, PSKH2, PYK2, QIK, QSK, RAF1, RAF1ps, RET, RHOK, RIPK1, RIPK2, RIPK3, RNAseL, ROCK1, ROCK2, RON, ROR1, ROR2, ROS, RSK1, RSK12, RSK2, RSK22, RSK3, RSK32, RSK4, RSK42, RSKL1, RSKL2, RYK, RYKps, SAKps, SBK, SCYL1, SCYL2, SCYL2ps, SCYL3, SGK, SgK050ps, SgK069, SgK071, SgK085, SgK110, SgK196, SGK2, SgK223, SgK269, SgK288, SGK3, SgK307, SgK384ps, SgK396, SgK424, SgK493, SgK494, SgK495, SgK496, SIK, skM-LCK, SLK, Slob, smMLCK, SNRK, SPEG, SPEG2, SRC, SRM, SRPK1, SRPK2, SRPK2ps, SSTK, STK33, STK33ps, STLK3, STLK5, STLK6, STLK6ps1, STLK6-rs, SuRTK106, SYK, TAK1, TAO1, TAO2, TAO3, TBCK, TBK1, TEC, TESK1, TESK2, TGFbR1, TGFbR2, TIE1, TIE2, TLK1, TLK1ps, TLK2, TLK2ps1, TLK2ps2, TNK1, Trad, Trb1, Trb2, Trb3, Trio, TRKA, TRKB, TRKC, TSSK1, TSSK2, TSSK3, TSSK4, TSSKps1, TSSKps2, TTBK1, TTBK2, TTK, TTN, TXK, TYK2, TYK22, TYRO3, TYRO3ps, ULK1, ULK2, ULK3, ULK4, VACAMKL, VRK1, VRK2, VRK3, VRK3ps, Wee1, Wee1B, Wee1Bps, Wee1ps1, Wee1ps2, Wnk1, Wnk2, Wnk3, Wnk4, YANK1, YANK2, YANK3, YES, YESps, YSK1, ZAK, ZAP70, ZC1/HGK, ZC2/TNIK, ZC3/MINK, ZC4/NRK. In certain embodiments, the kinase is HER3/ErbB3 ("Her3 kinase").

As used herein, "hydrophobic," in the context of a "hydrophobic" group —$R^H$ refers to a group —$R^H$ which comprises zero hydrogen bond donors (e.g., zero —NH, —OH, and/or —SH groups) and optionally zero hydrogen bond acceptors (e.g., O, N, and/or S atoms). In certain embodiments, the hydrophobic group —$R^H$ comprises zero hydrogen bond donors and zero hydrogen bond acceptors. For example, in certain embodiments, the hydrophobic group —$R^H$ is an unsubstituted hydrocarbon (carbocyclyl-alkyl, carbocyclyl, aralkyl, or aryl) group, i.e., comprising only carbon and hydrogen. In certain embodiments, the hydrophobic group —$R^H$ comprises at least 6 carbon atoms, e.g., between 6 and 50 carbon atoms, between 6 and 40 carbon atoms, between 6 and 30 carbon atoms, between 6 and 20 carbon atoms, or between 6 and 15 carbon atoms. In certain embodiments, the hydrophobic group —$R^H$ comprises 6, 7, 8, 9, 10, 11, 12, 13, 14, 15, 16, 17, 18, 19, or 20 carbon atoms.

A "small organic molecule," (M) as used herein, refers to an alkyl, alkenyl, alknyl, aryl, heteroaryl, carbocyclic, or heterocyclic moiety, as defined herein, comprising carbon and hydrogen, and optionally comprising one or more heteroatoms as a part of the molecule (in the case of heteroaryl and heterocyclic groups) and/or attached to the molecule selected from oxygen, nitrogen, sulfur, phosphorus, boron, silicon, and selenium.

"Molecular weights." The molecular weight of said small organic molecule (M), in the absence of the group -$L^1$-$R^H$ (such that the group -$L^1$-$R^H$ is replaced with hydrogen to provide M-H), is between about 100 g/mol and about 800 g/mol, inclusive, e.g., between about 100 and about 750 g/mol, between about 100 and about 700 g/mol, between about 100 and about 650 g/mol, between about 100 and about 600 g/mol, between about 100 and about 550 g/mol, between about 100 and about 500 g/mol, between about 100 and about 450 g/mol, between about 100 and about 400 g/mol, between about 100 and about 350 g/mol, between about 100 and about 300 g/mol, between about 100 and about 250 g/mol, between about 100 and about 200 g/mol, between about 100 and about 150 g/mol, between about 200 g/mol to about 800 g/mol, between about 200 g/mol to about 700 g/mol, between about 200 g/mol to about 600 g/mol, between about 200 g/mol to about 500 g/mol, between about 200 g/mol to about 400 g/mol, between about 200 g/mol to about 300 g/mol, between about 300 g/mol to about 800 g/mol, between about 300 g/mol to about 700 g/mol, between about 300 g/mol to about 600 g/mol, between about 300 g/mol to about 500 g/mol, between about 300 g/mol to about 400 g/mol, between about 400 g/mol to about 800 g/mol, between about 400 g/mol to about 700 g/mol, between about 400 g/mol to about 600 g/mol, between about 400 g/mol to about 500 g/mol, or between about 400 g/mol to about 400 g/mol, inclusive.

The molecular weight of the group -$L^1$-$R^H$ is, in certain embodiments, between about 50 g/mol and about 600 g/mol, inclusive, e.g., between about 50 g/mol and about 500 g/mol, between about 100 g/mol and about 500 g/mol, between about 100 g/mol and about 400 g/mol, between about 100 g/mol and about 300 g/mol, between about 100 g/mol and about 200 g/mol, between about 200 g/mol and about 400 g/mol, or between about 200 g/mol and about 300 g/mol, inclusive.

The molecular weight of the hydrophobic group —$R^H$ is, in certain embodiments, between about 100 g/mol and about 300 g/mol, inclusive, e.g., between about 100 g/mol and about 200 g/mol, between about 100 g/mol and about 180 g/mol, between about 110 g/mol and about 180 g/mol, between about 120 g/mol and about 180 g/mol, or between about 130 g/mol and about 180 g/mol, inclusive.

The total molecular weight of the compound of Formula (I), is the cumulative molecular weight of the small molecule (M) and group -$L^1$-$R^H$. In certain embodiments, the total molecular weight of the compound of Formula (I) is between about 200 g/mol to about 1000 g/mol, inclusive, e.g., between about 200 g/mol to about 900 g/mol, between about 200 g/mol to about 800 g/mol, between about 200 g/mol to about 700 g/mol, between about 200 g/mol to about 600 g/mol, between about 200 g/mol to about 500 g/mol, between about 200 g/mol to about 400 g/mol, between about 200 g/mol to about 300 g/mol, between about 300 g/mol to about 800 g/mol, between about 400 g/mol to about 1000 g/mol, between about 400 g/mol to about 900 g/mol, between about 400 g/mol to about 800 g/mol, between about 400 g/mol to about 700 g/mol, between about 400 g/mol to about 600 g/mol, between about 400 g/mol to about 500 g/mol, between about 500 g/mol to about 1000 g/mol, between about 500 g/mol to about 900 g/mol, between about 500 g/mol to about 800 g/mol, between about 500 g/mol to about 700 g/mol, or between about 500 g/mol to about 600 g/mol, inclusive.

For example, the molecular weight of the small molecule of Formula (II'), which is the small molecule as defined in Formula (II) in the absence of the group -$L^1$-$R^H$ (wherein -$L^1$-$R^H$ is replaced with hydrogen to provide M-H):

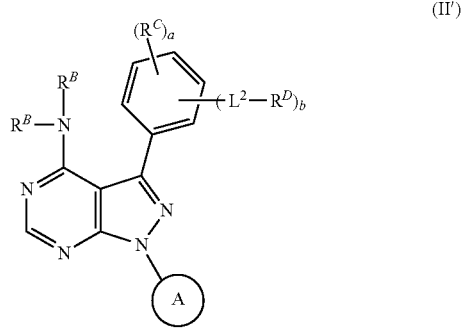

is between about 251 g/mol and about 800 g/mol, inclusive. 251 g/mol is the lowest molecular weight contemplated for this particular formula, wherein a and b are each 0, both instances of $R^B$ are hydrogen, and Ring A is unsubstituted cyclopropyl.

In certain embodiments, the molecular weight of the small molecule (M-H) of Formula (II') is between about 251 g/mol to about 800 g/mol, between about 251 g/mol to about 700 g/mol, between about 251 g/mol to about 600 g/mol, between about 251 g/mol to about 500 g/mol, between about 251 g/mol to about 400 g/mol, between about 300 g/mol to about 800 g/mol, between about 300 g/mol to about 700 g/mol, between about 300 g/mol to about 600 g/mol, between about 300 g/mol to about 500 g/mol, between about 300 g/mol to about 400 g/mol, between about 400 g/mol to about 800 g/mol, between about 400 g/mol to about 700 g/mol, between about 400 g/mol to about 600 g/mol, or between about 400 g/mol to about 500 g/mol, inclusive.

Furthermore, in the instance of the total molecular weight of a compound of Formula (II), which is the cumulative molecular weight of the small molecule (M) and the group -$L^1$-$R^H$, is, in certain embodiments, between about 351 g/mol and about 1000 g/mol, inclusive, e.g., between about 400 g/mol to about 1000 g/mol, between about 400 g/mol to about 900 g/mol, between about 400 g/mol to about 800 g/mol, between about 400 g/mol to about 700 g/mol, between about 400 g/mol to about 600 g/mol, between about 400 g/mol to about 500 g/mol, between about 500 g/mol to about 1000 g/mol, between about 500 g/mol to about 900 g/mol, between about 500 g/mol to about 800 g/mol, between about 500 g/mol to about 700 g/mol, or between about 500 g/mol to about 600 g/mol, inclusive.

Furthermore, in the instance of a compound of Formula (II), in certain embodiments, the molecular weight of the group -$L^1$-$R^H$ provided in Formula (II) is between about 50 g/mol and about 400 g/mol, e.g., between about 100 g/mol and about 400 g/mol, between about 100 g/mol and about 300 g/mol, between about 100 g/mol and about 200 g/mol, between about 200 g/mol and about 400 g/mol, or between about 200 g/mol and about 300 g/mol, inclusive.

In certain embodiments, the total molecular weight of the compound of Formula (II) is between about 500 g/mol to about 1000 g/mol, inclusive, and the molecular weight of the group -$L^1$-$R^H$ provided in Formula (II) is between about 100 g/mol and about 400 g/mol, inclusive.

In certain embodiments, the total molecular weight of the compound of Formula (II) is between about 500 g/mol to about 1000 g/mol, inclusive, and the molecular weight of the small molecule (M-H) of Formula (II') is between about 400 g/mol to about 600 g/mol, inclusive.

DETAILED DESCRIPTION OF CERTAIN EMBODIMENTS OF THE INVENTION

As generally described herein, the present invention is based on the development of bifunctional compounds (i.e., a kinase binding small molecule tagged with a hydrophobic moiety) that can induce the degradation of a kinase, e.g., a protein kinase, of interest. These bifunctional compounds possess a kinase recognition element that can bind either covalently or non-covalently and a 'hydrophobic' tag element that signals to the intracellular protein homeostasis machinery to induce degradation of the targeted kinase.

Bifunctional compounds contemplated herein may be generally represented by Formula (I):

or a pharmaceutically acceptable salt thereof;
wherein:

M represents a small organic molecule which binds to a kinase;

$L^1$ represents a linker selected from the group consisting of substituted and unsubstituted alkylene, substituted and unsubstituted alkenylene, substituted and unsubstituted alkynylene, substituted and unsubstituted heteroalkylene, substituted and unsubstituted heteroalkenylene, substituted and unsubstituted heteroalkynylene, substituted and unsubstituted heterocyclylene, substituted and unsubstituted carbocyclylene, substituted and unsubstituted arylene, substituted and unsubstituted heteroarylene, and combinations thereof; and $R^H$ represents a hydrophobic group selected from the group consisting of substituted and unsubstituted aryl, substituted and unsubstituted heteroaryl, substituted and unsubstituted carbocyclyl, substituted and unsubstituted heterocyclyl, substituted and unsubstituted aralkyl, substituted and unsubstituted heteroarylalkyl, substituted and unsubstituted carbocycylalkyl, and substituted and unsubstituted heterocyclylalkyl.

As described herein, M represents a small organic molecule which binds, covalently or non-covalently, to a particular kinase even when the group -$L^1$-$R^H$ is absent, i.e., wherein the group -$L^1$-$R^H$ is replaced, for example, with hydrogen (M-H). In certain embodiments, the small organic molecule (M or M-H) covalently binds the kinase. In certain embodiments, the small organic molecule (M or M-H) non-covalently binds the kinase. In certain embodiments, the non-covalent binding affinity of the small organic molecule (M or M-H) to the kinase is between about 0.1 nanomolar and 1000 nanomolar, inclusive, e.g., between about 1 nanomolar and 1000 nanomolar, between about 10 nanomolar and 1000 nanomolar, between about 100 nanomolar and 1000 nanomolar, between about 500 nanomolar and 1000 nanomolar, between about 0.1 nanomolar and 500 nanomolar, between about 0.1 nanomolar and 100 nanomolar, between about 0.1 nanomolar and 50 nanomolar, inclusive.

In certain embodiments the kinase is a protein kinase. In certain embodiments the kinase is a human protein kinase. In certain embodiments, the human protein kinase is HER3/ErbB3 ("Her3 kinase").

Linker $L^1$

As described herein, $L^1$ represents a linker selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof.

As used herein, reference to a linker consisting of a combination refers to a linker comprising 1, 2, 3, 4 or more of the recited moieties. For example, the linker may consist of an alkylene attached to a heteroalkylene, which may be further optionally attached to another alkylene. As used herein "at least one instance" refers to 1, 2, 3, 4, or more instances of the recited moiety.

In certain embodiments, $L^1$ comprises at least one instance of substituted or unsubstituted alkylene, e.g., substituted or unsubstituted $C_{1-6}$alkylene, substituted or unsubstituted $C_{1-2}$alkylene, substituted or unsubstituted $C_{2-3}$alkylene, substituted or unsubstituted $C_{3-4}$alkylene, substituted or unsubstituted $C_{4-5}$alkylene, substituted or unsubstituted $C_{5-6}$alkylene, substituted or unsubstituted $C_{3-6}$alkylene, or substituted or unsubstituted $C_{4-6}$alkylene. Exemplary alkylene groups include unsubstituted alkylene groups such as methylene —$CH_2$—, ethylene —$(CH_2)_2$—, n-propylene —$(CH_2)_3$—, n-butylene —$(CH_2)_4$—, n-pentylene —$(CH_2)_5$—, and n-hexylene —$(CH_2)_6$—.

In certain embodiments, $L^1$ comprises at least one instance of substituted or unsubstituted alkenylene, e.g., substituted or unsubstituted $C_{2-6}$alkenylene, substituted or unsubstituted $C_{2-3}$alkenylene, substituted or unsubstituted $C_{3-4}$alkenylene, substituted or unsubstituted $C_{4-5}$alkenylene, or substituted or unsubstituted $C_{5-6}$alkenylene.

In certain embodiments, $L^1$ comprises at least one instance of substituted or unsubstituted alkynylene, e.g., substituted or unsubstituted $C_{2-6}$alkynylene, substituted or unsubstituted $C_{2-3}$alkynylene, substituted or unsubstituted $C_{3-4}$alkynylene, substituted or unsubstituted $C_{4-5}$alkynylene, or substituted or unsubstituted $C_{5-6}$alkynylene.

In certain embodiments, $L^1$ comprises at least one instance of substituted or unsubstituted heteroalkylene, e.g., substituted or unsubstituted hetero$C_{1-6}$alkylene, substituted or unsubstituted hetero$C_{1-2}$alkylene, substituted or unsubstituted hetero$C_{2-3}$alkylene, substituted or unsubstituted hetero$C_{3-4}$alkylene, substituted or unsubstituted hetero$C_{4-5}$alkylene, or substituted or unsubstituted hetero$C_{5-6}$alkylene. Exemplary heteroalkylene groups include unsubstituted alkylene groups such as —$(CH_2)_2$—$O(CH_2)_2$—, —$OCH_2$—, —$CH_2O$—, —$O(CH_2)_2$—, —$(CH_2)_2O$—, —$O(CH_2)_3$—, —$(CH_2)_3O$—, —$O(CH_2)_4$—, —$(CH_2)_4O$—, —$O(CH_2)_5$—, —$(CH_2)_5O$—, —$O(CH_2)_6$—, and —$O(CH_2)_6O$—.

In certain embodiments, $L^1$ comprises at least one instance of substituted or unsubstituted heteroalkenylene, e.g., substituted or unsubstituted hetero$C_{2-6}$alkenylene, substituted or unsubstituted hetero$C_{2-3}$alkenylene, substituted or unsubstituted hetero$C_{3-4}$alkenylene, substituted or unsubstituted hetero$C_{4-5}$alkenylene, or substituted or unsubstituted hetero$C_{5-6}$alkenylene.

In certain embodiments, $L^1$ comprises at least one instance of substituted or unsubstituted heteroalkynylene, e.g., substituted or unsubstituted hetero$C_{2-6}$alkynylene, substituted or unsubstituted hetero$C_{2-3}$alkynylene, substituted or unsubstituted hetero$C_{3-4}$alkynylene, substituted or unsubstituted hetero$C_{4-5}$alkynylene, or substituted or unsubstituted hetero$C_{5-6}$alkynylene.

In certain embodiments, $L^1$ comprises at least one instance of substituted or unsubstituted carbocyclylene, e.g., substituted or unsubstituted $C_{3-6}$carbocyclylene, substituted or unsubstituted $C_{3-4}$carbocyclylene, substituted or unsubstituted $C_{4-5}$ carbocyclylene, or substituted or unsubstituted $C_{5-6}$ carbocyclylene.

In certain embodiments, $L^1$ comprises at least one instance of substituted or unsubstituted heterocyclylene, e.g., substituted or unsubstituted $C_{3-6}$ heterocyclylene, substituted or unsubstituted $C_{3-4}$ heterocyclylene, substituted or unsubstituted $C_{4-5}$ heterocyclylene, or substituted or unsubstituted $C_{5-6}$ heterocyclylene.

In certain embodiments, $L^1$ comprises at least one instance of substituted or unsubstituted arylene, e.g., substituted or unsubstituted phenylene.

In certain embodiments, $L^1$ comprises at least one instance of substituted or unsubstituted heteroarylene, e.g., substituted or unsubstituted 5- to 6-membered heteroarylene.

In certain embodiments, $L^1$ is a linker that contains an asymmetric carbon/stereocenter, i.e., an $sp^3$ hybridized carbon atom bearing 4 different groups attached thereto. In certain embodiments, the compound comprising such an $L^1$ group is enantiomerically enriched or substantially enantiomerically enriched, as defined herein. However, in certain embodiments, the compound comprising such an $L^1$ group is racemic.

In certain embodiments, $L^1$ represents a linker consisting of a combination of one or more consecutive covalently bonded groups of the formulae:

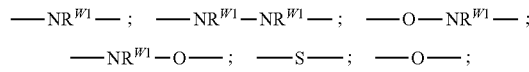

-continued
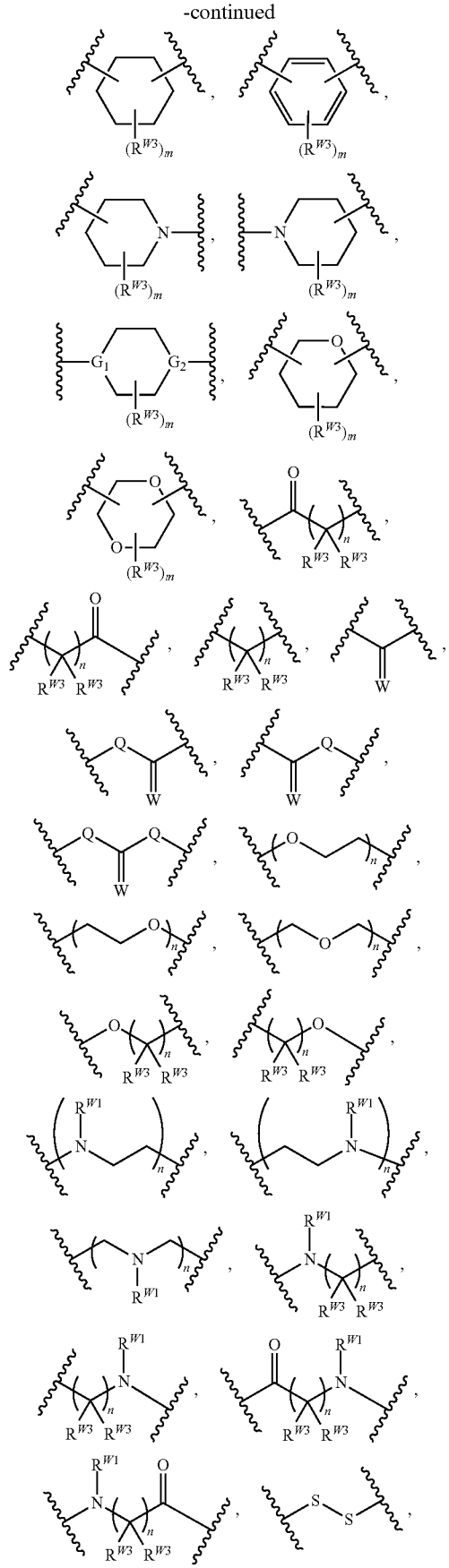
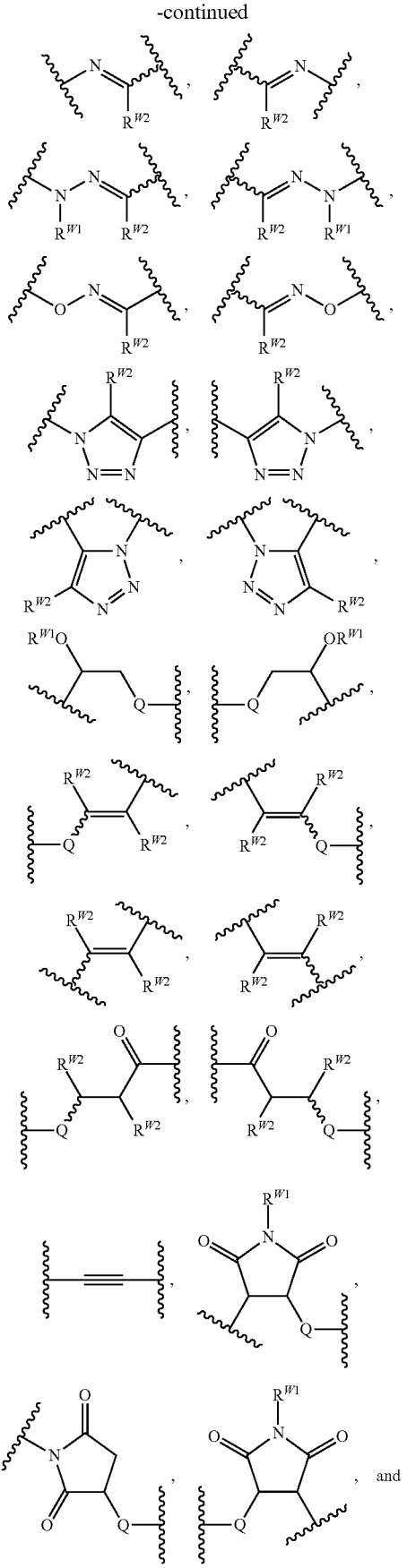
and

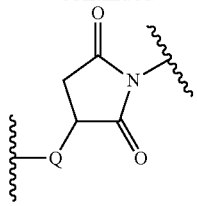

wherein:
each instance of n is independently an integer between 1 to 10, inclusive;
each instance of m is independently 0, 1, or 2;
each instance of Q is independently —NR$^{W1}$—; —NR$^{W1}$—NR$^{W1}$—; —O—NR$^{W1}$—; —NR$^{W1}$—O—; —S—; or —O—;
each instance of W is independently O, S, or NR$^{W1}$;
each instance of G$_1$ and G$_2$ are independently N or CH;
each instance of R$^{W1}$ is independently hydrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; a nitrogen protecting group if attached to a nitrogen atom, or an oxygen protecting group if attached to an oxygen atom;
each instance of R$^{W2}$ is independently hydrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or two R$^{W2}$ groups are joined to form a 5-6 membered ring; and
each instance of R$^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two R$^{W3}$ groups are joined to form a 3-6 membered ring;
or R$^{W1}$ and R$^{W3}$ are joined to form a 5-6 membered heterocyclic ring.

As described herein, n of any of the below formulae is independently an integer between 1 to 10, inclusive, e.g., 1, 2, 3, 4, 5, 6, 7, 8, 9, or 10:

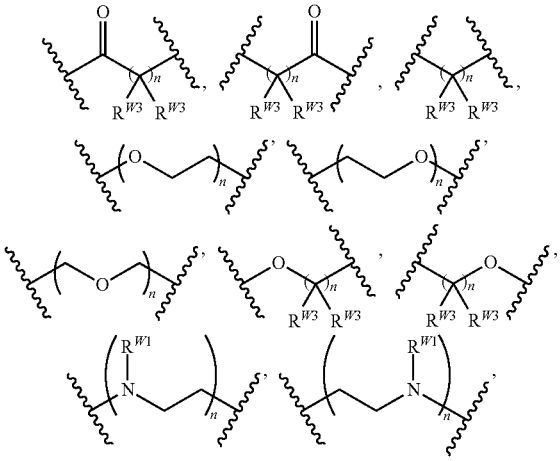

In certain embodiments, n is 1, 2, or 3. In certain embodiments, each instance of R$^{W3}$ is independently hydrogen; halogen; or substituted or unsubstituted alkyl (e.g., methyl).

As described herein, m of any of the below formulae is independently 0, 1, or 2, and G$_1$ and G$_2$ are independently N or CH:

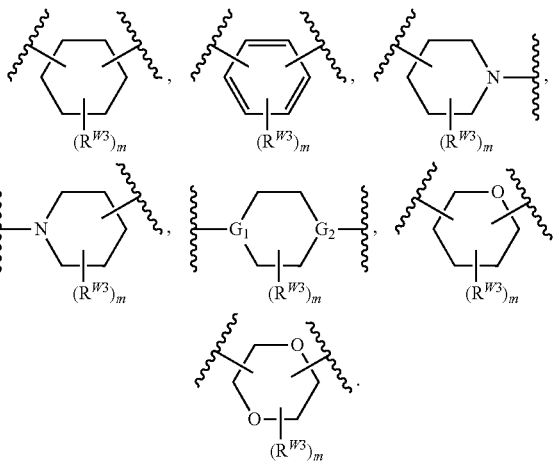

In certain embodiments, m is 0, and R$^{W3}$ is absent. In certain embodiments, m is 1. In certain embodiments, m is 2. In certain embodiments, G$_1$ is N. In certain embodiments, G$_1$ is CH. In certain embodiments, G$_2$ is N. In certain embodiments, G$_2$ is CH. In certain embodiments, G$_1$ is N and G$_2$ is CH. In certain embodiments, G$_1$ is CH and G$_2$ is CH. In certain embodiments, G$_1$ is N and G$_2$ is N. In certain embodiments, G$_1$ is CH and G$_2$ is N. In certain embodiments, each instance of R$^{W3}$ is independently hydrogen; halogen; or substituted or unsubstituted alkyl (e.g., methyl).

As described herein, each instance of Q of any of the below formulae is independently —NR$^{W1}$—; —NR$^{W1}$—NR$^{W1}$—; —O—NR$^{W1}$—; —NR$^{W1}$—O—; —S—; or —O—, and each instance of W of any of the below formulae is independently O, S, or NR$^{W1}$:

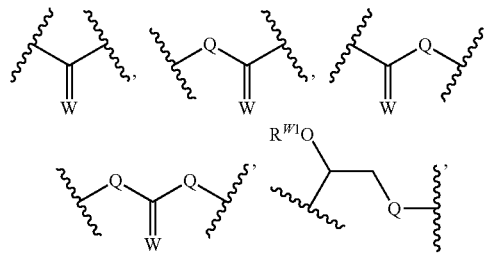

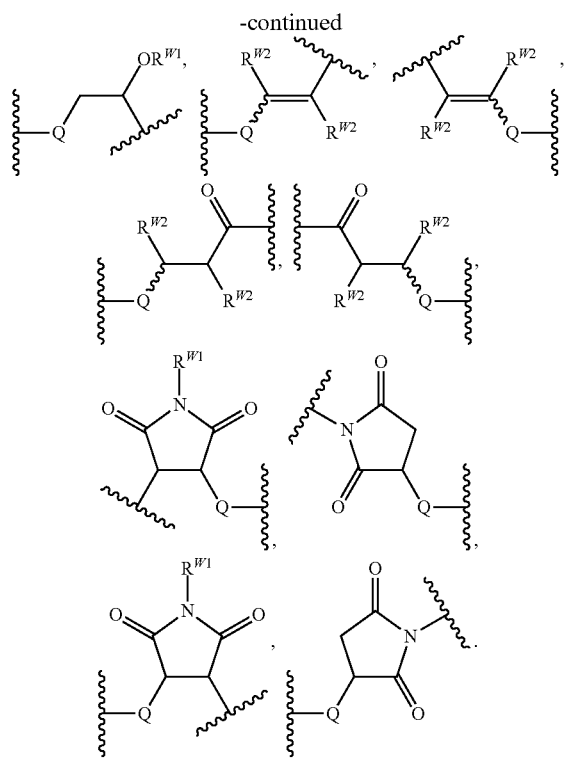

In certain embodiments, Q is —NR$^{W1}$—. In certain embodiments, Q is —NR$^{W1}$—NR$^{W1}$—. In certain embodiments, Q is —O—NR$^{W1}$—. In certain embodiments, Q is —NR$^{W1}$—O—. In certain embodiments, Q is —S—. In certain embodiments, Q is —O—. In certain embodiments, W is O. In certain embodiments, W is S. In certain embodiments, W is NR$^{W1}$. In certain embodiments, W is O and Q is independently —S—, —NR$^{W1}$—, or —O—. In certain embodiments, R$^{W1}$ is not hydrogen. In certain embodiments, R$^{W2}$ is hydrogen or substituted or unsubstituted alkyl (e.g., methyl).

As described herein, each instance of R$^{W1}$ is independently hydrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; a nitrogen protecting group if attached to a nitrogen atom, or an oxygen protecting group if attached to an oxygen atom. In any of the above formulae, as described herein, each instance of R$^{W1}$ is independently hydrogen; substituted or unsubstituted alkyl (e.g., methyl); a nitrogen protecting group if attached to a nitrogen atom, or an oxygen protecting group if attached to an oxygen atom.

As described herein, each instance of R$^{W2}$ is independently hydrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or two R$^{W2}$ groups are joined to form a 5-6 membered ring. In any of the above formulae, as described herein, each instance of R$^{W2}$ is independently hydrogen or substituted or unsubstituted alkyl (e.g., methyl).

As described herein, each instance of R$^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two R$^{W3}$ groups are joined to form a 3-6 membered ring. In any of the above formulae, as described herein, each instance of R$^{W3}$ is independently hydrogen; halogen; substituted or unsubstituted alkyl (e.g., methyl).

In certain embodiments, L$^1$ represents a linker consisting of a combination of one or more consecutively covalently bonded groups of the formula:

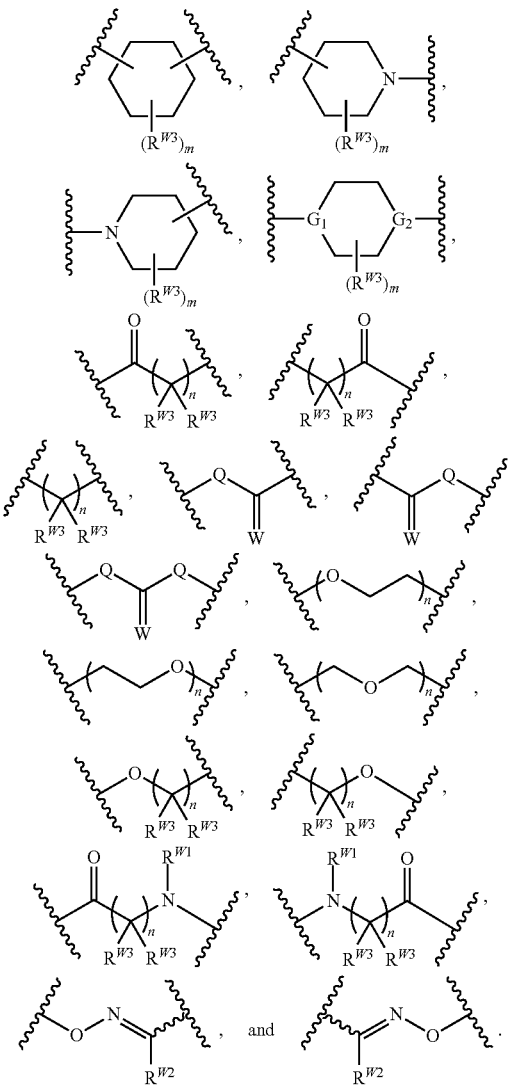

In certain embodiments, L$^1$ represents a linker consisting of a combination of 1 to 20 consecutive covalently bonded groups of the above described formulae, e.g., 2 to 20, 3 to 20, 4 to 20, 5 to 20, 6 to 20, 8 to 20, 9 to 20, 10 to 20, 2 to 10, 2 to 9, 2 to 8, 2 to 7, 2 to 6, or 2 to 5 groups, inclusive. In certain embodiments, L$^1$ represents a linker consisting of a combination of 1, 2, 3, 4, 5, 6, 7, 8, 9, 10, 11, 12, 13, 14, 15, 16, 17, 18, 19, or 20 consecutive covalently bonded groups of the above described formulae.

In certain embodiments, L$^1$ represents a linker 4 to 20 consecutive covalently bonded atoms in length, inclusive, e.g., 4 to 19, 4 to 18, 4 to 17, 4 to 16, 4 to 15, 4 to 14, 4 to 13, 4 to 12, 4 to 11, 4 to 10, 4 to 9, 4 to 8, 4 to 7, 4 to 6, or 5 to 11 consecutive covalently bonded atoms in length, inclusive. In certain embodiments, $L^1$ represents a linker 4, 5, 6, 7, 8, 9, 10, 11, 12, 13, 14, 15, 16, 17, 18, 19, or 20 consecutive covalently bonded atoms in length. In certain embodiments, $L^1$ represents a linker 5, 6, 7, 8, 9, 10, 11, 12, 13, 14, or 15 consecutive covalently bonded atoms in length.

It should be generally understood that multiple instances of a given variable or group present in a linker may optionally differ. Thus, in further defining the linker $L^1$, it is generally helpful to further distinguish multiple instances of a given variable with different numbers.

For example, in certain embodiments, $-L^1-R^H$ represents a group of the formula:

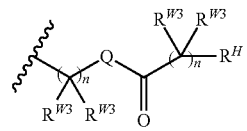

which may also be depicted as:

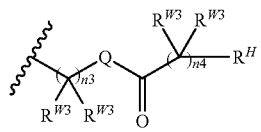

wherein n3 and n4 are as defined for variable n, and are each independently an integer between 1 to 10, inclusive, and wherein Q, $R^{W3}$ and $R^H$ are as defined herein. In certain embodiments, n3 is 2 or 3 and n4 is 1, 2, or 3.

In certain embodiments, $-L^1-R^H$ represents a group of the formula:

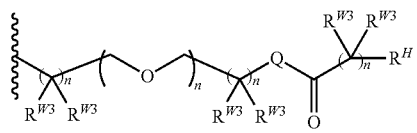

which may also be depicted as:

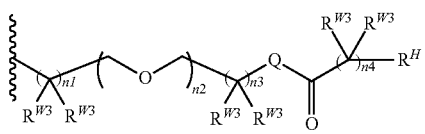

wherein n1, n2, n3, and n4 are as defined for variable n, and are each independently an integer between 1 to 10, inclusive, and wherein Q, $R^{W3}$ and $R^H$ are as defined herein. In certain embodiments, n1 is 1, n2 is 1 or 2, n3 is 1, and n4 is 1, 2, or 3.

In certain embodiments, $-L^1-R^H$ represents a group of the formula:

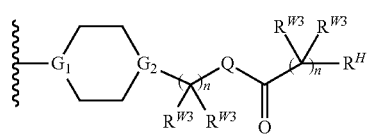

which may also be depicted as:

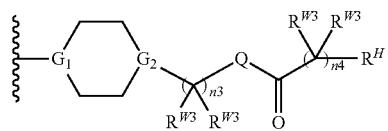

wherein n3 and n4 are as defined for variable n, and are each independently an integer between 1 to 10, inclusive, and wherein $G_1$, $G_2$, Q, $R^{W3}$, and $R^H$ are as defined herein. In certain embodiments, n3 is 2 or 3 and n4 is 1, 2, or 3.

In certain embodiments, $-L^1-R^H$ represents a group of the formula:

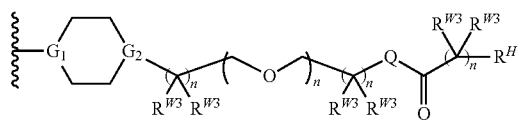

which may also be depicted as:

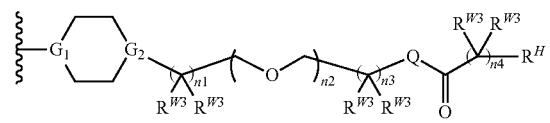

wherein n1, n2, n3, and n4 are as defined for variable n, and are each independently an integer between 1 to 10, inclusive, and wherein $G_1$, $G_2$, Q, $R^{W3}$ and $R^H$ are as defined herein. In certain embodiments, n1 is 1, n2 is 1 or 2, n3 is 1, and n4 is 1, 2, or 3.

In certain embodiments, $-L^1-R^H$ represents a group of the formula:

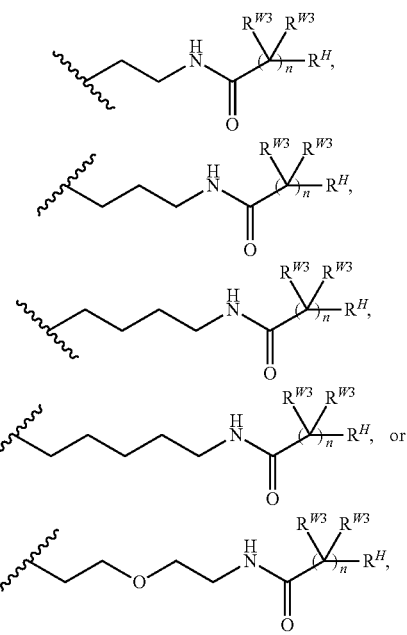

wherein n is an integer between 1 to 10, inclusive, and wherein $R^{W3}$ and $R^H$ are as defined herein. In certain embodiments, n is 1, 2, or 3.

In certain embodiments, -$L^1$-$R^H$ represents a group of the formula:

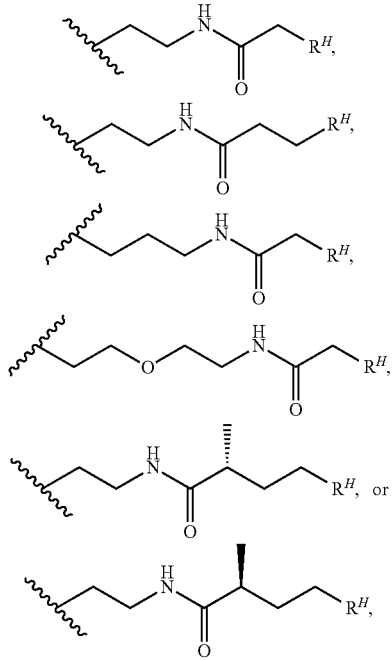

wherein $R^H$ is as defined herein.

In certain embodiments, -$L^1$-$R^H$ represents a group of the formula:

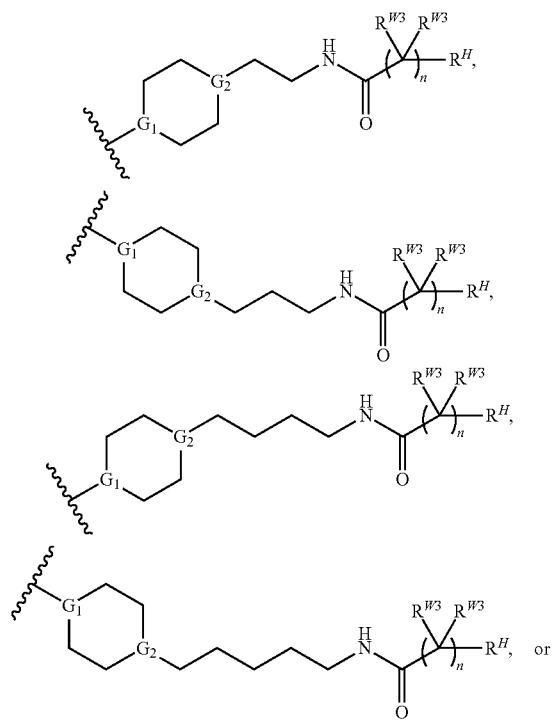

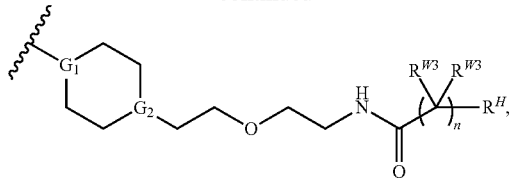

wherein n is an integer between 1 to 10, inclusive, and wherein $G_1$, $G_2$, Q, $R^{W3}$ and $R^H$ are as defined herein. In certain embodiments, n is 1, 2, or 3.

In certain embodiments, -$L^1$-$R^H$ represents a group of the formula:

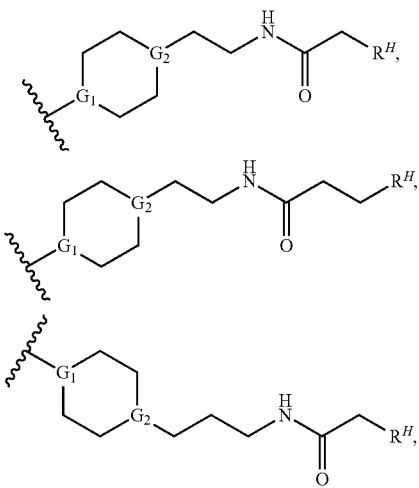

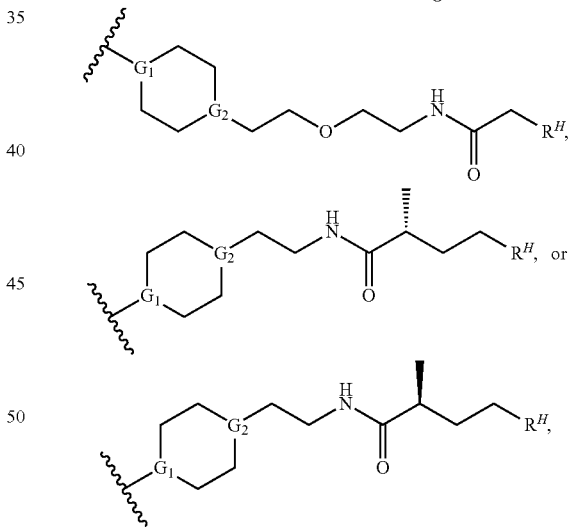

wherein $G_1$, $G_2$, and $R^H$ are as defined herein.

In certain embodiments, -$L^1$-$R^H$ represents a group of the formula:

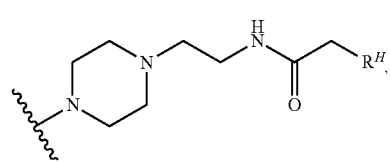

-continued

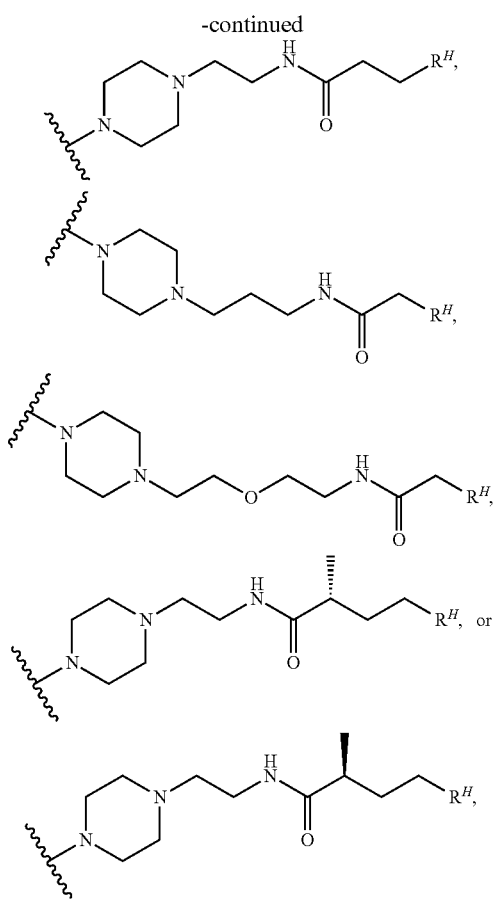

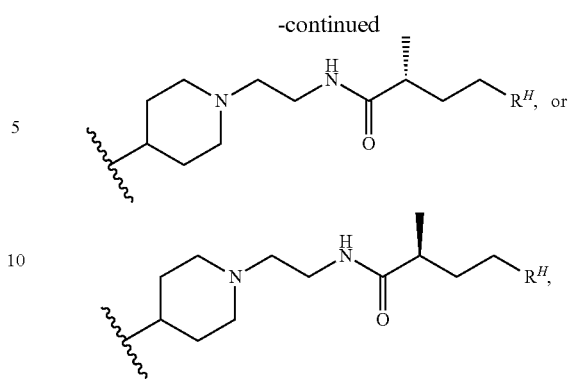

wherein $R^H$ is as defined herein.

Hydrophobic Group $R^H$

As described herein, $R^H$ represents a hydrophobic group selected from the group consisting of substituted and unsubstituted aryl, substituted and unsubstituted heteroaryl, substituted and unsubstituted carbocyclyl, substituted and unsubstituted heterocyclyl, substituted and unsubstituted aralkyl, substituted and unsubstituted heteroarylalkyl, substituted and unsubstituted carbocycylalkyl, and substituted and unsubstituted heterocyclylalkyl.

In certain embodiments, $R^H$ is a hydrophobic substituted or unsubstituted aryl or substituted or unsubstituted aralkyl moiety. In certain embodiments, $R^H$ is a hydrophobic substituted or unsubstituted aryl moiety, e.g., substituted or unsubstituted phenyl, substituted or unsubstituted biphenyl, substituted or unsubstituted naphthyl, or substituted or unsubstituted anthracenyl. In certain embodiments, $R^H$ is a hydrophobic substituted or unsubstituted aralkyl moiety, e.g., substituted or unsubstituted benzyl (—$CH_2$-phenyl), substituted or unsubstituted diphenylmethyl, substituted or unsubstituted trityl, substituted or unsubstituted biphenylmethyl, substituted or unsubstituted naphthylmethyl, or substituted or unsubstituted anthracenylmethyl.

In certain embodiments, $R^H$ is a hydrophobic substituted or unsubstituted aryl moiety, e.g., of the formula:

wherein $R^H$ is as defined herein.

In certain embodiments, $-L^1-R^H$ represents a group of the formula:

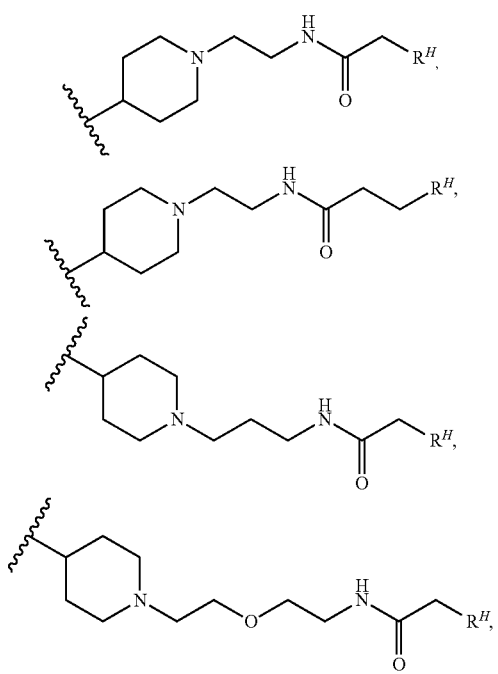

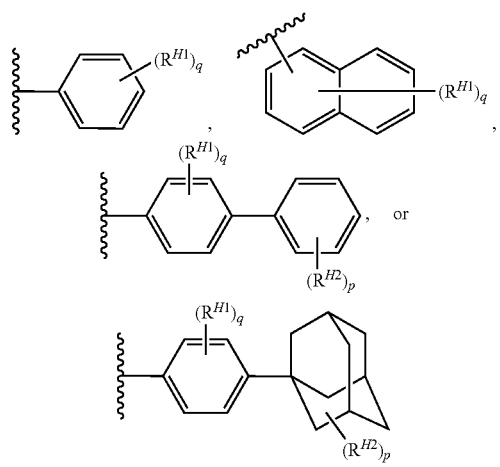

wherein each occurrence of $R^{H1}$ and $R^{H2}$ is independently halogen (e.g., fluoro, bromo, iodo, or chloro), alkyl (e.g., methyl, ethyl, propyl, isopropyl, tertbutyl), haloalkyl (e.g., difluoromethyl, perfluoromethyl), alkoxy (e.g., methoxy, ethoxy, isopropoxy), or dialkylamino (e.g., dimethylamino, diethylamino); and p and q are independently 0, 1, 2, or 3. In certain embodiments, each occurrence of $R^{H1}$ and $R^{H2}$ is independently fluoro, bromo, iodo, chloro, methyl, ethyl, propyl, isopropyl, tertbutyl, difluoromethyl, perfluoromethyl, methoxy, ethoxy, isopropoxy, dimethylamino, or diethylamino. In certain embodiments, p is 0 or 1. In certain embodiments, q is 0 or 1. In certain embodiments, p is 0. In certain embodiments, q is 0. In certain embodiments, p is 0, and q is 0.

In certain embodiments, $R^H$ is a hydrophobic substituted or unsubstituted aralkyl moiety, e.g., of the formula:

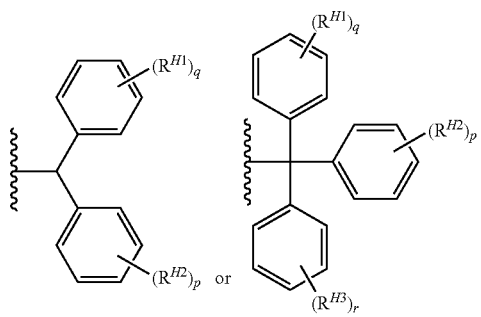

wherein each occurrence of $R^{H1}$, $R^{H2}$, and $R^{H3}$ is independently halogen (e.g., fluoro, bromo, iodo, or chloro), alkyl (e.g., methyl, ethyl, propyl, isopropyl, tertbutyl), haloalkyl (e.g., difluoromethyl, perfluoromethyl), alkoxy (e.g., methoxy, ethoxy, isopropoxy), or dialkylamino (e.g., dimethylamino, diethylamino); and p, q, and r are independently 0, 1, 2, or 3. In certain embodiments, each occurrence of $R^{H1}$, $R^{H2}$, and $R^{H3}$ is independently fluoro, bromo, iodo, chloro, methyl, ethyl, propyl, isopropyl, tertbutyl, difluoromethyl, perfluoromethyl, methoxy, ethoxy, isopropoxy, dimethylamino, or diethylamino. In certain embodiments, p is 0 or 1. In certain embodiments, q is 0 or 1. In certain embodiments, r is 0 or 1. In certain embodiments, p is 0. In certain embodiments, q is 0. In certain embodiments, r is 0. In certain embodiments, p is 0, q is 0, and r is 0.

In certain embodiments, $R^H$ is a hydrophobic substituted or unsubstituted heteroaryl or substituted or unsubstituted heteroarylalkyl moiety. In certain embodiments, $R^H$ is a hydrophobic substituted or unsubstituted heteroaryl moiety, e.g., substituted or unsubstituted 5-membered heteroaryl or substituted or unsubstituted 6-membered heteroaryl. In certain embodiments, $R^H$ is a hydrophobic substituted or unsubstituted heteroarylaralkyl moiety, e.g., substituted or unsubstituted 5-membered heteroarylmethyl or substituted or unsubstituted 6-membered heteroarylmethyl.

In certain embodiments, $R^H$ is a hydrophobic substituted or unsubstituted carbocyclyl or substituted or unsubstituted carbocyclylalkyl moiety. In certain embodiments, $R^H$ is a hydrophobic substituted or unsubstituted carbocyclyl moiety, e.g., a $C_{5-14}$carbocyclyl moiety which may be monocyclic, bicyclic, or tricyclic and/or fused, bridged, or spiro-fused, e.g., substituted or unsubstituted $C_{5-13}$carbocyclyl, substituted or unsubstituted $C_{5-12}$carbocyclyl, substituted or unsubstituted $C_{5-13}$carbocyclyl, substituted or unsubstituted $C_{5-10}$carbocyclyl, substituted or unsubstituted $C_{5-9}$carbocyclyl, substituted or unsubstituted $C_{5-8}$carbocyclyl, substituted or unsubstituted $C_{5-7}$carbocyclyl, substituted or unsubstituted $C_{3-6}$carbocyclyl, substituted or unsubstituted $C_{3-4}$carbocyclyl, substituted or unsubstituted $C_{4-5}$ carbocyclyl, or substituted or unsubstituted $C_{5-6}$ carbocyclyl. In certain embodiments, $R^H$ is a hydrophobic substituted or unsubstituted fused bicyclic carbocyclyl, e.g., substituted or unsubstituted cis- or trans-decalin. In certain embodiments, $R^H$ is a hydrophobic substituted or unsubstituted fused tricyclic carbocyclyl, e.g., substituted or unsubstituted fluorenyl. In certain embodiments, $R^H$ is a hydrophobic substituted or unsubstituted spiro-fused bicyclic carbocyclyl, e.g., substituted or unsubstituted spiropentane. In certain embodiments, $R^H$ is a hydrophobic substituted or unsubstituted bridged bicyclic carbocyclyl, e.g., substituted or unsubstituted norbornane, norbornene, bicyclo[2.2.2]octane, bicyclo[2.2.2]oct-2-ene, bicyclo[3.2.1]octane, or bicyclo[2.2.1]heptan-2-one. In certain embodiments, $R^H$ is a hydrophobic substituted or unsubstituted bridged tricyclic carbocyclyl moiety, e.g., substituted or unsubstituted adamantane. In certain embodiments, $R^H$ is a hydrophobic substituted or unsubstituted carbocycylalkyl moiety, e.g., hydrophobic substituted or unsubstituted carbocycylmethyl.

In certain embodiments, $R^H$ is a hydrophobic substituted or unsubstituted carbocyclyl moiety, e.g., of the formula:

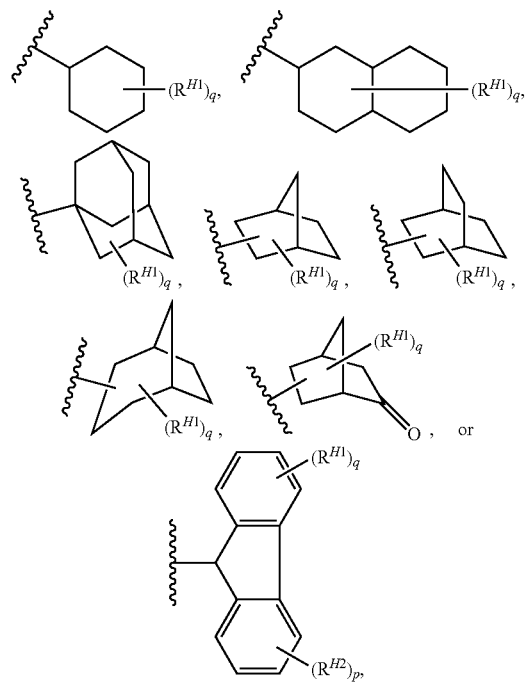

wherein each occurrence of $R^{H1}$ and $R^{H2}$ is independently halogen (e.g., fluoro, bromo, iodo, or chloro), alkyl (e.g., methyl, ethyl, propyl, isopropyl, tertbutyl), haloalkyl (e.g., difluoromethyl, perfluoromethyl), alkoxy (e.g., methoxy, ethoxy, isopropoxy), or dialkylamino (e.g., dimethylamino, diethylamino); and p and q are independently 0, 1, 2, or 3. In certain embodiments, each occurrence of $R^{H1}$ and $R^{H2}$ is independently fluoro, bromo, iodo, chloro, methyl, ethyl, propyl, isopropyl, tertbutyl, difluoromethyl, perfluoromethyl, methoxy, ethoxy, isopropoxy, dimethylamino, or diethylamino. In certain embodiments, p is 0 or 1. In certain embodiments, q is 0 or 1. In certain embodiments, p is 0. In certain embodiments, q is 0. In certain embodiments, p is 0, and q is 0.

In certain embodiments, $R^H$ is a hydrophobic substituted or unsubstituted carbocyclylalkyl moiety, e.g., of the formula:

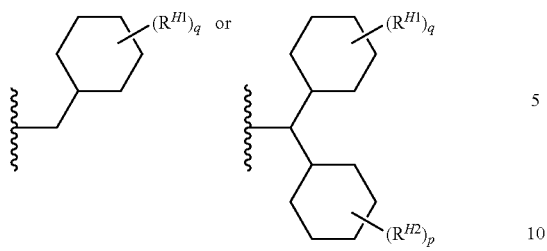

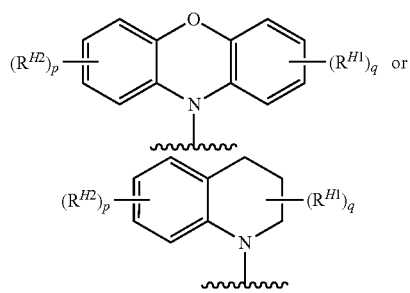

wherein each occurrence of $R^{H1}$ and $R^{H2}$ is independently halogen (e.g., fluoro, bromo, iodo, or chloro), alkyl (e.g., methyl, ethyl, propyl, isopropyl, tertbutyl), haloalkyl (e.g., difluoromethyl, perfluoromethyl), alkoxy (e.g., methoxy, ethoxy, isopropoxy), or dialkylamino (e.g., dimethylamino, diethylamino); and p and q are independently 0, 1, 2, or 3. In certain embodiments, each occurrence of $R^{H1}$ and $R^{H2}$ is independently fluoro, bromo, iodo, chloro, methyl, ethyl, propyl, isopropyl, tertbutyl, difluoromethyl, perfluoromethyl, methoxy, ethoxy, isopropoxy, dimethylamino, or diethylamino. In certain embodiments, p is 0 or 1. In certain embodiments, q is 0 or 1. In certain embodiments, p is 0. In certain embodiments, q is 0. In certain embodiments, p is 0, and q is 0.

In certain embodiments, $R^H$ is a hydrophobic substituted or unsubstituted heterocyclyl or substituted or unsubstituted heterocyclylalkyl moiety. In certain embodiments, $R^H$ is a hydrophobic substituted or unsubstituted heterocyclyl moiety, e.g., a 5-14-membered heterocyclyl which may be monocyclic, bicyclic, or tricyclic and/or a fused, bridged, or spiro-fused moiety, e.g., substituted or unsubstituted 5-13-membered heterocyclyl, substituted or unsubstituted 5-12-membered heterocyclyl, substituted or unsubstituted 5-11-membered heterocyclyl, substituted or unsubstituted 5-10-membered heterocyclyl, substituted or unsubstituted 5-9-membered heterocyclyl, substituted or unsubstituted 5-8-membered heterocyclyl, substituted or unsubstituted 5-7-membered heterocyclyl, substituted or unsubstituted 3-6-membered heterocyclyl, substituted or unsubstituted 3-4-membered heterocyclyl, substituted or unsubstituted 4-5-membered heterocyclyl, or substituted or unsubstituted 5-6-membered heterocyclyl. In certain embodiments, $R^H$ is a hydrophobic substituted or unsubstituted fused bicyclic heterocyclyl moiety. In certain embodiments, $R^H$ is a hydrophobic substituted or unsubstituted fused tricyclic heterocyclyl moiety. In certain embodiments, $R^H$ is a hydrophobic substituted or unsubstituted spiro-fused bicyclic heterocyclyl moiety. In certain embodiments, $R^H$ is a hydrophobic substituted or unsubstituted bridged bicyclic heterocyclyl moiety. In certain embodiments, $R^H$ is a hydrophobic substituted or unsubstituted bridged tricyclic heterocyclyl moiety. In certain embodiments, $R^H$ is a hydrophobic substituted or unsubstituted heterocyclyl alkyl moiety, e.g., hydrophobic substituted or unsubstituted heterocyclylmethyl. Exemplary heterocylyl groups include, but are not limited to, piperidinyl, tetrahydropyranyl, dihydropyridinyl, and thianyl, piperazinyl, morpholinyl, dithianyl, dioxanyl, and triazinanyl moieties, which may comprise one or more heterocycyl, carbocycyl, aryl or heteroaryl rings fused thereto.

In certain embodiments, $R^H$ is a hydrophobic substituted or unsubstituted heterocyclyl moiety, e.g., of the formula:

wherein each occurrence of $R^{H1}$ and $R^{H2}$ is independently halogen (e.g., fluoro, bromo, iodo, or chloro), alkyl (e.g., methyl, ethyl, propyl, isopropyl, tertbutyl), haloalkyl (e.g., difluoromethyl, perfluoromethyl), alkoxy (e.g., methoxy, ethoxy, isopropoxy), or dialkylamino (e.g., dimethylamino, diethylamino); and p and q are independently 0, 1, 2, or 3. In certain embodiments, each occurrence of $R^{H1}$ and $R^{H2}$ is independently fluoro, bromo, iodo, chloro, methyl, ethyl, propyl, isopropyl, tertbutyl, difluoromethyl, perfluoromethyl, methoxy, ethoxy, isopropoxy, dimethylamino, or diethylamino. In certain embodiments, p is 0 or 1. In certain embodiments, q is 0 or 1. In certain embodiments, p is 0. In certain embodiments, q is 0. In certain embodiments, p is 0, and q is 0.

In certain embodiments, $R^H$ is a hydrophobic group of the formula:

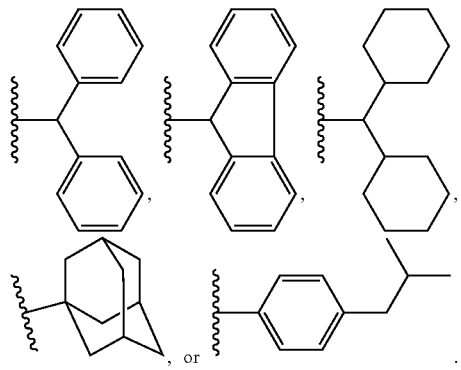

In certain embodiments, $R^H$ is a hydrophobic group of the formula:

Optional Warhead -$L^2$-$R^D$

As generally understood herein, M of Formula (I) represents a small organic molecule which covalently or non-covalently binds a kinase, e.g., a protein kinase.

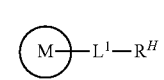

(I)

In certain embodiments, the small organic molecule M includes and is substituted with a group -$L^2$-$R^D$, wherein $L^2$ is a bond or a linker, and $R^D$ is a group that covalently or non-covalently binds to the kinase.

In certain embodiments, $L^2$ is a bond or a linker selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof.

In certain embodiments, $L^2$ is a bond.

In certain embodiments, $L^2$ is a linker comprising at least one instance of substituted or unsubstituted alkylene, e.g., substituted or unsubstituted $C_{1-6}$alkylene, substituted or unsubstituted $C_{2-6}$alkylene, substituted or unsubstituted $C_{3-6}$alkylene, substituted or unsubstituted $C_{4-6}$alkylene, substituted or unsubstituted $C_{5-6}$alkylene, substituted or unsubstituted $C_{2-5}$alkylene, substituted or unsubstituted $C_{2-4}$alkylene, substituted or unsubstituted $C_{2-3}$alkylene, substituted or unsubstituted $C_1$alkylene, substituted or unsubstituted $C_2$alkylene, substituted or unsubstituted $C_3$alkylene, substituted or unsubstituted $C_4$alkylene, substituted or unsubstituted $C_5$alkylene, or substituted or unsubstituted $C_6$alkylene. In certain embodiments, $L^2$ is substituted or unsubstituted alkylene.

In certain embodiments, $L^2$ is linker comprising at least one instance of substituted or unsubstituted alkenylene, e.g., substituted or unsubstituted $C_{2-6}$ alkenylene, substituted or unsubstituted $C_{3-6}$ alkenylene, substituted or unsubstituted $C_{4-6}$alkenylene, substituted or unsubstituted $C_{5-6}$alkenylene, substituted or unsubstituted $C_{2-5}$ alkenylene, substituted or unsubstituted $C_{2-4}$alkenylene, substituted or unsubstituted $C_{2-3}$ alkenylene, substituted or unsubstituted $C_2$alkenylene, substituted or unsubstituted $C_3$alkenylene, substituted or unsubstituted $C_4$alkenylene, substituted or unsubstituted $C_5$alkenylene, or substituted or unsubstituted $C_6$alkenylene. In certain embodiments, $L^2$ is substituted or unsubstituted alkenylene.

In certain embodiments, $L^2$ is linker comprising at least one instance of substituted or unsubstituted alkynylene, e.g., substituted or unsubstituted $C_{2-6}$alkynylene, substituted or unsubstituted $C_{3-6}$alkynylene, substituted or unsubstituted $C_{4-6}$alkynylene, substituted or unsubstituted $C_{5-6}$alkynylene, substituted or unsubstituted $C_{2-5}$alkynylene, substituted or unsubstituted $C_{2-4}$alkynylene, substituted or unsubstituted $C_{2-3}$alkynylene, substituted or unsubstituted $C_2$alkynylene, substituted or unsubstituted $C_3$alkynylene, substituted or unsubstituted $C_4$alkynylene, substituted or unsubstituted $C_5$alkynylene, or substituted or unsubstituted $C_6$alkynylene. In certain embodiments, $L^2$ is substituted or unsubstituted alkynylene.

In certain embodiments, $L^2$ is a linker comprising at least one instance of substituted or unsubstituted heteroalkylene, e.g., substituted or unsubstituted hetero$C_{1-6}$alkylene, substituted or unsubstituted hetero$C_{2-4}$alkylene, substituted or unsubstituted hetero$C_{3-6}$alkylene, substituted or unsubstituted hetero$C_{4-6}$alkylene, substituted or unsubstituted hetero$C_{5-6}$alkylene, substituted or unsubstituted hetero$C_{2-5}$alkylene, substituted or unsubstituted hetero$C_{2-4}$alkylene, substituted or unsubstituted hetero$C_{2-3}$alkylene, substituted or unsubstituted hetero$C_1$alkylene, substituted or unsubstituted hetero$C_2$alkylene, substituted or unsubstituted hetero$C_3$alkylene, substituted or unsubstituted hetero$C_4$alkylene, substituted or unsubstituted hetero$C_5$alkylene, or substituted or unsubstituted hetero$C_6$alkylene. In certain embodiments, $L^2$ is substituted or unsubstituted heteroalkylene.

In certain embodiments, $L^2$ is a linker comprising at least one instance of substituted or unsubstituted heteroalkenylene, e.g., substituted or unsubstituted hetero$C_{2-6}$alkenylene, substituted or unsubstituted hetero$C_{3-6}$alkenylene, substituted or unsubstituted hetero$C_{4-6}$alkenylene, substituted or unsubstituted hetero$C_{5-6}$alkenylene, substituted or unsubstituted hetero$C_{2-5}$alkenylene, substituted or unsubstituted hetero$C_{2-4}$alkenylene, substituted or unsubstituted hetero$C_{2-3}$alkenylene, substituted or unsubstituted hetero$C_2$alkenylene, substituted or unsubstituted hetero$C_3$alkenylene, substituted or unsubstituted hetero$C_4$alkenylene, substituted or unsubstituted hetero$C_5$alkenylene, or substituted or unsubstituted hetero$C_6$alkenylene. In certain embodiments, $L^2$ is substituted or unsubstituted heteroalkenylene.

In certain embodiments, $L^2$ is a linker comprising at least one instance of substituted or unsubstituted heteroalkynylene, e.g., substituted or unsubstituted hetero$C_{2-6}$alkynylene, substituted or unsubstituted hetero$C_{3-6}$alkynylene, substituted or unsubstituted hetero$C_{4-6}$alkynylene, substituted or unsubstituted hetero$C_{5-6}$alkynylene, substituted or unsubstituted hetero$C_{2-5}$alkynylene, substituted or unsubstituted hetero$C_{2-4}$alkynylene, substituted or unsubstituted hetero$C_{2-3}$alkynylene, substituted or unsubstituted hetero$C_2$alkynylene, substituted or unsubstituted hetero$C_3$alkynylene, substituted or unsubstituted hetero$C_4$alkynylene, substituted or unsubstituted hetero$C_5$alkynylene, or substituted or unsubstituted hetero$C_6$alkynylene. In certain embodiments, $L^2$ is substituted or unsubstituted heteroalkynylene.

In certain embodiments, $L^2$ is a linker comprising at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, $L^2$ is substituted or unsubstituted heterocyclylene.

In certain embodiments, $L^2$ is a linker comprising at least one instance of substituted or unsubstituted carbocyclylene, e.g., substituted or unsubstituted $C_{3-6}$ carbocyclylene, substituted or unsubstituted $C_{3-5}$ carbocyclylene, substituted or unsubstituted $C_{3-4}$ carbocyclylene, substituted or unsubstituted $C_3$ carbocyclylene, substituted or unsubstituted $C_4$ carbocyclylene, substituted or unsubstituted $C_5$ carbocyclylene, or substituted or unsubstituted $C_6$ carbocyclylene. In certain embodiments, $L^2$ is substituted or unsubstituted carbocyclylene.

In certain embodiments, $L^2$ is a linker comprising at least one instance of substituted or unsubstituted arylene, e.g., substituted or unsubstituted $C_6$ arylene (phenylene) or substituted or unsubstituted $C_{10}$ arylene (naphthylene). In certain embodiments, $L^2$ is substituted or unsubstituted arylene.

In certain embodiments, $L^2$ is a linker comprising at least one instance of substituted or unsubstituted heteroarylene, e.g., substituted or unsubstituted 5-membered heteroarylene or substituted or unsubstituted 6-membered heteroarylene. In certain embodiments, $L^2$ is substituted or unsubstituted heteroarylene.

In certain embodiments, $R^D$ is an electrophilic group that covalently binds a kinase, e.g., a protein kinase, by reaction with a nucleophilic moiety, e.g., such as a cysteine in the ATP binding pocket of the kinase. In this instance, in certain embodiments, $R^D$ is a group of formula:
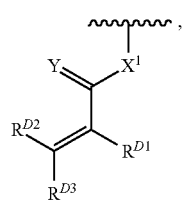
(i-1)
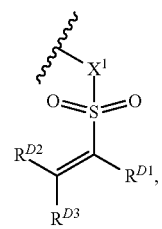
(i-2)
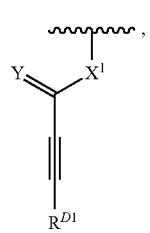
(i-3)
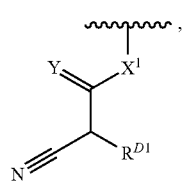
(i-4)
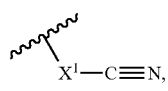
(i-5)
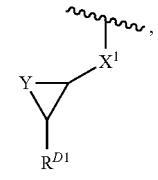
(i-6)
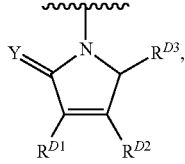
(i-7)
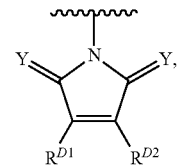
(i-8)
-continued
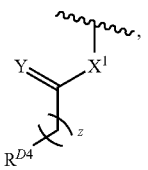
(i-9)
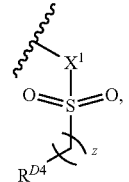
(i-10)
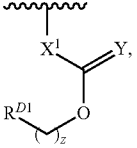
(i-11)
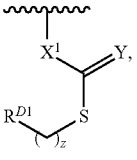
(i-12)
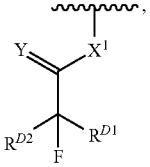
(i-13)
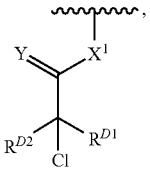
(i-14)
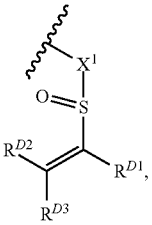
(i-15)
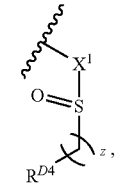
(i-16)

-continued

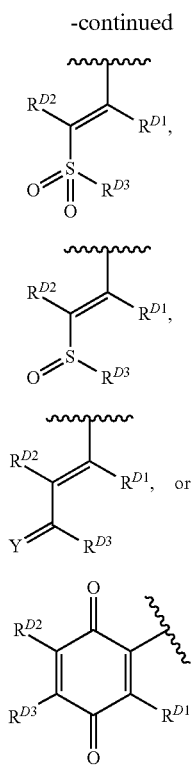

(i-17)

(i-18)

(i-19)

(i-20)

wherein:
$R^{D1}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of R$^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D1a}$ groups are joined to form an substituted or unsubstituted heterocyclic ring;

$R^{D2}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, and —C(=NR$^{D2a}$)N(R$^{D2a}$)$_2$, wherein each occurrence of R$^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, and substituted or unsubstituted heteroaryl, or two R$^{D2a}$ groups are joined to form an substituted or unsubstituted heterocyclic ring;

$R^{D3}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$ wherein each occurrence of R$^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D3a}$ groups are joined to form an substituted or unsubstituted heterocyclic ring;

optionally R$^{D1}$ and R$^{D3}$, or R$^{D2}$ and R$^{D3}$, or R$^{D1}$ and R$^{D2}$ are joined to form an substituted or unsubstituted carbocyclic or substituted or unsubstituted heterocyclic ring;

$R^{D4}$ is a leaving group selected from the group consisting of —Br, —Cl, —I, and —OS(=O)$_w$R$^{D4a}$, wherein w is 1 or 2, and R$^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

$X^1$ is a bond or NR$^{D5}$, wherein R$^{D5}$ is hydrogen, C$_{1-6}$ alkyl, or a nitrogen protecting group;

each instance of Y is independently O, S, or NR$^{D6}$, wherein R$^{D6}$ is hydrogen, C$_{1-6}$ alkyl, or a nitrogen protecting group; and z is 0, 1, 2, 3, 4, 5, or 6.

In certain embodiments, R$^D$ is a group of Formula (i-1), (i-3), or (i-20):

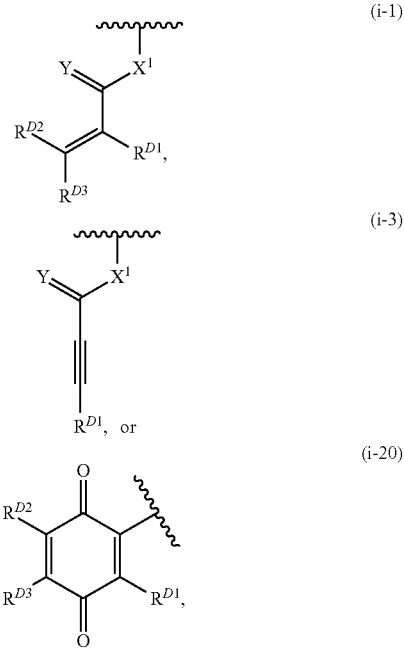

(i-1)

(i-3)

(i-20)

wherein each instance of $X^1$ is bond or $NR^{D5}$, Y is independently O, S, or $NR^{D6}$, and $R^{D1}$, $R^{D2}$, and $R^{D3}$ are as defined herein. In certain embodiments, $X^1$ is a bond. In certain embodiments, $X^1$ is $NR^{D5}$. In certain embodiments, Y is O. In certain embodiments, $R^{D1}$ is hydrogen. In certain embodiments, $R^{D1}$ is —CN. In certain embodiments, $R^{D2}$ is hydrogen. In certain embodiments, $R^{D3}$ is hydrogen. In certain embodiments, $R^{D2}$ is —$CH_2N(R^{D2a})_2$, and $R^{D3}$ is hydrogen. In certain embodiments, $R^{D2}$ is —$CH_2N(R^{D3a})_2$, and $R^{D3}$ is hydrogen. In certain embodiments, $R^{D2}$ and $R^{D3}$ are hydrogen. In certain embodiments, $R^{D1}$, $R^{D2}$ and $R^{D3}$ are hydrogen.

In certain embodiments, $R^D$ is a group of Formula (i-19), (i-17), or (i-18):

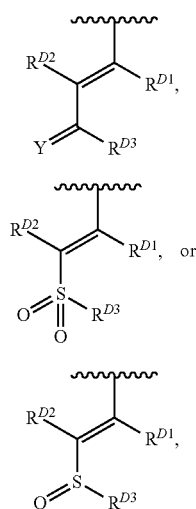

wherein Y is independently O, S, or $NR^{D6}$; and $R^{D1}$, $R^{D2}$, and $R^{D3}$ are as defined herein. In certain embodiments, Y is O. In certain embodiments, $R^{D1}$ is hydrogen. In certain embodiments, $R^{D2}$ is hydrogen. In certain embodiments, $R^{D2}$ is —CN. In certain embodiments, $R^{D3}$ is substituted or unsubstituted alkyl.

In certain embodiments, $R^D$ is a group of Formula (i-7) or (i-8):

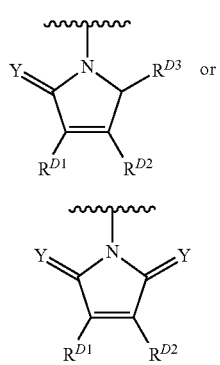

wherein Y is independently O, S, or $NR^{D6}$; and $R^{D1}$, $R^{D2}$, and $R^{D3}$ are as defined herein. In certain embodiments, Y is O. In certain embodiments, $R^D$ is hydrogen. In certain embodiments, $R^{D2}$ is hydrogen. In certain embodiments, $R^{D3}$ is hydrogen.

In certain embodiments, $R^D$ is a group of Formula (i-13) or (i-14):

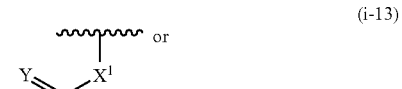

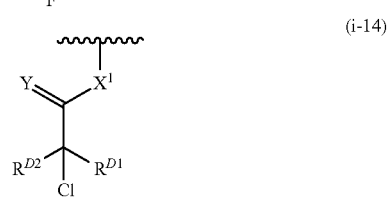

wherein each instance of $X^1$ is bond or $NR^{D5}$; Y is independently O, S, or $NR^{D6}$; and $R^{D1}$ and $R^{D2}$ are as defined herein. In certain embodiments, $X^1$ is a bond. In certain embodiments, $X^1$ is $NR^{D5}$. In certain embodiments, Y is O. In certain embodiments, $R^{D1}$ is hydrogen. In certain embodiments, $R^{D1}$ is halogen, e.g., —F or —Cl. In certain embodiments, $R^{D2}$ is hydrogen. In certain embodiments, $R^{D2}$ is halogen, e.g., —F or —Cl.

In certain embodiments, $R^D$ is a group of Formula (i-11) or (i-12):

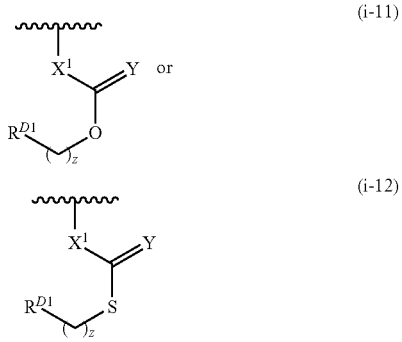

wherein each instance of $X^1$ is bond or $NR^{D5}$; Y is independently O, S, or $NR^{D6}$; z is 0, 1, 2, 3, 4, 5, or 6; and $R^{D1}$ is as defined herein. In certain embodiments, $X^1$ is a bond. In certain embodiments, $X^1$ is $NR^{D5}$. In certain embodiments, Y is O. In certain embodiments z is 0 or 1. In certain embodiments, $R^{D1}$ is substituted or unsubstituted alkyl.

In certain embodiments, $R^D$ is a group of Formula (i-10), (i-16), or (i-9):

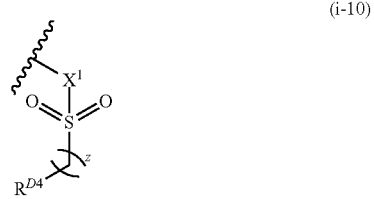

-continued

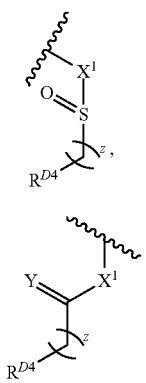

wherein each instance of $X^1$ is bond or $NR^{D5}$; Y is independently O, S, or $NR^{D6}$; z is 0, 1, 2, 3, 4, 5, or 6; and $R^D$ is a leaving group selected from the group consisting of —Br, —Cl, —I, and —OS(=O)$_w$R$^{D4a}$, wherein w is 1 or 2. In certain embodiments, $X^1$ is a bond. In certain embodiments, $X^1$ is $NR^{D5}$. In certain embodiments, Y is O. In certain embodiments, z is 0. In certain embodiments, z is 1.

In certain embodiments, $R^D$ is a group of Formula (i-4) or (i-5):

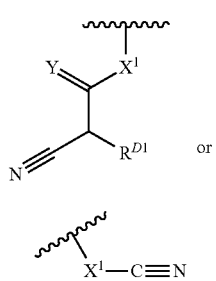

wherein each instance of $X^1$ is bond or $NR^{D5}$; and $R^{D1}$ is as defined herein. In certain embodiments, $X^1$ is a bond. In certain embodiments, $X^1$ is $NR^{D5}$. In certain embodiments, $R^{D1}$ is hydrogen.

In certain embodiments, $R^D$ is a group of Formula (i-6):

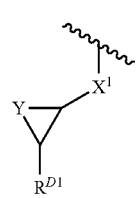

wherein each instance of $X^1$ is bond or $NR^{D5}$; Y is independently O, S, or $NR^{D6}$; and $R^{D1}$ is as defined herein. In certain embodiments, $X^1$ is a bond. In certain embodiments, $X^1$ is $NR^{D5}$. In certain embodiments, Y is O. In certain embodiments, $R^{D1}$ is hydrogen.

Her3 Protein Kinase

In certain embodiments, the small organic molecule, even in the absence of the hydrophobic moiety -L$^1$-R$^H$, covalently or non-covalently binds Her3 protein kinase.

Her3 (ErbB3) is a transmembrane receptor tyrosine protein kinase which is overexpressed and deregulated in many cancers such as breast, ovarian, and non-small cell lung cancers, and specifically Her2 driven breast cancer, 22% of gefitinib-resistant non-small cell lung cancer, and as much as 53% of ovarian cancer. See, e.g., Baselga et al., *Nat. Rev. Cancer* (2009) 9:463; Lee-Hoeflich et al., *Cancer Res.* (2008) 68:5878; Hammerman et al., *Clin. Cancer Res.* (2009) 15:7502; Tanner et al., *J. Clin. Oncol.* (2006) 24:4317. It is a member of the HER family which also includes: EGFR (ErbB1/Her1), Her2 (ErbB2), and Her4 (ErbB4). Among them, HER3 is unique because it has extremely low protein kinase activity and is considered to be a so-called "pseudo-kinase." See, e.g., Shi et al., *Proc. Natl. Acad. Sci. USA* (2010) 107:7692. Despite the lack of protein kinase activity, Her3 is often an essential heterodimerization partner with EGFR and Her2, resulting in recruitment and activation of PI3K to the plasma membrane. Her3 has been extensively validated as a promising oncology kinase target using genetic approaches and currently several antibodies directed against the extracellular ligand-binding domain of Her3 are under clinical evaluation. See, e.g., Sergina et al., *Nature* (2007) 445:437. Due to the weak kinase activity of Her3, there are currently no small molecules reported that can inhibit Her3 function, and the kinase is considered to be an "undruggable target." For example, many small molecules which covalently or non-covalently bind to the ATP site of Her3, due to the low kinase activity of Her3, neither inhibit Her3-dependent proliferation nor inhibit Her3 signaling. To overcome this problem, the inventors envisioned linking such small molecules to a hydrophobic tag such that the bi-functional molecule may, upon selectively binding Her3, then selectively induce Her3 protein degradation, e.g., by unfolding and subsequent degradation by the proteasome.

To discover chemical starting points for developing Her3 inhibitors, the inventors screened a library of 1,500 kinase-directed compounds using the LanthaScreen™ Eu methodology for compounds that could bind to the ATP-site of Her3. The most potent Her3 binder from this screen was KIN001-111, which evolved to TX-1-85-1 using structure-based drug design and iterative rounds of synthesis and evaluation. See, e.g., Stachlewitz et al., *J Pharmacol Exp Ther.* (2005) 315:36-41. TX1-85-1 possesses an acrylamide which forms a covalent bond with Cys721 in the Her3 ATP binding site (as shown by mass spectrometry). TX1-85-1 is a potent binder of Her3, and it can covalently label Her3 in cells.

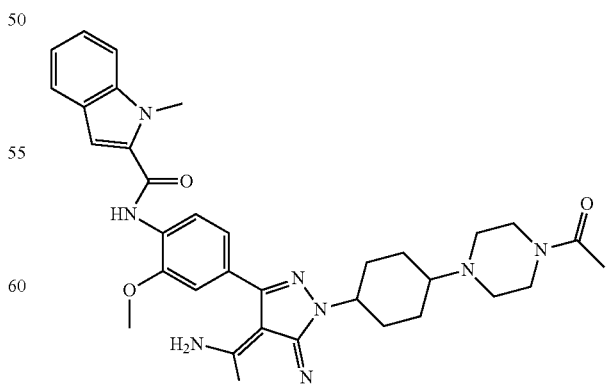

Kin001-111

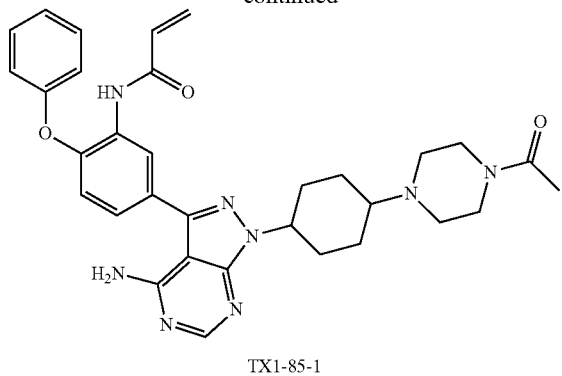

TX1-85-1

To evaluate the ability of covalent Her3 inhibitors to inhibit Her3-dependent growth, two established cells lines, PC9 GR4 and Ocvar8, were utilized that have been shown to be Her3-dependent using siRNA mediated depletion of Her3. At 5 µM of TX1-85-1, a concentration sufficient to fully label Her3 in cells, there was no observed growth inhibition of PC9 GR4 or Ovcar8 cells and no observed inhibition of the phosphorylation of downstream effectors of Her3, such as Erk and Akt. To overcome this problem, the inventors appended an adamantane hydrophobic tag via a linker to TX1-85-1 to yield TX2-62-1, which maintained potent and covalent Her3 binding ability. However, TX2-62-1 still did not inhibit Her3-dependent growth. Without wishing to be bound by any particular theory, the inventors hypothesize that this lack of inhibition is the result of poor cell penetration of TX2-62-1 due to its high molecular weight (MW=828.5). The inventors tested this hypothesis by designing a strategy whereby the two halves of TX2-62-1 (TX2-49-1 and TX2-57-1) were brought together inside of a cell via oxime formation. See Scheme 1 below. The inventors discovered that formation of TX2-62-1 via intracellular oxime formation resulted in efficient degradation of Her3, inhibition of Her3-dependent signaling, and loss of viability of Her3-addicted cells. As expected, when TX2-62-1 was washed out, Her3 protein was resynthesized and cell proliferation resumed.

Scheme 1.

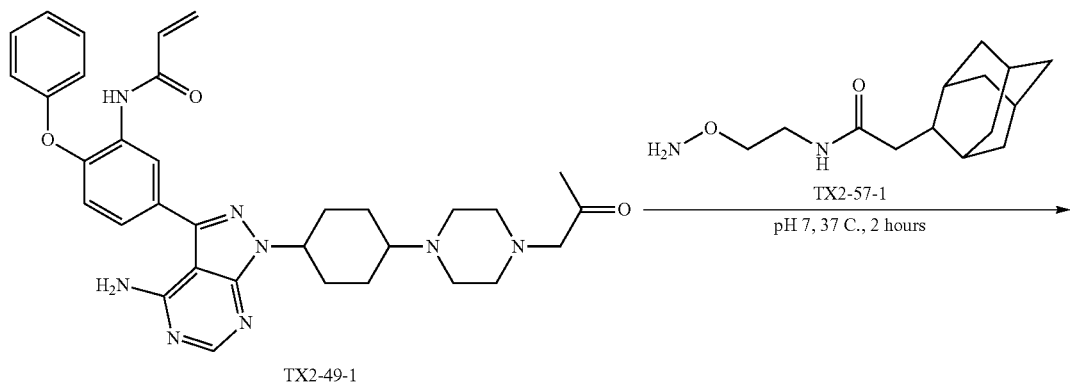

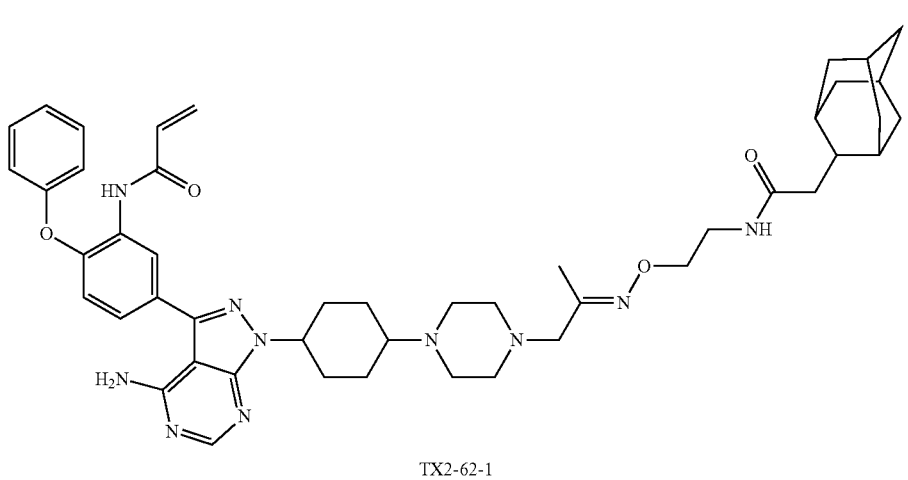

TX2-62-1

Based in part on the work with TX1-85-1 and TX2-62-1, the inventors envisioned certain desirable, but non-limiting, characteristics in a hydrophobically tagged compound of Formula (I), and specifically in a compound of Formula (II):

(1) In certain embodiments, the linker $L^1$, joining the small molecule (M) to the hydrophobic tag $R^H$, is long enough in order for the hydrophobic tag $R^H$ to be exposed for ligase recognition but short enough that the compound of Formula (I) or (II) will have a low enough molecular weight to be cell permeable, e.g., for example, in certain embodiments, the linker $L^1$ is 4 to 20 consecutive covalently bonded atoms in length, inclusive. In certain embodiments, the linker $L^1$ is 4, 5, 6, 7, 8, 9, 10, 11, 12, 13, 14, or 15 consecutive covalently bonded atoms in length.

(2) In certain embodiments, the compound of Formula (I) or (II) has a low enough molecular weight, e.g., between about 400 and about 800 g/mol, between about 500 and about 800 g/mol, between about 600 and about 800 g/mol, or between about 700 and about 800 g/mol, in order to ensure sufficient cell penetration.

(3) In certain embodiments, the compound of Formula (I) or (II) has a high enough polarity, e.g., as measured by a c log P of less than 5, in order to ensure cell penetration, e.g., between about −8 and about 4.9, between about −8 and about 4, between about −8 and about 3, between about −8 and about 2, between about −8 and about 1, or between about −8 and about 0, inclusive. The c log P value of a molecule, which is the logarithm of its partition coefficient between n-octanol and water $\log(c_{octanol}/c_{water})$, is a well-established measure of the molecule's hydrophilicity. Low hydrophilicities and therefore high log P values cause poor absorption or permeation.

(4) In certain embodiments, the terminal hydrophobic tag $R^H$ has enough hydrophobic character in order to induce the desired protein degradation of the target. Hydrophobic character of a particular group may be optimized by first limiting the number of hydrogen bond donors, e.g., to zero donors, and optionally by also limiting the number of hydrogen bond acceptors, e.g., optionally to zero acceptors.

(5) Of course, in its entirety, the compound of Formula (I) or (II) may comprise a number of hydrogen bond donors and acceptors, but in certain embodiments, the overall number of hydrogen bond donors and acceptors present is also limited, for example, to 5 or less hydrogen bond donors, and/or to 10 or less hydrogen bond acceptors. In certain embodiments, the compound of Formula (I) or (II) has 0, 1, 2, 3, 4, or 5 hydrogen bond donors; e.g., for example, 0, 1, 2, 3, 4, or 5 —OH, —SH, or —NH groups. In certain embodiments, the compound of Formula (I) or (II) has 0, 1, 2, 3, 4, 5, 6, 7, 8, 9, or 10 hydrogen bond acceptors, e.g., for example, 0, 1, 2, 3, 4, 5, 6, 7, 8, 9, or 10 O, S, or N atoms which do not comprise a hydrogen attached thereto.

(6) Furthermore, in certain embodiments, the compound of Formula (I) or (II) comprises an additional functionality which covalently or non-covalently binds the kinase, e.g., a protein kinase such as a Her3 protein kinase. This additional functionality, also referred to as a "warhead," is not attached to the linker or hydrophobic tag, but is appended to another area on the molecule such that the warhead does not interfere with the linker-tag's interaction with the protein kinase. In certain embodiments, the warhead non-covalently binds to the ATP binding site of kinase, e.g., the Her3 protein kinase. In certain embodiments, the warhead covalently binds to the ATP binding site of the kinase, e.g., the Her3 protein kinase. In certain embodiments, the warhead covalently binds to a cysteine residue in the ATP binding site of kinase, e.g., the Her3 protein kinase, e.g., Cys721 of the Her3 protein kinase.

Compounds of the present invention may comprise one or more of the above characteristics.

In certain embodiments, the compound of Formula (I) is a compound of Formula (II):

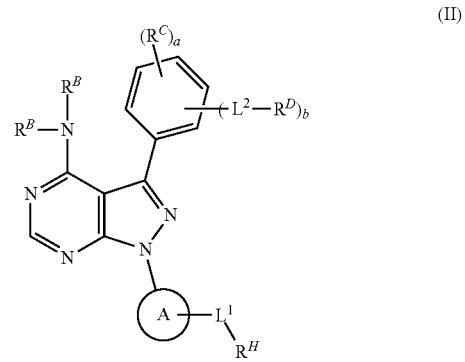

(II)

or a pharmaceutically acceptable salt thereof;
wherein:
$L^1$, $L^2$, $R^H$, and $R^D$ are as defined herein;
Ring A is substituted or unsubstituted carbocyclylene, substituted or unsubstituted heterocyclylene, substituted or unsubstituted arylene, or substituted or unsubstituted heteroarylene;

each occurrence of $R^B$ is independently selected from the group consisting of hydrogen, acyl, substituted and unsubstituted alkyl, substituted and unsubstituted alkenyl, substituted and unsubstituted alkynyl, substituted and unsubstituted carbocyclyl, substituted and unsubstituted heterocyclyl, substituted and unsubstituted aryl, substituted and unsubstituted heteroaryl, a nitrogen protecting group, or two $R^B$ groups are joined to form an substituted or unsubstituted heterocyclic or substituted or unsubstituted heteroaryl ring;

each instance of $R^C$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{C1}$, —$N(R^{C1})_2$, —$SR^{C1}$, —$C(=O)R^{C1}$, —$C(=O)OR^{C1}$, —$C(=O)SR^{C1}$, —$C(=O)N(R^{C1})_2$, —$NR^{C1}C(=O)R^{C1}$, —$NR^{C1}C(=O)OR^{C1}$, —$NR^{C1}C(=O)SR^{C1}$, or —$NR^{C1}C(=O)N(R^{C1})_2$, wherein each occurrence of $R^{C1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, and a sulfur protecting group when attached to a sulfur atom, or two $R^{C1}$ groups are joined to form an substituted or unsubstituted heterocyclic or substituted or unsubstituted heteroaryl ring;
a is 0, 1, 2, 3, or 4; and
b is 0 or 1.

As generally defined above, each occurrence of $R^B$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group, or two $R^B$ groups are joined to form an substituted or unsubstituted heterocyclic or substituted or unsubstituted heteroaryl ring.

In certain embodiments, each instance of $R^B$ is hydrogen. In certain embodiments, at least one instance of $R^B$ is hydrogen, and at least one instance of $R^B$ is a non-hydrogen group, i.e., acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group. In certain embodiments, two $R^B$ groups are joined to form an substituted or unsubstituted heterocyclic or substituted or unsubstituted heteroaryl ring.

As generally defined above, each instance of $R^C$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-C(=O)R^{C1}$, $-C(=O)OR^{C1}$, $-C(=O)SR^{C1}$, $-C(=O)N(R^{C1})_2$, $-NR^{C1}C(=O)R^{C1}$, $-NR^{C1}C(=O)OR^{C1}$, $-NR^{C1}C(=O)SR^{C1}$, or $-NR^{C1}C(=O)N(R^{C1})_2$; and a is 0, 1, 2, 3, or 4.

In certain embodiments, a is 0, and $R^C$ is absent. In certain embodiments, a is 1, 2, 3, or 4.

In certain embodiments, wherein a is 1, 2, 3, or 4, at least one instance of $R^C$ is $-OR^{C1}$, $-N(R^{C1})_2$, $-SR^{C1}$, $-C(=O)R^{C1}$, $-C(=O)OR^{C1}$, $-C(=O)SR^{C1}$, $-C(=O)N(R^{C1})_2$, $-NR^{C1}C(=O)R^{C1}$, $-NR^{C1}C(=O)OR^{C1}$, $-NR^{C1}C(=O)SR^{C1}$, or $-NR^{C1}C(=O)N(R^{C1})_2$. In certain embodiments, at least one instance of $R^C$ is $-OR^{C1}$. In certain embodiments, at least one instance of $R^C$ is $-N(R^{C1})_2$. In certain embodiments, at least one instance of $R^C$ is $-SR^{C1}$. In certain embodiments, at least one instance of $R^C$ is $-C(=O)R^{C1}$. In certain embodiments, at least one instance of $R^C$ is $-C(=O)OR^{C1}$. In certain embodiments, at least one instance of $R^C$ is $-C(=O)SR^{C1}$. In certain embodiments, at least one instance of $R^C$ is $-C(=O)N(R^{C1})_2$. In certain embodiments, at least one instance of $R^C$ is $-NR^{C1}C(=O)R^{C1}$. In certain embodiments, at least one instance of $R^C$ is $-NR^{C1}C(=O)OR^{C1}$. In certain embodiments, at least one instance of $R^C$ is $-NR^{C1}C(=O)SR^{C1}$. In certain embodiments, at least one instance of $R^C$ is $-NR^{C1}C(=O)N(R^{C1})_2$.

In certain embodiments, a is 1. In certain embodiments, a is 2.

In certain embodiments, a is 1, and b is 1. In this instance, in certain embodiments, the groups $R^C$ and $-L^2-R^D$ are ortho to each other. In certain embodiments, the groups $R^C$ and $-L^2-R^D$ are meta to each other. In certain embodiments, the groups $R^C$ and $-L^2-R^D$ are para to each other.

In certain embodiments, a is 2, and b is 0. In this instance, in certain embodiments, the two groups $R^C$ are ortho to each other. In certain embodiments, the two groups $R^C$ are meta to each other. In certain embodiments, the two groups $R^C$ are para to each other.

In certain embodiments, the compound of Formula (II) reduces protein kinase activity by targeted degradation of Her3. In certain embodiments, the compound of Formula (II) reduces protein kinase activity by inducing unfolding of the protein. In certain embodiments, the compound of Formula (II) reduces protein kinase activity by covalently binding to Her3. In certain embodiments, the compound of Formula (II) reduces protein kinase activity by non-covalently binding to Her3. In certain embodiments, wherein b is 1, and group $-L^2-R^D$ is present, the compound of Formula (II) covalently binds to Her3 protein kinase. In certain embodiments, wherein b is 0, and group $-L^2-R^D$ is absent, the compound of Formula (II) non-covalently binds to Her3 protein kinase. In certain embodiments, the reduction of protein kinase activity results in the inhibition of Her3-dependent signaling and/or loss of viability of Her3-addicted cells.

For example, in certain embodiments of Formula (II), wherein a is 1, and b is 1 (and thus the group $-L^2-R^D$ is present), provided is a compound of Formula (II-a):

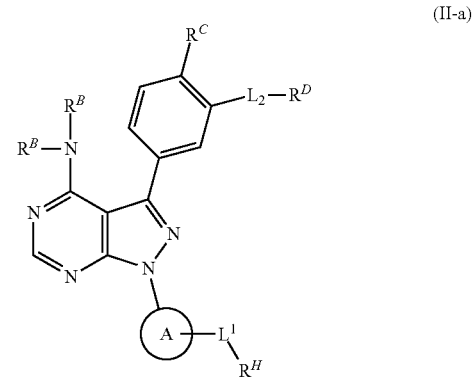

(II-a)

or a pharmaceutically acceptable salt thereof; wherein $R^C$ is as defined herein. In certain embodiments, $R^C$ is hydrogen, $-OR^{C1}$, $-N(R^{C1})_2$, or $-SR^{C1}$. In certain embodiments, $R^C$ is $-OR^{C1}$, wherein $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, $R^C$ is $-OR^{C1}$, wherein $R^{C1}$ is substituted or unsubstituted aryl, e.g., substituted or unsubstituted phenyl.

In certain embodiments of Formula (II-a), provided is a compound of Formula (II-a1):

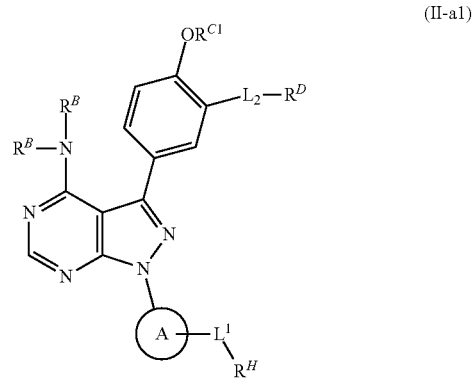

(II-a1)

or a pharmaceutically acceptable salt thereof. In certain embodiments, $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl.

In certain embodiments of Formula (II), wherein a is 2, and b is 0 (and thus the group $-L^2-R^D$ is absent), provided is a compound of Formula (II-b):

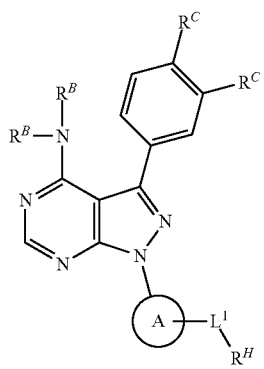

(II-b)

or a pharmaceutically acceptable salt thereof; wherein each instance of $R^C$ is as defined herein. In certain embodiments, one instance of $R^C$ is hydrogen, —$OR^{C1}$, —$N(R^{C1})_2$, or —$SR^{C1}$. In certain embodiments, one instance of $R^C$ is —$OR^{C1}$, wherein $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, $R^C$ is —$OR^{C1}$, wherein $R^{C1}$ is substituted or unsubstituted alkyl, e.g., methyl. In certain embodiments, one $R^C$ is —C(=O)$R^{C1}$, —C(=O)O$R^{C1}$, —C(=O)S$R^{C1}$, —C(=O)N($R^{C1}$)$_2$, —$NR^{C1}$C(=O)$R^{C1}$, —$NR^{C1}$C(=O)O$R^{C1}$, —$NR^{C1}$C(=O)S$R^{C1}$, or —$NR^{C1}$C(=O)N($R^{C1}$)$_2$. In certain embodiments, one $R^C$ is —C(=O)$R^{C1}$, —C(=O)O$R^{C1}$, —C(=O)S$R^{C1}$, —C(=O)N($R^{C1}$)$_2$, —NHC(=O)$R^{C1}$, —NHC(=O)O$R^{C1}$, —NHC(=O)S$R^{C1}$, or —NHC(=O)N($R^{C1}$)$_2$. In certain embodiments, one $R^C$ is —C(=O)$R^{C1}$, —C(=O)O$R^{C1}$, —C(=O)S$R^{C1}$, —C(=O)N($R^{C1}$)$_2$, —NHC(=O)$R^{C1}$, —NHC(=O)O$R^{C1}$, —NHC(=O)S$R^{C1}$, or —NHC(=O)N($R^{C1}$)$_2$, wherein one $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, one $R^C$ is —C(=O)$R^{C1}$, —C(=O)O$R^{C1}$, —C(=O)S$R^{C1}$, —C(=O)N($R^{C1}$)$_2$, —NHC(=O)$R^{C1}$, —NHC(=O)O$R^{C1}$, —NHC(=O)S$R^{C1}$, or —NHC(=O)N($R^{C1}$)$_2$, wherein one $R^{C1}$ is substituted or unsubstituted heteroaryl, e.g., a substituted or unsubstituted bicyclic heteroaryl moiety, such as indolyl.

In certain embodiments of Formula (II-b), provided is a compound of Formula (II-b1):

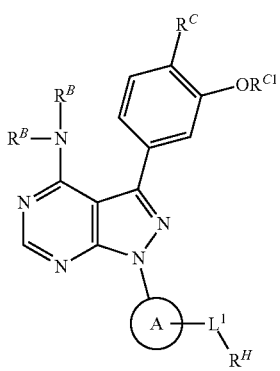

(II-b1)

or a pharmaceutically acceptable salt thereof. In certain embodiments, $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, $R^C$ is —C(=O)$R^{C1}$, —C(=O)O$R^{C1}$, —C(=O)S$R^{C1}$, —C(=O)N($R^{C1}$)$_2$, —NHC(=O)$R^{C1}$, —NHC(=O)O$R^{C1}$, —NHC(=O)S$R^{C1}$, or —NHC(=O)N($R^{C1}$)$_2$.

In certain embodiments of Formula (II-b), provided is a compound of Formula (II-b2):

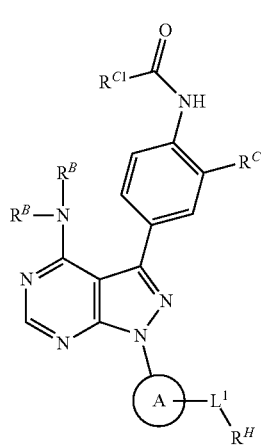

(II-b2)

or a pharmaceutically acceptable salt thereof. In certain embodiments, $R^C$ is —$OR^{C1}$, wherein $R^{C1}$ is substituted or unsubstituted alkyl, substituted or unsubstituted carbocyclyl, substituted or unsubstituted heterocyclyl, substituted or unsubstituted aryl, or substituted or unsubstituted heteroaryl. In certain embodiments, $R^{C1}$ of the amide moiety is a substituted or unsubstituted heteroaryl moiety, e.g., a substituted or unsubstituted bicyclic heteroaryl moiety, such as indolyl.

In certain embodiments of Formula (II-b), provided is a compound of Formula (II-b3):

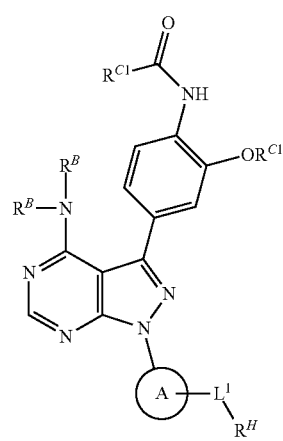

(II-b3)

or a pharmaceutically acceptable salt thereof. In certain embodiments, $R^{C1}$ of the —$OR^{C1}$ group is substituted or unsubstituted alkyl, substituted or unsubstituted carbocyclyl, substituted or unsubstituted heterocyclyl, substituted or unsubstituted aryl, or substituted or unsubstituted heteroaryl.

In certain embodiments, $R^{C1}$ of the amide moiety is a substituted or unsubstituted heteroaryl moiety, e.g., a substituted or unsubstituted bicyclic heteroaryl moiety, such as indolyl.

As generally defined above, Ring A is substituted or unsubstituted carbocyclylene, substituted or unsubstituted heterocyclylene, substituted or unsubstituted arylene, or substituted or unsubstituted heteroarylene. It is understood that Ring A is already substituted with the group -$L^1$-$R^H$. Thus, "substituted" in the context of Ring A refers to additional substitution(s) on the ring. In certain embodiments, Ring A is not further substituted (unsubstituted Ring A). In certain embodiments, Ring A is additionally substituted (substituted Ring A).

In certain embodiments, Ring A is substituted or unsubstituted arylene, e.g., substituted or unsubstituted phenylene or substituted or unsubstituted napthylene.

In certain embodiments, wherein Ring A is substituted or unsubstituted phenylene, the compound of Formula (II) is of Formula (II-c):

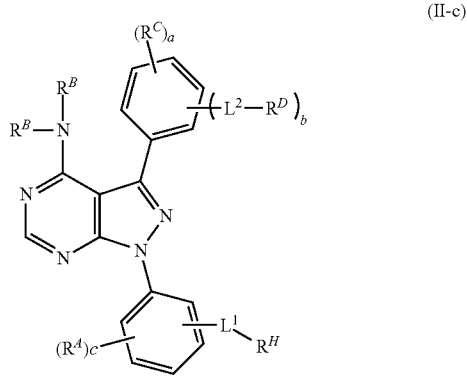

(II-c)

or a pharmaceutically acceptable salt thereof,
wherein:
each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{41}$, $-N(R^{41})_2$, $-SR^{41}$, $-C(=O)R^{41}$, or $-C(=O)OR^{41}$ wherein each occurrence of $R^{41}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{41}$ groups are joined to form an substituted or unsubstituted heterocyclic or substituted or unsubstituted heteroaryl ring; and
c is 0 or 1.

In certain embodiments of Formula (II-c), c is 0, and $R^A$ is absent. In certain embodiments, c is 1, and $R^A$ is present, either ortho, meta, or para to the point of attachment of the phenylene group to the pyrazolyl ring. In certain embodiments, the group $L^1$-$R^H$ is present either ortho, meta, or para to the point of attachment of the phenylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, L is 5 to 15 consecutive covalently bonded atoms in length. In certain embodiments, $R^H$ is a group of formula:

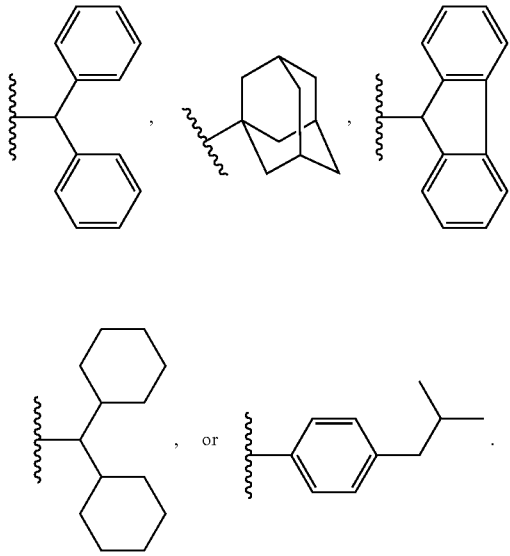

For example, in certain embodiments of Formula (II-c), wherein the group $L^1$-$R^H$ is para to the point of attachment of the phenylene group to the pyrazolyl ring, provided is a compound of Formula (II-c1):

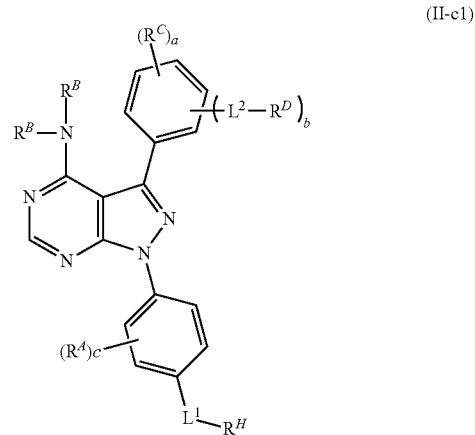

(II-c1)

or a pharmaceutically acceptable salt thereof. In certain embodiments of Formula (II-c1), c is 0, and $R^A$ is absent. In certain embodiments, c is 1, and $R^A$ is present, either ortho, meta, or para to the point of attachment of the phenylene group to the pyrazolyl ring. In certain embodiments, the group $L^1$-$R^H$ is present either ortho, meta, or para to the point of attachment of the phenylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

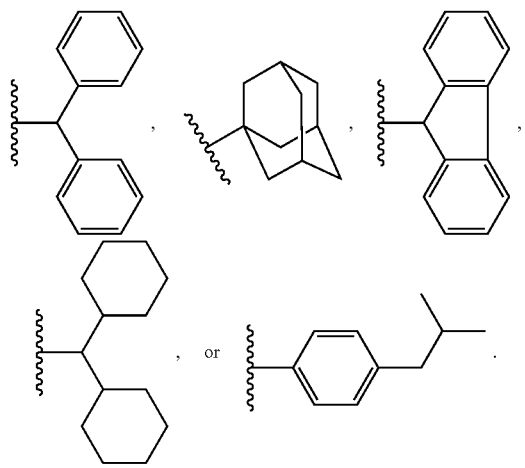

In certain embodiments, Ring A is substituted or unsubstituted heteroarylene, e.g., a substituted or unsubstituted 5- to 6-membered heteroarylene. In certain embodiments, Ring A is a 6-membered heteroarylene, e.g., pyridinylene.

For example, in certain embodiments, wherein Ring A is substituted or unsubstituted pyridinylene, provided is a compound of Formula (II-d):

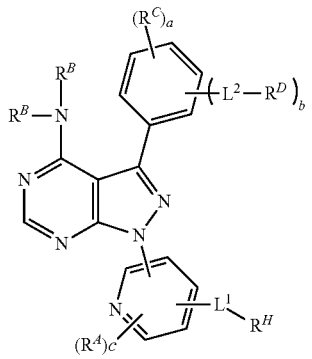

(II-d)

or a pharmaceutically acceptable salt thereof, wherein:

each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —$C(=O)R^{A1}$, or —$C(=O)OR^{A1}$, wherein each occurrence of $R^{A1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form an substituted or unsubstituted heterocyclic or substituted or unsubstituted heteroaryl ring; and c is 0 or 1.

In certain embodiments of Formula (II-d), c is 0, and $R^A$ is absent. In certain embodiments, c is 1, and $R^A$ is present, either ortho, meta, or para to the point of attachment of the pyridinylene group to the pyrazolyl ring. In certain embodiments, the group $L^1$-$R^H$ is present either ortho, meta, or para to the point of attachment of the pyridinylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, L1 is 5 to 15 consecutive covalently bonded atoms in length. In certain embodiments, $R^H$ is a group of formula:

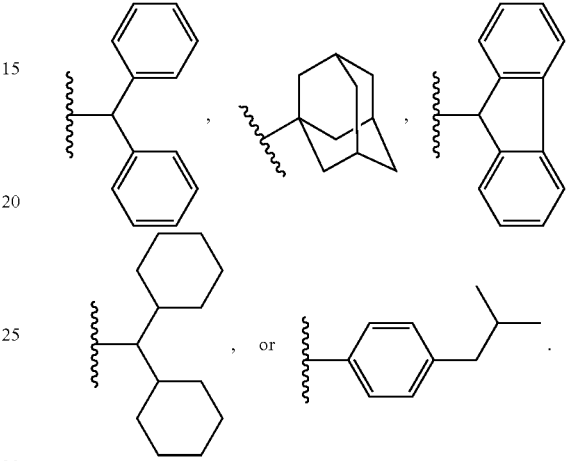

In certain embodiments, Ring A is substituted or unsubstituted carbocyclylene, e.g., a substituted or unsubstituted $C_{3-8}$ carbocyclylene. In certain embodiments, Ring A is a substituted or unsubstituted cyclopropylene, substituted or unsubstituted cyclobutylene, substituted or unsubstituted cyclopentylene, substituted or unsubstituted cyclohexylene, substituted or unsubstituted cycloheptylene, or substituted or unsubstituted cyclooctylene.

For example, in certain embodiments, wherein Ring A is substituted or unsubstituted $C_{3-8}$ carbocyclylene, provided is a compound of Formula (II-e):

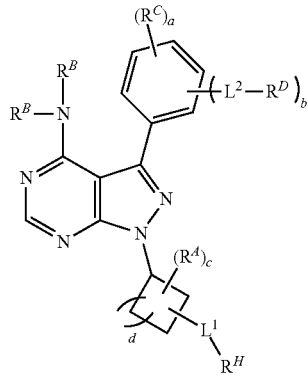

(II-e)

or a pharmaceutically acceptable salt thereof,
wherein:

each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR^{A1}, —N(R^{A1})_2, —SR^{A1}, —C(=O)R^{A1}, or —C(=O)OR^{A1}, wherein each occurrence of R^{A1} is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two R^{A1} groups are joined to form an substituted or unsubstituted heterocyclic or substituted or unsubstituted heteroaryl ring;

c is 0 or 1; and d is 0, 1, 2, 3, 4, or 5.

In certain embodiments of Formula (II-e), c is 0 and R^A is absent. In certain embodiments, c is 1. In certain embodiments, b is 0. In certain embodiments, b is 1, L^2 is a bond, and R^D is a group of Formula (i-1). In certain embodiments, each instance of R^B is hydrogen. In certain embodiments, L^1 is 5 to 15 consecutive covalently bonded atoms in length. In certain embodiments, R^H is a group of formula:

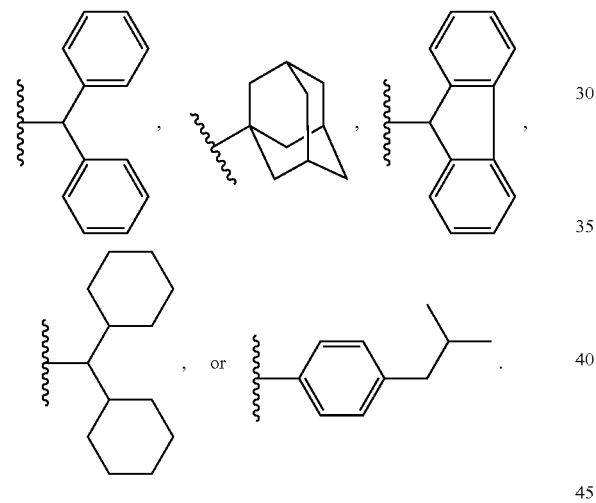

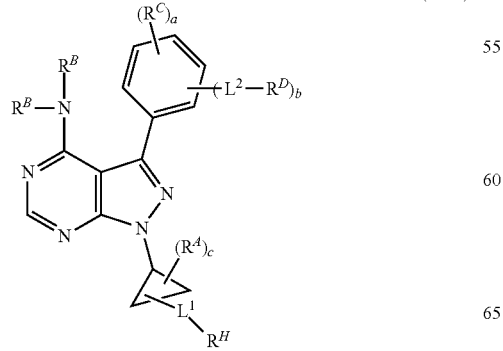

For example, in certain embodiments, wherein Ring A is substituted or unsubstituted C_{3-8} carbocyclylene, provided is a compound of Formula (II-e1), (II-e2), (II-e3), (II-e4), (II-e5), or (II-e6):

(II-e1)

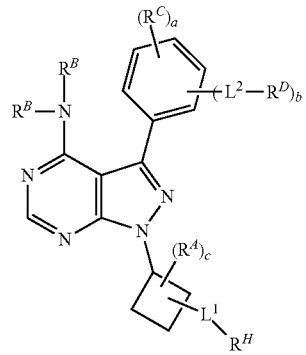

(II-e2)

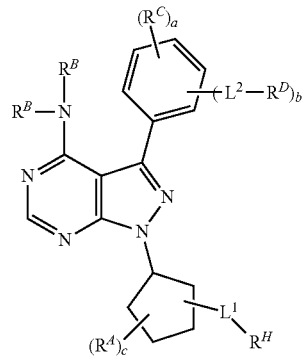

(II-e3)

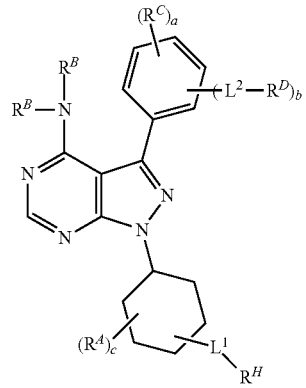

(II-e4)

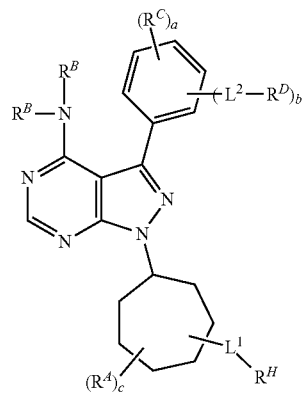

(II-e5)

-continued

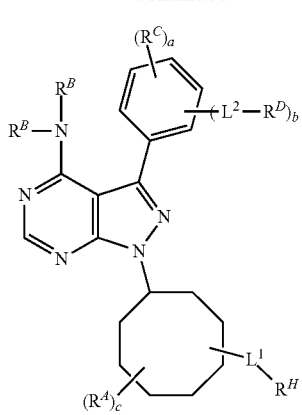
(II-e6)

or a pharmaceutically acceptable salt thereof.

In certain embodiments of Formula (II-e1), (II-e2), (II-e3), (II-e4), (II-e5), or (II-e6), c is 0, and $R^A$ is absent. In certain embodiments, c is 1. In certain embodiments, b is 0. In certain embodiments, b is 1, L is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

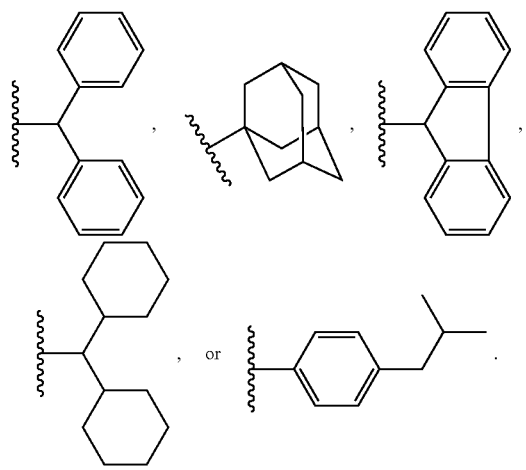

For example, in certain embodiments of Formula (II-e3) provided is a compound of Formula (II-e3a):

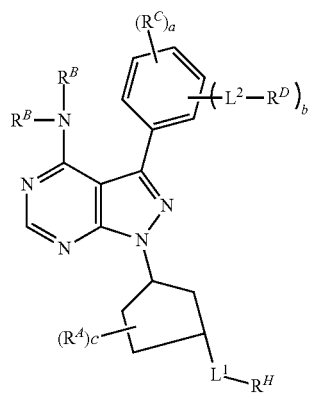
(II-e3a)

or a pharmaceutically acceptable salt thereof. In certain embodiments of Formula (II-e3) or (II-e3a), c is 0, and $R^A$ is absent. In certain embodiments, c is 1, and $R^A$ is present either at the 2 or 3 position from the point of attachment of the cyclopentylene group to the pyrazolyl ring. In certain embodiments, the group $L^1$-$R^H$ is present either at the 2 or 3 position from the point of attachment of the cyclopentylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

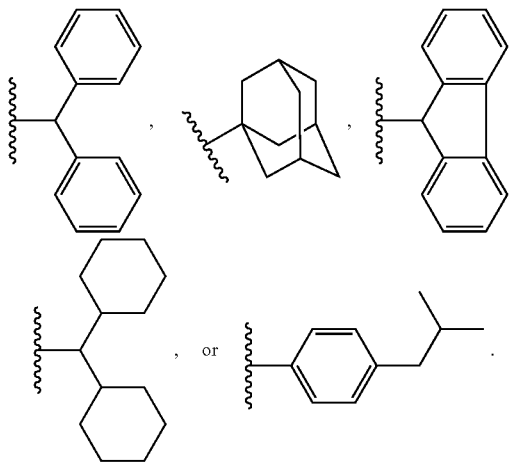

For example, in certain embodiments of Formula (II-e4) provided is a compound of Formula (II-e4a):

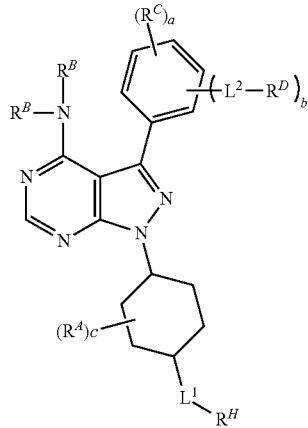
(II-e4a)

or a pharmaceutically acceptable salt thereof. In certain embodiments of Formula (II-e4) or (II-e4a), c is 0, and $R^A$ is absent. In certain embodiments, c is 1, and $R^A$ is present, either at the 2, 3, or 4 position from the point of attachment of the cyclohexylene group to the pyrazolyl ring. In certain embodiments, the group $L^1$-$R^H$ is present either at the 2, 3, or 4 position from the point of attachment of the cyclohexylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, L is 5 to 15 consecutive covalently bonded atoms in length. In certain embodiments, $R^H$ is a group of formula:

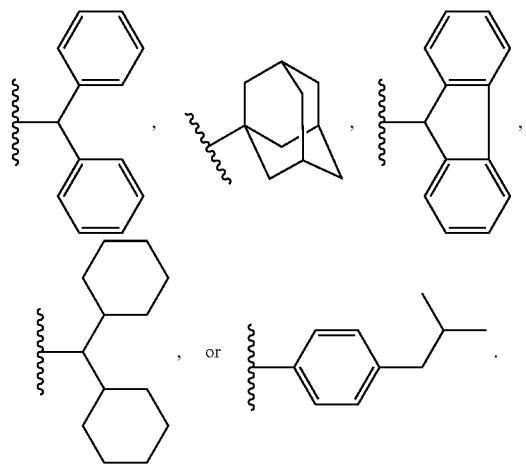

In certain embodiments, Ring A is substituted or unsubstituted heterocyclylene, e.g., substituted or unsubstituted 3- to 8-membered heterocyclylene, e.g., substituted or unsubstituted 3-membered heterocyclylene, substituted or unsubstituted 4-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene. In certain embodiments, Ring A is substituted or unsubstituted 5-membered heterocyclylene, e.g., substituted or unsubstituted pyrrolidinylene. In certain embodiments, Ring A is substituted or unsubstituted 6-membered heterocyclylene, e.g., substituted or unsubstituted morpholinylene, substituted or unsubstituted piperidinylene, or substituted or unsubstituted piperazinylene.

For example, in certain embodiments, wherein Ring A is substituted or unsubstituted pyrrolidinylene, provided is a compound of Formula (II-f):

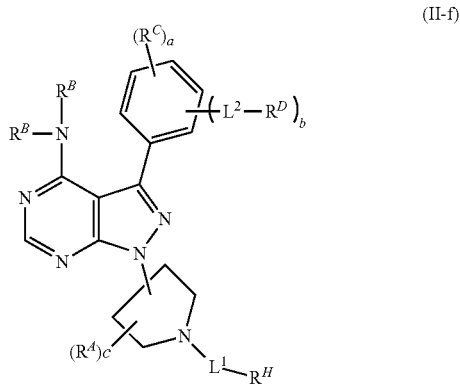

or a pharmaceutically acceptable salt thereof, wherein:

each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{A1}$, $-N(R^{A1})_2$, $-SR^{A1}$, $-C(=O)R^{A1}$, or $-C(=O)OR^{A1}$, wherein each occurrence of $R^{A1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form an substituted or unsubstituted heterocyclic or substituted or unsubstituted heteroaryl ring; and c is 0 or 1.

In certain embodiments of Formula (II-f), c is 0 and $R^A$ is absent. In certain embodiments, c is 1, and $R^A$ is present, either at the 2 or 3 position from the point of attachment of the pyrrolidinyl group to the pyrazolyl ring. In certain embodiments, the group $L^1$-$R^H$ is present either at the 2 or 3 position from the point of attachment of the pyrrolidinyl group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

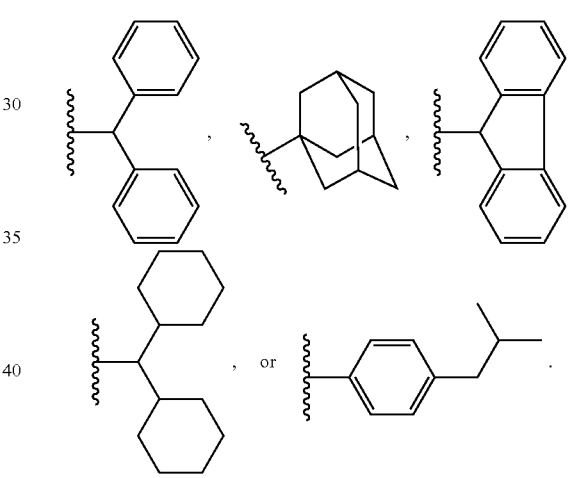

In certain embodiments of Formula (II-f) provided is a compound of Formula (II-f1):

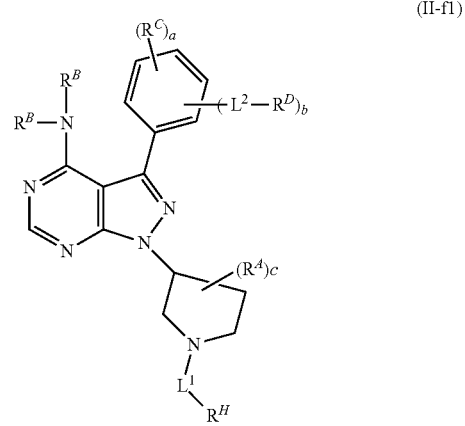

or a pharmaceutically acceptable salt thereof. In certain embodiments of Formula (II-f1), c is 0 and $R^A$ is absent. In certain embodiments, c is 1, and $R^A$ is present, either at the 2 or 3 position from the point of attachment of the pyrrolidinyl group to the pyrazolyl ring. In certain embodiments, the group $L^1$-$R^H$ is present either at the 2 or 3 position from the point of attachment of the pyrrolidinyl group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

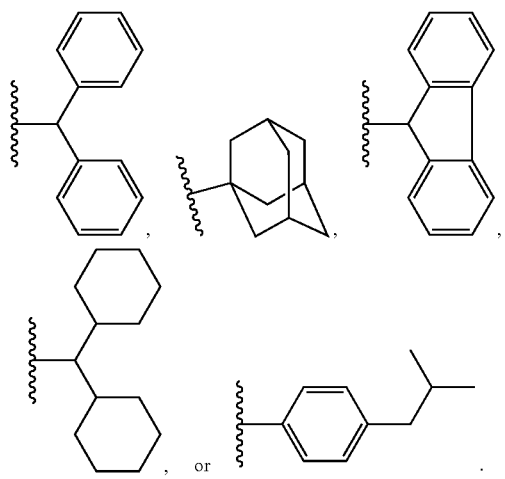

, or .

In certain embodiments, wherein Ring A is substituted or unsubstituted piperidinylene, provided is a compound of Formula (II-g):

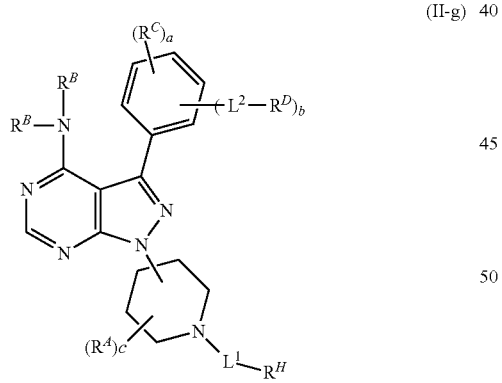

or a pharmaceutically acceptable salt thereof, wherein:

each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —$C(=O)R^{A1}$, or —$C(=O)OR^{A1}$, wherein each occurrence of $R^{A1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form an substituted or unsubstituted heterocyclic or substituted or unsubstituted heteroaryl ring; and c is 0 or 1.

In certain embodiments of Formula (II-g), c is 0, and $R^A$ is absent. In certain embodiments, c is 1 and $R^A$ is present, either at the 2, 3, or 4 position from the point of attachment of the piperidinylene group to the pyrazolyl ring. In certain embodiments, the group $L^1$-$R^H$ is present either at the 2, 3, or 4 position from the point of attachment of the piperidinylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

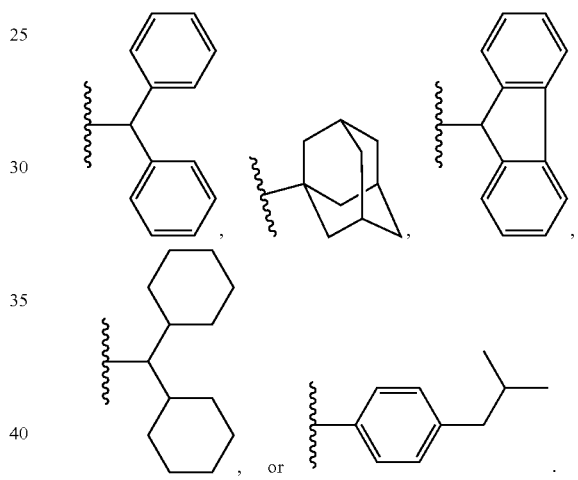

, or .

For example, in certain embodiments of Formula (II-g) provided is a compound of Formula (II-g1):

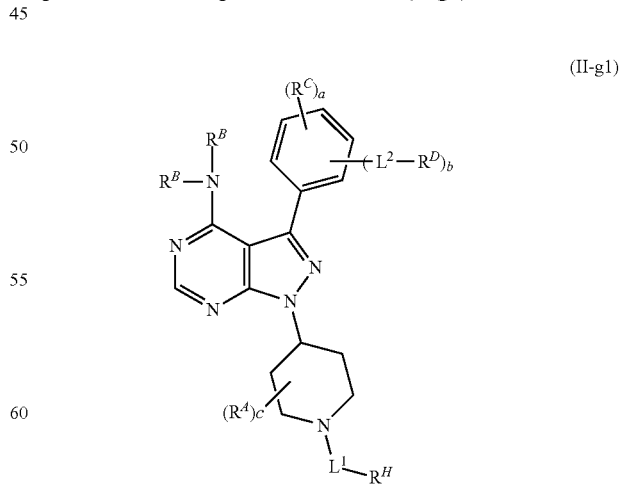

or a pharmaceutically acceptable salt thereof. In certain embodiments of Formula (II-g1), c is 0, and $R^A$ is absent. In certain embodiments, c is 1, and $R^A$ is present, either at the 2 or 3 position from the point of attachment of the piperidinylene group to the pyrazolyl ring. In certain embodiments, the group $L^1$-$R^H$ is present either at the 2 or 3 position from the point of attachment of the piperidinylene group to the pyrazolyl ring. In certain embodiments, b is 0. In certain embodiments, b is 1, $L^2$ is a bond, and $R^D$ is a group of Formula (i-1). In certain embodiments, each instance of $R^B$ is hydrogen. In certain embodiments, $L^1$ is 5 to 15 consecutive covalently bonded atoms in length. In certain embodiments, $R^H$ is a group of formula:

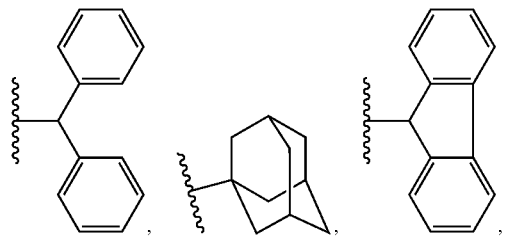

-continued

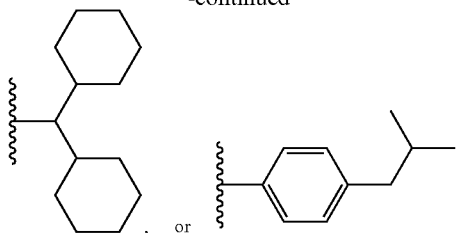

Non-limiting examples of compounds of Formula (I) and (II), and pharmaceutically acceptable salts, thereof are provided below in Table 1.

TABLE 1

| Structure |
|---|
| 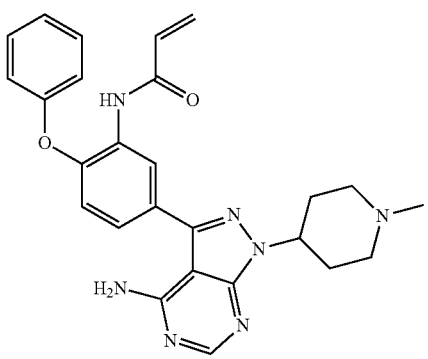 <br> Control <br> TX2-120-1 |
| 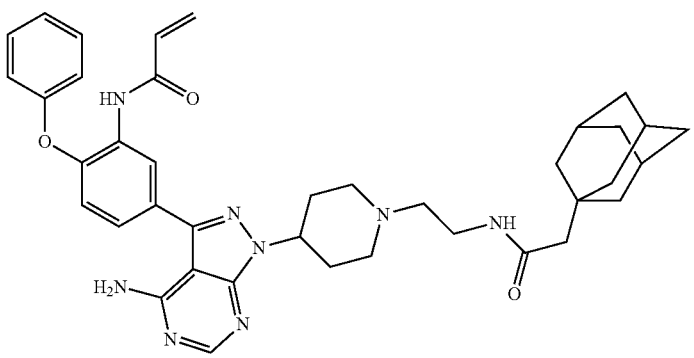 [SMILES: C=CC(=O)Nc1cc(-c2nn(C3CCN(CCNC(=O)CC45CC6CC(CC(C6)C4)C5)CC3)c3ncnc(N)c23)ccc1Oc1ccccc1] <br> TX2-112-1 <br> MW$_{total}$ = 674 g/mol <br> MW(—$L^1$—$R^H$) = 220 g/mol <br> MW(M—H) = 455 g/mol <br> $L^1$ = 5 atoms long |

TABLE 1-continued
| Structure | |
|---|---|
| 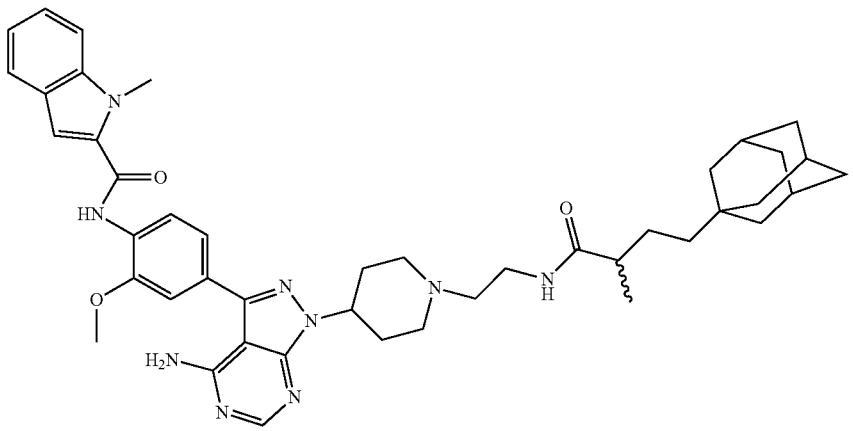 [SMILES: COc1cc(-c2nn(C3CCN(CCNC(=O)C(C)CCC45CC6CC(CC(C6)C4)C5)CC3)c3ncnc(N)c23)ccc1NC(=O)c1cc2ccccc2n1C] | TX2-126-1<br>MW$_{total}$ = 757 g/mol<br>MW(—L$^1$—R$^H$) = 262 g/mol<br>MW(M—H) = 496 g/mol<br>L$^1$ = 7 atoms |
| 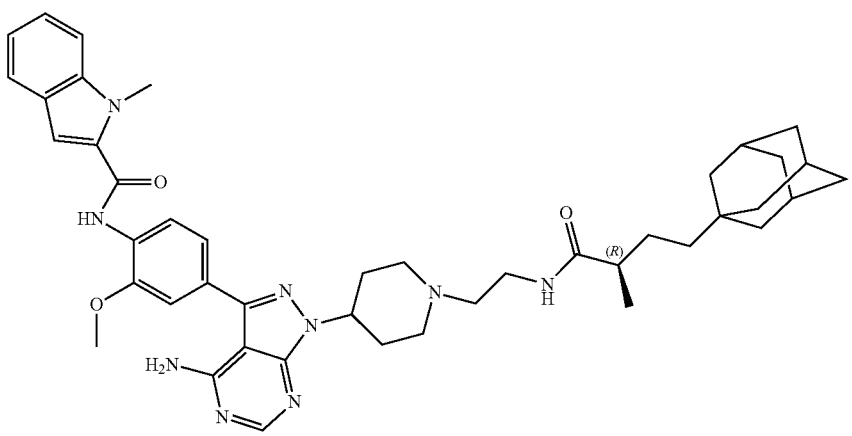 | (R)-TX2-126-1 |
| 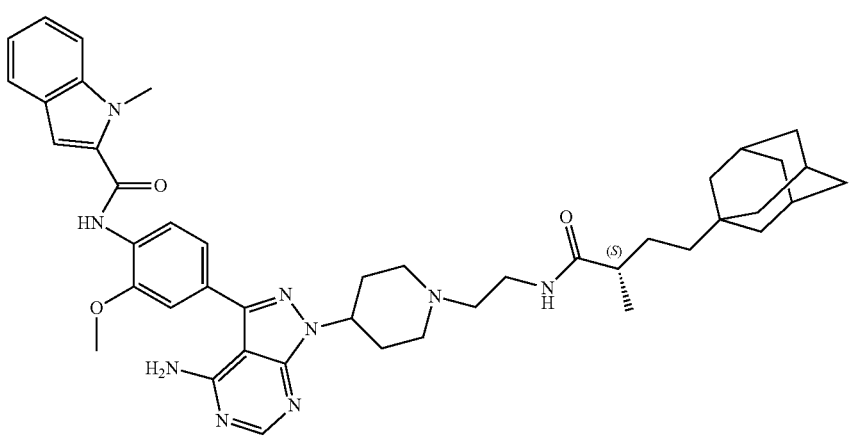 | (S)-TX2-126-1 |

TABLE 1-continued
Structure
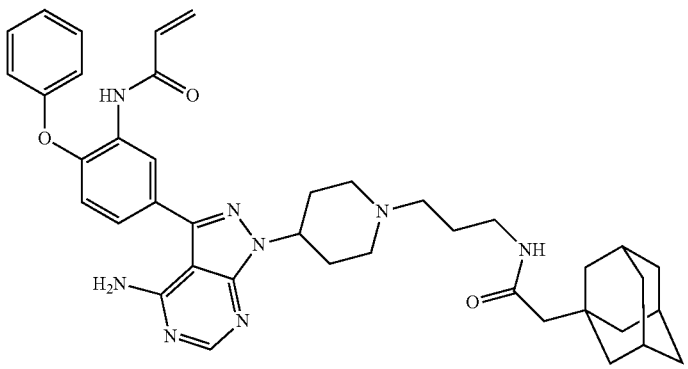 [SMILES: C=CC(=O)Nc1cc(-c2nn(C3CCN(CCCNC(=O)CC45CC6CC(CC(C6)C4)C5)CC3)c3ncnc(N)c23)ccc1Oc1ccccc1]
TX2-113-1
MW$_{total}$ = 688 g/mol
MW(—L$^1$—R$^H$) = 234 g/mol
MW(M—H) = 455 g/mol
L$^1$ = 6 atoms long
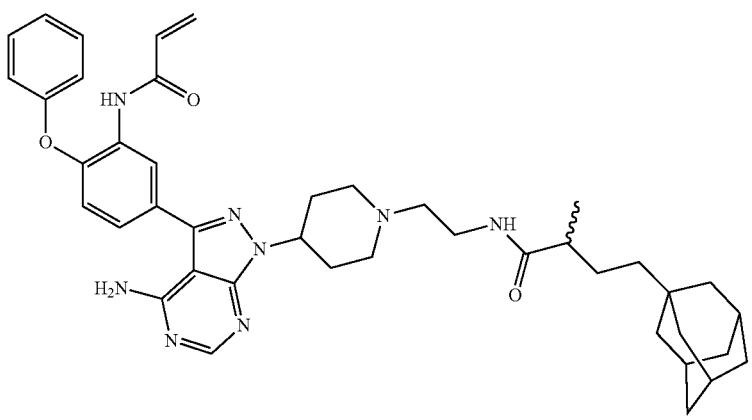 [SMILES: C=CC(=O)Nc1cc(-c2nn(C3CCN(CCNC(=O)C(C)CCC45CC6CC(CC(C6)C4)C5)CC3)c3ncnc(N)c23)ccc1Oc1ccccc1]
TX2-121-1
MW$_{total}$ = 716 g/mol
MW(—L$^1$—R$^H$) = 262 g/mol
MW(M—H) = 455 g/mol
L$^1$ = 7 atoms long
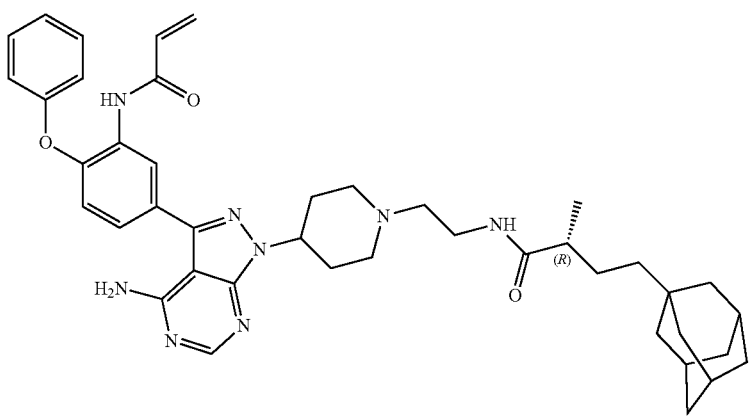
(R)-TX2-121-1
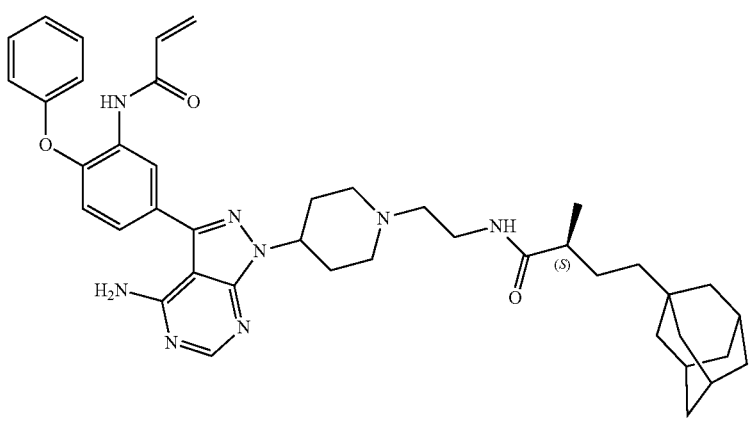
(S)-TX2-121-1

TABLE 1-continued
Structure
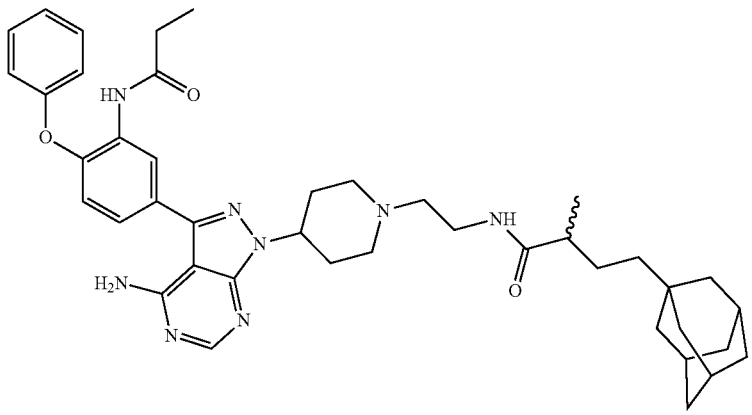 [SMILES: CCC(=O)Nc1cc(-c2nn(C3CCN(CCNC(=O)C(C)CCC45CC6CC(CC(C6)C4)C5)CC3)c3ncnc(N)c23)ccc1Oc1ccccc1]
TX2-121-3
MW$_{total}$ = 718 g/mol
MW(—L$^1$—R$^H$) = 262 g/mol
MW(M—H) = 457 g/mol
L$^1$ = 7 atoms long
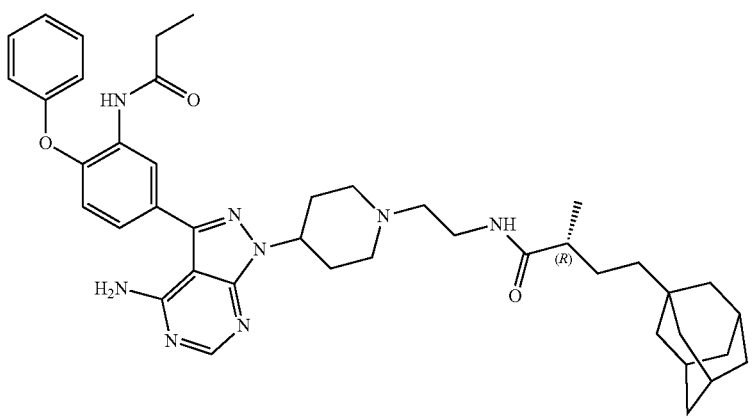
(R)-TX2-121-3
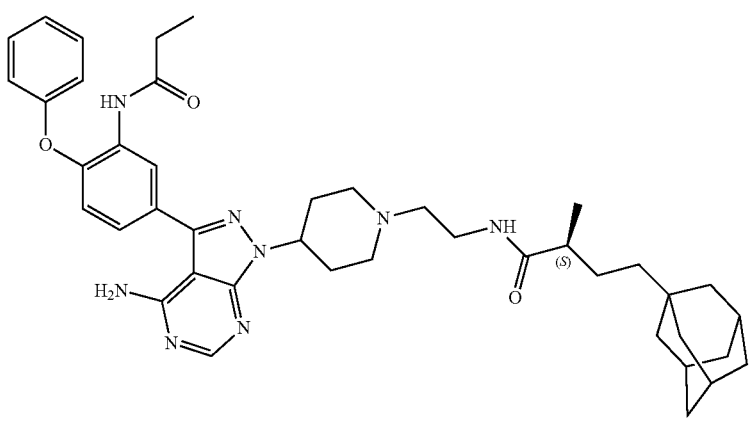
(S)-TX2-121-3

TABLE 1-continued
Structure
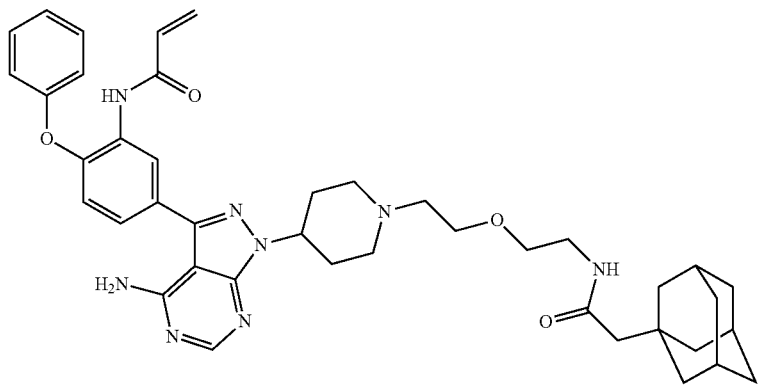 [SMILES: C=CC(=O)Nc1cc(-c2nn(C3CCN(CCOCCNC(=O)CC45CC6CC(CC(C6)C4)C5)CC3)c3ncnc(N)c23)ccc1Oc1ccccc1]
TX2-114-1
MW$_{total}$ = 718 g/mol
MW(—L$^1$—R$^H$) = 264 g/mol
MW(M—H) = 455 g/mol
L$^1$ = 8 atoms long
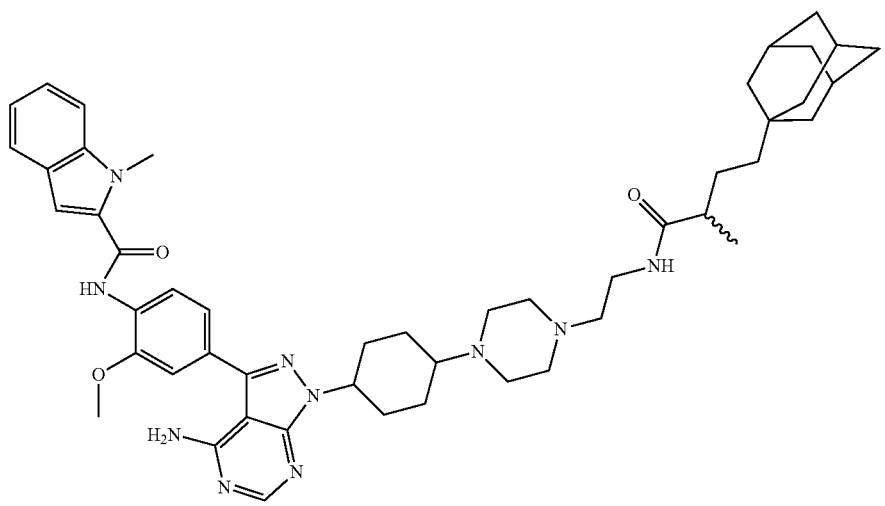 [SMILES: COc1cc(-c2nn(C3CCC(N4CCN(CCNC(=O)C(C)CCC56CC7CC(CC(C7)C5)C6)CC4)CC3)c3ncnc(N)c23)ccc1NC(=O)c1cc2ccccc2n1C]
SML-11-124-1
MW$_{total}$ = 841 g/mol
MW(—L$^1$—R$^H$) = 346 g/mol
MW(M—H) = 495 g/mol
L$^1$ = 11 atoms long
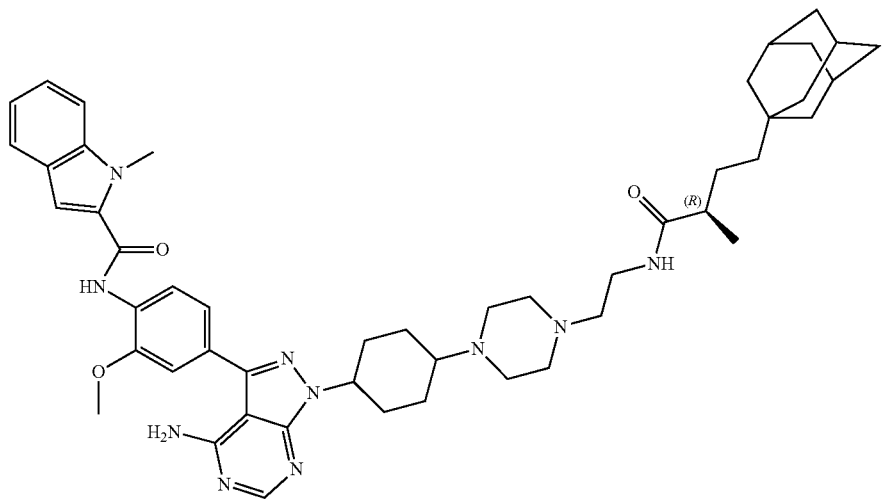
(R)-SML-11-124-1

TABLE 1-continued

Structure (S)-SML-11-124-1

Pharmaceutical Compositions

In certain embodiments, the present invention provides a pharmaceutical composition comprising a compound of Formula (I) or (II) or a pharmaceutically acceptable salt thereof and, optionally, a pharmaceutically acceptable excipient. In certain embodiments, the compound is present in an effective amount, e.g., a therapeutically effective amount or a prophylactically effective amount.

Pharmaceutically acceptable excipients include any and all solvents, diluents or other liquid vehicles, dispersion or suspension aids, surface active agents, isotonic agents, thickening or emulsifying agents, preservatives, solid binders, lubricants and the like, as suited to the particular dosage form desired. General considerations in the formulation and/or manufacture of pharmaceutical compositions agents can be found, for example, in Remington's Pharmaceutical Sciences, Sixteenth Edition, E. W. Martin (Mack Publishing Co., Easton, Pa., 1980), and Remington: The Science and Practice of Pharmacy, 21$^{st}$ Edition (Lippincott Williams & Wilkins, 2005).

Pharmaceutical compositions described herein can be prepared by any method known in the art of pharmacology. In general, such preparatory methods include the steps of bringing the compound of Formula (I) or (II) or a pharmaceutically acceptable salt thereof (the "active ingredient") into association with the excipient and/or one or more other accessory ingredients, and then, if necessary and/or desirable, shaping and/or packaging the product into a desired single- or multi-dose unit.

Pharmaceutical compositions can be prepared, packaged, and/or sold in bulk, as a single unit dose, and/or as a plurality of single unit doses. As used herein, a "unit dose" is discrete amount of the pharmaceutical composition comprising a predetermined amount of the active ingredient. The amount of the active ingredient is generally equal to the dosage of the active ingredient which would be administered to a subject and/or a convenient fraction of such a dosage such as, for example, one-half or one-third of such a dosage.

Relative amounts of the active ingredient, the pharmaceutically acceptable carrier, and/or any additional ingredients in a pharmaceutical composition of the invention will vary, depending upon the identity, size, and/or condition of the subject treated and further depending upon the route by which the composition is to be administered. By way of example, the composition may comprise between 0.1% and 100% (w/w) active ingredient.

Pharmaceutically acceptable excipients used in the manufacture of provided pharmaceutical compositions include inert diluents, dispersing and/or granulating agents, surface active agents and/or emulsifiers, disintegrating agents, binding agents, preservatives, buffering agents, lubricating agents, and/or oils. Excipients such as cocoa butter and suppository waxes, coloring agents, coating agents, sweetening, flavoring, and perfuming agents may also be present in the composition.

Exemplary diluents include calcium carbonate, sodium carbonate, calcium phosphate, dicalcium phosphate, calcium sulfate, calcium hydrogen phosphate, sodium phosphate lactose, sucrose, cellulose, microcrystalline cellulose, kaolin, mannitol, sorbitol, inositol, sodium chloride, dry starch, cornstarch, powdered sugar, etc., and combinations thereof.

Exemplary granulating and/or dispersing agents include potato starch, corn starch, tapioca starch, sodium starch glycolate, clays, alginic acid, guar gum, citrus pulp, agar, bentonite, cellulose and wood products, natural sponge, cation-exchange resins, calcium carbonate, silicates, sodium carbonate, cross-linked poly(vinyl-pyrrolidone) (crospovidone), sodium carboxymethyl starch (sodium starch glycolate), carboxymethyl cellulose, cross-linked sodium carboxymethyl cellulose (croscarmellose), methylcellulose, pregelatinized starch (starch 1500), microcrystalline starch, water insoluble starch, calcium carboxymethyl cellulose, magnesium aluminum silicate (Veegum), sodium lauryl sulfate, quaternary ammonium compounds, etc., and combinations thereof.

Exemplary surface active agents and/or emulsifiers include natural emulsifiers (e.g. acacia, agar, alginic acid, sodium alginate, tragacanth, chondrux, cholesterol, xanthan, pectin, gelatin, egg yolk, casein, wool fat, cholesterol, wax, and lecithin), colloidal clays (e.g. bentonite [aluminum silicate] and Veegum [magnesium aluminum silicate]), long chain amino acid derivatives, high molecular weight alcohols (e.g. stearyl alcohol, cetyl alcohol, oleyl alcohol, triacetin monostearate, ethylene glycol distearate, glyceryl monostearate, and propylene glycol monostearate, polyvinyl alcohol), carbomers (e.g. carboxy polymethylene, polyacrylic acid, acrylic acid polymer, and carboxyvinyl polymer), carrageenan, cellulosic derivatives (e.g. carboxymethylcellulose sodium, powdered cellulose, hydroxymethyl cellulose, hydroxypropyl cellulose, hydroxypropyl methylcellulose, methylcellulose), sorbitan fatty acid esters (e.g. polyoxyethylene sorbitan monolaurate [Tween 20], polyoxyethylene sorbitan [Tween 60], polyoxyethylene sorbitan monooleate [Tween 80], sorbitan monopalmitate [Span 40], sorbitan monostearate [Span 60], sorbitan tristearate [Span 65], glyceryl monooleate, sorbitan monooleate [Span 80]), polyoxyethylene esters (e.g. polyoxyethylene monostearate [Myrj 45], polyoxyethylene hydrogenated castor oil, polyethoxylated castor oil, polyoxymethylene stearate, and Solutol), sucrose fatty acid esters, polyethylene glycol fatty acid esters (e.g., Cremophor), polyoxyethylene ethers, (e.g. polyoxyethylene lauryl ether [Brij 30]), poly(vinyl-pyrrolidone), diethylene glycol monolaurate, triethanolamine oleate, sodium oleate, potassium oleate, ethyl oleate, oleic acid, ethyl laurate, sodium lauryl sulfate, Pluronic F 68, Poloxamer 188, cetrimonium bromide, cetylpyridinium chloride, benzalkonium chloride, docusate sodium, etc. and/or combinations thereof.

Exemplary binding agents include starch (e.g. cornstarch and starch paste), gelatin, sugars (e.g. sucrose, glucose, dextrose, dextrin, molasses, lactose, lactitol, mannitol, etc.), natural and synthetic gums (e.g. acacia, sodium alginate, extract of Irish moss, panwar gum, ghatti gum, mucilage of isapol husks, carboxymethylcellulose, methylcellulose, ethylcellulose, hydroxyethylcellulose, hydroxypropyl cellulose, hydroxypropyl methylcellulose, microcrystalline cellulose, cellulose acetate, poly(vinyl-pyrrolidone), magnesium aluminum silicate (Veegum), and larch araboga-lactan), alginates, polyethylene oxide, polyethylene glycol, inorganic calcium salts, silicic acid, polymethacrylates, waxes, water, alcohol, etc., and/or combinations thereof.

Exemplary preservatives include antioxidants, chelating agents, antimicrobial preservatives, antifungal preservatives, alcohol preservatives, acidic preservatives, and other preservatives.

Exemplary antioxidants include alpha tocopherol, ascorbic acid, acorbyl palmitate, butylated hydroxyanisole, butylated hydroxytoluene, monothioglycerol, potassium metabisulfite, propionic acid, propyl gallate, sodium ascorbate, sodium bisulfite, sodium metabisulfite, and sodium sulfite.

Exemplary chelating agents include ethylenediaminetetraacetic acid (EDTA) and salts and hydrates thereof (e.g., sodium edetate, disodium edetate, trisodium edetate, calcium disodium edetate, dipotassium edetate, and the like), citric acid and salts and hydrates thereof (e.g., citric acid monohydrate), fumaric acid and salts and hydrates thereof, malic acid and salts and hydrates thereof, phosphoric acid and salts and hydrates thereof, and tartaric acid and salts and hydrates thereof. Exemplary antimicrobial preservatives include benzalkonium chloride, benzethonium chloride, benzyl alcohol, bronopol, cetrimide, cetylpyridinium chloride, chlorhexidine, chlorobutanol, chlorocresol, chloroxylenol, cresol, ethyl alcohol, glycerin, hexetidine, imidurea, phenol, phenoxyethanol, phenylethyl alcohol, phenylmercuric nitrate, propylene glycol, and thimerosal.

Exemplary antifungal preservatives include butyl paraben, methyl paraben, ethyl paraben, propyl paraben, benzoic acid, hydroxybenzoic acid, potassium benzoate, potassium sorbate, sodium benzoate, sodium propionate, and sorbic acid.

Exemplary alcohol preservatives include ethanol, polyethylene glycol, phenol, phenolic compounds, bisphenol, chlorobutanol, hydroxybenzoate, and phenylethyl alcohol.

Exemplary acidic preservatives include vitamin A, vitamin C, vitamin E, beta-carotene, citric acid, acetic acid, dehydroacetic acid, ascorbic acid, sorbic acid, and phytic acid.

Other preservatives include tocopherol, tocopherol acetate, deteroxime mesylate, cetrimide, butylated hydroxyanisol (BHA), butylated hydroxytoluened (BHT), ethylenediamine, sodium lauryl sulfate (SLS), sodium lauryl ether sulfate (SLES), sodium bisulfite, sodium metabisulfite, potassium sulfite, potassium metabisulfite, Glydant Plus, Phenonip, methylparaben, Germall 115, Germaben II, Neolone, Kathon, and Euxyl. In certain embodiments, the preservative is an anti-oxidant. In other embodiments, the preservative is a chelating agent.

Exemplary buffering agents include citrate buffer solutions, acetate buffer solutions, phosphate buffer solutions, ammonium chloride, calcium carbonate, calcium chloride, calcium citrate, calcium glubionate, calcium gluceptate, calcium gluconate, D-gluconic acid, calcium glycerophosphate, calcium lactate, propanoic acid, calcium levulinate, pentanoic acid, dibasic calcium phosphate, phosphoric acid, tribasic calcium phosphate, calcium hydroxide phosphate, potassium acetate, potassium chloride, potassium gluconate, potassium mixtures, dibasic potassium phosphate, monobasic potassium phosphate, potassium phosphate mixtures, sodium acetate, sodium bicarbonate, sodium chloride, sodium citrate, sodium lactate, dibasic sodium phosphate, monobasic sodium phosphate, sodium phosphate mixtures, tromethamine, magnesium hydroxide, aluminum hydroxide, alginic acid, pyrogen-free water, isotonic saline, Ringer's solution, ethyl alcohol, etc., and combinations thereof.

Exemplary lubricating agents include magnesium stearate, calcium stearate, stearic acid, silica, talc, malt, glyceryl behanate, hydrogenated vegetable oils, polyethylene glycol, sodium benzoate, sodium acetate, sodium chloride, leucine, magnesium lauryl sulfate, sodium lauryl sulfate, etc., and combinations thereof.

Exemplary natural oils include almond, apricot kernel, avocado, babassu, bergamot, black current seed, borage, cade, camomile, canola, caraway, carnauba, castor, cinnamon, cocoa butter, coconut, cod liver, coffee, corn, cotton seed, emu, eucalyptus, evening primrose, fish, flaxseed, geraniol, gourd, grape seed, hazel nut, hyssop, isopropyl myristate, jojoba, kukui nut, lavandin, lavender, lemon, litsea cubeba, macademia nut, mallow, mango seed, meadowfoam seed, mink, nutmeg, olive, orange, orange roughy, palm, palm kernel, peach kernel, peanut, poppy seed, pumpkin seed, rapeseed, rice bran, rosemary, safflower, sandalwood, sasquana, savoury, sea buckthorn, sesame, shea butter, silicone, soybean, sunflower, tea tree, thistle, tsubaki, vetiver, walnut, and wheat germ oils. Exemplary synthetic oils include, but are not limited to, butyl stearate, caprylic triglyceride, capric triglyceride, cyclomethicone, diethyl sebacate, dimethicone 360, isopropyl myristate, mineral oil, octyldodecanol, oleyl alcohol, silicone oil, and combinations thereof.

Liquid dosage forms for oral and parenteral administration include pharmaceutically acceptable emulsions, microemulsions, solutions, suspensions, syrups and elixirs. In addition to the active ingredients, the liquid dosage forms may comprise inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can include adjuvants such as wetting agents, emulsifying and suspending agents, sweetening, flavoring, and perfuming agents. In certain embodiments for parenteral administration, the conjugates of the invention are mixed with solubilizing agents such as Cremophor, alcohols, oils, modified oils, glycols, polysorbates, cyclodextrins, polymers, and combinations thereof.

Injectable preparations, for example, sterile injectable aqueous or oleaginous suspensions can be formulated according to the known art using suitable dispersing or wetting agents and suspending agents. The sterile injectable preparation can be a sterile injectable solution, suspension or emulsion in a nontoxic parenterally acceptable diluent or solvent, for example, as a solution in 1,3-butanediol. Among the acceptable vehicles and solvents that can be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This can be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle.

Compositions for rectal or vaginal administration are typically suppositories which can be prepared by mixing the conjugates of this invention with suitable non-irritating excipients or carriers such as cocoa butter, polyethylene glycol or a suppository wax which are solid at ambient temperature but liquid at body temperature and therefore melt in the rectum or vaginal cavity and release the active ingredient.

Solid dosage forms for oral administration include capsules, tablets, pills, powders, and granules. In such solid dosage forms, the active ingredient is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may comprise buffering agents.

Solid compositions of a similar type can be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes. Solid compositions of a similar type can be employed as fillers in soft and hard-filled gelatin capsules using such excipients as lactose or milk sugar as well as high molecular weight polethylene glycols and the like.

The active ingredients can be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active ingredient can be admixed with at least one inert diluent such as sucrose, lactose or starch. Such dosage forms may comprise, as is normal practice, additional substances other than inert diluents, e.g., tableting lubricants and other tableting aids such a magnesium stearate and microcrystalline cellulose. In the case of capsules, tablets and pills, the dosage forms may comprise buffering agents. They may optionally comprise opacifying agents and can be of a composition that they release the active ingredient(s) only, or preferentially, in a certain part of the intestinal tract, optionally, in a delayed manner. Examples of embedding compositions which can be used include polymeric substances and waxes.

Dosage forms for topical and/or transdermal administration of a compound of this invention may include ointments, pastes, creams, lotions, gels, powders, solutions, sprays, inhalants and/or patches. Generally, the active ingredient is admixed under sterile conditions with a pharmaceutically acceptable carrier and/or any needed preservatives and/or buffers as can be required. Additionally, the present invention contemplates the use of transdermal patches, which often have the added advantage of providing controlled delivery of an active ingredient to the body. Such dosage forms can be prepared, for example, by dissolving and/or dispensing the active ingredient in the proper medium. Alternatively or additionally, the rate can be controlled by either providing a rate controlling membrane and/or by dispersing the active ingredient in a polymer matrix and/or gel.

Suitable devices for use in delivering intradermal pharmaceutical compositions described herein include short needle devices such as those described in U.S. Pat. Nos. 4,886,499; 5,190,521; 5,328,483; 5,527,288; 4,270,537; 5,015,235; 5,141,496; and 5,417,662. Intradermal compositions can be administered by devices which limit the effective penetration length of a needle into the skin, such as those described in PCT publication WO 99/34850 and functional equivalents thereof. Jet injection devices which deliver liquid vaccines to the dermis via a liquid jet injector and/or via a needle which pierces the stratum corneum and produces a jet which reaches the dermis are suitable. Jet injection devices are described, for example, in U.S. Pat.

Nos. 5,480,381; 5,599,302; 5,334,144; 5,993,412; 5,649,912; 5,569,189; 5,704,911; 5,383,851; 5,893,397; 5,466,220; 5,339,163; 5,312,335; 5,503,627; 5,064,413; 5,520,639; 4,596,556; 4,790,824; 4,941,880; 4,940,460; and PCT publications WO 97/37705 and WO 97/13537. Ballistic powder/particle delivery devices which use compressed gas to accelerate vaccine in powder form through the outer layers of the skin to the dermis are suitable. Alternatively or additionally, conventional syringes can be used in the classical mantoux method of intradermal administration.

Formulations suitable for topical administration include, but are not limited to, liquid and/or semi liquid preparations such as liniments, lotions, oil in water and/or water in oil emulsions such as creams, ointments and/or pastes, and/or solutions and/or suspensions. Topically-administrable formulations may, for example, comprise from about 1% to about 10% (w/w) active ingredient, although the concentration of the active ingredient can be as high as the solubility limit of the active ingredient in the solvent. Formulations for topical administration may further comprise one or more of the additional ingredients described herein.

A pharmaceutical composition of the invention can be prepared, packaged, and/or sold in a formulation suitable for pulmonary administration via the buccal cavity. Such a formulation may comprise dry particles which comprise the active ingredient and which have a diameter in the range from about 0.5 to about 7 nanometers or from about 1 to about 6 nanometers. Such compositions are conveniently in the form of dry powders for administration using a device comprising a dry powder reservoir to which a stream of propellant can be directed to disperse the powder and/or using a self propelling solvent/powder dispensing container such as a device comprising the active ingredient dissolved and/or suspended in a low-boiling propellant in a sealed container. Such powders comprise particles wherein at least 98% of the particles by weight have a diameter greater than 0.5 nanometers and at least 95% of the particles by number have a diameter less than 7 nanometers. Alternatively, at least 95% of the particles by weight have a diameter greater than 1 nanometer and at least 90% of the particles by number have a diameter less than 6 nanometers. Dry powder compositions may include a solid fine powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic and/or solid anionic surfactant and/or a solid diluent (which may have a particle size of the same order as particles comprising the active ingredient).

Pharmaceutical compositions of the invention formulated for pulmonary delivery may provide the active ingredient in the form of droplets of a solution and/or suspension. Such formulations can be prepared, packaged, and/or sold as aqueous and/or dilute alcoholic solutions and/or suspensions, optionally sterile, comprising the active ingredient, and may conveniently be administered using any nebulization and/or atomization device. Such formulations may further comprise one or more additional ingredients including, but not limited to, a flavoring agent such as saccharin sodium, a volatile oil, a buffering agent, a surface active agent, and/or a preservative such as methylhydroxybenzoate. The droplets provided by this route of administration may have an average diameter in the range from about 0.1 to about 200 nanometers.

The formulations described herein as being useful for pulmonary delivery are useful for intranasal delivery of a pharmaceutical composition of the invention. Another formulation suitable for intranasal administration is a coarse powder comprising the active ingredient and having an average particle from about 0.2 to 500 micrometers. Such a formulation is administered, by rapid inhalation through the nasal passage from a container of the powder held close to the nares.

Formulations for nasal administration may, for example, comprise from about as little as 0.1% (w/w) and as much as 100% (w/w) of the active ingredient, and may comprise one or more of the additional ingredients described herein. A pharmaceutical composition of the invention can be prepared, packaged, and/or sold in a formulation for buccal administration. Such formulations may, for example, be in the form of tablets and/or lozenges made using conventional methods, and may contain, for example, 0.1 to 20% (w/w) active ingredient, the balance comprising an orally dissolvable and/or degradable composition and, optionally, one or more of the additional ingredients described herein. Alternately, formulations for buccal administration may comprise a powder and/or an aerosolized and/or atomized solution and/or suspension comprising the active ingredient. Such powdered, aerosolized, and/or aerosolized formulations, when dispersed, may have an average particle and/or droplet size in the range from about 0.1 to about 200 nanometers, and may further comprise one or more of the additional ingredients described herein.

A pharmaceutical composition of the invention can be prepared, packaged, and/or sold in a formulation for ophthalmic administration. Such formulations may, for example, be in the form of eye drops including, for example, a 0.1/1.0% (w/w) solution and/or suspension of the active ingredient in an aqueous or oily liquid carrier. Such drops may further comprise buffering agents, salts, and/or one or more other of the additional ingredients described herein. Other opthalmically administrable formulations which are useful include those which comprise the active ingredient in microcrystalline form and/or in a liposomal preparation. Ear drops and/or eye drops are contemplated as being within the scope of this invention.

Although the descriptions of pharmaceutical compositions provided herein are principally directed to pharmaceutical compositions which are suitable for administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and/or perform such modification with ordinary experimentation. General considerations in the formulation and/or manufacture of pharmaceutical compositions can be found, for example, in *Remington: The Science and Practice of Pharmacy* 21$^{st}$ ed., Lippincott Williams & Wilkins, 2005.

Still further encompassed by the invention are pharmaceutical packs and/or kits. Pharmaceutical packs and/or kits provided may comprise a provided composition and a container (e.g., a vial, ampoule, bottle, syringe, and/or dispenser package, or other suitable container). In some embodiments, provided kits may optionally further include a second container comprising a suitable aqueous carrier for dilution or suspension of the provided composition for preparation of administration to a subject. In some embodiments, contents of provided formulation container and solvent container combine to form at least one unit dosage form.

Optionally, a single container may comprise one or more compartments for containing a provided composition, and/or appropriate aqueous carrier for suspension or dilution. In some embodiments, a single container can be appropriate for modification such that the container may receive a physical modification so as to allow combination of compartments and/or components of individual compartments. For example, a foil or plastic bag may comprise two or more compartments separated by a perforated seal which can be broken so as to allow combination of contents of two individual compartments once the signal to break the seal is generated. A pharmaceutical pack or kit may thus comprise such multi-compartment containers including a provided composition and appropriate solvent and/or appropriate aqueous carrier for suspension.

Optionally, instructions for use are additionally provided in such kits of the invention. Such instructions may provide, generally, for example, instructions for dosage and administration. In other embodiments, instructions may further provide additional detail relating to specialized instructions for particular containers and/or systems for administration. Still further, instructions may provide specialized instructions for use in conjunction and/or in combination with additional therapy.

Methods of Treatment

The present invention also provides methods of using the compounds of Formula (I) or (II) as described herein for treating a condition associated with aberrant activity of a kinase. "Aberrant activity" of a kinase refers to any undesired activity, and includes, but is not limited to, overactivity and/or over-expression of the kinase compared to a normal cell. Such methods include therapeutic as well as prophylactic (preventative) methods.

For example, in one aspect, provided is a method of treating a condition associated with aberrant activity of a kinase, the method comprising administering an effective amount of a compound of Formula (I) or (II), or pharmaceutical composition thereof, to a subject in need thereof in an amount sufficient to reduce kinase activity.

In certain embodiments, the compound reduces or prevents kinase activity by targeted degradation of the kinase. In certain embodiments, the compound reduces kinase activity by inducing unfolding of the kinase. In certain embodiments, the compound reduces kinase activity by inducing degradation of the kinase. In certain embodiments, the compound reduces kinase activity by covalently binding to the kinase. In certain embodiments, compound reduces kinase activity by non-covalently binding to the kinase.

Exemplary conditions associated with aberrant activity of a kinase includes, but are not limited to, proliferative disorders, inflammatory disorders, autoimmune disorders, painful conditions, metabolic disorders, CNS disorders, and viral infections.

In certain embodiments, the condition associated with aberrant activity of a kinase is a proliferative disorder. Exemplary proliferative diseases include, but are not limited to, tumors, begnin neoplasms, pre-malignant neoplasms (carcinoma in situ), and malignanat neoplasms (cancers).

Exemplary cancers include, but are not limited to, acoustic neuroma, adenocarcinoma, adrenal gland cancer, anal cancer, angiosarcoma (e.g., lymphangiosarcoma, lymphangioendotheliosarcoma, hemangiosarcoma), appendix cancer, benign monoclonal gammopathy, biliary cancer (e.g., cholangiocarcinoma), bladder cancer, breast cancer (e.g., adenocarcinoma of the breast, papillary carcinoma of the breast, mammary cancer, medullary carcinoma of the breast), brain cancer (e.g., meningioma; glioma, e.g., astrocytoma, oligodendroglioma; medulloblastoma), bronchus cancer, carcinoid tumor, cervical cancer (e.g., cervical adenocarcinoma), choriocarcinoma, chordoma, craniopharyngioma, colorectal cancer (e.g., colon cancer, rectal cancer, colorectal adenocarcinoma), epithelial carcinoma, ependymoma, endotheliosarcoma (e.g., Kaposi's sarcoma, multiple idiopathic hemorrhagic sarcoma), endometrial cancer (e.g., uterine cancer, uterine sarcoma), esophageal cancer (e.g., adenocarcinoma of the esophagus, Barrett's adenocarinoma), Ewing's sarcoma, eye cancer (e.g., intraocular melanoma, retinoblastoma), familiar hypereosinophilia, gall bladder cancer, gastric cancer (e.g., stomach adenocarcinoma), gastrointestinal stromal tumor (GIST), head and neck cancer (e.g., head and neck squamous cell carcinoma, oral cancer (e.g., oral squamous cell carcinoma (OSCC), throat cancer (e.g., laryngeal cancer, pharyngeal cancer, nasopharyngeal cancer, oropharyngeal cancer)), hematopoietic cancers (e.g., leukemia such as acute lymphocytic leukemia (ALL) (e.g., B-cell ALL, T-cell ALL), acute myelocytic leukemia (AML) (e.g., B-cell AML, T-cell AML), chronic myelocytic leukemia (CML) (e.g., B-cell CML, T-cell CML), and chronic lymphocytic leukemia (CLL) (e.g., B-cell CLL, T-cell CLL); lymphoma such as Hodgkin lymphoma (HL) (e.g., B-cell HL, T-cell HL) and non-Hodgkin lymphoma (NHL) (e.g., B-cell NHL such as diffuse large cell lymphoma (DLCL) (e.g., diffuse large B-cell lymphoma (DLBCL)), follicular lymphoma, chronic lymphocytic leukemia/small lymphocytic lymphoma (CLL/SLL), mantle cell lymphoma (MCL), marginal zone B-cell lymphomas (e.g., mucosa-associated lymphoid tissue (MALT) lymphomas, nodal marginal zone B-cell lymphoma, splenic marginal zone B-cell lymphoma), primary mediastinal B-cell lymphoma, Burkitt lymphoma, lymphoplasmacytic lymphoma (i.e., "Waldenström's macroglobulinemia"), hairy cell leukemia (HCL), immunoblastic large cell lymphoma, precursor B-lymphoblastic lymphoma and primary central nervous system (CNS) lymphoma; and T-cell NHL such as precursor T-lymphoblastic lymphoma/leukemia, peripheral T-cell lymphoma (PTCL) (e.g., cutaneous T-cell lymphoma (CTCL) (e.g., mycosis fungiodes, Sezary syndrome), angioimmunoblastic T-cell lymphoma, extranodal natural killer T-cell lymphoma, enteropathy type T-cell lymphoma, subcutaneous panniculitis-like T-cell lymphoma, anaplastic large cell lymphoma); a mixture of one or more leukemia/lymphoma as described above; and multiple myeloma (MM)), heavy chain disease (e.g., alpha chain disease, gamma chain disease, mu chain disease), hemangioblastoma, inflammatory myofibroblastic tumors, immunocytic amyloidosis, kidney cancer (e.g., nephroblastoma a.k.a. Wilms' tumor, renal cell carcinoma), liver cancer (e.g., hepatocellular cancer (HCC), malignant hepatoma), lung cancer (e.g., bronchogenic carcinoma, small cell lung cancer (SCLC), non-small cell lung cancer (NSCLC), adenocarcinoma of the lung), leiomyosarcoma (LMS), mastocytosis (e.g., systemic mastocytosis), myelodysplastic syndrome (MDS), mesothelioma, myeloproliferative disorder (MPD) (e.g., polycythemia Vera (PV), essential thrombocytosis (ET), agnogenic myeloid metaplasia (AMM) a.k.a. myelofibrosis (MF), chronic idiopathic myelofibrosis, chronic myelocytic leukemia (CML), chronic neutrophilic leukemia (CNL), hypereosinophilic syndrome (HES)), neuroblastoma, neurofibroma (e.g., neurofibromatosis (NF) type 1 or type 2, schwannomatosis), neuroendocrine cancer (e.g., gastroenteropancreatic neuroendoctrine tumor (GEP-NET), carcinoid tumor), osteosarcoma, ovarian cancer (e.g., cystadenocarcinoma, ovarian embryonal carcinoma, ovarian adenocarcinoma), papillary adenocarcinoma, pancreatic cancer (e.g., pancreatic andenocarcinoma, intraductal papillary mucinous neoplasm (IPMN), Islet cell tumors), penile cancer (e.g., Paget's disease of the penis and scrotum), pinealoma, primitive neuroectodermal tumor (PNT), prostate cancer (e.g., prostate adenocarcinoma), rectal cancer, rhabdomyosarcoma, salivary gland cancer, skin cancer (e.g., squamous cell carcinoma (SCC), keratoacanthoma (KA), melanoma, basal cell carcinoma (BCC)), small bowel cancer (e.g., appendix cancer), soft tissue sarcoma (e.g., malignant fibrous histiocytoma (MFH), liposarcoma, malignant peripheral nerve sheath tumor (MPNST), chondrosarcoma, fibrosarcoma, myxosarcoma), sebaceous gland carcinoma, sweat gland carcinoma, synovioma, testicular cancer (e.g., seminoma, testicular embryonal carcinoma), thyroid cancer (e.g., papillary carcinoma of the thyroid, papillary thyroid carcinoma (PTC), medullary thyroid cancer), urethral cancer, vaginal cancer and vulvar cancer (e.g., Paget's disease of the vulva).

In certain embodiments, the condition associated with aberrant activity of a kinase is an inflammatory disorder. The term "inflammatory disorder" refers to those diseases, disorders or conditions that are characterized by signs of pain (dolor, from the generation of noxious substances and the stimulation of nerves), heat (calor, from vasodilatation), redness (rubor, from vasodilatation and increased blood flow), swelling (tumor, from excessive inflow or restricted outflow of fluid), and/or loss of function (functio laesa, which can be partial or complete, temporary or permanent. Inflammation takes on many forms and includes, but is not limited to, acute, adhesive, atrophic, catarrhal, chronic, cirrhotic, diffuse, disseminated, exudative, fibrinous, fibrosing, focal, granulomatous, hyperplastic, hypertrophic, interstitial, metastatic, necrotic, obliterative, parenchymatous, plastic, productive, proliferous, pseudomembranous, purulent, sclerosing, seroplastic, serous, simple, specific, subacute, suppurative, toxic, traumatic, and/or ulcerative inflammation.

Exemplary inflammatory disorders include, but are not limited to, inflammation associated with acne, anemia (e.g., aplastic anemia, haemolytic autoimmune anaemia), asthma, arteritis (e.g., polyarteritis, temporal arteritis, periarteritis nodosa, Takayasu's arteritis), arthritis (e.g., crystalline arthritis, osteoarthritis, psoriatic arthritis, gouty arthritis, reactive arthritis, rheumatoid arthritis and Reiter's arthritis), ankylosing spondylitis, amylosis, amyotrophic lateral sclerosis, autoimmune diseases, allergies or allergic reactions, atherosclerosis, bronchitis, bursitis, chronic prostatitis, conjunctivitis, Chagas disease, chronic obstructive pulmonary disease, cermatomyositis, diverticulitis, diabetes (e.g., type I diabetes mellitus, type 2 diabetes mellitus), a skin condition (e.g., psoriasis, eczema, burns, dermatitis, pruritus (itch)), endometriosis, Guillain-Barre syndrome, infection, ischaemic heart disease, Kawasaki disease, glomerulonephritis, gingivitis, hypersensitivity, headaches (e.g., migraine headaches, tension headaches), ileus (e.g., postoperative ileus and ileus during sepsis), idiopathic thrombocytopenic purpura, interstitial cystitis (painful bladder syndrome), gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), lupus, multiple sclerosis, morphea, myesthenia gravis, myocardial ischemia, nephrotic syndrome, pemphigus vulgaris, pernicious aneaemia, peptic ulcers, polymyositis, primary biliary cirrhosis, neuroinflammation associated with brain disorders (e.g., Parkinson's disease, Huntington's disease, and Alzheimer's disease), prostatitis, chronic inflammation associated with cranial radiation injury, pelvic inflammatory disease, reperfusion injury, regional enteritis, rheumatic fever, systemic lupus erythematosus, schleroderma, scierodoma, sarcoidosis, spondyloarthopathies, Sjogren's syndrome, thyroiditis, transplantation rejection, tendonitis, trauma or injury (e.g., frostbite, chemical irritants, toxins, scarring, burns, physical injury), vasculitis, vitiligo and Wegener's granulomatosis.

In certain embodiments, the inflammatory disorder is inflammation associated with a proliferative disorder, e.g., inflammation associated with cancer.

In certain embodiments, the condition associated with aberrant activity of a kinase is an autoimmune disorder. Exemplary autoimmune disorders include, but are not limited to, arthritis (including rheumatoid arthritis, spondyloarthopathies, gouty arthritis, degenerative joint diseases such as osteoarthritis, systemic lupus erythematosus, Sjogren's syndrome, ankylosing spondylitis, undifferentiated spondylitis, Behcet's disease, haemolytic autoimmune anaemias, multiple sclerosis, amyotrophic lateral sclerosis, amylosis, acute painful shoulder, psoriatic, and juvenile arthritis), asthma, atherosclerosis, osteoporosis, bronchitis, tendonitis, bursitis, skin condition (e.g., psoriasis, eczema, burns, dermatitis, pruritus (itch)), enuresis, eosinophilic disease, gastrointestinal disorder (e.g., selected from peptic ulcers, regional enteritis, diverticulitis, gastrointestinal bleeding, eosinophilic gastrointestinal disorders (e.g., eosinophilic esophagitis, eosinophilic gastritis, eosinophilic gastroenteritis, eosinophilic colitis), gastritis, diarrhea, gastroesophageal reflux disease (GORD, or its synonym GERD), inflammatory bowel disease (IBD) (e.g., Crohn's disease, ulcerative colitis, collagenous colitis, lymphocytic colitis, ischaemic colitis, diversion colitis, Behcet's syndrome, indeterminate colitis) and inflammatory bowel syndrome (IBS)), and disorders ameliorated by a gastroprokinetic agent (e.g., ileus, postoperative ileus and ileus during sepsis; gastroesophageal reflux disease (GORD, or its synonym GERD); eosinophilic esophagitis, gastroparesis such as diabetic gastroparesis; food intolerances and food allergies and other functional bowel disorders, such as nonulcerative dyspepsia (NUD) and non-cardiac chest pain (NCCP, including costo-chondritis)).

In certain embodiments, the condition associated with aberrant activity of a kinase is a painful condition. A "painful condition" includes, but is not limited to, neuropathic pain (e.g., peripheral neuropathic pain), central pain, deafferentiation pain, chronic pain (e.g., chronic nociceptive pain, and other forms of chronic pain such as post-operative pain, e.g., pain arising after hip, knee, or other replacement surgery), pre-operative pain, stimulus of nociceptive receptors (nociceptive pain), acute pain (e.g., phantom and transient acute pain), noninflammatory pain, inflammatory pain, pain associated with cancer, wound pain, burn pain, postoperative pain, pain associated with medical procedures, pain resulting from pruritus, painful bladder syndrome, pain associated with premenstrual dysphoric disorder and/or premenstrual syndrome, pain associated with chronic fatigue syndrome, pain associated with pre-term labor, pain associated with withdrawl symptoms from drug addiction, joint pain, arthritic pain (e.g., pain associated with crystalline arthritis, osteoarthritis, psoriatic arthritis, gouty arthritis, reactive arthritis, rheumatoid arthritis or Reiter's arthritis), lumbosacral pain, musculo-skeletal pain, headache, migraine, muscle ache, lower back pain, neck pain, toothache, dental/maxillofacial pain, visceral pain and the like. One or more of the painful conditions contemplated herein can comprise mixtures of various types of pain provided above and herein (e.g. nociceptive pain, inflammatory pain, neuropathic pain, etc.). In some embodiments, a particular pain can dominate. In other embodiments, the painful condition comprises two or more types of pains without one dominating. A skilled clinician can determine the dosage to achieve a therapeutically effective amount for a particular subject based on the painful condition.

In certain embodiments, the painful condition is inflammatory pain. In certain embodiments, the painful condition (e.g., inflammatory pain) is associated with an inflammatory disorder and/or an autoimmune disorder.

In certain embodiments, the condition associated with aberrant activity of a kinase is a metabolic disorder (e.g., a wasting condition, an obesity-related condition or complication thereof).

In certain embodiments, the metabolic disorder is a wasting condition. A "wasting condition," as used herein, includes but is not limited to, anorexia and cachexias of various natures (e.g., weight loss associated with cancer, weight loss associated with other general medical conditions, weight loss associated with failure to thrive, and the like). In certain embodiments, the metabolic disorder is an obesity-related condition or a complication thereof. An "obesity-related condition" as used herein, includes, but is not limited to, obesity, undesired weight gain (e.g., from medication-induced weight gain, from cessation of smoking) and an over-eating disorder (e.g., binge eating, bulimia, compulsive eating, or a lack of appetite control each of which can optionally lead to undesired weight gain or obesity). "Obesity" and "obese" as used herein, refers to class I obesity, class II obesity, class III obesity and pre-obesity (e.g., being "over-weight") as defined by the World Health Organization.

In certain embodiments, the condition associated with aberrant activity of a kinase is a CNS disorder. Exemplary CNS disorders include, but are not limited to, neurotoxicity and/or neurotrauma, stroke, multiple sclerosis, spinal cord injury, epilepsy, a mental disorder, a sleep condition, a movement disorder, nausea and/or emesis, amyotrophic lateral sclerosis, Alzheimer's disease and drug addiction.

In certain embodiments, the CNS disorder is neurotoxicity and/or neurotrauma, e.g., for example, as a result of acute neuronal injury (e.g., tramatic brain injury (TBI), stroke, epilepsy) or a chronic neurodegenerative disorder (e.g., multiple sclerosis, Parkinson's disease, Huntington's disease, amyotrophic lateral sclerosis, Alzheimer's disease).

In certain embodiments, the CNS disorder is a mental disorder, e.g., for example, depression, anxiety or anxiety-related conditions, a learning disability or schizophrenia.

In certain embodiments, the CNS disorder is depression. "Depression," as used herein, includes, but is not limited to, depressive disorders or conditions, such as, for example, major depressive disorders (e.g., unipolar depression), dysthymic disorders (e.g., chronic, mild depression), bipolar disorders (e.g., manic-depression), seasonal affective disorder, and/or depression associated with drug addiction (e.g., withdrawal). The depression can be clinical or subclinical depression. The depression can be associated with or prementrual syndrome and/or premenstrual dysphoric disorder.

In certain embodiments, the CNS disorder is anxiety. "Anxiety," as used herein, includes, but is not limited to anxiety and anxiety-related conditions, such as, for example, clinical anxiety, panic disorder, agoraphobia, generalized anxiety disorder, specific phobia, social phobia, obsessive-compulsive disorder, acute stress disorder, post-traumatic stress disorder, adjustment disorders with anxious features, anxiety disorder associated with depression, anxiety disorder due to general medical conditions, and substance-induced anxiety disorders, anxiety associated with drug addiction (e.g., withdrawal, dependence, reinstatement) and anxiety associated with nausea and/or emesis. This treatment may also be to induce or promote sleep in a subject (e.g., for example, a subject with anxiety).

In certain embodiments, the CNS disorder is a learning disorder (e.g., attention deficit disorder (ADD)).

In certain embodiments, the CNS disorder is Schizophrenia.

In certain embodiments, the CNS disorder is a sleep condition. "Sleep conditions" include, but are not limited to, insomia, narcolepsy, sleep apnea, restless legs syndrome (RLS), delayed sleep phase syndrome (DSPS), periodic limb movement disorder (PLMD), hypopnea syndrome, rapid eye movement behavior disorder (RBD), shift work sleep condition (SWSD), and sleep problems (e.g., parasomnias) such as nightmares, night terrors, sleep talking, head banging, snoring, and clenched jaw and/or grinding of teeth (bruxism).

In certain embodiments, the CNS disorder is a movement disorder, e.g., basal ganglia disorders, such as, for example, Parkinson's disease, levodopa-induced dyskinesia, Huntington's disease, Gilles de Ia Tourette's syndrome, tardive diskinesia and dystonia.

In certain embodiments, the CNS disorder is Alzheimer's disease.

In certain embodiments, the CNS disorder is amyotrophic lateral sclerosis (ALS).

In certain embodiments, the CNS disorder is nausea and/or emesis.

In certain embodiments, the CNS disorder is drug addiction (e.g., for instance, addiction to opiates, nicotine, cocaine, psychostimulants or alcohol).

In certain embodiments, the condition associated with aberrant activity of a kinase is a viral infection.

In certain embodiments of Formula (I) and (II), the kinase is Her3 protein kinase. In this instance, in certain embodiments, the condition associated with aberrant activity of Her3 protein kinase is a proliferative disorder. In certain embodiments, the proliferative disorder associated with aberrant activity of Her3 protein kinase is cancer. In certain embodiments, the cancer associated with aberrant activity of Her3 protein kinase is breast cancer, lung cancer, or ovarian cancer. In certain embodiments, the breast cancer associated with aberrant activity of Her3 protein kinase is Her2 driven breast cancer. In certain embodiments, the lung cancer associated with aberrant activity of Her3 protein kinase is gefitinib resistant lung cancer. In certain embodiments, the lung cancer is NSCLC.

Compounds of Formula (I) or (II) may be formulated in dosage unit form for ease of administration and uniformity of dosage. It will be understood, however, that the total daily usage of the compositions comprising a compound of Formula (I) or (II) will be decided by the attending physician within the scope of sound medical judgment. The specific therapeutically effective dose level for any particular subject or organism will depend upon a variety of factors including the disease, disorder, or condition being treated and the severity of the disorder; the activity of the specific active ingredient employed; the specific composition employed; the age, body weight, general health, sex and diet of the subject; the time of administration, route of administration, and rate of excretion of the specific active ingredient employed; the duration of the treatment; drugs used in combination or coincidental with the specific active ingredient employed; and like factors well known in the medical arts.

The compounds and compositions provided herein can be administered by any route, including enteral (e.g., oral), parenteral, intravenous, intramuscular, intra-arterial, intramedullary, intrathecal, subcutaneous, intraventricular, transdermal, interdermal, rectal, intravaginal, intraperitoneal, topical (as by powders, ointments, creams, and/or drops), mucosal, nasal, bucal, sublingual; by intratracheal instillation, bronchial instillation, and/or inhalation; and/or as an oral spray, nasal spray, and/or aerosol. Specifically contemplated routes are oral administration, intravenous administration (e.g., systemic intravenous injection), regional administration via blood and/or lymph supply, and/or direct administration to an affected site. In general the most appropriate route of administration will depend upon a variety of factors including the nature of the agent (e.g., its stability in the environment of the gastrointestinal tract), the condition of the subject (e.g., whether the subject is able to tolerate oral administration).

The exact amount of a compound required to achieve an effective amount will vary from subject to subject, depending, for example, on species, age, and general condition of a subject, severity of the side effects or disorder, identity of the particular compound(s), mode of administration, and the like. The desired dosage can be delivered three times a day, two times a day, once a day, every other day, every third day, every week, every two weeks, every three weeks, or every four weeks. In certain embodiments, the desired dosage can be delivered using multiple administrations (e.g., two, three, four, five, six, seven, eight, nine, ten, eleven, twelve, thirteen, fourteen, or more administrations).

In certain embodiments, an effective amount of a compound for administration one or more times a day to a 70 kg adult human may comprise about 0.0001 mg to about 3000 mg, about 0.0001 mg to about 2000 mg, about 0.0001 mg to about 1000 mg, about 0.001 mg to about 1000 mg, about 0.01 mg to about 1000 mg, about 0.1 mg to about 1000 mg, about 1 mg to about 1000 mg, about 1 mg to about 100 mg, about 10 mg to about 1000 mg, or about 100 mg to about 1000 mg, of a compound per unit dosage form.

In certain embodiments, the compounds of the invention may be administered orally or parenterally at dosage levels sufficient to deliver from about 0.001 mg/kg to about 100 mg/kg, from about 0.01 mg/kg to about 50 mg/kg, preferably from about 0.1 mg/kg to about 40 mg/kg, preferably from about 0.5 mg/kg to about 30 mg/kg, from about 0.01 mg/kg to about 10 mg/kg, from about 0.1 mg/kg to about 10 mg/kg, and more preferably from about 1 mg/kg to about 25 mg/kg, of subject body weight per day, one or more times a day, to obtain the desired therapeutic effect.

It will be appreciated that dose ranges as described herein provide guidance for the administration of provided pharmaceutical compositions to an adult. The amount to be administered to, for example, a child or an adolescent can be determined by a medical practitioner or person skilled in the art and can be lower or the same as that administered to an adult.

It will be also appreciated that a compound or composition, as described herein, can be administered in combination with one or more additional therapeutically active agents. The compounds or compositions can be administered in combination with additional therapeutically active agents that improve their bioavailability, reduce and/or modify their metabolism, inhibit their excretion, and/or modify their distribution within the body. It will also be appreciated that the therapy employed may achieve a desired effect for the same disorder (for example, a compound can be administered in combination with an anti-inflammatory agent, anti-cancer agent, etc.), and/or it may achieve different effects (e.g., control of adverse side-effects, e.g., emesis controlled by an anti-emetic).

The compound or composition can be administered concurrently with, prior to, or subsequent to, one or more additional therapeutically active agents. In general, each agent will be administered at a dose and/or on a time schedule determined for that agent. In will further be appreciated that the additional therapeutically active agent utilized in this combination can be administered together in a single composition or administered separately in different compositions. The particular combination to employ in a regimen will take into account compatibility of the inventive compound with the additional therapeutically active agent and/or the desired therapeutic effect to be achieved. In general, it is expected that additional therapeutically active agents utilized in combination be utilized at levels that do not exceed the levels at which they are utilized individually. In some embodiments, the levels utilized in combination will be lower than those utilized individually. Additional therapeutically active agents include, but are not limited to, small organic molecules such as drug compounds (e.g., compounds approved by the Food and Drugs Administration as provided in the Code of Federal Regulations (CFR)), peptides, proteins, carbohydrates, monosaccharides, oligosaccharides, polysaccharides, nucleoproteins, mucoproteins, lipoproteins, synthetic polypeptides or proteins, small molecules linked to proteins, glycoproteins, steroids, nucleic acids, DNAs, RNAs, nucleotides, nucleosides, oligonucleotides, antisense oligonucleotides, lipids, hormones, vitamins and cells. In certain embodiments, the additional therapeutically agent is a cancer agent (e.g., a biotherapeutic or chemotherapeutic cancer agent). In other embodiments, the additional therapeutically active agent is an anti-inflammatory agent.

Methods of Preparation

Compounds of the present invention may be prepared by coupling a compound substituted with a group -L$^3$-X* with a compound of formula Y*-L$^4$-R$^H$, wherein X* and Y* react together to form a group A, thus providing a compound substituted with a group of formula -L$^3$-A-L$^4$-R$^H$. It should be understood that the group of formula -L$^3$-A-L$^4$- is encompassed by the group of formula -L$^1$- as defined herein.

Scheme 2.

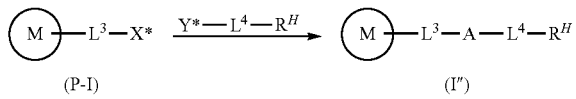

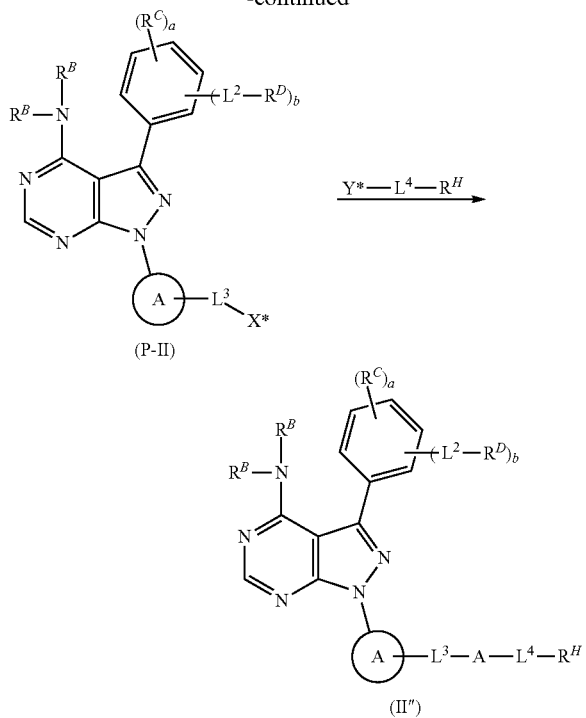

(P-II)

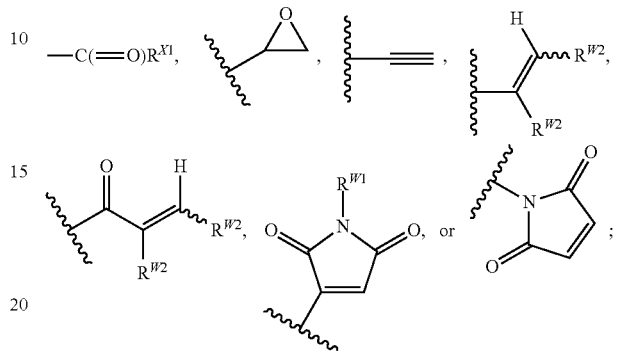

(II″)

It should also be understood that, for a compound of Formula (P-I) or (P-II), the group $Y^*$ of the compound of formula $Y^*$-$L^4$-$R^H$, should be complimentary and reactive with the group $X^*$ present on the precursor compound in order to form the compound of Formula (I″) or (II″). For example, if the group $Y^*$ is a nucleophilic group, the group $X^*$ must be a electrophilic group. Likewise, if the group $Y^*$ is an electrophilic group, the group $X^*$ must be a nucleophilic group. While $X^*$ and $Y^*$ are defined the same in the present invention, it is thus understood that such groups are paired compliments.

In certain embodiments, the coupling of a compound substituted with a group -$L^3$-$X^*$ with a compound of formula $Y^*$-$L^4$-$R^H$ is via "click chemistry." Click chemistry is a chemical philosophy introduced by Sharpless in 2001 and describes chemistry tailored to generate substances quickly and reliably by joining small units together. See, e.g., Kolb, Finn and Sharpless, *Angewandte Chemie International Edition* (2001) 40: 2004-2021; Evans, *Australian Journal of Chemistry* (2007) 60: 384-395. Exemplary coupling reactions (some of which may be classified as "click chemistry") include, but are not limited to, formation of esters, thioesters, amides (e.g., such as peptide coupling) from activated acids or acyl halides; nucleophilic displacement reactions (e.g., such as nucleophilic displacement of a halide or ring opening of strained ring systems); azide-alkyne Huisgen cycloaddition; thiol-yne addition; imine formation; and Michael additions (e.g., maleimide addition).

In any of the above and below embodiments, $L^3$ and $L^4$ represent a bond or a linker selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof. Groups of formula A, $X^*$, and $Y^*$ are further defined herein.

In any of the embodiments herein, $X^*$ and $Y^*$ independently represent a group —SH, —OH, —$NH_2$, —NH—$NH_2$, —$N_3$, —O—$NH_2$, halogen (or other leaving group), wherein:

$R^{X1}$ is hydrogen, halogen, or —$OR^2$, wherein $R^{X2}$ is hydrogen, substituted or unsubstituted alkyl, substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or an oxygen protecting group;

W is O, S, or $NR^{W1}$;

$R^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or a nitrogen protecting group; and $R^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^{W2}$ groups are joined to form a 5-6 membered ring.

In certain embodiments, $Y^*$ is —SH. In certain embodiments, $X^*$ is —SH.

In certain embodiments, $Y^*$ is —OH. In certain embodiments, $X^*$ is —OH.

In certain embodiments, $Y^*$ is —$NH_2$. In certain embodiments, $X^*$ is —$NH_2$.

In certain embodiments, $Y^*$ is —NH—$NH_2$. In certain embodiments, $X^*$ is —NH—$NH_2$.

In certain embodiments, $Y^*$ is —O—$NH_2$. In certain embodiments, $X^*$ is —O—$NH_2$.

In certain embodiments, $Y^*$ is —$N_3$. In certain embodiments, $X^*$ is —$N_3$.

In certain embodiments, $Y^*$ is halogen, e.g., —Cl, —Br, or —I. In certain embodiments, $X^*$ is halogen, e.g., —Cl, —Br, or —I.

In certain embodiments, $Y^*$ is —C(=O)$R^{X1}$, wherein $R^{X1}$ is hydrogen, i.e., to provide $Y^*$ as an aldehyde —CHO. In certain embodiments, $X^*$ is —C(=O)$R^{X1}$, wherein $R^{X1}$ is hydrogen, i.e., to provide $X^*$ as an aldehyde —CHO.

In certain embodiments, Y* is —C(=O)R$^{X1}$, wherein R$^{X1}$ is halogen (e.g., "Hal" representing —Cl, —Br, and —I), i.e., to provide Y* as an acyl halide —C(=O)—Hal.

In certain embodiments, X* is —C(=O)R$^{X1}$, wherein R$^{X1}$ is halogen (e.g., "Hal" representing —Cl, —Br, and —I), i.e., to provide X* as an acyl halide —C(=O)—Hal.

In certain embodiments, Y* is —C(=O)R$^{X1}$, wherein R$^{X1}$ is —OR$^{X2}$, and wherein R$^{X2}$ is hydrogen, i.e., to provide Y* as a carboxylic acid —C(=O)OH.

In certain embodiments, X* is —C(=O)R$^{X1}$, wherein R$^{X1}$ is —OR$^{X2}$, and wherein R$^{X2}$ is hydrogen, i.e., to provide X* as a carboxylic acid —C(=O)OH.

In certain embodiments, Y* is —C(=O)R$^{X1}$, wherein R$^{Z1}$ is —OR$^{X2}$, and wherein R$^{X2}$ is substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or an oxygen protecting group, i.e., to provide Y* as an ester —C(=O)OR$^{X2}$.

In certain embodiments, X* is —C(=O)R$^{X1}$, wherein R$^{Z1}$ is —OR$^{X2}$, and wherein R$^{X2}$ is substituted or unsubstituted alkyl; substituted or unsubstituted alkenyl; substituted or unsubstituted alkynyl; substituted or unsubstituted heteroalkyl; substituted or unsubstituted heteroalkenyl; substituted or unsubstituted heteroalkynyl; substituted or unsubstituted carbocyclyl; substituted or unsubstituted heterocyclyl; substituted or unsubstituted aryl; substituted or unsubstituted heteroaryl; or an oxygen protecting group, i.e., to provide X* as an ester —C(=O)OR$^{X2}$.

In certain embodiments, X* or Y* is an oxiranyl of formula:

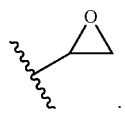

In certain embodiments, X* or Y* is ethynyl:

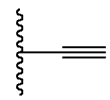

In certain embodiments, X* or Y* is ethenyl:

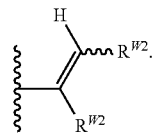

In certain embodiments, X* or Y* is an α,β-unsaturated carbonyl:

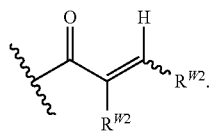

In certain embodiments, X* or Y* is a maleimide group:

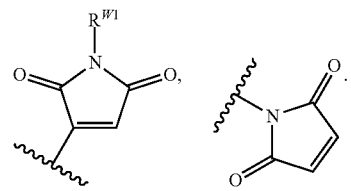

Furthermore, as generally understood herein, X* and Y* may react together to form a group A, wherein A is a group of the formula:

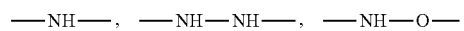

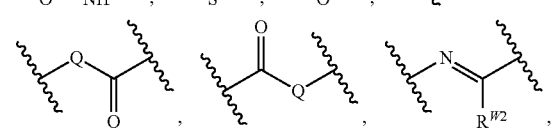

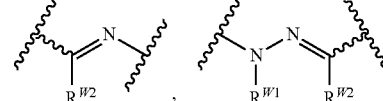

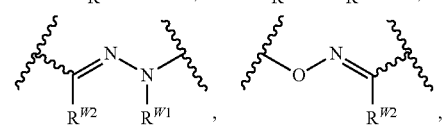

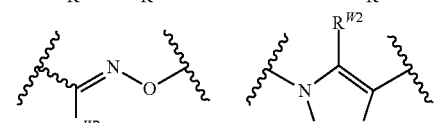

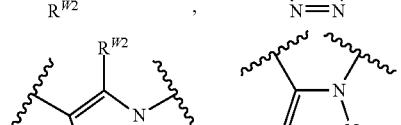

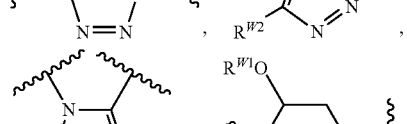

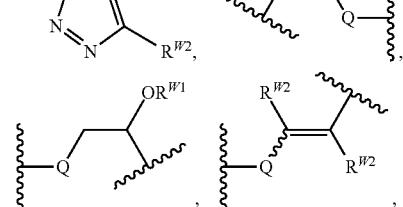

-continued

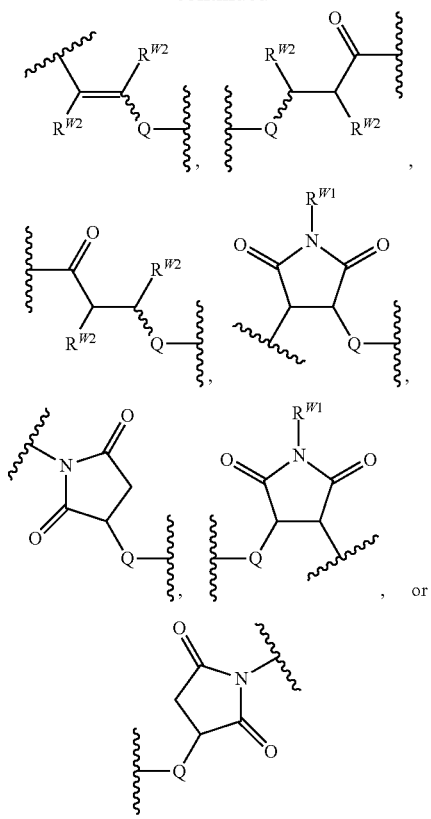

wherein:

Q is —NH—, —NH—NH—, —O—NH—, —NH—O—, —S—, —O—;

W is O, S, or NR$^{W1}$;

R$^{W1}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; a nitrogen protecting group if attached to a nitrogen atom, or an oxygen group if attached to an oxygen atom; and R$^{W2}$ is hydrogen, substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl, or two R$^{W2}$ groups are joined to form a 5-6 membered ring;

In certain embodiments, A is —NH—.
In certain embodiments, A is —NH—NH—.
In certain embodiments, A is —S—.
In certain embodiments, A is —O—.
In certain embodiments, A is a disulfide group

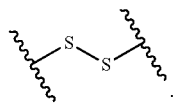 [SMILES: *SS*]

In certain embodiments, A is

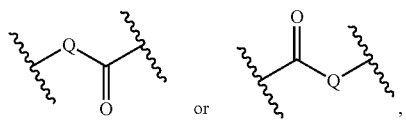

wherein Q is —NH—, —NH—NH—, —O—NH—, —NH—O—, —S—, —O—. For example, in certain embodiments, wherein Q is —NH—, A is an amide group of the formula

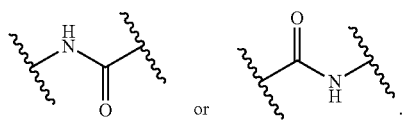

In certain embodiments, wherein Q is —NH—NH—, A is an amide hydrazide group of the formula

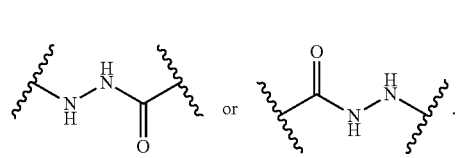 [SMILES: *NNC(*)=O ; *NNC(*)=O]

In certain embodiments, wherein Q is —S—, A is an thioester group of the formula

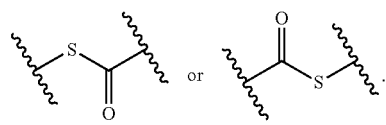 [SMILES: *SC(*)=O ; *SC(*)=O]

In certain embodiments, wherein Q is —O—, A is an ester group of the formula

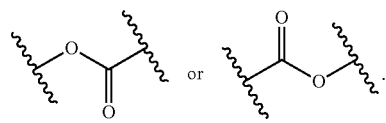 [SMILES: *OC(*)=O ; *OC(*)=O]

In certain embodiments, A is

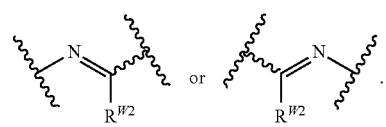

In certain embodiments, R$^{W2}$ is alkyl, e.g., methyl.
In certain embodiments, A is

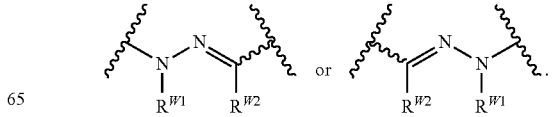

In certain embodiments, $R^{W2}$ is alkyl, e.g., methyl. In certain embodiments, $R^{W1}$ is hydrogen.

In certain embodiments, A is

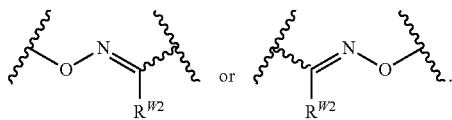

In certain embodiments, $R^{W2}$ is alkyl, e.g., methyl.

In certain embodiments, A is:

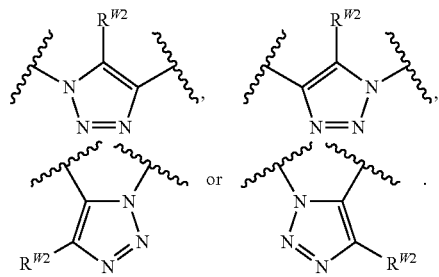

In certain embodiments, A is:

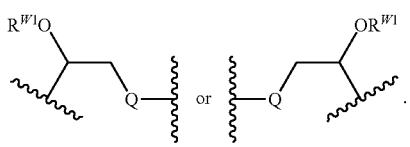

wherein $R^{W1}$ is hydrogen, substituted or unsubstituted alkyl, or an amino protecting group; and Q is —NH—, —NH—NH—, —O—NH—, —NH—O—, —S—, —O—. In certain embodiments, Q is —NH—. In certain embodiments, Q is —NH—NH—. In certain embodiments, Q is —S—. In certain embodiments, Q is —O—.

In certain embodiments, A is:

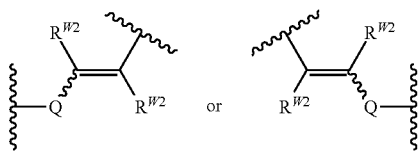

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

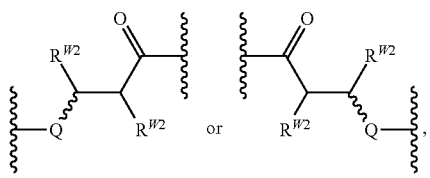

wherein Q is —NH—, —NH—NH—, —O—NH—, —NH—O—, —S—, or —O—. In certain embodiments, Q is —NH—. In certain embodiments, Q is —NH—NH—. In certain embodiments, Q is —S—. In certain embodiments, Q is —O—.

In certain embodiments, A is:

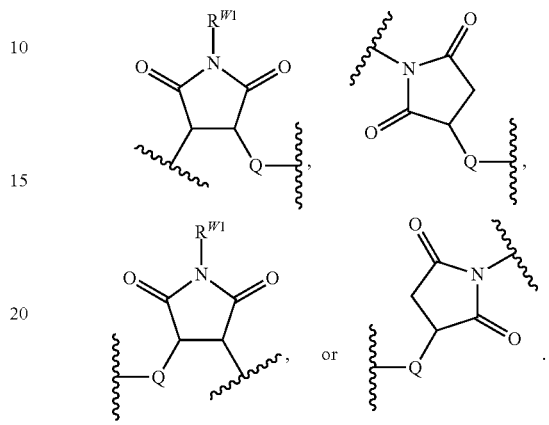

wherein W is O, S, or $NR^{W1}$, $R^{W1}$ is hydrogen, substituted or unsubstituted alkyl, or an amino protecting group; and Q is —NH—, —NH—NH—, —O—NH—, —NH—O—, —S—, or —O—. In certain embodiments, W is O. In certain embodiments, W is S. In certain embodiments, W is $NR^{W1}$. In certain embodiments, Q is —NH—. In certain embodiments, Q is —NH—NH—. In certain embodiments, Q is —S—. In certain embodiments, Q is —O—.

In one aspect, provided is a method of preparing a compound of Formula (I") or (II"), or pharmaceutically acceptable salt thereof, the method comprising coupling of a precursor compound of Formula (P-I) or (P-II) or pharmaceutically acceptable salt thereof with a compound of formula $Y^*$-$L^4$-$R^H$.

In certain embodiments, the method of preparing a compound of Formula (I") or (II"), or pharmaceutically acceptable salt thereof, comprises coupling a precursor compound of Formula (P-I) or (P-II), or pharmaceutically acceptable salt thereof, with a compound of formula $Y^*$-$L^4$-$R^H$, wherein one of $X^*$ and $Y^*$ is —C(=O)$R^{X1}$, wherein $R^{X1}$ is halogen or —$OR^{X2}$, and one of $X^*$ and $Y^*$ is —SH, —OH, —NH$_2$, or —NH—NH$_2$ to provide a compound of Formula (I") or (II"), wherein A is an amide, thioester, or ester group. See, e.g., Table 2.

TABLE 2

| $R^{X1}$ | $Y^*$ | $X^*$ | A<br>—C(=O)Q—,<br>—QC(=O)— |
|---|---|---|---|
| halogen or —$OR^{X2}$ | —SH | | —C(=O)S— |
| | | —SH | —SC(=O)— |
| | —OH | | —C(=O)O— |
| | | —OH | —OC(=O)— |
| | —NH$_2$ | | —C(=O)NH— |
| | | —NH$_2$ | —NHC(=O)— |
| | —NH—NH$_2$ | | —C(=O)NHNH— |
| | | —NH—NH$_2$ | —NHNHC(=O)— |

In certain embodiments, the method of preparing a compound of Formula (I") or (II"), or pharmaceutically acceptable salt thereof, comprises coupling a precursor compound of Formula (P-I) or (P-II), or pharmaceutically acceptable salt thereof, with a compound of formula Y*-L$^4$-R$^H$, wherein one of X* and Y* is halogen or another leaving group, and one of X* and Y* is —SH, —OH, —NH$_2$, or —NH—NH$_2$ to provide a compound of Formula (I') or (II'), wherein A is, respectively, —S—, —O—, —NH—, or —NH—NH—. See, e.g., Table 3.

TABLE 3

| Y* | X* | A |
|---|---|---|
| Hal or other leaving group | —SH | —S— |
|  | —OH | —O— |
|  | —NH$_2$ | —NH— |
|  | —NH—NH$_2$ | —NH—NH— |
|  | —O—NH$_2$ | —O—NH— |
| —SH | Hal or other leaving group | —S— |
| —OH |  | —O— |
| —NH$_2$ |  | —NH— |
| —NH—NH$_2$ |  | —NH—NH— |
| —O—NH$_2$ |  | —NH—O— |

In certain embodiments, the method of preparing a compound of Formula (I'') or (II''), or pharmaceutically acceptable salt thereof, comprises coupling (azide-alkyne Huisgen cycloaddition of) a precursor compound of Formula (P-I) or (P-II), or pharmaceutically acceptable salt thereof, with a compound of formula Y*-L$^4$-R$^H$, wherein one of X* and Y* is

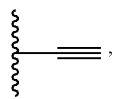

and one of X* and Y* is —N$_3$. See, e.g., Table 4.

TABLE 4

| X* | Y* | A 1,4-adduct | A 1,5-adduct |
|---|---|---|---|
| — | —N$_3$ | (structure) | (structure) |
| —N$_3$ | — | (structure) | (structure) |

In certain embodiments, the method of preparing a compound of Formula (I'') or (II''), or pharmaceutically acceptable salt thereof, comprises coupling (via thiol-yne addition of) a precursor compound of Formula (P-I) or (P-II), or pharmaceutically acceptable salt thereof, with a compound of formula Y*-L$^4$-R$^H$, wherein one of X* and Y* is

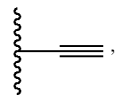

and one of X* and Y* is —SH. See, e.g., Table 5.

TABLE 5

| X* | Y* | A |
|---|---|---|
| — | —SH | (structure) |
| —SH | — | (structure) |

In certain embodiments, the method of preparing a compound of Formula (I'') or (II''), or pharmaceutically acceptable salt thereof, comprises coupling a precursor compound of Formula (P-I) or (P-II), or pharmaceutically acceptable salt thereof, with a compound of formula Y*-L$^4$-R$^H$, wherein one of X* and Y* is an aldehyde —CHO or ketone, and one of X* and Y* is —NH$_2$, —NH—NH$_2$, or —O—NH$_2$. See, e.g., Table 6.

TABLE 6

| X* | Y* | A |
|---|---|---|
| — | —NH$_2$ | (structure with R$^{W2}$) |
| — | —NH—NH$_2$ | (structure with R$^{W2}$, R$^{W1}$) |
| — | —O—NH$_2$ | (structure with R$^{W2}$) |
| —NH$_2$ | — | (structure with R$^{W2}$) |
| —NH—NH$_2$ | — | (structure with R$^{W1}$, R$^{W2}$) |

TABLE 6-continued

| X* | Y* | A |
|---|---|---|
| —O—NH₂ | — | (structure: O—N=C—R^W2) |

In certain embodiments, the method of preparing a compound of Formula (I″) or (II″), or pharmaceutically acceptable salt thereof, comprises coupling a precursor compound of Formula (P-I) or (P-II), or pharmaceutically acceptable salt thereof, with a compound of formula $Y^*-L^4-R^H$, wherein one of X* and Y* is an α,β-unsaturated carbonyl, and one of X* and Y* is —OH, —SH, —NH₂, —NHNH₂, or —O—NH₂. See, e.g., Table 7.

TABLE 7

| X* | Y* | A |
|---|---|---|
| (α,β-unsaturated ketone with R^W2) | —OH, —SH, —NH₂, —NHNH₂, —O—NH₂ | (saturated ketone with R^W2 and Q linkage) |
| —OH, —SH, —NH₂, —NHNH₂, —O—NH₂ | (α,β-unsaturated ketone with R^W2) | (saturated ketone with R^W2 and Q linkage) |

In certain embodiments, the method of preparing a compound of Formula (I′) or (II′) or pharmaceutically acceptable salt thereof comprises coupling a precursor compound of Formula (P-I) or (P-II) or pharmaceutically acceptable salt thereof with a compound of formula $Y^*-L^4-R^H$, wherein one of X* and Y* is a maleimide group, and one of X* and Y* is —OH, —SH, —NH₂, —NHNH₂, or —O—NH₂. See, e.g., Table 8.

TABLE 8

| X* | Y* | A |
|---|---|---|
| (maleimide with R^W1) | —OH, —SH, —NH₂, —NHNH₂, —O—NH₂ | (succinimide with R^W1 and Q) |
| (maleimide) | —OH, —SH, —NH₂, —NHNH₂, —O—NH₂ | (succinimide with Q) |

TABLE 8-continued

| X* | Y* | A |
|---|---|---|
| —OH, —SH, —NH₂, —NHNH₂, —O—NH₂ | (maleimide with R^W1) | (succinimide with R^W1 and Q) |
| —OH, —SH, —NH₂, —NHNH₂, —O—NH₂ | (maleimide) | (succinimide with Q) |

In certain embodiments, the method of preparing a compound of Formula (I″) or (II″), or pharmaceutically acceptable salt thereof, comprises coupling a precursor compound of Formula (P-I) or (P-II), or pharmaceutically acceptable salt thereof, with a compound of formula $Y^*-L^4-R^H$, wherein each of X* and Y* is —SH to provide, upon treatment with an oxidant, a compound of Formula (I′) or (II′), or pharmaceutically acceptable salt thereof, wherein A is a disulfide (—S—S—) bond.

EXAMPLES

In order that the invention described herein may be more fully understood, the following examples are set forth. It should be understood that these examples are for illustrative purposes only and are not to be construed as limiting this invention in any manner.

Synthetic Procedures

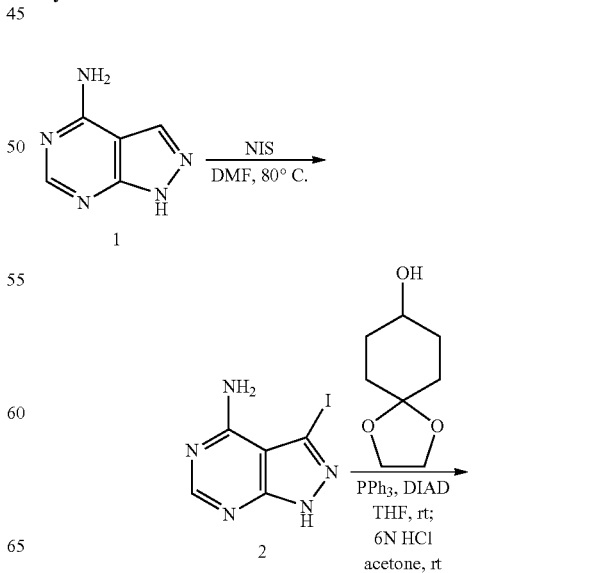

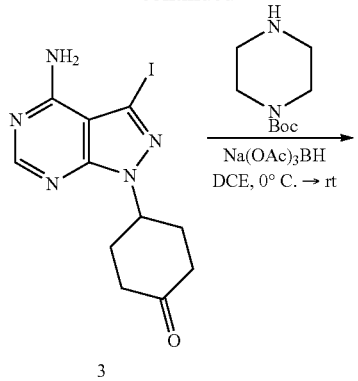

3

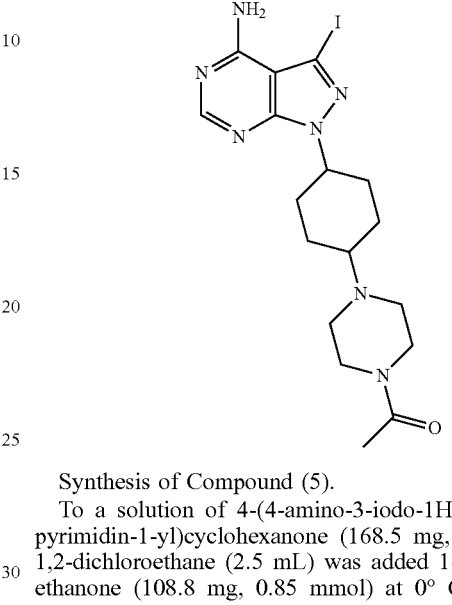

4

Synthesis of Compound (2).

To a suspension of 1H-pyrazolo[3,4-d]pyrimidin-4-amine (1) (2.8 g, 20.7 mmol) in DMF (12 mL) was added N-iodosuccinimide (5.59 g, 24.8 mmol) at ambient temperature. The reaction mixture was heated to 80° C. and stirred for 14 hr. The resulting solid was collected by filtration, rinsed with ice-cold ethanol (20 mL), and concentrated invacuo to provide 3-iodo-1H-pyrazolo[3,4-d]pyrimidin-4-amine (3.9 g, 72%) as an off-white solid. MS m/z: 261.92 (M+1).

Synthesis of Compound (3).

To a solution of 3-iodo-1H-pyrazolo[3,4-d]pyrimidin-4-amine (531.8 mg, 2.04 mmol) in THF (12 mL) under argon atmosphere were added 1,4-dioxaspiro[4.5]decan-8-ol (826.4 µL, 6.11 mmol), triphenylphosphine (1.07 g, 4.07 mmol) and diisopropyl azodicarboxylate (802.3 µL, 4.07 mmol) at ambient temperature in this order. The reaction mixture was stirred at ambient temperature for 16 hr and concentrated in vacuo. The crude mixture was taken up in acetone (15 mL) and 6N HCl (5 mL) was added dropwise. The solution was stirred at ambient temperature for 4 hr and concentrated in vacuo. The residue was purified by flash-column chromatography (5% methanol-dichloromethane) to provide 4-(4-amino-3-iodo-1H-pyrazolo[3,4-d]pyrimidin-1-yl)cyclohexanone (337.2 mg, 46.3%) as a yellow oil. MS m/z: 357.90 (M).

Synthesis of Compound (4).

To a solution of 4-(4-amino-3-iodo-1H-pyrazolo[3,4-d]pyrimidin-1-yl)cyclohexanone (168.5 mg, 0.47 mmol) in 1,2-dichloroethane (2.5 mL) was added tert-butyl piperazine-1-carboxylate (158.2 mg, 0.85 mmol) at 0° C. After 5 min, sodium triacetoxyborohydride (180.0 mg, 0.849 mmol) was added to the reaction mixture which was warmed up to ambient temperature and stirred for 14 hr. The mixture was diluted with dichloromethane (10 mL), washed with a saturated aqueous sodium bicarbonate (10 mL) and brine (10 mL) and concentrated invacuo. The residue was purified by flash-column chromatography (10% methanol-dichloromethane) to provide tert-butyl-4-(4-(4-amino-3-iodo-1H-pyrazolo[3,4-d]pyrimidin-1-yl)cyclohexyl)piperazine-1-carboxylate (89.5 mg, 36.0%) as a white solid. MS m/z: 528.06 (M+1).

5

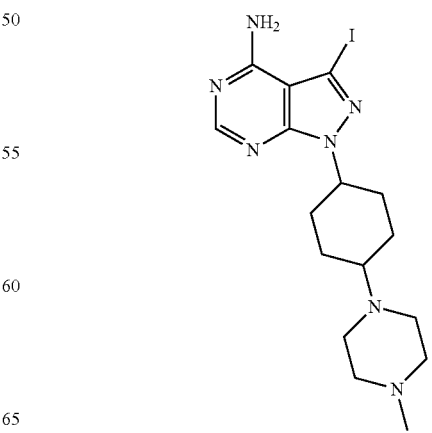

Synthesis of Compound (5).

To a solution of 4-(4-amino-3-iodo-1H-pyrazolo[3,4-d]pyrimidin-1-yl)cyclohexanone (168.5 mg, 0.47 mmol) in 1,2-dichloroethane (2.5 mL) was added 1-(piperazin-1-yl)ethanone (108.8 mg, 0.85 mmol) at 0° C. After 5 min, sodium triacetoxyborohydride (180.0 mg, 0.849 mmol) was added to the reaction mixture which was warmed up to ambient temperature and stirred for 14 hr. The mixture was diluted with dichloromethane (10 mL), washed with a saturated aqueous sodium bicarbonate (10 mL) and brine (10 mL) and concentrated invacuo. The residue was purified by flash-column chromatography (10% methanol-dichloromethane) to cis-1-(4-(4-(4-amino-3-iodo-1H-pyrazolo[3,4-d]pyrimidin-1-yl)cyclohexyl)piperazin-1-yl)ethanone (55 mg, 25%). $^1$H NMR: (600 MHz, DMSO-d$_6$) δ (ppm): 8.31 (s, 1H); 6.05 (m, 2H); 4.83 (s, 1H); 3.65 (m, 5H); 2.58 (m, 4H); 2.39 (m, 3H); 2.10 (m, 8H); MS m/z: 470.36 (M+1). trans-1-(4-(4-(4-amino-3-iodo-1H-pyrazolo[3,4-d]pyrimidin-1-yl)cyclohexyl)piperazin-1-yl)ethanone (78 mg, 35%). $^1$H NMR: (600 MHz, DMSO-d$_6$) δ (ppm): 8.33 (s, 1H); 6.02 (m, 2H); 4.65 (s, 1H); 3.62 (m, 5H); 2.62 (m, 7H); 2.13 (m, 8H); MS m/z: 470.36 (M+1). MS m/z: 470.72 (M+1).

6

Synthesis of Compound (6).

To a solution of 4-(4-amino-3-iodo-1H-pyrazolo[3,4-d]pyrimidin-1-yl)cyclohexanone (168.5 mg, 0.47 mmol) in 1,2-dichloroethane (2.5 mL) was added 1-methylpiperazine (85 mg, 0.85 mmol) at 0° C. After 5 min, sodium triacetoxyborohydride (180.0 mg, 0.849 mmol) was added to the reaction mixture which was warmed up to ambient temperature and stirred for 14 hr. The mixture was diluted with dichloromethane (10 mL), washed with a saturated aqueous sodium bicarbonate (10 mL) and brine (10 mL) and concentrated in vacuo. The residue was purified by flash-column chromatography (10% methanol-dichloromethane) to 1-(4-(4-(4-amino-3-iodo-1H-pyrazolo[3,4-d]pyrimidin-1-yl)cyclohexyl)piperazin-1-yl)ethanone (105 mg, 51%). MS m/z: 442.45 (M+1).

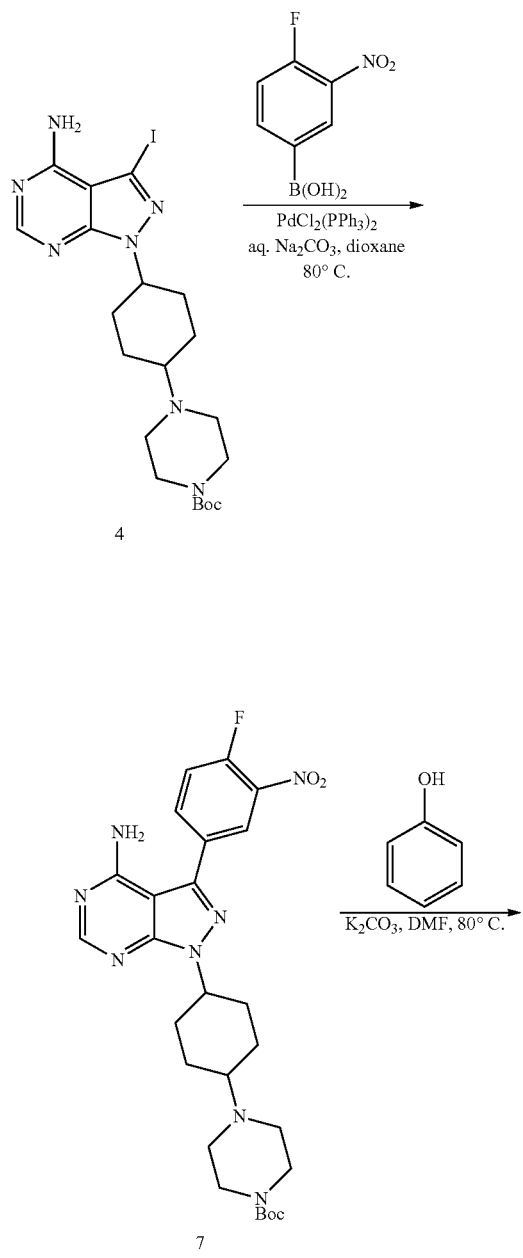

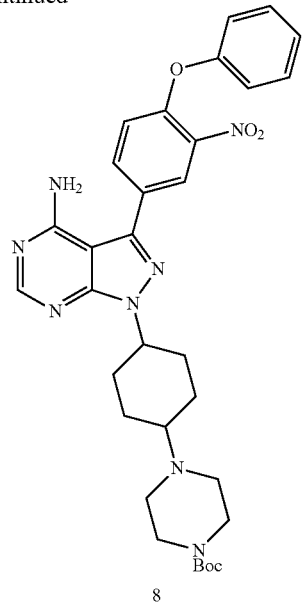

Synthesis of Compound (7).

To a solution of tert-butyl 4-(4-(4-amino-3-iodo-1H-pyrazolo[3,4-d]pyrimidin-1-yl)cyclohexyl)piperazine-1-carboxylate (360 mg, 0.68 mmol) in dioxane (6 mL) were added (4-fluoro-3-nitrophenyl)boronic acid (177 mg, 0.96 mmol) and 1M aqueous solution of sodium carbonate (2 mL) at ambient temperature. The resulting suspension was degassed with argon for 3 min and bis(triphenylphosphine)palladium(II) dichloride (35 mg, 0.05 mmol) was added. The mixture was heated to 80° C. and stirred for 2 hr. It was diluted with dichloromethane (30 mL), washed with water (30 mL) and concentrated in vacuo. The residue was purified by flash-column chromatography (10% methanol-dichloromethane) to provide tert-butyl 4-(4-(4-amino-3-(4-fluoro-3-nitrophenyl)-1H-pyrazolo[3,4-d]pyrimidin-1-yl)cyclohexyl)piperazine-1-carboxylate (312 mg, 85%). MS m/z: 541.75 (M+1).

Synthesis of Compound (8).

To a solution of tert-butyl 4-(4-(4-amino-3-(4-fluoro-3-nitrophenyl)-1H-pyrazolo[3,4-d]pyrimidin-1-yl)cyclohexyl)piperazine-1-carboxylate (312 mg, 0.58 mmol) in dimethylformamide (3 ml) were added phenol (81.7 mg 0.87 mmol) and potassium carbonate (120 mg, 0.87 mmol) at ambient temperature. The mixture was heated up to 80° C. and stirred overnight. Worked up with dichloromethane and water, concentrated in vacuo. The residue was purified by flash-column chromatography (10% methanol-dichloromethane) to tert-butyl 4-(4-(4-amino-3-(3-nitro-4-phenoxyphenyl)-1H-pyrazolo[3,4-d]pyrimidin-1-yl)cyclohexyl)piperazine-1-carboxylate (268.2 mg 75.4%). MS m/z: 615.49 (M+1).

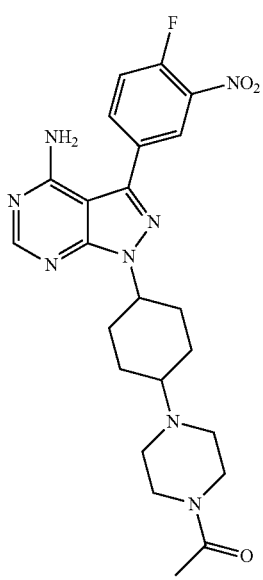

9

Synthesis of Compound (9).

To a solution of tert-butyl 4-(4-(4-amino-3-iodo-1H-pyrazolo[3,4-d]pyrimidin-1-yl)cyclohexyl)piperazine-1-carboxylate (234 mg, 0.50 mmol) in dioxane (6 mL) were added (4-fluoro-3-nitrophenyl)boronic acid (136 mg, 0.74 mmol) and 1M aqueous solution of sodium carbonate (2 mL) at ambient temperature. The resulting suspension was degassed with argon for 3 min and bis(triphenylphosphine)palladium(II) dichloride (47 mg, 0.07 mmol) was added. The mixture was heated to 80° C. and stirred for 2 hr. It was diluted with dichloromethane (30 mL), washed with water (30 mL) and concentrated in vacuo. The residue was purified by flash-column chromatography (10% methanol-dichloromethane) to 1-(4-(4-(4-amino-3-(4-fluoro-3-nitrophenyl)-1H-pyrazolo[3,4-d]pyrimidin-1-yl)cyclohexyl)piperazin-1-yl)ethanone (188 mg, 78%). MS m/z: 482.63 (M+1).

Synthesis of Compound (10).

To a solution of tert-butyl 4-(4-(4-amino-3-(4-fluoro-3-nitrophenyl)-1H-pyrazolo[3,4-d]pyrimidin-1-yl)cyclohexyl)piperazine-1-carboxylate (188 mg, 0.39 mmol) in dimethylformamide (3 ml) were added phenol (56.4 mg 0.60 mmol) and potassium carbonate (82.8 mg, 0.60 mmol) at ambient temperature. The mixture was heated up to to 80° C. and stirred overnight. The mixture was worked up with dichloromethane and water, concentrated in vacuo. The residue was purified by flash-column chromatography (10% methanol-dichloromethane) to 1-(4-(4-(4-amino-3-(3-nitro-4-phenoxyphenyl)-1H-pyrazolo[3,4-d]pyrimidin-1-yl)cyclohexyl)piperazin-1-yl)ethanone (148.7 mg 68.4%). MS m/z: 557.59 (M+1).

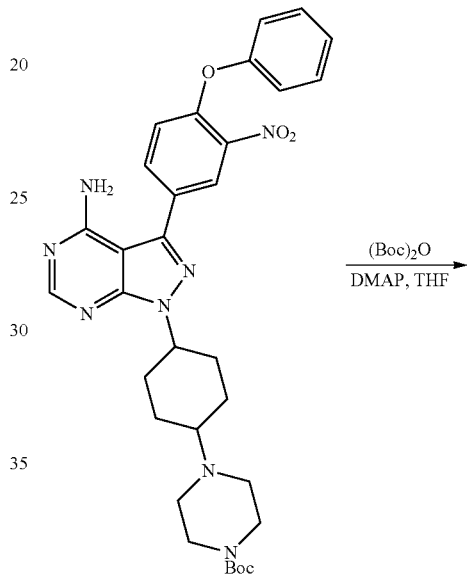

8

(Boc)₂O
DMAP, THF
⟶

10

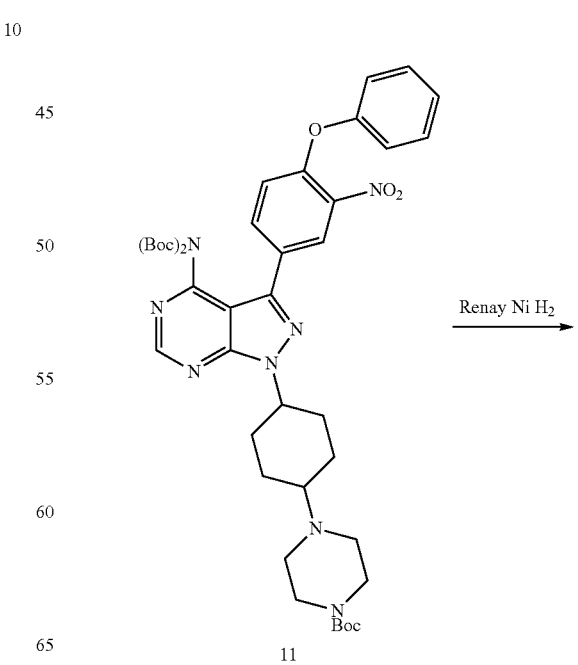

11

Renay Ni H₂
⟶

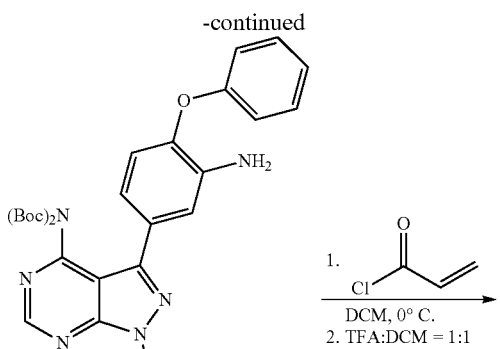

Synthesis of Compound (11).

To a solution of tert-butyl 4-(4-(4-amino-3-(3-nitro-4-phenoxyphenyl)-1H-pyrazolo[3,4-d]pyrimidin-1-yl)cyclohexyl)piperazine-1-carboxylate (268 mg, 0.44 mmol) in tetrahydrofuran (5 mL) were added di-tert-butyl dicarbonate (477 mg, 2.1 mmol) and 4-dimethylaminopyridine (5.3 mg, 0.04 mmol) at ambient temperature. The mixture was stirred for approximately 4 hours, concentrated in vacuo. The residue was purified by flash-column chromatography (10% methanol-dichloromethane) to tert-butyl 4-(4-(4-((tert-butoxycarbonyl)amino)-3-(3-nitro-4-phenoxyphenyl)-1H-pyrazolo[3,4-d]pyrimidin-1-yl)cyclohexyl)piperazine-1-carboxylate (326 mg, 91%) MS m/z: 816.07 (M+1).

Synthesis of Compound (12).

To a solution of to tert-butyl 4-(4-(4-((tert-butoxycarbonyl)amino)-3-(3-nitro-4-phenoxyphenyl)-1H-pyrazolo[3,4-d]pyrimidin-1-yl)cyclohexyl)piperazine-1-carboxylate (50 mg, 0.06 mmol) in methanol (4 mL) was added renay nichel (100 mg) which was dispersed in methanol at ambient temperature. The round bottom flash with the mixture was degrassed with vacuum and inserted with hydrogen balloon. Repeat to degrass and supply hydrogen for 3 times. The mixture was vigorously stirred for 2 hours, and filtered with celite. Celite was washed with methanol quickly for 3 times. All elute solvent was collected and concentration in vacu. tert-butyl 4-(4-(3-(3-amino-4-phenoxyphenyl)-4-((tert-butoxycarbonyl)amino)-1H-pyrazolo[3,4-d]pyrimidin-1-yl)cyclohexyl)piperazine-1-carboxylate was obtained. (45 mg, 95%) MS m/z: 786.28 (M+1).

Synthesis of Compound (13).

To a solution tert-butyl 4-(4-(3-(3-amino-4-phenoxyphenyl)-4-((tert-butoxycarbonyl)amino)-1H-pyrazolo[3,4-d]pyrimidin-1-yl)cyclohexyl)piperazine-1-carboxylate (60 mg, 0.076 mmol) in dichloromethane (0.5 mL) were added acryloyl chloride (8 μL, 0.10 mmol) and 4-dimethylaminopyridine (4.0 mg, 0.033 mmol) at ambient temperature. The mixture was stirred for 2 hours. Then, trifluoroacetic acid (0.5 mL) was added and stirred for another 2 hours at ambient temperature and concentrated. N-(5-(4-amino-1-(4-(piperazin-1-yl)cyclohexyl)-1H-pyrazolo[3,4-d]pyrimidin-3-yl)-2-phenoxyphenyl)acrylamide was obtained (35 mg, 85%) MS m/z: 540.07 (M+1).

Synthesis of Compound (14).

To a solution of 1-(4-(4-(4-amino-3-(3-nitro-4-phenoxyphenyl)-1H-pyrazolo[3,4-d]pyrimidin-1-yl)cyclohexyl)piperazin-1-yl)ethanone (148.7 mg, 0.267 mmol) in tetrahydrofuran (5 mL) were added di-tert-butyl dicarbonate (238 mg, 1.1 mmol) and 4-dimethylaminopyridine (5.3 mg, 0.04 mmol) at ambient temperature. The mixture was stirred for approximately 4 hours, concentrated in vacuo. The residue was purified by flash-column chromatography (10% methanol-dichloromethane) to tert-butyl (1-(4-(4-acetylpiperazin-1-yl)cyclohexyl)-3-(3-nitro-4-phenoxyphenyl)-1H-pyrazolo[3,4-d]pyrimidin-4-yl)carbamate (188 mg, 93%) MS m/z: 757.91 (M+1).

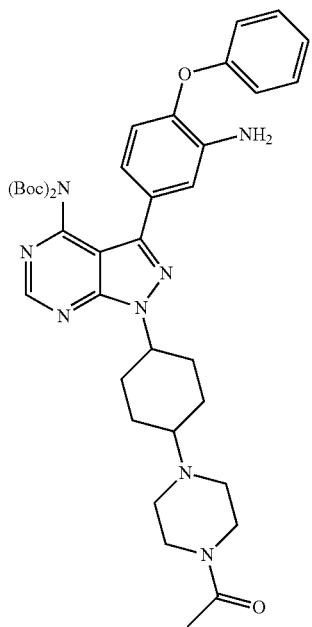

Synthesis of Compound (15).

To a solution of to tert-butyl (1-(4-(4-acetylpiperazin-1-yl)cyclohexyl)-3-(3-nitro-4-phenoxyphenyl)-1H-pyrazolo[3,4-d]pyrimidin-4-yl)carbamate (50 mg, 0.066 mmol) in methanol (4 mL) was added renay nichel (100 mg) which was dispersed in methanol at ambient temperature. The round bottom flash with the mixture was degrassed with vacuum and inserted with hydrogen balloon. Repeat to degrass and supply hydrogen for 3 times. The mixture was vigorously stirred for 2 hours, and filtered with celite. Celite was washed with methanol quickly for 3 times. All elute solvent was collected and concentration in vacu. tert-butyl (1-(4-(4-acetylpiperazin-1-yl)cyclohexyl)-3-(3-amino-4-phenoxyphenyl)-1H-pyrazolo[3,4-d]pyrimidin-4-yl)carbamate was obtained (48 mg, 98%) MS m/z: 728.04 (M+1).

16

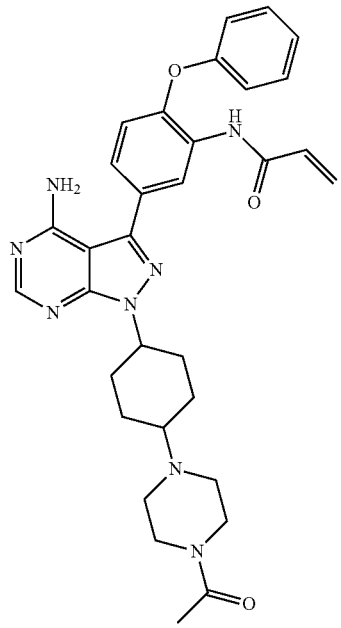

Synthesis of Compound (16).

To a tert-butyl (1-(4-(4-acetylpiperazin-1-yl)cyclohexyl)-3-(3-amino-4-phenoxyphenyl)-1H-pyrazolo[3,4-d]pyrimidin-4-yl)carbamate (30 mg, 0.041 mmol) in dichloromethane (0.5 mL) were added acryloyl chloride (4 µL, 0.05 mmol) and 4-dimethylaminopyridine (4.0 mg, 0.033 mmol) at ambient temperature. The mixture was stirred for 2 hours. Then, trifluoroacetic acid (0.5 mL) was added and stirred for another 2 hours at ambient temperature and concentrated. The crude mixture was diluted with dimethyl sulfoxide DMSO (1 mL) and directly purified by preparative reverse-phase HPLC (methanol/water gradient) to provide N-(5-(4-amino-1-(4-(piperazin-1-yl)cyclohexyl)-1H-pyrazolo[3,4-d]pyrimidin-3-yl)-2-phenoxyphenyl)acrylamide as a TFA salt. (TX1-85-1) (12 mg, 50%)$^1$H NMR: (600 MHz, DMSO-$d_6$) δ (ppm): 9.94 (s, 1H); 8.38 (s, 1H); 8.32 (s, 2H); 8.23 (s, 1H); 7.37 (m, 3H); 7.06 (d, J=8.4 Hz, 2H); 6.96 (d, J=8.4 Hz, 2H); 6.64 (dd, J=17.4 and 10.8 Hz, 1H); 6.19 (dd, J=17.4 and 1.8 Hz, 1H); 5.69 (dd, J=10.8 and 1.8 Hz, 1H); 4.91 (s, 1H); 3.42 (br m, 5H); 2.56 (br m, 4H); 2.39 (s, 3H); 2.05 (m, 4H); 1.91 (br m, 4H); MS m/z: 581.43 (M+1)

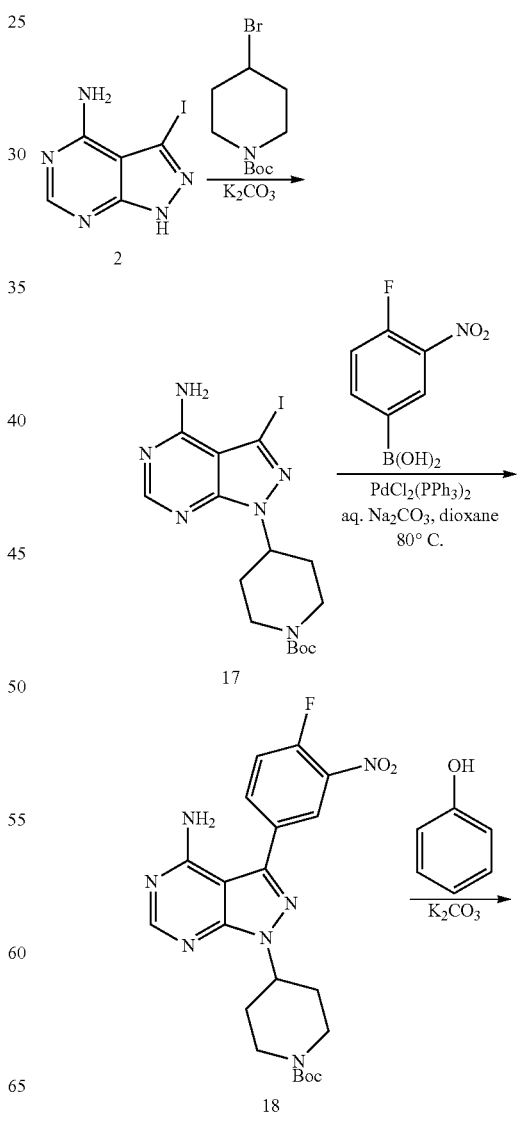

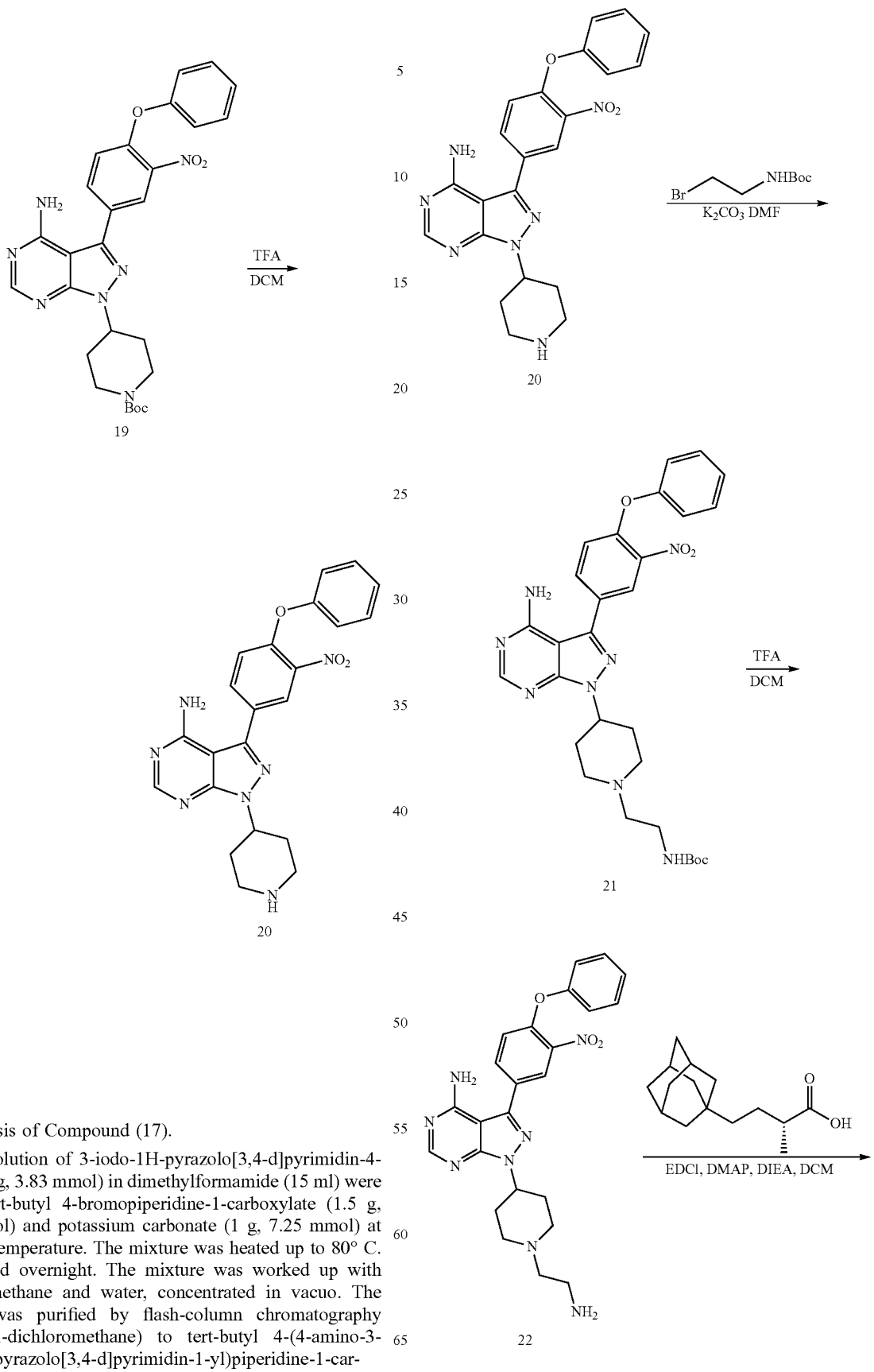

Synthesis of Compound (17).

To a solution of 3-iodo-1H-pyrazolo[3,4-d]pyrimidin-4-amine (1 g, 3.83 mmol) in dimethylformamide (15 ml) were added tert-butyl 4-bromopiperidine-1-carboxylate (1.5 g, 5.68 mmol) and potassium carbonate (1 g, 7.25 mmol) at ambient temperature. The mixture was heated up to 80° C. and stirred overnight. The mixture was worked up with dichloromethane and water, concentrated in vacuo. The residue was purified by flash-column chromatography (methanol-dichloromethane) to tert-butyl 4-(4-amino-3-iodo-1H-pyrazolo[3,4-d]pyrimidin-1-yl)piperidine-1-carboxylate (918.5 mg 53.8%). MS m/z: 445.76 (M+1).

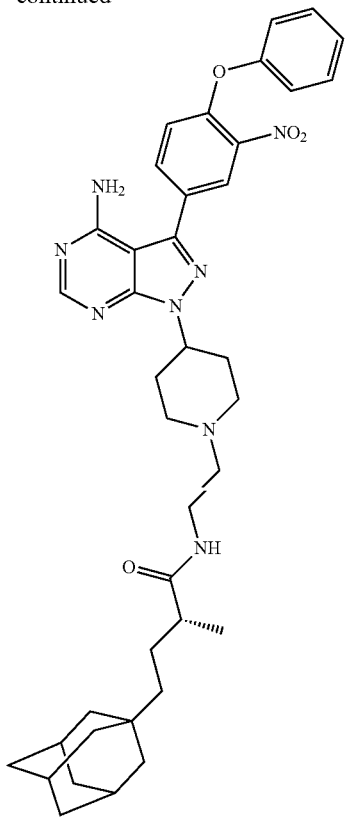

23

Synthesis of Compound (21).

To a solution of 3-(3-nitro-4-phenoxyphenyl)-1-(piperidin-4-yl)-1H-pyrazolo[3,4-d]pyrimidin-4-amine (100 mg, 0.23 mmol) in dimethylformamide (3 mL) were added tert-butyl(2-bromoethyl)carbamate (78 mg, 0.35 mmol) and potassium carbonate (128 mg, 0.93 mmol) at ambient temperature. The reaction mixture was heated to 80° C. stirred at ambient temperature overnight. The crude was worked up with dichloromethane and water. The product was purified by flash-column chromatography (8% methanol-dichloromethane) to provide tert-butyl (2-(4-(4-amino-3-(3-nitro-4-phenoxyphenyl)-1H-pyrazolo[3,4-d]pyrimidin-1-yl)piperidin-1-yl)ethyl)carbamate (135.2 mg, 67.2%) as a yellow solid. MS m/z: 575.62 (M+1).

Synthesis of Compounds (22) and (23).

To a solution of tert-butyl (2-(4-(4-amino-3-(3-nitro-4-phenoxyphenyl)-1H-pyrazolo[3,4-d]pyrimidin-1-yl)piperidin-1-yl)ethyl)carbamate (30 mg, 0.05 mmol) in dichloromethane (1.2 mL) was added trifluoroacetic acid (500 µL) at ambient temperature. The reaction mixture was stirred at ambient temperature for 2 hr and concentrated invacuo. The crude product was taken up in dimethylformamide (1.0 mL), and to that solution were added (2R)-4-((1r,3S)-adamantan-1-yl)-2-methylbutanoic acid (10 mg, 0.042 mmol), N-Ethyl-N'-(3-dimethylaminopropyl)carbodiimide hydrochloride (30.8 mg, 0.16 mmol) and 4-(dimethylamino)pyridine (4 mg, 0.03 mmol) at ambient temperature in this order. The reaction mixture was stirred at ambient temperature for 3 hr.

The residue was purified by flash-column chromatography (methanol-dichloromethane) to provide (R)-4-((3R,5R,7R)-adamantan-1-yl)-N-(2-(4-(4-amino-3-(3-nitro-4-phenoxyphenyl)-1H-pyrazolo[3,4-d]pyrimidin-1-yl)piperidin-1-yl)ethyl)-2-methylbutanamide (17.4 mg 50.2%). MS m/z: 693.45 (M+1).

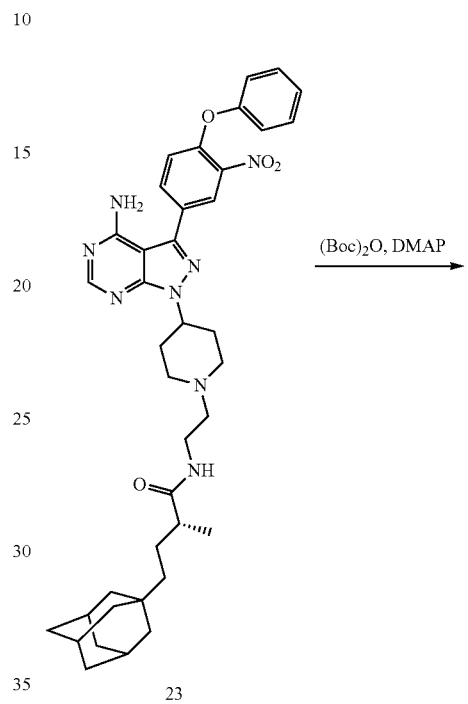

23

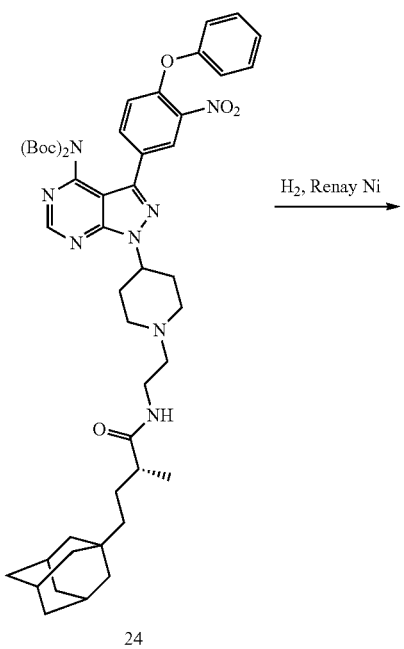

24

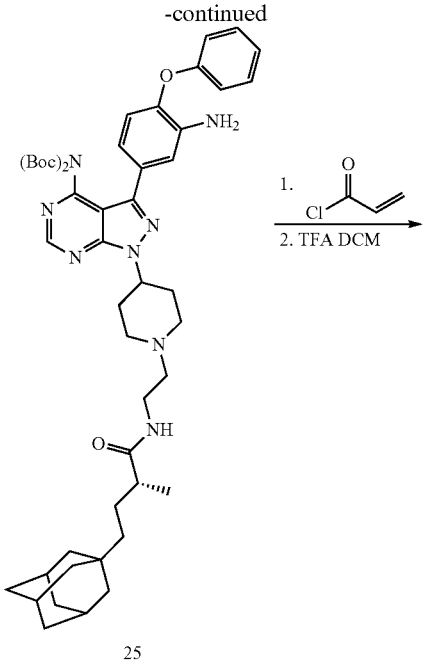

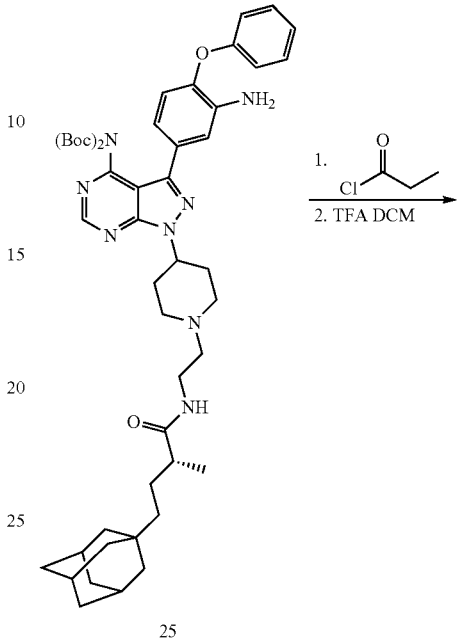

Hz, 1H); 4.91 (s, 1H); 3.42 (br m, 5H); 2.56 (br m, 4H); 2.39 (s, 3H); 2.05 (m, 4H); 1.91 (br m, 4H); MS m/z: 717.42 (M+1).

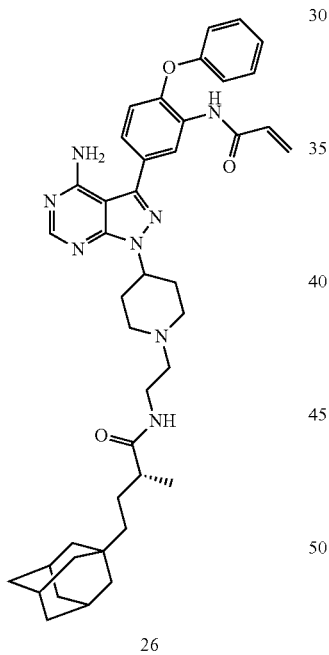

26

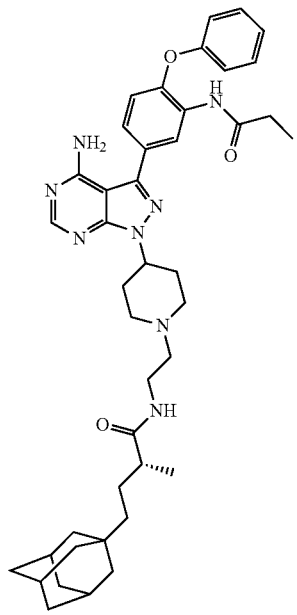

36

Synthesis of Compound (26).

Following synthetic procedures described above, (R)—N-(2-(4-(3-(3-acrylamido-4-phenoxyphenyl)-4-amino-1H-pyrazolo[3,4-d]pyrimidin-1-yl)piperidin-1-yl)ethyl)-4-((3R,5R,7R)-adamantan-1-yl)-2-methylbutanamide (7.3 mg) ((R)-TX2-121-1) was purified by preparative reverse-phase HPLC (methanol/water gradient). $^1$H NMR: (600 MHz, DMSO-$d_6$) δ (ppm): 9.94 (s, 1H); 9.74 (s, 1H); 8.33 (s, 1H); 8.22 (s, 1H); 7.37 (t, J=8.4 Hz, 2H); 7.33 (dd, J=8.4 Hz and 1.8 Hz, 1H); 7.11 (d, J=8.4 Hz, 1H); 7.07 (d, J=8.4 Hz, 2H); 6.96 (d, J=8.4 Hz, 1H); 6.64 (dd, J=17.4 and 10.8 Hz, 1H); 6.19 (dd, J=17.4 and 1.8 Hz, 1H); 5.69 (dd, J=10.8 and 1.8

Synthesis of Compound (36).

Following synthetic procedures described above, but using propionyl chloride instead of acyryloyl chloride, compound 36 ((R)-TX2-121-3) was prepared.

27

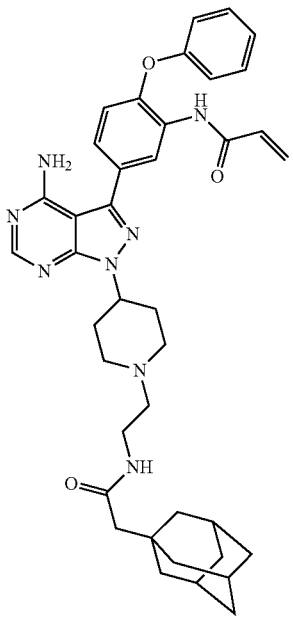

Synthesis of Compound (27).
N-(5-(1-(1-(2-(2-(2-((1s,3s)-adamantan-1-yl)acetamido)ethyl)piperidin-4-yl)-4-amino-1H-pyrazolo[3,4-d]pyrimidin-3-yl)-2-phenoxyphenyl)acrylamide (15.8 mg) (TX2-112-1) was purified by preparative reverse-phase HPLC (methanol/water gradient). $^1$H NMR: (600 MHz, DMSO-$d_6$) δ (ppm): 9.95 (s, 1H); 9.50 (br s, 1H); 8.37 (s, 1H); 8.29 (s, 1H); 7.37 (t, J=8.4 Hz, 2H); 7.33 (dd, J=8.4 Hz and 1.8 Hz, 1H); 7.13 (d, J=8.4 Hz, 1H); 7.07 (d, J=8.4 Hz, 2H); 6.76 (d, J=8.4 Hz, 1H); 6.64 (dd, J=17.4 and 10.8 Hz, 1H); 6.20 (dd, J=17.4 and 1.8 Hz, 1H); 5.70 (dd, J=10.8 and 1.8 Hz, 1H); 4.99 (br m, 1H); 3.66 (m, 5H); 3.38 (br m); 3.24 (br m); 2.43 (s, 3H); 2.35 (m); 2.14 (br m); 1.85 (br m); MS m/z: 675.41 (M+1).

28

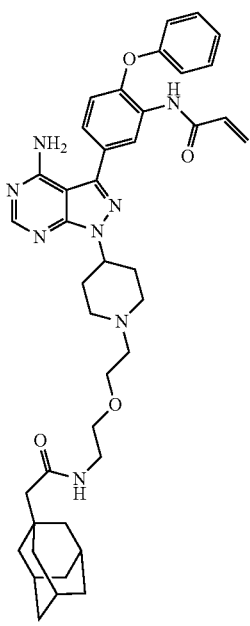

Synthesis of Compound (28).
N-(5-(1-(1-(2-(2-(2-((1s,3s)-adamantan-1-yl)acetamido)ethoxy)ethyl)piperidin-4-yl)-4-amino-1H-pyrazolo[3,4-d]pyrimidin-3-yl)-2-phenoxyphenyl)acrylamide (12.3 mg) (TX2-114-1) was purified by preparative reverse-phase HPLC (methanol/water gradient). $^1$H NMR: (600 MHz, DMSO-$d_6$) δ (ppm): 10.0 (s, 1H); 9.66 (br s, 1H); 8.47 (s, 1H); 8.38 (s, 1H); 7.47 (t, J=8.4 Hz, 2H); 7.42 (dd, J=8.4 Hz and 1.8 Hz, 1H); 7.23 (t, J=8.4 Hz, 1H); 7.16 (d, J=8.4 Hz, 2H); 7.05 (d, J=8.4 Hz, 1H); 6.74 (dd, J=17.4 and 10.8 Hz, 1H); 6.30 (dd, J=17.4 and 1.8 Hz, 1H); 5.79 (dd, J=10.8 and 1.8 Hz, 1H); 5.10 (br m, 1H); 3.80 (m, 5H); 3.73 (br m, 4H); 3.51 (br m, 4H); 3.27 (br m) 2.57 (s); 2.23 (m); 1.90 (br m); MS m/z: 719.44 (M+1).

29

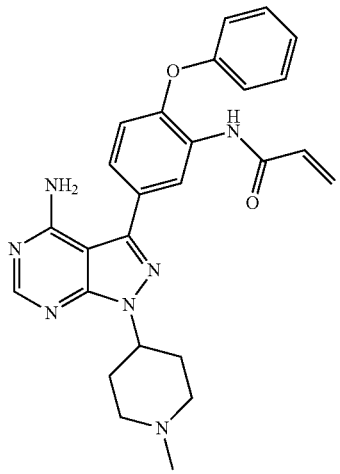

Synthesis of Compound (29).
N-(5-(4-amino-1-(1-methylpiperidin-4-yl)-1H-pyrazolo[3,4-d]pyrimidin-3-yl)-2-phenoxyphenyl)acrylamide (5.0 mg) (TX2-120-1) was purified by preparative reverse-phase HPLC (methanol/water gradient). $^1$H NMR: (600 MHz, DMSO-$d_6$) δ (ppm): 10.0 (s, 1H); 9.56 (br s, 1H); 8.42 (s, 1H); 8.30 (s, 1H); 7.473 (t, J=8.4 Hz, 2H); 7.39 (dd, J=8.4 Hz and 1.8 Hz, 1H); 7.19 (t, J=8.4 Hz, 1H); 7.11 (d, J=8.4 Hz, 2H); 7.03 (d, J=8.4 Hz, 1H); 6.70 (dd, J=17.4 and 10.8 Hz, 1H); 6.26 (dd, J=17.4 and 1.8 Hz, 1H); 5.76 (dd, J=10.8 and 1.8 Hz, 1H); 5.05 (br m, 1H); 3.80 (m); 3.70 (br m); 3.16 (br m); 2.49 (s); MS m/z: 470.34 (M+1).

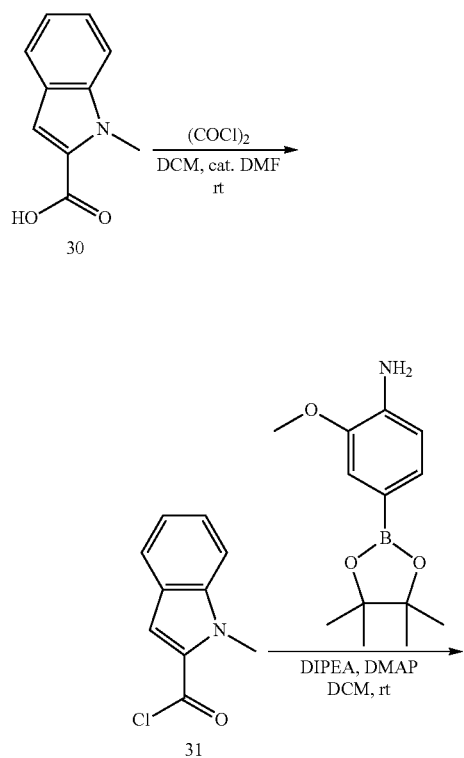

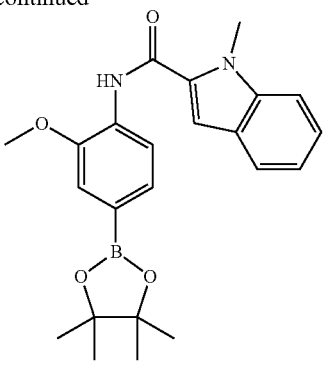

Synthesis of Compound (32).

To a solution of 1-methyl-1H-indole-2-carboxylic acid (75.0 mg, 0.43 mmol) in dichloromethane (1.2 mL) were added oxalyl chloride (44.8 L, 0.51 mmol) and a catalytic amount of dimethylformamide at ambient temperature. The reaction mixture was stirred at ambient temperature for 2 h, and concentrated invacuo. The crude material was taken up with dichloromethane (2.0 mL), and to that solution were added 4-amino-3-methoxyphenylboronic acid pinacol ester (106.6 mg, 0.43 mmol), N,N-diisopropylethylamine (111.9 L, 0.64 mmol) and 4-(dimethylamino)pyridine (5.2 mg, 0.043 mmol) sequentially. The reaction mixture was stirred at ambient temperature for 3 hr. The mixture was diluted with dichloromethane (10 mL), washed with water and concentrated invacuo. The residue was directly used for the next step without further purification. MS m/z: 406.98 (M).

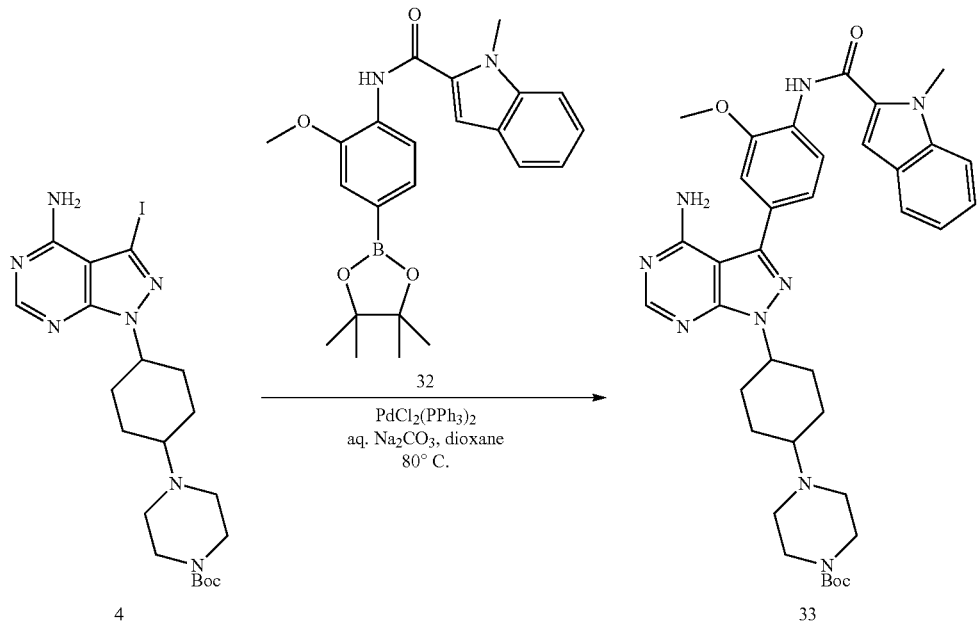

-continued

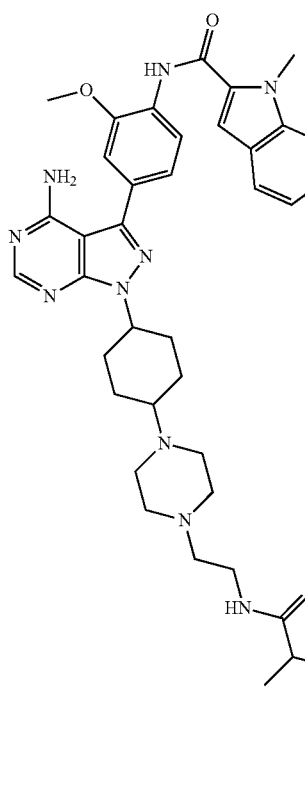

35

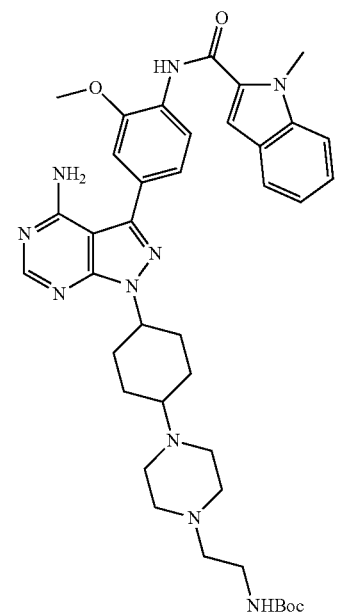

34

Synthesis of Compound (33).

To a solution of tert-butyl-4-(4-(4-amino-3-iodo-1H-pyrazolo[3,4-d]pyrimidin-1-yl)cyclohexyl)piperazine-1-carboxylate (64.0 mg, 0.12 mmol) in dioxane (1.94 mL) were added N-(2-methoxy-4-(4,4,5,5-tetramethyl-1,3,2-dioxaborolan-2-yl)phenyl)-1-methyl-1H-indole-2-carboxamide (59.5 mg, 0.15 mmol) and 1M aqueous solution of sodium carbonate (485 µL) at ambient temperature. The resulting suspension was degassed with argon for 3 min and bis(triphenylphosphine)palladium(II) dichloride (8.5 mg, 0.012 mmol) was added. The mixture was heated to 80° C. and stirred for 2 hr. It was diluted with dichloromethane (10 mL), washed with water (10 mL) and concentrated invacuo. The residue was purified by flash-column chromatography (10% methanol-dichloromethane) to provide tert-butyl 4-(4-(4-amino-3-(3-methoxy-4-(1-methyl-1H-indole-2-carboxamido)phenyl)-1H-pyrazolo[3,4-d]pyrimidin-1-yl)cyclohexyl)piperazine-1-carboxylate (55.2 mg, 66.9%) as a brown solid. MS m/z: 680.30 (M+1).

Synthesis of compound (34). To a solution of tert-butyl 4-(4-(4-amino-3-(3-methoxy-4-(1-methyl-1H-indole-2-carboxamido)phenyl)-1H-pyrazolo[3,4-d]pyrimidin-1-yl)cyclohexyl)piperazine-1-carboxylate (33.1 mg, 0.049 mmol) in dichloromethane (1.1 mL) was added trifluoroacetic acid (250 µL) at ambient temperature. The reaction mixture was stirred at ambient temperature for 2 hr and concentrated. The crude product was taken up in acetonitrile (1.2 mL), and to that solution were added tert-Butyl N-(2-bromoethyl)carbamate (16.4 mg, 0.073 mmol) and potassium carbonate (26.9 mg, 0.20 mmol) sequentially. The mixture was heated to reflux and stirred for 1 hr. The residual solid was filtered and washed with ethyl acetate (10 mL), and the filtrated was concentrated invacuo. This residue was purified by flash-column chromatography (8% methanol-dichloromethane) to provide tert-butyl (2-(4-(4-(4-amino-3-(3-methoxy-4-(1-methyl-1H-indole-2-carboxamido)phenyl)-1H-pyrazolo[3,4-d]pyrimidin-1-yl)cyclohexyl)piperazin-1-yl)ethyl)carbamate (21.6 mg, 61.6%) as a yellow solid. MS m/z: 723.33 (M+1).

Synthesis of compound (35). To a solution of tert-butyl (2-(4-(4-(4-amino-3-(3-methoxy-4-(1-methyl-1H-indole-2-carboxamido)phenyl)-1H-pyrazolo[3,4-d]pyrimidin-1-yl)cyclohexyl)piperazin-1-yl)ethyl)carbamate (21.6 mg, 0.03 mmol) in dichloromethane (1.2 mL) was added trifluoroacetic acid (300 L) at ambient temperature. The reaction mixture was stirred at ambient temperature for 2 hr and concentrated invacuo. The crude product was taken up in dimethylformamide (1.0 mL), and to that solution were added 4-(adamantan-1-yl)-2-methylbutanoic acid (8.5 mg, 0.036 mmol), N-Ethyl-N'-(3-dimethylaminopropyl)carbodiimide hydrochloride (17.3 mg, 0.09 mmol) and 4-(dimethylamino)pyridine (0.4 mg, 0.003 mmol) at ambient temperature in this order. The reaction mixture was stirred at ambient temperature for 3 hr. The crude mixture was diluted with water (1 mL) and directly purified by preparative reverse-phase HPLC (methanol/water gradient) to provide (R)—N-(4-(1-(4-(4-(2-(4-(adamantan-1-yl)-2-methylbutanamido)ethyl)piperazin-1-yl)cyclohexyl)-4-amino-1H-pyrazolo[3,4-d]pyrimidin-3-yl)-2-methoxyphenyl)-1-methyl-1H-indole-2-carboxamide (SML-11-124-1) as a mixture of cis/trans isomers (6.3 mg, 25.0%) as a TFA salt. MS m/z: 841.38 (M+1).

Biological Assays

Invitrogen LanthaScreen™ Eu Kinase Binding Assay

Figure 2:
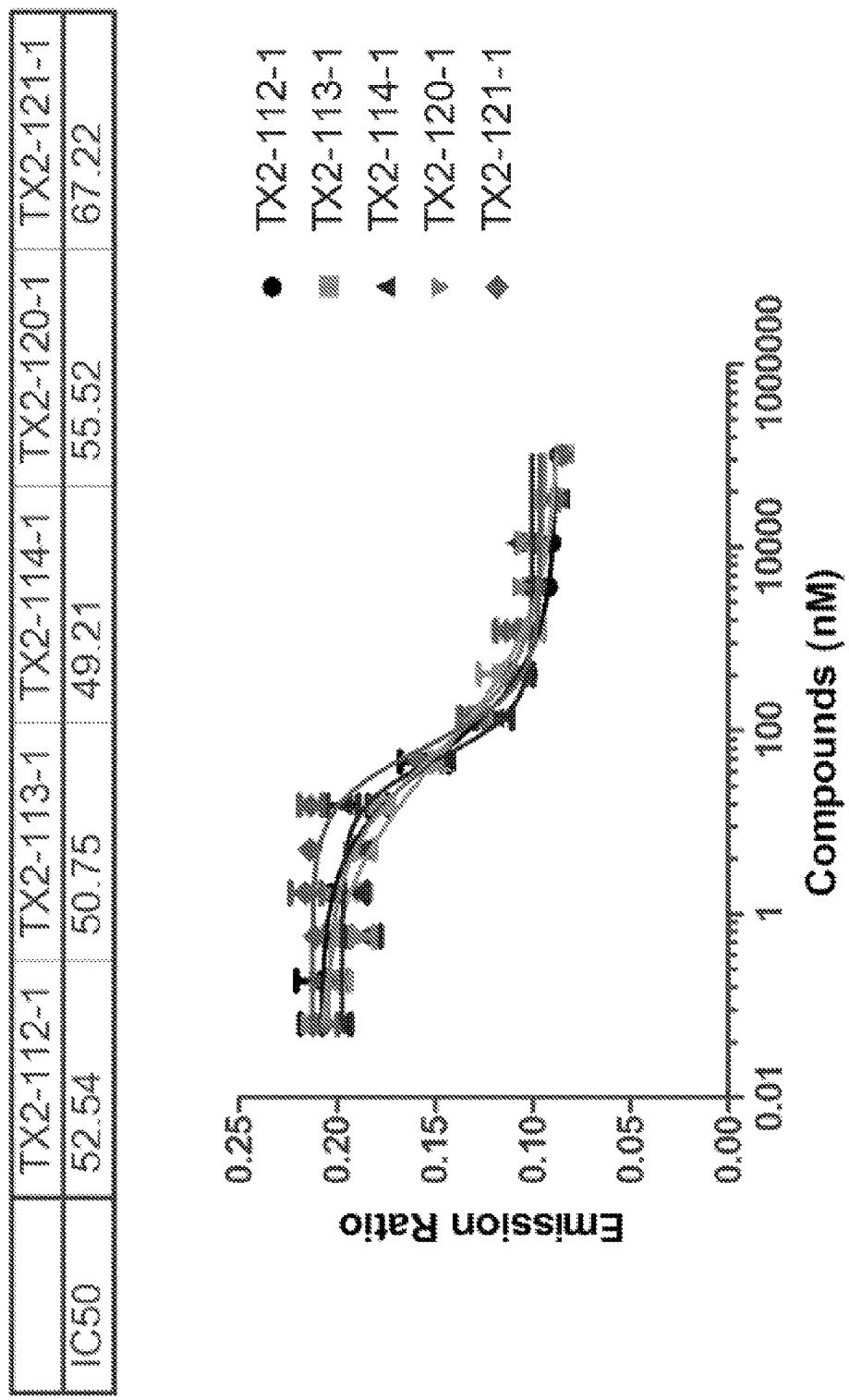
FIG. 2 depicts the results of a Invitrogen LanthaScreen™ Eu kinase binding assay of TX2-112-1, TX2-113-1, TX2-114-1, TX2-120-1, and TX2-121-1 (depicted in Table 1).

FIG. 2 depicts binding affinity data for exemplary compounds of Formula (II). Binding affinity ($IC_{50}$) was measured by Invitrogen LanthaScreen™ Eu kinase binding assay which is based on the binding and displacement of Alexa Fluor 647 labeled ATP-competitive kinase inhibitor scaffold (Kinase Tracer 178). Binding of the tracer to the kinase is detected using a europium-labeled anti-tag antibody (anti-GST). The binding of both the tracer and antibody to the kinase results in a high degree of FRET (fluorescenece resonance energy transfer) from the europium donor fluorophore to the Alexa Fluor 647 acceptor fluoropore on the kinase tracer. Binding of an inhibitor to the kinase competes for binding with the tracer, resulting in a loss of FRET. The typical experiment procedure is shown below:

(1) Purified ErbB3(667-1053) protein was obtained from Invitrogen at a concentration of 1.19 mg/ml. The buffer is 50 mM Tris (pH 7.5), 150 mM NaCl, 0.5 mM EDTA, 0.02% Triton® X-100, 2 mM DTT, 50% Glycerol. Dilute to 30 nM with Kinase Buffer A (50 mM HEPES ph 7.5, 10 mM $MgCl_2$, 1 mM EGTA, 0.01% Brij-35).

(2) 1 to 1 mix ErbB3 protein with 12 nM LanthaScreen™ Eu-anti-GST antibody solution which was also dilute in Kinase Buffer A. Prior to use, the antibody tube should be thawed and centrifuged at approximately 10,000 g for 5 minutes, and the solution needed for the assay should be aspirated from the top of the solution. This centrifugation step will eliminate spurious data points that can arise on occasion due to any particulates in the product.

(3) Add 5 ul the mixture of ErbB3 protein and Eu-anti-GST to 5 ul test compound solution per well in coming 384 plates.

(4) Add 5 ul tracer 178 at concentration of 39 nM per well.

(5) Incubate for 3 hours at 4° C. and read plate with Perkin Elmer EnVision.

CellTiter-Glo® Luminescent Assay

Figure 3:
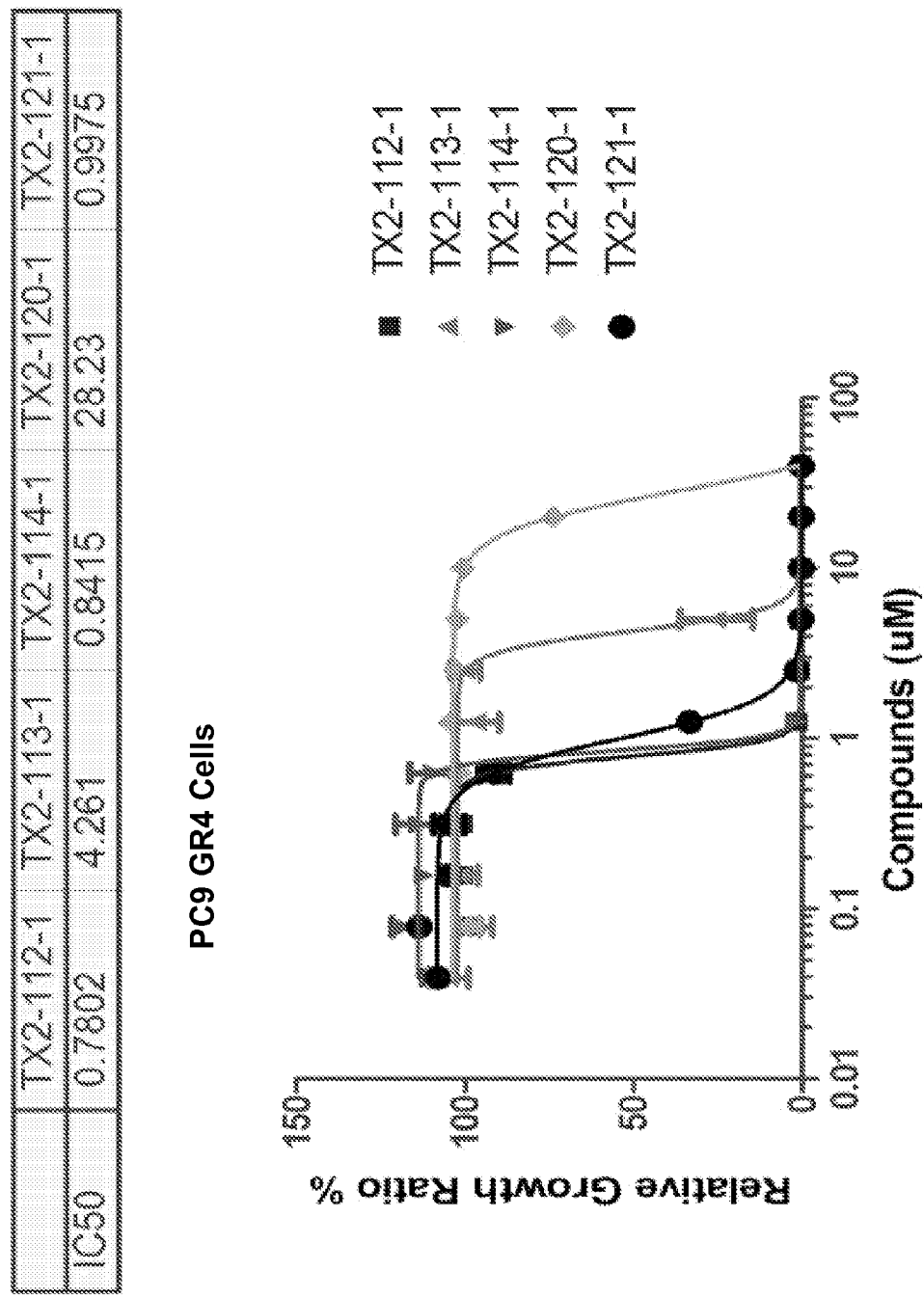
FIG. 3 depicts results of a CellTiterGlo® Luminescent Assay (anti proliferation assay) of TX2-112-1, TX2-113-1, TX2-114-1, TX2-120-1, and TX2-121-1 (depicted in Table 1).

FIG. 3 depicts anti-proliferation data for exemplary compounds of Formula (II). The anti-proliferation assay was carried out by using 96 well white bottom plates. 2000-4000 cells were seeded per well, and the medium volume per well was about 100 ul. Incubate for 3 days after adding and titrating indicated concentration of compounds. The cell viability was test by CellTiter-Glo® Luminescent Assay. In a typical experiment, add 10 ul CellTiter-Glo® reagent per well. Mix and shake the plate for 2 minutes to induce cell lysis at room temperature. Allow the plate to incubate at room temperature for approximately 10 minutes to stabilize luminescent signal. Read plate with Perkin Elmer EnVision. The cell numbers were normalized by the DMSO control. And the $EC_{50}$s were calculated by GraphPad Prism.

Electrophoretic Gel (SDS-PAGE)

Figure 4A:
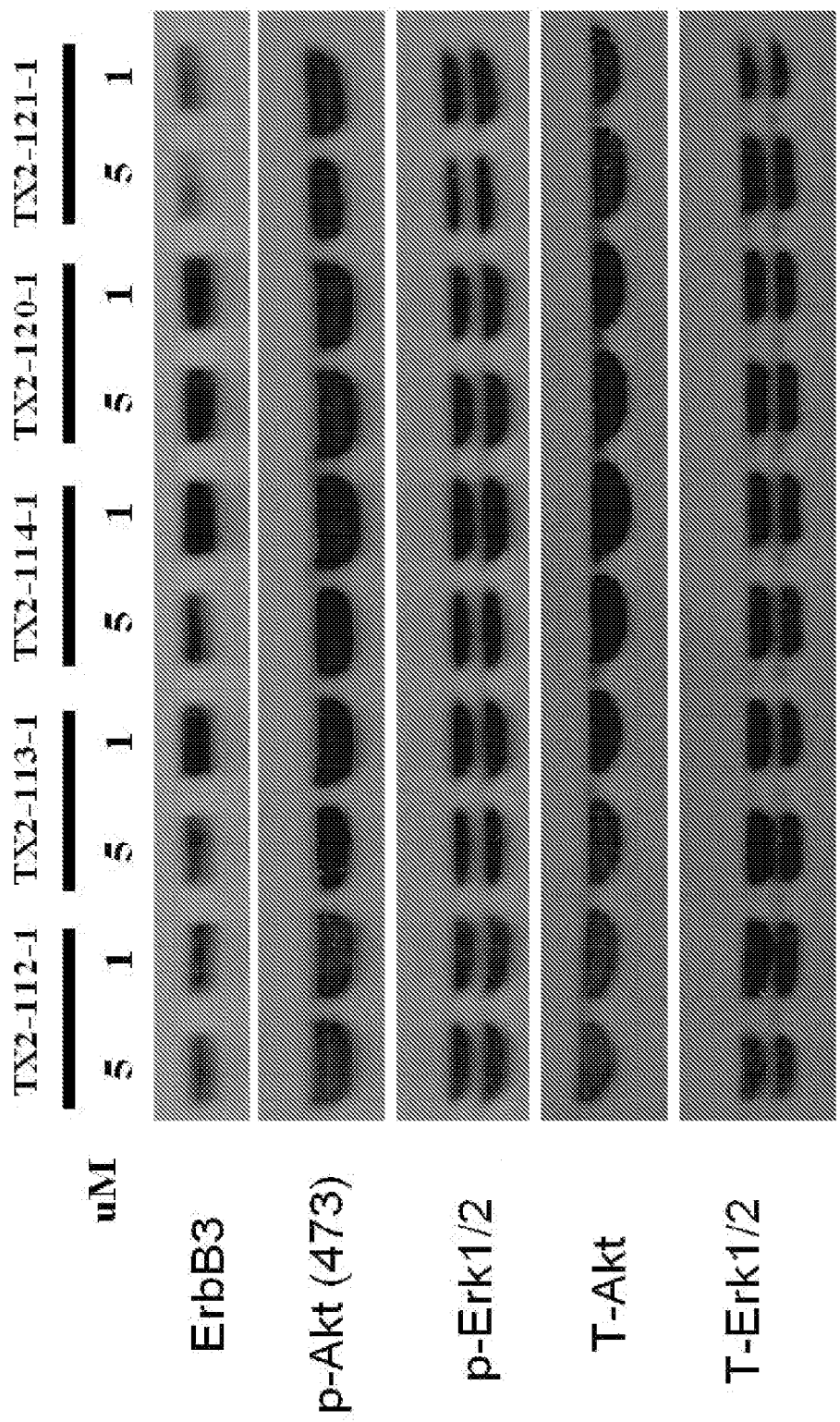
FIGS. 4A and 4B depict electrophoretic gel image (SD-SPAGE) results of compounds TX2-112-1, TX2-113-1, TX2-114-1, TX2-120-1, and TX2-121-1 (FIG. 4A) and SML-11-124-1 and TX2-126-1 (FIG. 4B) immunoblotted against various antibodies; line 1: ErbB3 antibody; line 2: Phospho-Akt (Ser473) antibody; line 3: p44/42 MAPK (p-Erk1/2) antibody; line 4: T-Akt antibody; and line 5: Phospho-p44/42 MAPK (T-Erk1/2) (Thr202/Thr204) antibody.
Figure 4B:
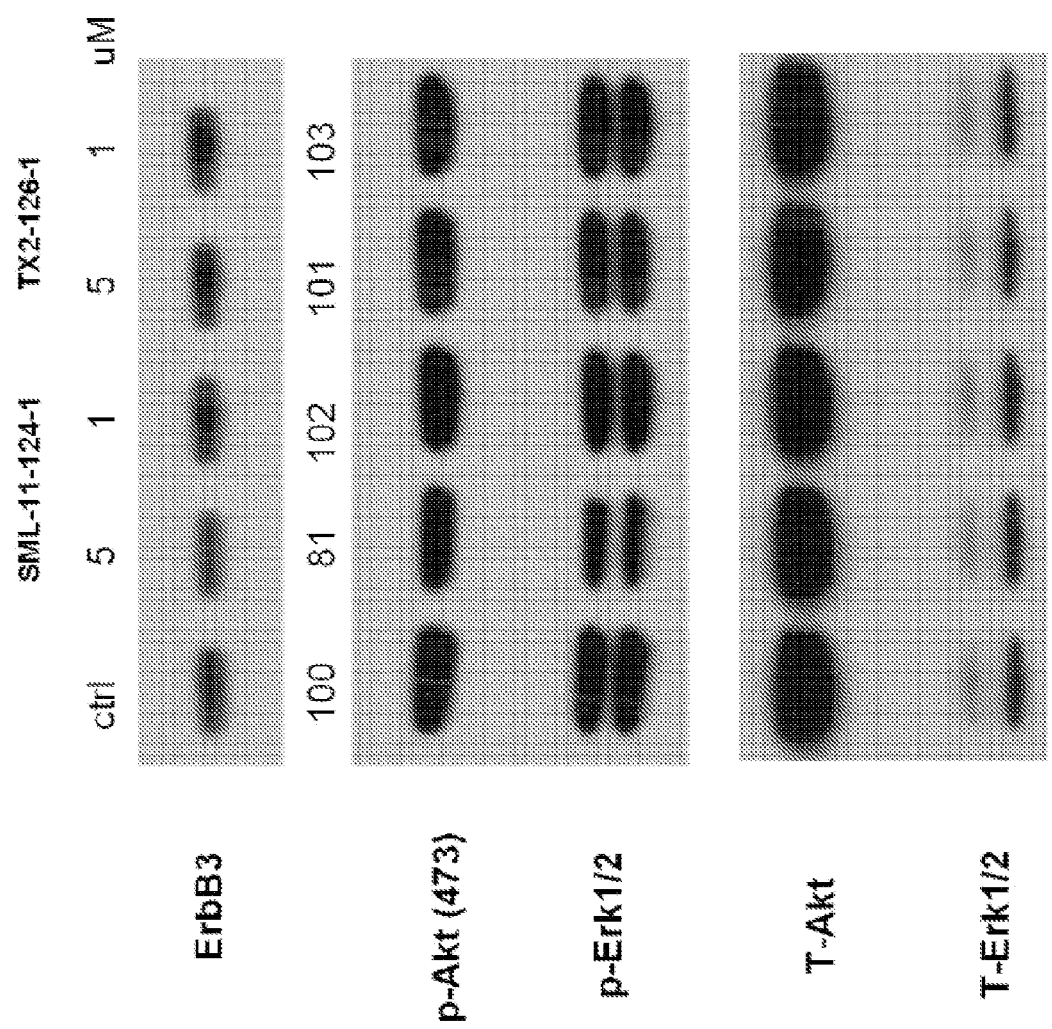

FIGS. 4A and 4B depict electrophoretic gel image (SDS-PAGE) results of compounds TX2-112-1, TX2-113-1, TX2-114-1, TX2-120-1, and TX2-121-1 (FIG. 4A) and SML-11-124-1 and TX2-126-1 (FIG. 4B) immunoblotted against various antibodies; line 1: ErbB3 antibody; line 2: Phospho-Akt (Ser473) antibody; line 3: p44/42 MAPK (p-Erk1/2) antibody; line 4: T-Akt antibody; and line 5: Phospho-p44/42 MAPK (T-Erk1/2) (Thr202/Thr204) antibody. The general procedure for running this gel is provided below.

PC9 Gefitinib Resistant 4 (GR4) cells were cultured in 60 mm plate with 10% fetal bovine serum (FBS), Roswell Park Memorial Institute medium (RPMI) medium. When the confluence reached 80%, cells were treated with compounds in indicated concentration. After 4 hours, wash cells with medium for three times. Cells were cultured for another 4 hours, followed by 3 times PBS washes. Cells were lysed with lysis buffer (25 mM Tris-HCl pH 7.4, 150 mM NaCl, 1 mM EDTA, 1% NP-40, 5% glycerol, Roche PhosSTOP phosphatase inhibitor cocktail tablets and Roche Complete Protease inhibitor cocktail tablets). The cell lysate was rotated end-to-end for approximately 30 min, centrifuged at 10,000 g for 15 minutes at 4° C. The supernatant was transferred to new tubes. The total protein concentration was measure by Pierce BCA protein assay: BCA reagent A and B were mixed with the ration of 20:1. Pipette 1 ml the mixture to each disposal plastic cuvette, add 2 ul lysate. Incubate at 37° C. for approximately 30 minutes. Cool all tubes to room temperature.

With the spectrophotometer set to 562 nm, zero the instrument on a cuvette filled only with water. Subsequently, measure the absorbance of all the samples with 10 minutes. Subtract the average 562 nm absorbance measurement of the Blank standard replicates from the 562 nm absorbance measurement of all other individual standard and unknown sample replicates. Prepare a standard curve by plotting the average Blank-corrected 562 nm measurement for each BSA standard vs. its concentration. Use the standard curve to determine the protein concentration of each unknown sample. Dilute all samples to 1.0 mg/ml with lysis buffer. Add same volume 1:1 loading buffer to samples, heat samples at 95° C. for 10 min. Run samples on an SDS-PAGE gel at 110V.

After transferred, the membrane was immunoblotted with antibodies: ErbB3 antibody, Santa Cruz sc-285; Phospho-Akt (Ser473) antibody, Cell Signaling 4058; Akt antibody, Cell Signaling 4685; Phospho-p44/42 MAPK (Erk1/2) (Thr202/Thr204), Cell Signaling 4377; p44/42 MAPK (Erk1/2), Cell Signaling 4695.

OTHER EMBODIMENTS

In the claims articles such as "a," "an," and "the" may mean one or more than one unless indicated to the contrary or otherwise evident from the context. Claims or descriptions that include "or" between one or more members of a group are considered satisfied if one, more than one, or all of the group members are present in, employed in, or otherwise relevant to a given product or process unless indicated to the contrary or otherwise evident from the context. The invention includes embodiments in which exactly one member of the group is present in, employed in, or otherwise relevant to a given product or process. The invention includes embodiments in which more than one, or all of the group members are present in, employed in, or otherwise relevant to a given product or process.

Furthermore, the invention encompasses all variations, combinations, and permutations in which one or more limitations, elements, clauses, and descriptive terms from one or more of the listed claims is introduced into another claim. For example, any claim that is dependent on another claim can be modified to include one or more limitations found in any other claim that is dependent on the same base claim. Where elements are presented as lists, e.g., in Markush group format, each subgroup of the elements is also disclosed, and any element(s) can be removed from the group. It should it be understood that, in general, where the invention, or aspects of the invention, is/are referred to as comprising particular elements and/or features, certain embodiments of the invention or aspects of the invention consist, or consist essentially of, such elements and/or features. For purposes of simplicity, those embodiments have not been specifically set forth in haec verba herein. It is also noted that the terms "comprising" and "containing" are intended to be open and permits the inclusion of additional elements or steps. Where ranges are given, endpoints are included. Furthermore, unless otherwise indicated or otherwise evident from the context and understanding of one of ordinary skill in the art, values that are expressed as ranges can assume any specific value or sub-range within the stated ranges in different embodiments of the invention, to the tenth of the unit of the lower limit of the range, unless the context clearly dictates otherwise.

This application refers to various issued patents, published patent applications, journal articles, and other publications, all of which are incorporated herein by reference. If there is a conflict between any of the incorporated references and the instant specification, the specification shall control. In addition, any particular embodiment of the present invention that falls within the prior art may be explicitly excluded from any one or more of the claims. Because such embodiments are deemed to be known to one of ordinary skill in the art, they may be excluded even if the exclusion is not set forth explicitly herein. Any particular embodiment of the invention can be excluded from any claim, for any reason, whether or not related to the existence of prior art.

Those skilled in the art will recognize or be able to ascertain using no more than routine experimentation many equivalents to the specific embodiments described herein. The scope of the present embodiments described herein is not intended to be limited to the above Description, but rather is as set forth in the appended claims. Those of ordinary skill in the art will appreciate that various changes and modifications to this description may be made without departing from the spirit or scope of the present invention, as defined in the following claims.

What is claimed is:

1. A compound of Formula (II):

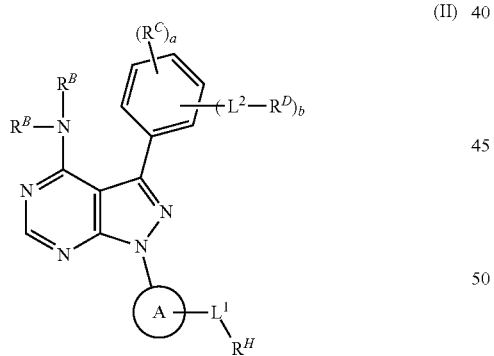

(II)

or a pharmaceutically acceptable salt thereof;
wherein:
Ring A is substituted or unsubstituted carbocyclyl, substituted or unsubstituted heterocyclyl, substituted or unsubstituted aryl, or substituted or unsubstituted heteroaryl;
each occurrence of $R^B$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, or a nitrogen protecting group, or two $R^B$ groups are joined to form an substituted or unsubstituted heterocyclic or substituted or unsubstituted heteroaryl ring;
each instance of $R^C$ is independently hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, $-OR^{C1}$, $-N(R^{C1})_2$, $-SR^{C1}$, $-C(=O)R^{C1}$, $-C(=O)OR^{C1}$, $-C(=O)SR^{C1}$, $-C(=O)N(R^{C1})_2$, $-NR^{C1}C(=O)R^{C1}$, $-NR^{C1}C(=O)OR^{C1}$, $-NR^{C1}C(=O)SR^{C1}$, or $-NR^{C1}C(=O)N(R^{C1})_2$, wherein each occurrence of $R^{C1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{C1}$ groups are joined to form a substituted or unsubstituted heterocyclic or substituted or unsubstituted heteroaryl ring;
a is 0, 1, 2, 3, or 4;
b is 1;
$L^1$ represents a linker of 4 to 20, inclusive, consecutive, covalently bonded atoms in length, selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof;
$L^2$ represents a bond or a linker selected from the group consisting of substituted and unsubstituted alkylene; substituted and unsubstituted alkenylene; substituted and unsubstituted alkynylene; substituted and unsubstituted heteroalkylene; substituted and unsubstituted heteroalkenylene; substituted and unsubstituted heteroalkynylene; substituted and unsubstituted heterocyclylene; substituted and unsubstituted carbocyclylene; substituted and unsubstituted arylene; substituted and unsubstituted heteroarylene; and combinations thereof;
$R^H$ represents a hydrophobic group selected from the group consisting of substituted and unsubstituted aryl, substituted and unsubstituted heteroaryl, substituted and unsubstituted carbocyclyl, substituted and unsubstituted heterocyclyl, substituted and unsubstituted aralkyl, substituted and unsubstituted heteroarylalkyl, substituted and unsubstituted carbocycylalkyl, and substituted and unsubstituted heterocyclylalkyl;
wherein the hydrophobic group refers to a group comprising zero hydrogen bond donors; and
$R^D$ is of formula:

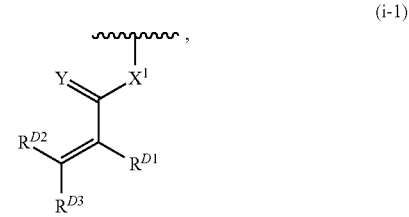

(i-1)

-continued
(i-2)
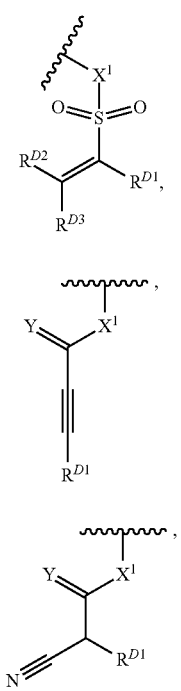
(i-3)
(i-4)
(i-5)
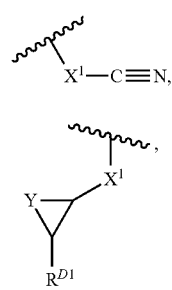
(i-6)
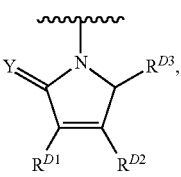
(i-7)
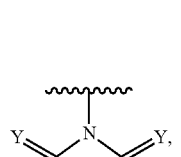
(i-8)
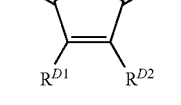
(i-9)
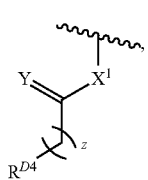
-continued
(i-10)
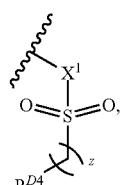
(i-11)
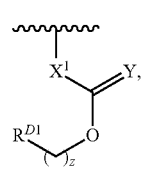
(i-12)
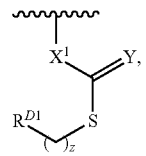
(i-13)
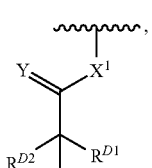
(i-14)
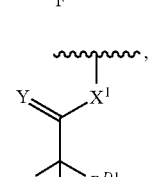
(i-15)
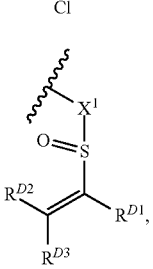
(i-16)
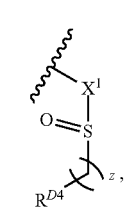
(i-17)
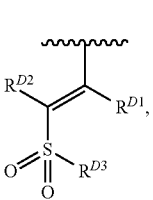

147
-continued

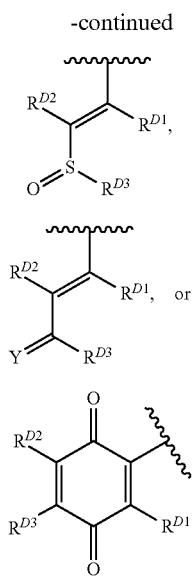

(i-18)

(i-19)

(i-20)

wherein:
R$^{D1}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D1a}$, —N(R$^{D1a}$)$_2$, —SR$^{D1a}$, —CH$_2$OR$^{D1a}$, —CH$_2$N(R$^{D1a}$)$_2$, —CH$_2$SR$^{D1a}$, —C(=O)R$^{D1a}$, —C(=O)OR$^{D1a}$, —C(=O)SR$^{D1a}$, —C(=O)N(R$^{D1a}$)$_2$, —C(=S)R$^{D1a}$, —C(=S)OR$^{D1a}$, —C(=S)SR$^{D1a}$, —C(=S)N(R$^{D1a}$)$_2$, —C(=NR$^{D1a}$)R$^{D1a}$, —C(=NR$^{D1a}$)OR$^{D1a}$, —C(=NR$^{D1a}$)SR$^{D1a}$, or —C(=NR$^{D1a}$)N(R$^{D1a}$)$_2$, wherein each occurrence of R$^{D1a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D1a}$ groups are joined to form an substituted or unsubstituted heterocyclic ring;

R$^{D2}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —CN, —NO$_2$, —OR$^{D2a}$, —N(R$^{D2a}$)$_2$, —SR$^{D2a}$, —CH$_2$OR$^{D2a}$, —CH$_2$N(R$^{D2a}$)$_2$, —CH$_2$SR$^{D2a}$, —C(=O)R$^{D2a}$, —C(=O)OR$^{D2a}$, —C(=O)SR$^{D2a}$, —C(=O)N(R$^{D2a}$)$_2$, —C(=S)R$^{D2a}$, —C(=S)OR$^{D2a}$, —C(=S)SR$^{D2a}$, —C(=S)N(R$^{D2a}$)$_2$, —C(=NR$^{D2a}$)R$^{D2a}$, —C(=NR$^{D2a}$)OR$^{D2a}$, —C(=NR$^{D2a}$)SR$^{D2a}$, or —C(=NR$^{D2a}$)N(R$^{D2a}$)$_2$, wherein each occurrence of R$^{D2a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D2a}$ groups are joined to form an substituted or unsubstituted heterocyclic ring;

148

R$^{D3}$ is hydrogen, halogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —OR$^{D3a}$, —N(R$^{D3a}$)$_2$, —SR$^{D3a}$, —CH$_2$OR$^{D3a}$, —CH$_2$N(R$^{D3a}$)$_2$, —CH$_2$SR$^{D3a}$, —C(=O)R$^{D3a}$, —C(=O)OR$^{D3a}$, —C(=O)SR$^{D3a}$, —C(=O)N(R$^{D3a}$)$_2$, —C(=S)R$^{D3a}$, —C(=S)OR$^{D3a}$, —C(=S)SR$^{D3a}$, —C(=S)N(R$^{D3a}$)$_2$, —C(=NR$^{D3a}$)R$^{D3a}$, —C(=NR$^{D3a}$)OR$^{D3a}$, —C(=NR$^{D3a}$)SR$^{D3a}$, or —C(=NR$^{D3a}$)N(R$^{D3a}$)$_2$, wherein each occurrence of R$^{D3a}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl, or two R$^{D3a}$ groups are joined to form an substituted or unsubstituted heterocyclic ring;

optionally R$^{D1}$ and R$^{D3}$, or R$^{D2}$ and R$^{D3}$, or R$^{D1}$ and R$^{D2}$ are joined to form an substituted or unsubstituted carbocyclic or substituted or unsubstituted heterocyclic ring;

R$^{D4}$ is a leaving group selected from the group consisting of —Br, —Cl, —I, and —OS(=O)$_w$R$^{D4a}$, wherein w is 1 or 2, and R$^{D4a}$ is substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, or substituted or unsubstituted heteroaryl;

X$^1$ is a bond or NR$^{D5}$, wherein R$^{D5}$ is hydrogen, C$_{1-6}$ alkyl, or a nitrogen protecting group;

each instance of Y is independently O, S, or NR$^{D6}$, wherein R$^{D6}$ is hydrogen, C$_{1-6}$ alkyl, or a nitrogen protecting group; and z is 0, 1, 2, 3, 4, 5, or 6.

2. The compound of claim 1, wherein Ring A is substituted or unsubstituted phenyl.

3. The compound of claim 1, wherein Ring A is a substituted or unsubstituted 5- to 6-membered heteroaryl ring.

4. The compound of claim 1, wherein Ring A is a substituted or unsubstituted C$_{3-8}$carbocyclyl ring.

5. The compound of claim 1, wherein Ring A is a substituted or unsubstituted 3- to 8-membered heterocyclyl ring.

6. The compound of claim 1 of Formula (II-g):

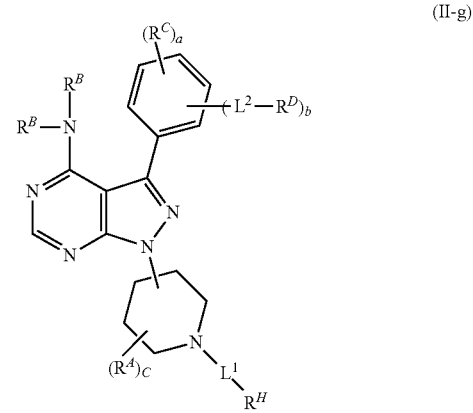

(II-g)

or a pharmaceutically acceptable salt thereof, wherein:
each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —$C(\!=\!O)R^{A1}$, or —$C(\!=\!O)OR^{A1}$, wherein each occurrence of $R^{A1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring; and
c is 0 or 1.

7. The compound of claim 1 of Formula (II-e4):

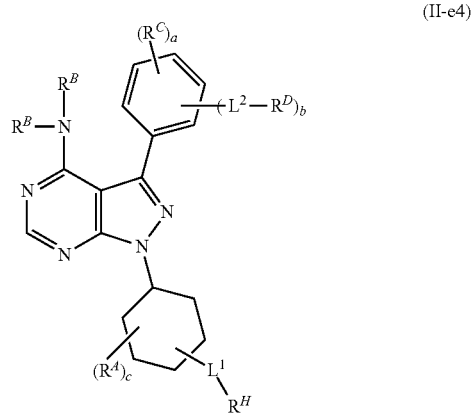

(II-e4)

or a pharmaceutically acceptable salt thereof,
wherein:
each occurrence of $R^A$ is, independently, hydrogen, halogen, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, —$OR^{A1}$, —$N(R^{A1})_2$, —$SR^{A1}$, —$C(\!=\!O)R^{A1}$, or —$C(\!=\!O)OR^{A1}$, wherein each occurrence of $R^{A1}$ is independently hydrogen, acyl, substituted or unsubstituted alkyl, substituted or unsubstituted alkenyl, substituted or unsubstituted alkynyl, substituted or unsubstituted carbocyclyl, substituted or unsubstituted heterocyclyl, substituted or unsubstituted aryl, substituted or unsubstituted heteroaryl, a nitrogen protecting group when attached to a nitrogen atom, an oxygen protecting group when attached to an oxygen atom, or a sulfur protecting group when attached to a sulfur atom, or two $R^{A1}$ groups are joined to form a substituted or unsubstituted heterocyclic or substituted or unsubstituted heteroaryl ring; and
c is 0 or 1.

8. The compound of claim 1, wherein $R^H$ is a hydrophobic substituted or unsubstituted aryl, or a hydrophobic substituted or unsubstituted aralkyl.

9. The compound of claim 8, wherein $R^H$ is a group of formula:

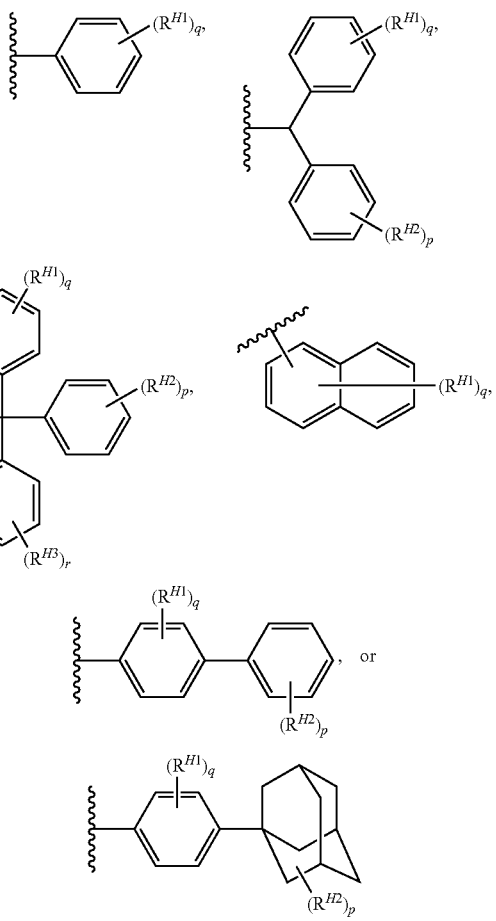

wherein each occurrence of $R^{H1}$, $R^{H2}$, and $R^{H3}$ is independently halogen, alkyl, haloalkyl, alkoxy, or dialkylamino; and p, q, and r are independently 0, 1, 2, or 3.

10. The compound of claim 1, wherein $R^H$ is a hydrophobic substituted or unsubstituted carbocyclyl, or a hydrophobic substituted or unsubstituted carbocyclylalkyl.

11. The compound of claim 10, wherein $R^H$ is a group of formula:

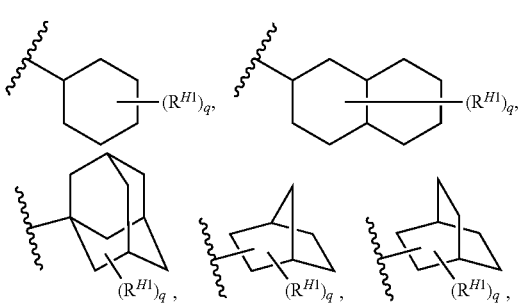

-continued

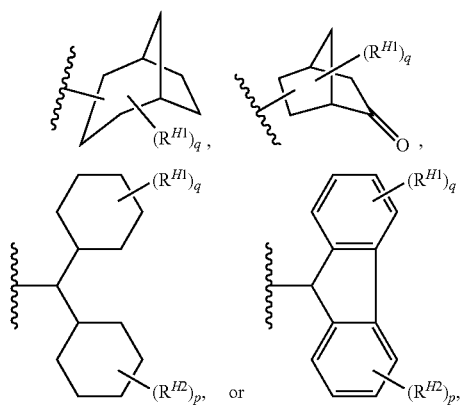

wherein each occurrence of $R^{H1}$ and $R^{H2}$ is independently halogen, alkyl, haloalkyl, alkoxy, or dialkylamino; and p and q are independently 0, 1, 2, or 3.

12. The compound of claim 1, wherein $R^H$ is a hydrophobic substituted or unsubstituted heterocyclyl, or a hydrophobic substituted or unsubstituted heterocyclylalkyl.

13. The compound of claim 12, wherein $R^H$ is a group of formula:

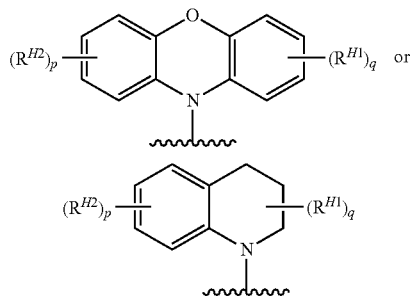

wherein each occurrence of $R^{H1}$ and $R^{H2}$ is independently halogen, alkyl, haloalkyl, alkoxy, or dialkylamino; and p and q are independently 0, 1, 2, or 3.

14. The compound of claim 1, wherein $L^1$ represents a linker consisting of one group, or a combination of 2 to 20 consecutive covalently bonded groups, of the formula:

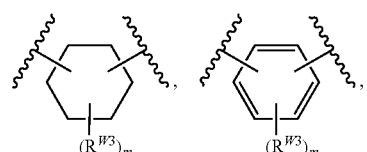

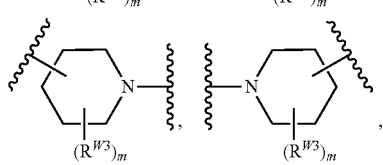

-continued

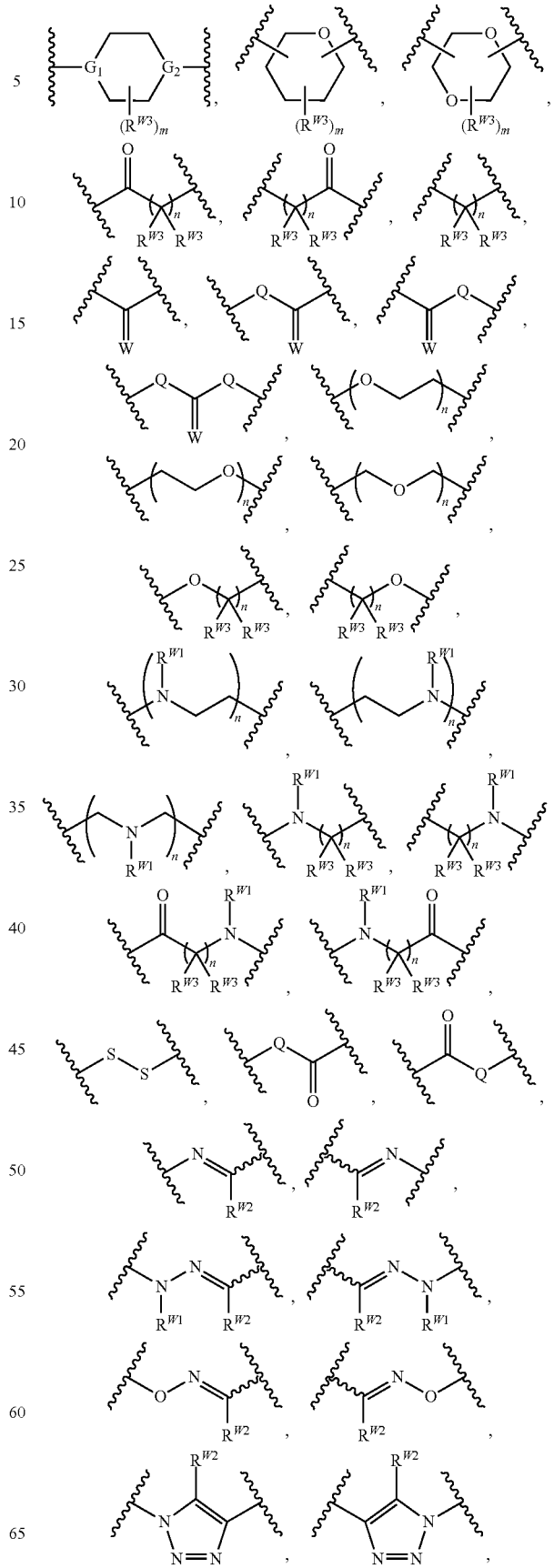

153

-continued

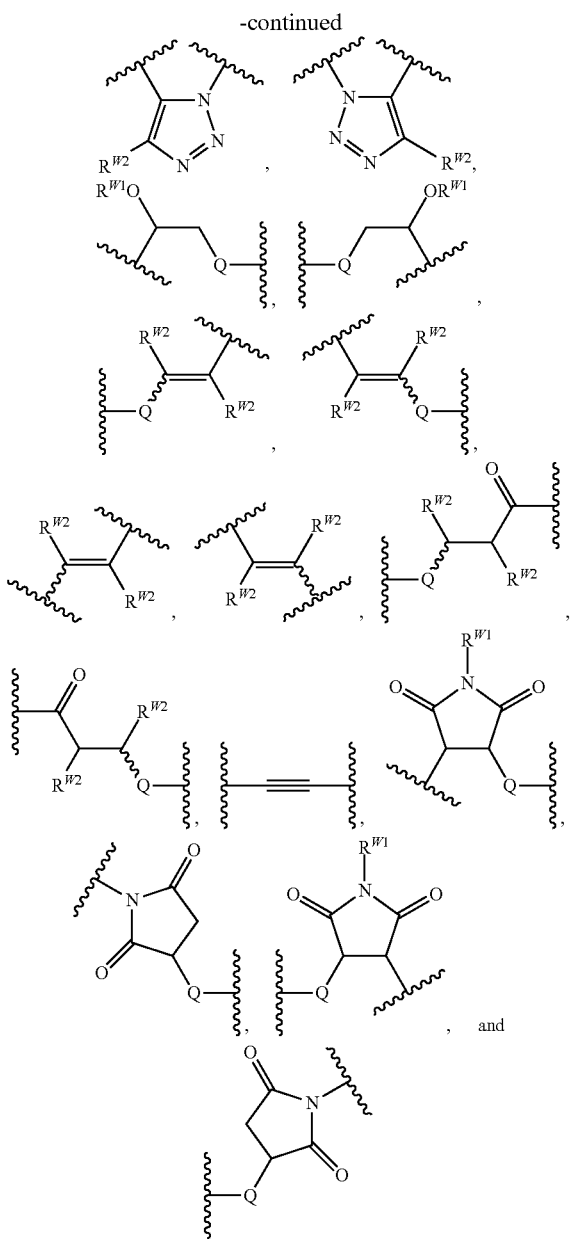

wherein:
each instance of n is independently an integer between 1 to 10, inclusive;
each instance of m is independently 0, 1 or 2;
each instance of Q is independently —$NR^{W1}$—; —$NR^{W1}$—$NR^{W1}$—; —O—$NR^{W1}$—; —$NR^{W1}$—O—; —S—; or —O—;
each instance of W is independently O, S, or $NR^{W1}$;
each instance of $G_1$ and $G_2$ are independently N or CH;
each instance of $R^{W1}$ is independently hydrogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; a nitrogen protecting group if attached to a nitrogen atom, or an oxygen protecting group if attached to an oxygen atom;
each instance of $R^{W2}$ is independently hydrogen; substituted or unsubstituted alkyl; substituted or unsubsti-

154 tuted alkenyl; substituted or unsubstituted alkynyl; substituted or unsubstituted carbocyclyl; substituted or unsubstituted heterocyclyl; substituted or unsubstituted aryl; substituted or unsubstituted heteroaryl; or two $R^{W2}$ groups are joined to form a 5-6 membered ring; and
each instance of $R^{W3}$ is independently hydrogen; halogen; substituted or unsubstituted alkyl; substituted or unsubstituted alkenyl; substituted or unsubstituted alkynyl; substituted or unsubstituted carbocyclyl; substituted or unsubstituted heterocyclyl; substituted or unsubstituted aryl; or substituted or unsubstituted heteroaryl, or two $R^{W3}$ groups are joined to form a 3-6 membered ring;
or $R^{W1}$ and $R^{W3}$ are joined to form a 5-6 membered heterocyclic ring; provided $L^1$ is a linker of 4 to 20, inclusive, consecutive, covalently bonded atoms in length.

15. The compound of claim 14, wherein -$L^1$-$R^H$ represents a group of the formula:

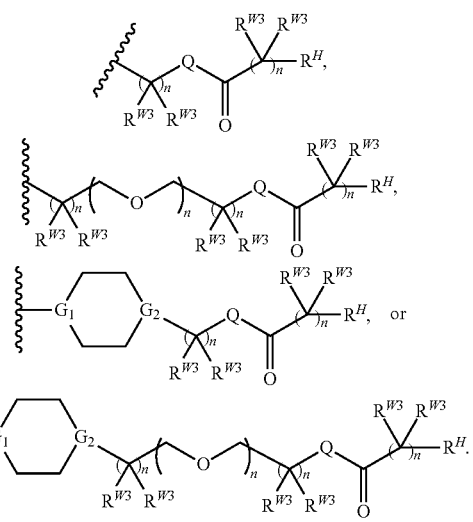

16. A pharmaceutical composition comprising a compound of claim 1, or a pharmaceutically acceptable salt thereof, and a pharmaceutically acceptable excipient.

17. A method of treating breast cancer, ovarian cancer, or lung cancer, the method comprising administering a compound of claim 1, or a pharmaceutically acceptable salt thereof, to a subject in need thereof in an amount sufficient to treat the breast cancer, ovarian cancer, or lung cancer.

18. The compound of claim 1 selected from the group consisting of:

TX2-112-1

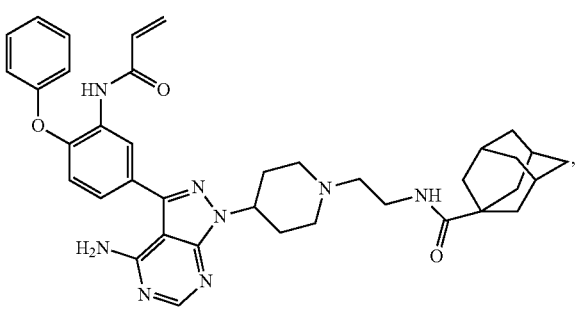

-continued
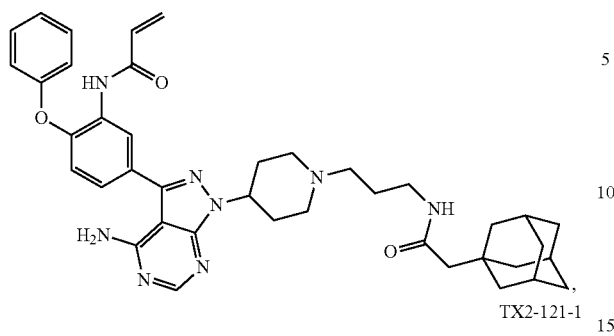
TX2-113-1
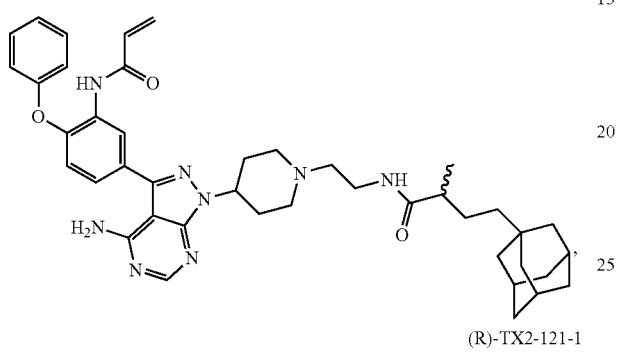
(R)-TX2-121-1
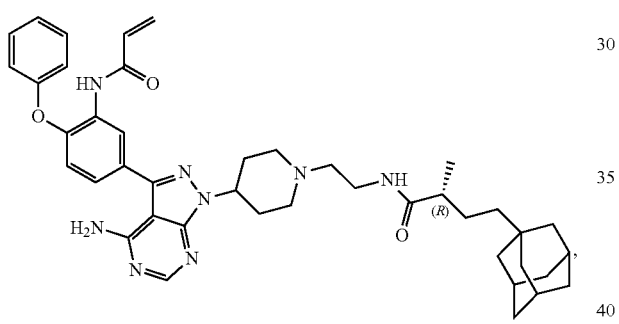
-continued
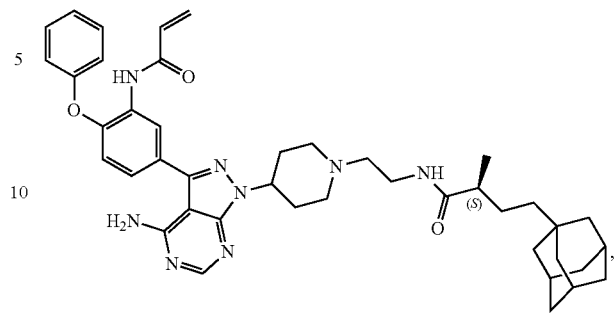
(S)-TX2-121-1
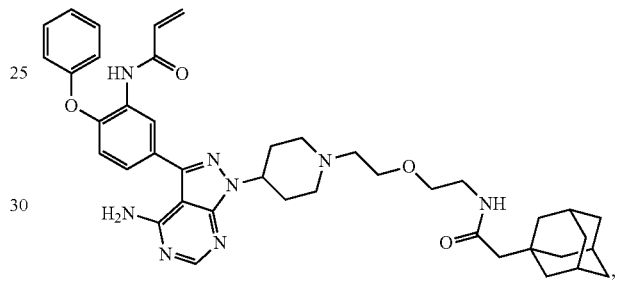
TX2-114-1
and pharmaceutically acceptable salts thereof.
19. A compound selected from the group consisting of:
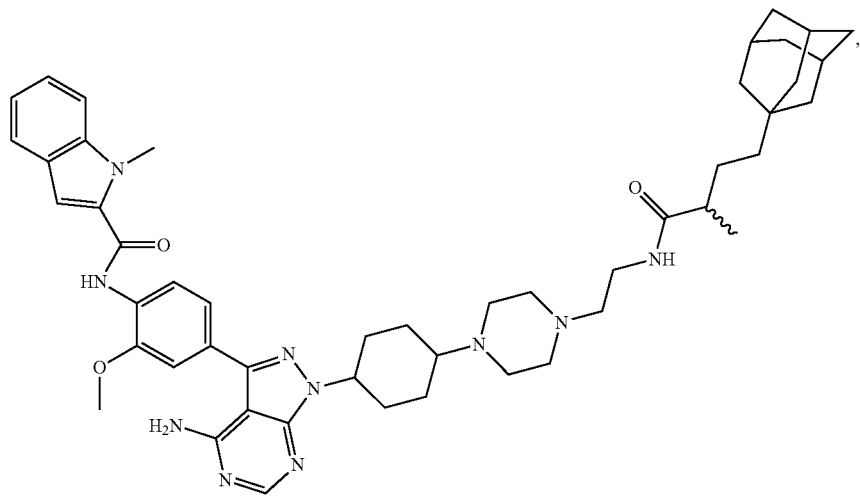
SML-11-124-1

-continued
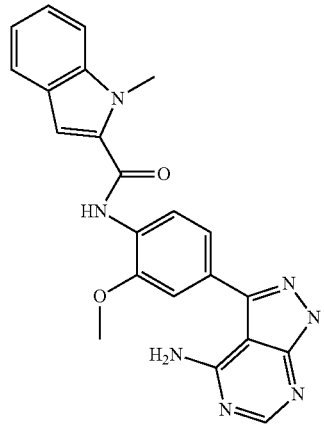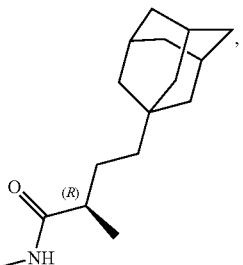
(R)-SML-11-124-1
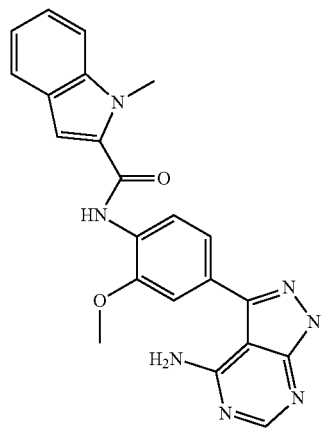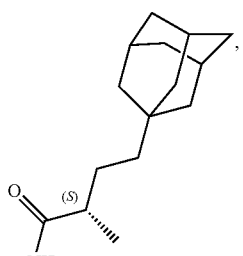
(S)-SML-11-124-1
and pharmaceutically acceptable salts thereof.
20. A compound selected from the group consisting of:
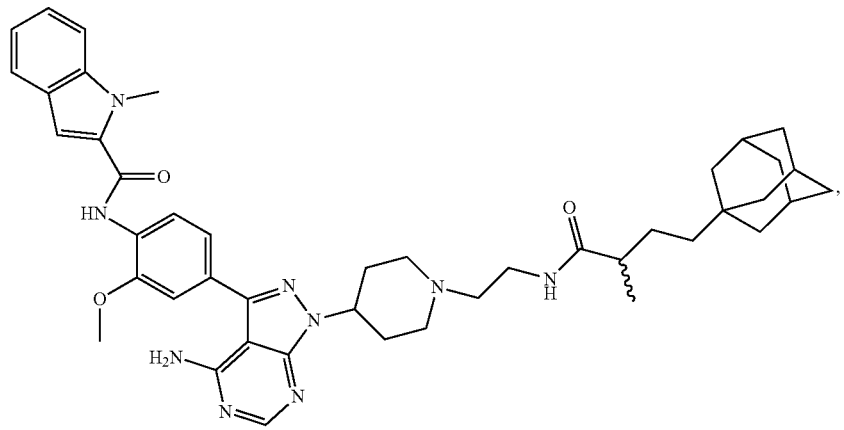
TX2-126-1

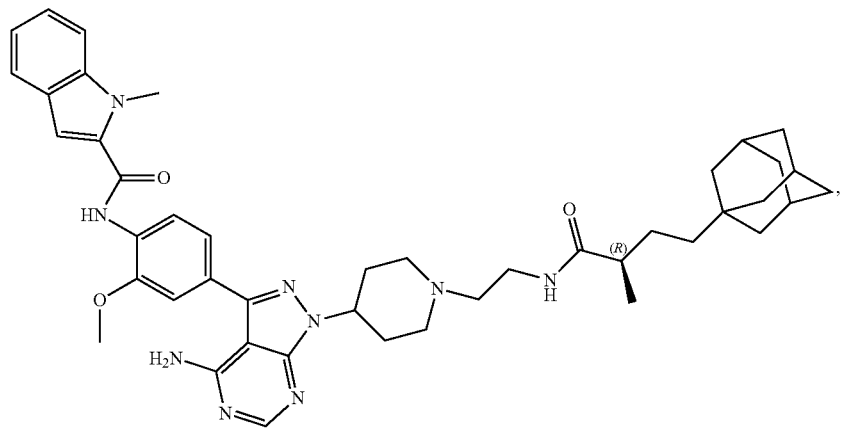
(R)-TX2-126-1
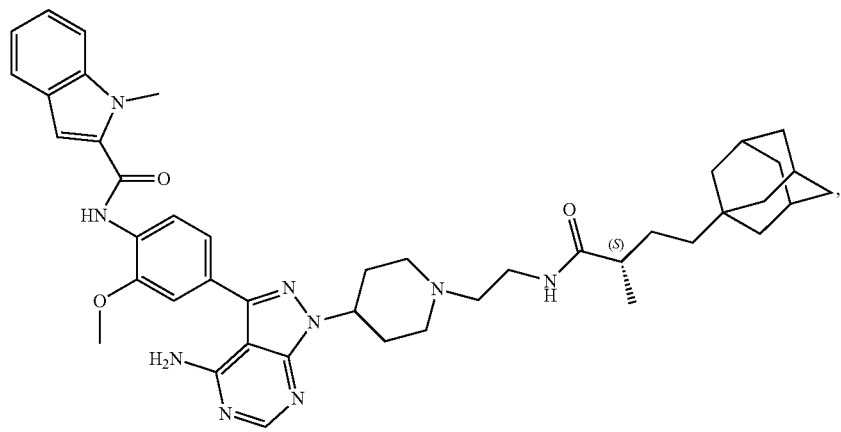
(S)-TX2-126-1
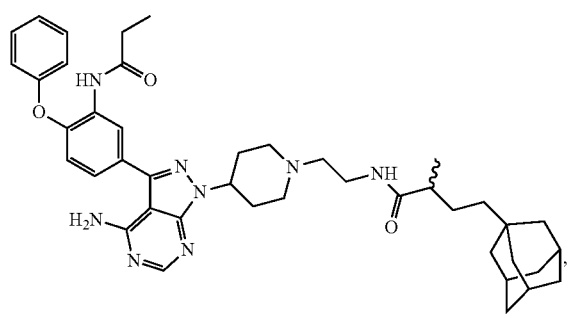
TX2-121-3
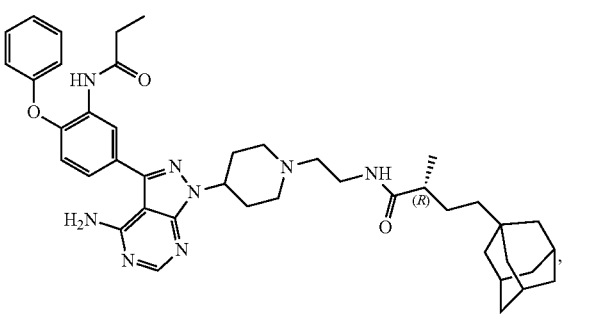
(R)-TX2-121-3
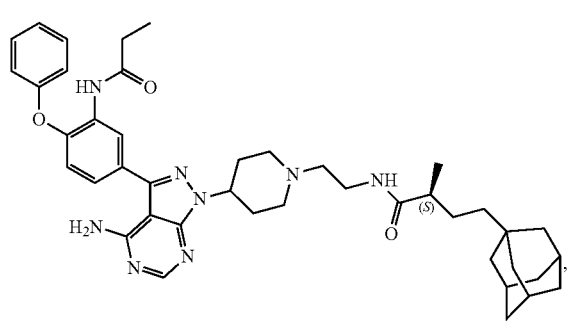
(S)-TX2-121-3
and pharmaceutically acceptable salts thereof.
21. The compound of claim 1, wherein $L^1$ represents a linker of 5 to 15, inclusive, consecutive, covalently bonded atoms in length.
22. The compound of claim 1, wherein $L^1$ represents a linker of 5 to 11, inclusive, consecutive, covalently bonded atoms in length.
* * * * *

UNITED STATES PATENT AND TRADEMARK OFFICE
CERTIFICATE OF CORRECTION

PATENT NO. : 9,758,522 B2
APPLICATION NO. : 14/436657
DATED : September 12, 2017
INVENTOR(S) : Nathanael S. Gray et al.

It is certified that error appears in the above-identified patent and that said Letters Patent is hereby corrected as shown below:

In the Claims

In Claim 14, at Column 153, Line 39, the term "and" should be replaced with the term --or--.

Signed and Sealed this
Fourteenth Day of November, 2017

Joseph Matal
*Performing the Functions and Duties of the*
*Under Secretary of Commerce for Intellectual Property and*
*Director of the United States Patent and Trademark Office*